(12) United States Patent
Hannoush et al.

(10) Patent No.: US 10,428,125 B2
(45) Date of Patent: Oct. 1, 2019

(54) CYSTINE KNOT SCAFFOLD PLATFORM

(71) Applicant: Genentech, Inc., South San Francisco, CA (US)

(72) Inventors: Rami Hannoush, San Mateo, CA (US); Harini Kaluarachchi, South San Francisco, CA (US); Aaron Nile, San Bruno, CA (US); Cameron Noland, South San Francisco, CA (US); Yingnan Zhang, Fremont, CA (US); Lijuan Zhou, Belmont, CA (US); Xinxin Gao, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/267,087

(22) Filed: Sep. 15, 2016

(65) Prior Publication Data
US 2017/0129927 A1 May 11, 2017

Related U.S. Application Data

(60) Provisional application No. 62/219,063, filed on Sep. 15, 2015.

(51) Int. Cl.
| | | |
|---|---|---|
| *C07K 14/415* | (2006.01) | |
| *C07K 14/00* | (2006.01) | |
| *A61K 38/16* | (2006.01) | |
| *A61K 9/00* | (2006.01) | |
| *A61K 47/34* | (2017.01) | |
| *A61K 38/00* | (2006.01) | |
| *C07K 14/81* | (2006.01) | |
| *C07K 14/47* | (2006.01) | |
| *A61K 9/50* | (2006.01) | |

(52) U.S. Cl.
CPC .......... *C07K 14/415* (2013.01); *A61K 9/0051* (2013.01); *A61K 9/5031* (2013.01); *A61K 38/00* (2013.01); *A61K 38/168* (2013.01); *A61K 47/34* (2013.01); *C07K 14/001* (2013.01); *C07K 14/4702* (2013.01); *C07K 14/811* (2013.01); *C07K 2319/70* (2013.01)

(58) Field of Classification Search
CPC ...... A61K 38/00; A61K 38/168; A61K 47/34; A61K 9/0051; A61K 9/5031; C07K 14/001; C07K 14/415; C07K 14/4702; C07K 14/811; C07K 2319/70
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,485,045 A | 11/1984 | Regen | |
| 4,496,689 A | 1/1985 | Mitra | |
| 4,544,545 A | 10/1985 | Ryan et al. | |
| 4,640,835 A | 2/1987 | Shimizu et al. | |
| 4,670,417 A | 6/1987 | Iwashita et al. | |
| 4,703,039 A | 10/1987 | Hawiger et al. | |
| 4,791,192 A | 12/1988 | Nakagawa et al. | |
| 5,013,556 A | 5/1991 | Woodle et al. | |
| 5,428,130 A | 6/1995 | Capon et al. | |
| 5,605,793 A | 2/1997 | Stemmer | |
| 5,747,035 A | 5/1998 | Presta et al. | |
| 5,811,238 A | 9/1998 | Stemmer et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,869,046 A | 2/1999 | Presta et al. | |
| 7,918,814 B2 | 4/2011 | Prausnitz et al. | |
| 2005/0281861 A1 | 12/2005 | Hughes et al. | |
| 2006/0182783 A1 | 8/2006 | Hughes et al. | |
| 2008/0107694 A1 | 5/2008 | Trogden et al. | |
| 2008/0181929 A1 | 7/2008 | Robinson et al. | |
| 2009/0263460 A1 | 10/2009 | McDonald | |
| 2009/0305994 A1 | 12/2009 | D'Andrea et al. | |
| 2010/0015158 A1 | 1/2010 | Robinson et al. | |
| 2010/0216702 A1 | 8/2010 | Szkudlinski et al. | |
| 2011/0136740 A1 | 6/2011 | Cochran et al. | |
| 2011/0207653 A1 | 8/2011 | Raiche et al. | |
| 2014/0154321 A1 | 6/2014 | Ashton | |

(Continued)

FOREIGN PATENT DOCUMENTS

| | | |
|---|---|---|
| WO | WO-1991/14438 A1 | 10/1991 |
| WO | WO-1994/11026 A2 | 5/1994 |
| WO | WO-1994/11026 A3 | 5/1994 |

(Continued)

OTHER PUBLICATIONS

Abou-Nadler, M. et al. (2010, e-pub. Sep. 1, 2010). "Rapid Generation of Random Mutant Libraries," *Bioengineered Bugs* 1(5):337-340.
Achouri, D. et al. (2012). "Recent Advances in Ocular Drug Delivery," *Drug Dev. Indust. Pharm.* 39:1599-1617, 19 pages.
Alberts, B. et al. (2008). "The Cytoskeleton," Chapter 16 in *Molecular Biology of the Cell.* 5th Ed., Garland Science, pp. 1-88.
Amblard, M. et al. (2005). "Fundamentals of Modern Peptide Synthesis," Chapter 1 in *Methods in Molecular Biology: Peptide Synthesis and Applications,* vol. 298, Humana Press, Howl, J. ed., 273 pages.
Arnon, R et al. (1985). "Monoclonal Antibodies for Immunotargeting of Drugs in Cancer Therapy," in *Monoclonal Antibodies and Cancer Therapy,* Reisfeld et al., eds., Alan R. Liss, Inc., pp. 243-256.

(Continued)

*Primary Examiner* — Rachael E Bredefeld
*Assistant Examiner* — Erinne R Dabkowski
(74) *Attorney, Agent, or Firm* — Morrison & Foerster LLP

(57) ABSTRACT

Provided are non-naturally occurring cystine knot peptides (CKPs) that bind to VEGF-A. Additionally, provided are methods of using non-naturally occurring CKPs that bind to VEGF-A, including diagnostic and therapeutic compositions and methods. Non-naturally CKPs that bind low density lipoprotein receptor-related protein 6 (LRP6) are also provided.

39 Claims, 18 Drawing Sheets
(18 of 18 Drawing Sheet(s) Filed in Color)
Specification includes a Sequence Listing.

(56) References Cited

U.S. PATENT DOCUMENTS

2018/0291069 A1 10/2018 Hannoush et al.

FOREIGN PATENT DOCUMENTS

| WO | WO 1996/32478 A1 | 10/1996 | |
|---|---|---|---|
| WO | WO-1997/43316 A1 | 11/1997 | |
| WO | WO-1999/43713 A1 | 9/1999 | |
| WO | WO-2000/09560 A2 | 2/2000 | |
| WO | WO-2000/09560 A3 | 2/2000 | |
| WO | WO-2002/100318 A2 | 12/2002 | |
| WO | WO-2002/100318 A3 | 12/2002 | |
| WO | WO-2006/093758 A1 | 9/2006 | |
| WO | WO-2007/038619 A2 | 4/2007 | |
| WO | WO-2007/038619 A3 | 4/2007 | |
| WO | WO-2008/045252 A2 | 4/2008 | |
| WO | WO-2008/045252 A3 | 4/2008 | |
| WO | WO-2009/026461 A2 | 2/2009 | |
| WO | WO-2009/026461 A3 | 2/2009 | |
| WO | WO-2010/088548 A1 | 8/2010 | |
| WO | WO-2012/064658 A1 | 5/2012 | |
| WO | WO-2014/033184 A1 | 3/2014 | |
| WO | WO-2014057284 A2 * | 4/2014 | ........... C07K 14/415 |

OTHER PUBLICATIONS

Ausubel, F.M. et al. (2003). *Current Protocols in Molecular Biology*, John Wiley & Sons, Inc., Supplement 64, pp. 1-4648.

Avery, R.L. et al. (Dec. 2014). "Intravitreal Injection Technique and Monitoring: Updated Guidelines of an Expert PaneL," *Retina* 34(12)S1-S18.

Banta, S. et al. (2013, e-pub. Apr. 29, 2013). "Replacing Antibodies: Engineering New Binding Proteins," *Annu. Rev. Biomed. Eng.* 15:93-113.

Baranowski, P. et al. (2014). "Ophthalmic Drug Dosage Forms: Characterisation and Research Methods," *Sci. World J.* pp. 1-14.

Binz, H.K. et al. (Oct. 2005, E-Pub. Oct. 6, 2005). "Engineering Novel Binding Proteins From Nonimmunoglobulin Domains," *Nat. Biotechnol.* 23(10):1257-1268.

Binz, H.K. et al. (2005, e-pub. Jul. 6, 2005). "Engineered Proteins as Specific Binding Reagents," *Curr. Opin. Biotechnol.* 16:459-469.

Boddu, S.H.S. et al. (2014). "Drug Delivery to the Back of the Eye Following Topical Administration: An Update on Research and Patenting Activity," *Recent Patents on Drug Delivery and Formulation* 8:27-36.

Bourhis, E. et al. (Mar. 19, 2010). "Reconstitution of a Frizzled8 Wnt3a LRP6 Signaling Complex Reveals Multiple Wnt and Dkk1 Binding Sites on LRP6," *The Journal of Biological Chemistry* 285(12):9172-9179.

Caricasole, A. et al. (Jun. 30, 2004). "Induction of Dickkopf-1, a Negative Modulator of the Wnt Pathway, Is Associated with Neuronal Degeneration in Alzheimer's Brain," *J. Neurosci.* 24(26):6021-6027.

Cemazar, M. et al. (Jun. 11, 2008). "The Structure of a Two-Disulfide Intermediate Assists in Elucidating the Oxidative Folding Pathway of a Cyclic Cystine Knot Protein," *Structure* 16(6):842-851.

Cirino, P.C. et al. (2003). "Generating Mutant Libraries Using Error-Prone PCR," Chapter 1 in *Methods in Molecular Biology*, Arnold, F.H. et al., Human Press, New Jersey, 231:3-9.

Clevers, H. (Nov. 3, 2006). "Wnt/β-Catenin Signaling in Development and Disease," *Cell* 127:469-480.

Creighton, T.E. (1983). Proteins: Structure and Molecular Properties, W.H. Freeman & Co., San Francisco, pp. 70-87.

Davis, J.L. et al. (Apr. 1, 2004) "Novel Approaches to Ocular Drug Delivery," *Curr. Opin. Mol. Therap.* 6(2):195-205.

De Ferrari, G.V. et al. (May 29, 2007). "Common Genetic Variation Within the Low-Density Lipoprotein Receptor-Related Protein 6 and Late-Onset Alzheimer's Disease," *Proc. Natl. Acad. Sci. USA* 104(22):9434-9439.

Denardo, G.L. et al. (Oct. 1998). "Comparison of 1,4, 7 ,10-Tetraazacyciododecane-N,N',N", N'''-Tetraacetic Acid (DOTA)-Peptide-ChL6, A Novel Immunoconjugate with Catabolizabie Linker, to 2-Iminothiolane-2-[p-(Bromoacetamido)Benzyl]-DOTA-ChL6 in Breast Cancer Xenografts," *Clin. Cancer Res.* 4:2483-24990.

Donnelly, R.F. et al. (2010, e-pub. Mar. 18, 2010). "Microneedle-Based Drug Delivery Systems: Microfabrication, Drug Delivery, and Safety," *Drug Deliv.* 17(4):187-207.

Doshi, R.R. et al. (2011). "Intravitreal Injection Technique," *Seminars Ophthalmol.* 26(3):104-113.

Eljarrat-Binstock, E. et al. (Feb. 21, 2006, e-pub. Dec. 15, 2005). "Iontophoresis: A Non-Invasive Ocular Drug Delivery," *J. Controlled Release* 110:479-489.

Epstein, D.A. et al.(Jun. 1985). "Biological Activity of Liposome-Encapsulated Murine Interferon γ is Mediated by a Cell Membrane Receptor," *Proc. Natl. Acad. Sci. USA* 82:3688-3692.

Evan, G.I. et al. (Dec. 1985). "Isolation of Monoclonal Antibodies Specific for Human c-myc Proto-Oncogene Product," *Mol. Cell. Biol.* 5(12):3610-3616.

Fagan, X.J. et al. (2013). "Intravitreal Injections: a Review of the Evidence for Best Practice," *Clin. Exp. Ophthalmol.* 41:500-507.

Field, J. et al. (May 1988). "Purification of a RAS-Responsive Adenylyl Cyclase Complex from *Saccharomyces cerevisiae* by Use of an Epitope Addition Method," *Mol. Cell. Biol.* 8(5):2159-2165.

Firth, A.E. et al. (2005, e-pub. Jun. 2, 2005). "Statistics of Protein Library Construction," *Bioinformatics* 21(15):3314-3315.

Freeman, P.D. et al. (2009). "Preservatives in Topical Ophthalmic Medications: Historical and Clinical Perspectives," *Exp. Rev. Ophthalmol.* 4(1):59-64.

Fuh, G. et al. (Mar. 10, 2006). "Structure-Function Studies of Two Synthetic Anti-vascular Endothelial Growth Factor Fabs and Comparison with the Avastin™ Fab," *J. Biol. Chem.* 281(10):6625-6631.

Gabizon, A. et al. (Oct. 4, 1989). "Pharmacokinetics and Tissue Distribution of Doxorubicin Encapsulated in Stable Liposomes With Long Circulation Times," *J. National Cancer Inst.* 81(19):1484-1488.

Gaikwad, D.R. et al. (2013). "Recent Advances in Ocular Drug Delivery Systems," *Indo Amer. J. Pharm. Res.* 3(2):3216-3232.

Gao, Y. (2012). "Development of a Label-Free Competitive Ligand Binding Assay With Human Serum Albumin on a Molecularly Engineered Surface Plasmon Resonance Sensor Chip," *Analytical Methods* 4:3718-3723.

Gaudana, R. et al. (Sep. 2010). "Ocular Drug Delivery," *AAPS J.* 12(3):348-360.

Ghate, D. et al. (2006, e-pub. Feb. 28, 2006). "Ocular Drug Delivery," *Expert Opin. Drug Deliv.* 3(2):275-287.

Gong, Y. et al. (Sep. 13, 2010). "Wnt isoform-Specific interactions With Coreceptor Specify Inhibition or Potentiation of Signaling by LRP6 Antibodies," *PLoS ONE* 5(9):e12682), 17 pages.

Gong, Y. et al. (Nov. 16, 2001). "LDL Receptor-Related Protein 5 (LRP5) Affects Bone Accrual and Eye Development," *Cell* 107:513-523.

Gronwall, C. et al. (Mar. 25, 2009). "Engineered Affinity Proteins—Generation and Applications," *J. Biotechnol.* 140(3-4):254-269.

Gunasekera, S. et al. (2008, e-pub. Dec. 3, 2008). "Engineering Stabilized Vascular Endothelial Growth Factor-A Antagonists: Synthesis, Structural Characterization, and Bioactivity of Grafted Analogues of Cyclotides," *Journal of Medicinal Chemistry* 51(24):7697-7704.

Hansson, L.O. et al. (Mar. 26, 1999). "Evolution of Differential Substrate Specificities in Mu Class Glutathione Transferases Probed by DNA Shuffling," *J. Mol. Biol.* 287(2):265-276.

Harayama, S. (Feb. 1, 1998). "Artificial Evolution by DNA shuffling," *Trends Biotechnol.* 16(2):76-82.

Hellström, K.R. et al. (1987). "Antibodies for Drug Delivery," Chapter 15 in *Controlled Drug Delivery*, 2nd Ed., Robinson et al. (eds.), Marcel Dekker, Inc., pp. 623-653.

Hope, I.A. et al. (Nov. 1985). "GCN4 Protein, Synthesized In Vitro, Binds HIS3 Regulatory Sequences: Implications for General Control of Amino Acid Biosynthetic Genes in Yeast," *Cell* 43:177-188.

Hope, I.A. et al. (Sep. 12, 1986). "Functional Dissection of a Eukaryotic Transcriptional Activator Protein, GCN4 of Yeast," *Cell* 46:885-894.

(56) References Cited

OTHER PUBLICATIONS

Hope, I.A. et al. (1987). "GCN4, a Eukaryotic Transcriptional Activator Protein, Binds as a Dimer to Target DNA," *EMBO J.* 6(9):2781-2784.

Hope, I.A. et al. (Jun. 16, 1988). "Structural and Functional Characterization of the Short Acidic Transcriptional Activation region of Yeast GCN4 Protein," *Nature* 333:635-640.

Hopp, T.P. et al. (1988). "A Short Polypeptide Marker Sequence Useful for Recombinant Protein Identification and Purification," *BioTechnology* 6:1204-1210.

Hsu, J. (May 2007). "Drug Delivery Methods for Posterior Segment Disease" *Curr. Opin. Ophthalmol.* 18(3):235-239.

Hwang, K.L. et al. (Jul. 1980). "Hepatic Uptake and Degradation of Unilamellar Sphingomyelin/ Cholesterol Liposomes: A Kinetic Study," *Proc. Natl. Acad. Sci. USA* 77(7):4030-4034.

Katoh, M. et al. (Jul. 15, 2007). "WNT Signaling Pathway and Stem Cell Signaling Network," *Clin Cancer Res* 13(14):4042-4045.

Kawai, M. et al. (Feb. 2011). "Emerging Therapeutic Opportunities for Skeletal Restoration," *Nat. Rev. Drug Discov.* 10(2):141-156, 32 pages.

Krätzner, R. et al. (Sep. 1, 2005). "Structure of *Ecballium elaterium* Trypsin Inhibitor II (EETI-II): A Rigid Molecular Scaffold," *Acta Cryst.* D61(Pt 9):1255-1262.

Kreig, P.A. et al. (1984). "Functional Messenger RNAs are Produced by SP6 in vitro Transcription of Cloned CDNAs," *Nucleic Acids Research* 12(18):7057-7077.

Kunkel, T.A. (Jan. 1987). "Rapid and Efficient Site-Specific Mutagenesis Without Phenotypic Selection," *Methods Enzymol* 82:488-492.

Kuno, N. et al. (Jan. 6, 2011). "Recent Advances in Ocular Drug Delivery Systems," *Polymers* 3:193-221.

Lang, J.C. (1995). "Ocular Drug Delivery Conventional Ocular Formulations," *Adv. Drug Deliv. Rev.* 16:39-43.

Lehmann, M. et al. (2001). "Engineering Proteins for Thermostability: The Use of Sequence Alignments Versus Rational Design and Directed Evolution," *Cur. Open Biotechnology* 12:371-375.

Li, Y. et al. (2004, e-pub. Oct. 25, 2004), "LRP6 Expression Promotes Cancer Cell Proliferation and Tumorigenesis by Altering β-Catenin Subcellular Distribution," *Oncogene* 23:9129-9135.

Liu, C.-C. et al. (Mar. 16, 2010). "LRP6 Overexpression Defines a Class of Breast Cancer Subtype and Is a Target for Therapy," *Proc. Natl. Acad. Sci. USA* 107(11):5136-5141.

Lock, J.H. et al. (Mar. 2010). "Retinal Laser Photocoagulation," *Med. J. Malaysia* 65(1):88-95.

Loftsson, T. et al. (2012). "Topical Drug Delivery to the Eye: Dorzolamide," *Acta Ophthalmologica* 90:603-608.

Lorenzo, M. del M. et al. (Feb. 1998). "PCR-Based Method for the Introduction of Mutations in Genes Cloned and Expressed in Vaccinia Virus," *Biotechniques* 24(2):308-313.

Lu, G.W. (Jan. 2010). "Recent Advances in Developing Ophthalmic Formulations: A Patent Review," *Recent Pat. Drug Deliv. Formul.* 4(1):49-57.

Lutz-Freyermuth, C. et al. (Aug. 1990). "Quantitative Determination That One of Two Potential RNA-Binding Domains of the a Protein Component of the U1 Small Nuclear Ribonucleoprotein Complex Binds With High Affinity to Stem-Loop of U1 RNA," *Proc. Natl. Acad. Sci. USA* 87:6393-6397.

MacDonald, B.T. et al. (Jul. 2009). "Wnt/β-Catenin Signaling: Components, Mechanisms, and Diseases," *Dev. Cell* 17(1):9-26, 33 pages.

Mani, A. et al. (Mar. 2, 2007). "LRP6 Mutation in a Family With Early Coronary Disease and Metabolic Risk Factors," *Science* 315(5816):1278-1282, 10 pages.

Martin, G.A. et al. (Jan. 10, 1992). "GAP Domains Responsible for Ras p21-Dependent Inhibition of Muscarinic Atrial K+ Channel Currents," *Science* 255(5041):192-194.

Mason, J.J. et al. (2010). "SOST and DKK: Antagonists of LRP Family Signaling as Targets for Treating Bone Disease," *J. Osteoporosis* 2010:Article ID 460120, 9 pages.

Melton, D.A. et al. (1984). "Efficient in vitro Synthesis of Biologically Active RNA and RNA Hybridization Probes From Plasmids Containing a Bacteriophage SP6 Promoter," *Nucl. Acids Res.* 12(18):7057-7070.

Monfardini, C. et al. (Jan. 1995). "A Branched Monomethoxypoly(Ethylene Glycol) for Protein Modification," *Bioconjugate Chem.* 6(1):62-69.

Myles, M.E. et al. (Dec. 13, 2005, e-pub. Nov. 28, 2005). "Recent Progress in Ocular Drug Delivery for Posterior Segment Disease: Emphasis on Transscleral Iontophoresis," *Adv. Drug Deliv. Rev.* 57:2063-2079.

Nusse, R. (2008, e-pub. Apr. 8, 2008). "Wnt Signaling and Stem Cell Control," *Cell Res.* 18:523-527.

Ominsky, M.S. et al. (May 2010, e-pub. Dec. 21, 2009). "Two Doses of Sclerostin Antibody in Cynomolgus Monkeys Increases Bone Formation, Bone Mineral Density, and Bone Strength," *J. Bone Miner. Res.* 25(5):948-959.

Order, S.E. (1985). "Analysis, Results, and Future Prospective of the Therapeutic Use of Radio labeled Antibody in Cancer Therapy," Chapter 15 in *Monoclonal Antibodies for Cancer Detection and Therapy*, Baldwin, et al. eds., Academic Press, London, pp. 303-316.

Paborsky, L.R. et al. (1990). "Mammalian Cell Transient Expression of Tissue Factor for the Production of Antigen," *Protein Eng.* 3(6):547-553.

Padhi, D. et al. (Jan. 2011). "Single-Does, Placebo-Controlled, Randomized Study of AMG 785, A Sclerostin Monoclonal Antibody," *J. Bone Miner. Res.* 26(1):19-26.

Patel, A. et al. (2013). "Ocular Drug Delivery System: An Overview," *World J. Pharmacol.* 2(2):47-64, 35 pages.

Patten, P.A. et al. (Dec. 1997). "Applications of DNA Shuffling to Pharmaceuticals and Vaccines," *Curr. Opinion Biotechnol.* 8(6):724-733.

Peterson, J.J. et al. (1999, e-pub. May 20, 1999). "Enzymatic Cleavage of Peptide-Linked Radiolabels From Immunoconjugates," *Bioconjug. Chem.* 10:553-557.

Pirakitikulr, N. et al. (2010, e-pub. Oct. 8, 2010). "PCRless Library Mutagenesis Via Oligonucleotide Recombination in Yeast," *Protein Sci.* 19:2336-2346.

Polakis, P. (2007). "The Many Ways of Wnt in Cancer," *Curr. Opin. Genet. Dev.* 17:45-51.

Reinwarth, M. et al. (Oct. 24, 2012) "Chemical Synthesis, Backbone Cyclization and Oxidative Folding of Cystine-knot Peptides—Promising Scaffolds for Applications in Drug Design," *Molecules* 17(12):12533-12552.

Sampoli, B.B.A. et al. (Jul. 2000). "Disulfide Bond Plasticity in Epidermal Growth Factor," *Proteins Struct. Funct. Gen.* 40(1):168-174.

Schwarze, S.R. et al. (Sep. 3, 1999). "In Vivo Protein Transduction: Delivery of a Biologically Active Protein Into the Mouse," *Science* 285:1569-1572.

Seneci, P. (2000). *Solid-Phase Synthesis and Combinational Technologies*, A John Wiley & Sons, Inc. New York, New York, 28 pages, (Table of Contents).

Short, B.G. (2008). "Safety Evaluation of Ocular Drug Delivery Formulations: Techniques and Practical Considerations," *Toxicologic Path.* 36:49-62.

Sidhu, S.S. et al. (Aug. 2007). "Phage Display for Engineering and Analyzing Protein Interaction Interfaces," *Curr. Opin. Struct. Biol.* 17(4):481-487.

Skelton, N. J. et al. (Feb. 28, 2003). "Origins of PDZ Domain Ligand Specificity. Structure Determination and Mutagenesis of the Erbin PDZ Domain," *J. Biol .Chem.* 278(9):7645-7654.

Skerra, A. (Aug. 2007). "Alternative Non-Antibody Scaffolds for Molecular Recognition," *Curr. Opin. Biotechnol.* 18(4):295-304.

Skinner, R.H. et al. (Aug. 5, 1991). "Use of the Glu-Glu-Phe C-Terminal Epitope for Rapid Purification of the Catalytic Domain of Normal and Mutant ras GTPase-Activatin Proteins," *J. Biol. Chem.* 266(22):15163-15166.

Stanger, K. et al. (2014, e-pub. Oct. 27, 2014). "Backbone Cyclization of a Recombinant Cystine-Knot Peptide by Engineered Sortase A," *FEBS Lett.* 588(23):4487-4496.

(56) References Cited

OTHER PUBLICATIONS

Steffens, D.L. et al. (Jul. 2007). "Efficient Site-Directed Saturation Mutagenesis Using Degenerate Oligonucleotides," *J. Biomol. Tech.* 18(3):147-149.

Tonikian, R. et al. (2007, e-pub. May 24, 2007). "Identifying Specificity Profiles for Peptide Recognition Modules From Phage-Displayed Peptide Libraries," *Nat. Protoc.* 2(6):1368-1386.

Tung, E. K.-K. et al. (May 3, 2012). "Upregulation of the Wnt Co-Receptor LRP6 Promotes Hepatocarcinogenesis and Enhances Cell Invasion," *PLoS One* 7(5):e36565, 10 pages.

Vitetta, E.S. et al. (Nov. 20, 1987). "Redesigning Natures's Poisons to Create Anti-Tumor Reagents," *Science* 238:1098-1104. (1987).

Welsch, M.E. et al. (2010). "Privileged Scaffolds for Library Design and Drug Discovery," *Current Opinion in Chemical Biology* 14:1-15.

Wurch, T. et al. (Nov. 2012). "Novel Protein Scaffolds as Emerging Therapeutic Proteins: From Discovery to Clinical Proof-of-Concept," *Trends Biotechnol* 30(11):575-582.

Yavuz, B. et al. (2013). "Dendrimeric System and Their Applications in Ocular Drug Delivery," *Sci. World J.* 2013:Article II 7362340, 13 pages.

Zettner, A. (1973). "Principles of Competitive Binding Assays (Saturation Analyses): I. Equilibrium Techniques," *Clin. Chem.* 19(7):699-705.

Zimmerman, K. et al. (1999). "A Triglycine Linder Improves Tumor Uptake and Biodistribution of 67-Cu-Labeled Anti-Neuroblastoma Mab chCE7 F(ab')$_2$ Fragments," *Nucl. Med. Biol.* 26:943-950.

International Search Report dated Feb. 13, 2017, for PCT Application No. PCT/US2016/052012, filed on Sep. 15, 2016, 9 pages.

Written Opinion dated Feb. 13, 2017, for PCT Application No. PCT/US2016/052012, filed on Sep. 15, 2016, 15 pages.

Chan, L.Y. et al. (Dec. 15, 2011, e-pub. Oct. 28, 2011). "Engineering Pro-Angiogenic Peptides Using Stable, Disulfide-Rich Cyclic Scaffolds," *Blood* 118(25):6709-6717.

Sommerhofft, C.P. et al. (2010, e-pub. Oct. 21, 2009). "Engineered Cystine Knot Miniproteins as Potent Inhibitors of Human Mast Cell Tryptase β," *J. Mol. Biol.* 395:167-175.

Thorpe, P.E. et al. (Feb. 1982). "The Preparation and Cytotoxic Properties of Antibody-Toxin Conjugates," *Immunol. Rev.* 62(1):119-158.

Thorpe, P.E. (1985). "Antibody Carriers of Cytotoxic Agents in Cancer Therapy: A Review," in *Monoclonal Antibodies 84: Biological and Clinical Applications* pp. 475-506.

\* cited by examiner (SEQ ID NO: 1) G C P R I L M R C K Q D S D C L A G - C V C G P N G F C G

WT EETI    G C P R I L M R   C K Q D S D C L A G C V C G P N G F C G 54.90      G C N I M L P F W G C G R D F E C L A G C V C Q Y Y Q S C G

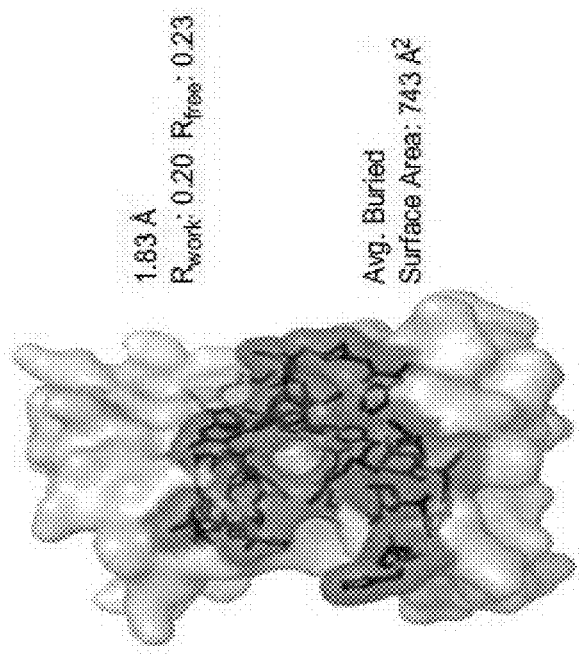
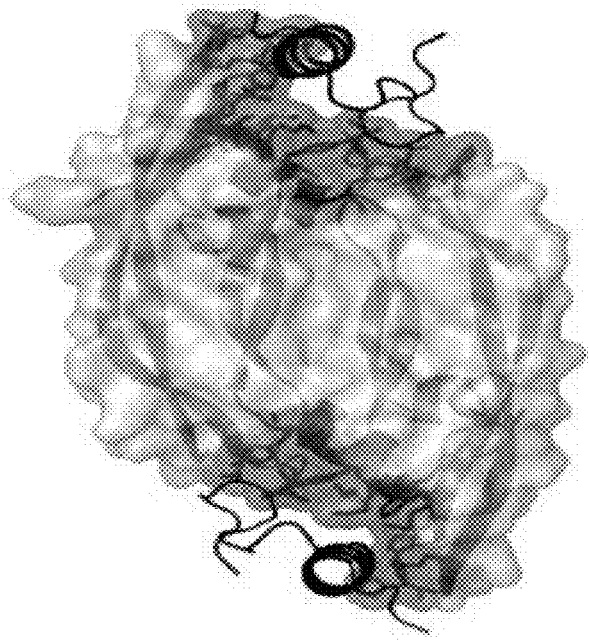
FIG. 6A    FIG. 6B

Binding Epitope:
Atoms <4.5 Å (Yellow),
<4 Å (Orange),
<3.5 Å (Red)

54.90

G6 Fab

Domain 2 of FLT-1

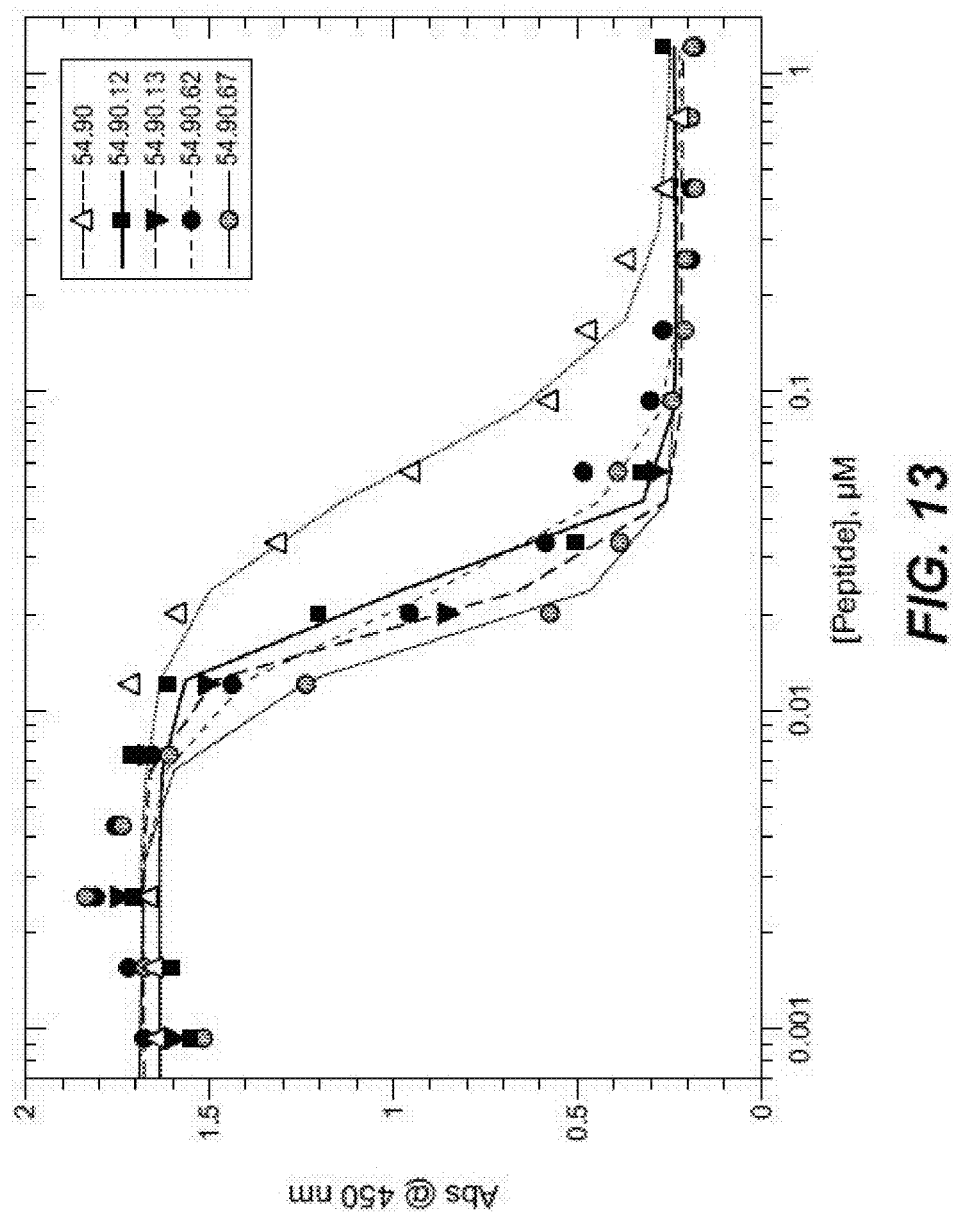

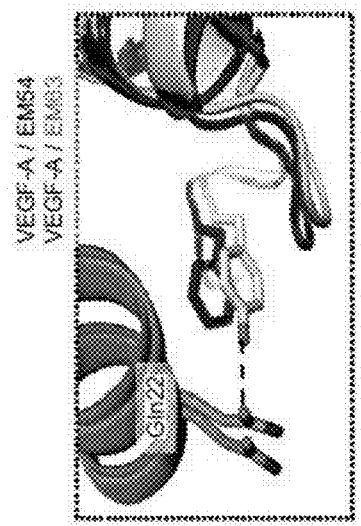
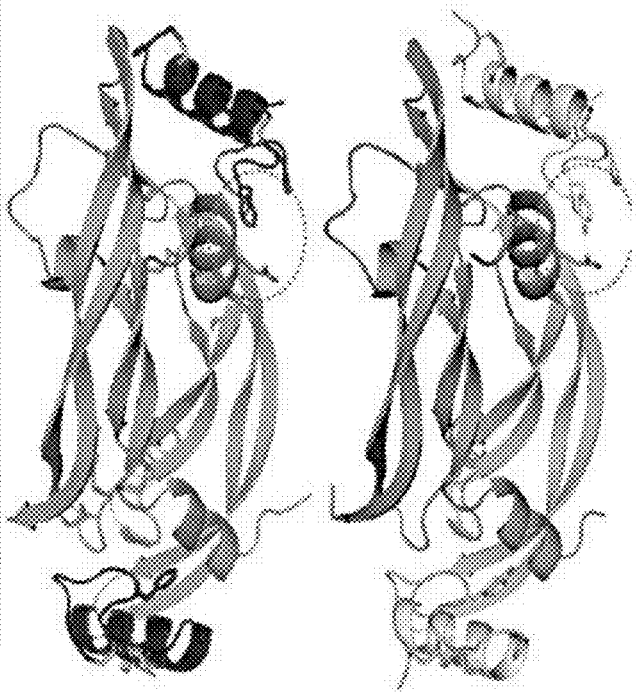
FIG. 14A
FIG. 14B
FIG. 14C
FIG. 14D

SEQUENCE LISTING

```
<160> NUMBER OF SEQ ID NOS: 568

<210> SEQ ID NO 1
<211> LENGTH: 28
<212> TYPE: PRT
<213> ORGANISM: Ecballium elaterium

<400> SEQUENCE: 1

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6
<223> OTHER INFORMATION: Xaa = Any Amino Acid

<400> SEQUENCE: 2

Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7
<223> OTHER INFORMATION: Xaa = Any Amino Acid

<400> SEQUENCE: 3

Xaa Xaa Xaa Xaa Xaa Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8
```

<223> OTHER INFORMATION: Xaa = Any Amino Acid

<400> SEQUENCE: 4

Xaa Xaa Xaa Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9
<223> OTHER INFORMATION: Xaa = Any Amino Acid

<400> SEQUENCE: 5

Xaa Xaa Xaa Xaa Xaa Xaa Xaa Xaa Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10
<223> OTHER INFORMATION: Xaa = Any Amino Acid

<400> SEQUENCE: 6

Xaa Xaa Xaa Xaa Xaa Xaa Xaa Xaa Xaa Xaa
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Xaa = any amino acid or an unnatural amino acid

<400> SEQUENCE: 7

Xaa Xaa Xaa Xaa Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Pro Thr Thr Arg Phe Lys Gln Tyr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Gln Asp Pro Thr Phe Asn Trp Ala Leu Tyr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Gln Leu Met Gln Pro Phe Trp Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

Arg Asp Leu Asp Val Lys Trp Asp
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Arg Thr Pro Trp Glu Pro His Asp Ile Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Thr Thr Pro Trp Pro Pro His Glu Ile Met
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Val Thr Pro Trp Lys Pro His Trp Ile Asn
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

```
Gly Pro Asn Gly Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Gln Met Tyr Gln Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

His Trp Tyr Gln Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Gln Tyr Tyr Ser Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Gly Pro Asn Gly Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or E or Y or Q or H
<220> FEATURE:
<221> NAME/KEY: VARIANT
<222> LOCATION: 2
<223> OTHER INFORMATION: Xaa = P or M or W or Y
<220> FEATURE:
<221> NAME/KEY: VARIANT
<222> LOCATION: 3
<223> OTHER INFORMATION: Xaa = N or Y or W
<220> FEATURE:
<221> NAME/KEY: VARIANT
<222> LOCATION: 4
<223> OTHER INFORMATION: Xaa = G or D or T or Q or R or S
```

```
<220> FEATURE:
<221> NAME/KEY: VARIANT
<222> LOCATION: 5
<223> OTHER INFORMATION: Xaa = F or A or E or S

<400> SEQUENCE: 20

Xaa Xaa Xaa Xaa Xaa
1               5

<210> SEQ ID NO 21
<211> LENGTH: 30
<212> TYPE: PRT
<213> ORGANISM: Artificial Sequence
<220> FEATURE:
<223> OTHER INFORMATION: Synthetic Construct

<400> SEQUENCE: 21

Gly Cys Pro Thr Thr Arg Phe Lys Gln Tyr Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Synthetic Construct

<400> SEQUENCE: 22

Gly Cys Gln Asp Pro Thr Phe Asn Trp Ala Leu Tyr Cys Lys Gln Asp
1               5                   10                  15

Ser Asp Cys Leu Ala Gly Cys Val Cys Gln Met Tyr Gln Ser Cys Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic Construct

<400> SEQUENCE: 23

Gly Cys Gln Leu Met Gln Pro Phe Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic Construct

<400> SEQUENCE: 24

Gly Cys Arg Asp Leu Asp Val Lys Trp Asp Cys Lys Gln Asp Ser Asp
1               5                   10                  15

Cys Leu Ala Gly Cys Phe Cys Gln Tyr Tyr Ser Ser Cys Gly
            20                  25                  30

<210> SEQ ID NO 25
<211> LENGTH: 32
<212> TYPE: PRT
<213> ORGANISM: Artificial Sequence
```

```
<220> FEATURE:
<223> OTHER INFORMATION: Synthetic Construct

<400> SEQUENCE: 25

Gly Cys Arg Thr Pro Trp Glu Pro His Asp Ile Thr Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Synthetic Construct

<400> SEQUENCE: 26

Gly Cys Thr Thr Pro Trp Pro Pro His Glu Ile Met Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Gly Cys Val Thr Pro Trp Lys Pro His Trp Ile Asn Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Asp Val Leu Gln Pro Phe Trp Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Gln Ile Ser Gln Pro Phe Trp Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30
```

Asp Arg Met Gln Pro Leu Trp Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Asn Leu Met Leu Pro Phe Trp Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Gln Arg Thr Gln Pro Phe Trp Gly
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Asn Ile Met Leu Pro Phe Trp Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Asp Pro Met Gln Pro Phe Trp Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Asp Val Met Gln Pro Tyr Trp Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Asp Ile Met Gln Pro Leu Trp Gly

```
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gln Leu Leu Gln Pro Leu Trp Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Asn Pro Met Leu Pro Leu Trp Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct

<400> SEQUENCE: 39

Lys Leu Phe Glu Pro Leu Trp Gly
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or D or K or N or A or R or H
<220> FEATURE:
<221> NAME/KEY: VARIANT
<222> LOCATION: 2
<223> OTHER INFORMATION: Xaa = L or V or I or R or P or V
<220> FEATURE:
<221> NAME/KEY: VARIANT
<222> LOCATION: 3
<223> OTHER INFORMATION: Xaa = M or L or S or T or F
<220> FEATURE:
<221> NAME/KEY: VARIANT
<222> LOCATION: 4
<223> OTHER INFORMATION: Xaa = Q or E or L or H
<220> FEATURE:
<221> NAME/KEY: VARIANT
<222> LOCATION: 6
<223> OTHER INFORMATION: Xaa = F or L or M or Y or S

<400> SEQUENCE: 40

Xaa Xaa Xaa Xaa Pro Xaa Trp Gly
1               5

<210> SEQ ID NO 41
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 41

His Phe Tyr Asn Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Construct

<400> SEQUENCE: 42

Leu Trp Tyr Lys Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Arg Trp Tyr His Ser
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Arg Trp Tyr Gln Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Construct

<400> SEQUENCE: 45

Gln Tyr Tyr Gln Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct

<400> SEQUENCE: 46

His Trp Tyr Asn Ser
1               5

<210> SEQ ID NO 47
<211> LENGTH: 30
<212> TYPE: PRT
<213> ORGANISM: Artificial Sequence
<220> FEATURE:
```

<223> OTHER INFORMATION: Synthetic Construct

<400> SEQUENCE: 47

Gly Cys Asp Val Leu Gln Pro Phe Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic Construct

<400> SEQUENCE: 48

Gly Cys Gln Ile Ser Gln Pro Phe Trp Gly Cys Lys Gln Asp Ser Asp
1               5                   10                  15

Cys Leu Ala Gly Cys Val Cys His Phe Tyr Asn Ser Cys Gly
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic Construct

<400> SEQUENCE: 49

Gly Cys Asp Arg Met Gln Pro Leu Trp Gly Cys Lys Gln Asp Ser Asp
1               5                   10                  15

Cys Leu Ala Gly Cys Val Cys Leu Trp Tyr Lys Ser Cys Gly
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic Construct

<400> SEQUENCE: 50

Gly Cys Asn Leu Met Leu Pro Phe Trp Gly Cys Lys Gln Asp Ser Asp
1               5                   10                  15

Cys Leu Ala Gly Cys Val Cys Arg Trp Tyr His Ser Cys Gly
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic Construct

<400> SEQUENCE: 51

Gly Cys Gln Arg Thr Gln Pro Phe Trp Gly Cys Lys Gln Asp Ser Asp
1               5                   10                  15

Cys Leu Ala Gly Cys Val Cys Arg Trp Tyr Gln Ser Cys Gly
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic Construct

<400> SEQUENCE: 53

Gly Cys Asn Pro Met Leu Pro Phe Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic Construct

<400> SEQUENCE: 54

Gly Cys Asp Pro Met Gln Pro Phe Trp Gly Cys Lys Gln Asp Ser Asp
1               5                   10                  15

Cys Leu Ala Gly Cys Val Cys Arg Trp Tyr Gln Ser Cys Gly
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic Construct

<400> SEQUENCE: 55

Gly Cys Asp Val Met Gln Pro Tyr Trp Gly Cys Lys Gln Asp Ser Asp
1               5                   10                  15

Cys Leu Ala Gly Cys Val Cys His Trp Tyr Asn Ser Cys Gly
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic Construct

<400> SEQUENCE: 56

Gly Cys Asp Ile Met Gln Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 57
<211> LENGTH: 30
<212> TYPE: PRT

<213> ORGANISM: Artificial Sequence
<220> FEATURE:
<223> OTHER INFORMATION: Synthetic Construct

<400> SEQUENCE: 57

Gly Cys Gln Leu Leu Gln Pro Leu Trp Gly Cys Lys Gln Asp Ser Asp
1               5                   10                  15

Cys Leu Ala Gly Cys Val Cys Arg Trp Tyr Gln Ser Cys Gly
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Synthetic Construct

<400> SEQUENCE: 58

Gly Cys Asn Pro Met Leu Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Synthetic Construct

<400> SEQUENCE: 59

Gly Cys Lys Leu Phe Glu Pro Leu Trp Gly Cys Lys Gln Asp Ser Asp
1               5                   10                  15

Cys Leu Ala Gly Cys Val Cys Arg Trp Tyr Glu Ser Cys Gly
            20                  25                  30

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Lys Asn Pro Leu Phe Asn Trp Ala Leu Tyr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Gln Asp Pro Thr Val Asn Trp Ala Val Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

```
Gln Asp Pro Thr Phe Asn Trp Ala Glu Tyr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63

Gln Asp Pro Ser Leu Asn Trp Ala Asp Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Leu Asp Arg Thr Leu Asn Trp Ala Leu Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Leu Asp Pro Ser Phe Asn Trp Ser Leu Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Arg Asp Leu Thr Ile Asn Trp Ala Leu Phe
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Leu Asp Pro Thr Val Asn Trp Ala Leu Phe
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68
```

```
Gln Asp Pro Lys Leu Asn Trp Ala Val Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Leu Asp Pro Ser Phe Asp Trp Ala Leu Tyr
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or D or K or W or E or L or R
<220> FEATURE:
<221> NAME/KEY: VARIANT
<222> LOCATION: 2
<223> OTHER INFORMATION: Xaa = D or N
<220> FEATURE:
<221> NAME/KEY: VARIANT
<222> LOCATION: 3
<223> OTHER INFORMATION: Xaa = P or R or L or T
<220> FEATURE:
<221> NAME/KEY: VARIANT
<222> LOCATION: 4
<223> OTHER INFORMATION: Xaa = T or S or L or K
<220> FEATURE:
<221> NAME/KEY: VARIANT
<222> LOCATION: 5
<223> OTHER INFORMATION: Xaa = F or V or L or I
<220> FEATURE:
<221> NAME/KEY: VARIANT
<222> LOCATION: 6
<223> OTHER INFORMATION: Xaa = N or D
<220> FEATURE:
<221> NAME/KEY: VARIANT
<222> LOCATION: 8
<223> OTHER INFORMATION: Xaa = A or S or G
<220> FEATURE:
<221> NAME/KEY: VARIANT
<222> LOCATION: 9
<223> OTHER INFORMATION: Xaa = L or V or E or T or Q or D
<220> FEATURE:
<221> NAME/KEY: VARIANT
<222> LOCATION: 10
<223> OTHER INFORMATION: Xaa = F or Y

<400> SEQUENCE: 70

Xaa Xaa Xaa Xaa Xaa Xaa Trp Xaa Xaa Xaa
1               5                   10

<210> SEQ ID NO 71
<211> LENGTH: 5
<212> TYPE: PRT
<213> ORGANISM: Artificial Sequence
<220> FEATURE:
<223> OTHER INFORMATION: Synthetic Construct

<400> SEQUENCE: 71

Gln Leu Phe Asp Ser
1               5
```

```
<210> SEQ ID NO 72
<211> LENGTH: 5
<212> TYPE: PRT
<213> ORGANISM: Artificial Sequence
<220> FEATURE:
<223> OTHER INFORMATION: Synthetic Construct

<400> SEQUENCE: 72

Gln Phe Tyr Gln Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic Construct

<400> SEQUENCE: 73

Gln Leu Tyr Gln Ser
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Construct

<400> SEQUENCE: 74

Gln Met His Gln Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic Construct

<400> SEQUENCE: 75

Gln Met Tyr Asn Ser
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct

<400> SEQUENCE: 76

Gln Met Tyr Asp Ser
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct

<400> SEQUENCE: 77

Gln His Tyr Lys Thr
1               5

<210> SEQ ID NO 78
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 78

Gln Leu Phe Asn Ser
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Construct

<400> SEQUENCE: 79

Gln Leu Tyr Asn Ser
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or R
<220> FEATURE:
<221> NAME/KEY: VARIANT
<222> LOCATION: 2
<223> OTHER INFORMATION: Xaa = M or L or F or H
<220> FEATURE:
<221> NAME/KEY: VARIANT
<222> LOCATION: 3
<223> OTHER INFORMATION: Xaa = Y or F or H
<220> FEATURE:
<221> NAME/KEY: VARIANT
<222> LOCATION: 4
<223> OTHER INFORMATION: Xaa = D or Q or N or K
<220> FEATURE:
<221> NAME/KEY: VARIANT
<222> LOCATION: 5
<223> OTHER INFORMATION: Xaa = S or T

<400> SEQUENCE: 80

Xaa Xaa Xaa Xaa Xaa
1               5

<210> SEQ ID NO 81
<211> LENGTH: 32
<212> TYPE: PRT
<213> ORGANISM: Artificial Sequence
<220> FEATURE:
<223> OTHER INFORMATION: Synthetic Construct

<400> SEQUENCE: 81

Gly Cys Lys Asn Pro Leu Phe Asn Trp Ala Leu Tyr Cys Lys Gln Asp
1               5                   10                  15

Ser Asp Cys Leu Ala Gly Cys Val Cys Gln Leu Phe Asp Ser Cys Gly
            20                  25                  30

<210> SEQ ID NO 82
<211> LENGTH: 32
<212> TYPE: PRT
<213> ORGANISM: Artificial Sequence
<220> FEATURE:
```

<223> OTHER INFORMATION: Synthetic Construct

<400> SEQUENCE: 82

Gly Cys Gln Asp Pro Thr Val Asn Trp Ala Val Tyr Cys Lys Gln Asp
1               5                   10                  15

Ser Asp Cys Leu Ala Gly Cys Val Cys Gln Phe Tyr Gln Ser Cys Gly
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Synthetic Construct

<400> SEQUENCE: 83

Gly Cys Gln Asp Pro Thr Phe Asn Trp Ala Glu Tyr Cys Lys Gln Asp
1               5                   10                  15

Ser Asp Cys Leu Ala Gly Cys Val Cys Gln Leu Tyr Gln Ser Cys Gly
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Synthetic Construct

<400> SEQUENCE: 84

Gly Cys Gln Asp Pro Thr Phe Asn Trp Ala Glu Tyr Cys Lys Gln Asp
1               5                   10                  15

Ser Asp Cys Leu Ala Gly Cys Val Cys Gln Met Tyr Gln Ser Cys Gly
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: Synthetic Construct

<400> SEQUENCE: 85

Gly Cys Gln Asp Pro Ser Leu Asn Trp Ala Asp Tyr Cys Lys Gln Asp
1               5                   10                  15

Ser Asp Cys Leu Ala Gly Cys Val Cys Gln Met His Gln Ser Cys Gly
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic Construct

<400> SEQUENCE: 86

Gly Cys Leu Asp Arg Thr Leu Asn Trp Ala Leu Tyr Cys Lys Gln Asp
1               5                   10                  15

Ser Asp Cys Leu Ala Gly Cys Val Cys Gln Met Tyr Asn Ser Cys Gly
            20                  25                  30

<210> SEQ ID NO 87
<211> LENGTH: 32
<212> TYPE: PRT
<213> ORGANISM: Artificial Sequence

```
<220> FEATURE:
<223> OTHER INFORMATION: Synthetic Construct

<400> SEQUENCE: 87

Gly Cys Leu Asp Pro Ser Phe Asn Trp Ser Leu Tyr Cys Lys Gln Asp
1               5                   10                  15

Ser Asp Cys Leu Ala Gly Cys Val Cys Gln Met Tyr Asp Ser Cys Gly
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Synthetic Construct

<400> SEQUENCE: 88

Gly Cys Arg Asp Leu Thr Ile Asn Trp Ala Leu Phe Cys Lys Gln Asp
1               5                   10                  15

Ser Asp Cys Leu Ala Gly Cys Val Cys Gln Met Phe Asn Ser Cys Gly
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic Construct

<400> SEQUENCE: 89

Gly Cys Leu Asp Pro Thr Val Asn Trp Ala Leu Phe Cys Lys Gln Asp
1               5                   10                  15

Ser Asp Cys Leu Ala Gly Cys Val Cys Gln His Tyr Lys Thr Cys Gly
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic Construct

<400> SEQUENCE: 90

Gly Cys Gln Asp Pro Lys Leu Asn Trp Ala Val Tyr Cys Lys Gln Asp
1               5                   10                  15

Ser Asp Cys Leu Ala Gly Cys Val Cys Gln Leu Phe Asn Ser Cys Gly
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Synthetic Construct

<400> SEQUENCE: 91

Gly Cys Leu Asp Pro Ser Phe Asp Trp Ala Leu Tyr Cys Lys Gln Asp
1               5                   10                  15

Ser Asp Cys Leu Ala Gly Cys Val Cys Gln Leu Tyr Asn Ser Cys Gly
            20                  25                  30

<210> SEQ ID NO 92
<211> LENGTH: 6
<212> TYPE: PRT
```

```
<213> ORGANISM: Artificial Sequence
<220> FEATURE:
<223> OTHER INFORMATION: Synthetic Construct

<400> SEQUENCE: 92

Pro Arg Ile Leu Met Arg
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Construct

<400> SEQUENCE: 93

Lys Gln Asp Ser Asp
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Construct

<400> SEQUENCE: 94

Gly Gln Ser Phe Glu
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic Construct

<400> SEQUENCE: 95

Gly Leu Asp Tyr Asp
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Construct

<400> SEQUENCE: 96

Gly Pro Asp Leu Gln
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct

<400> SEQUENCE: 97

Gly Arg Asp Phe Glu
1               5

<210> SEQ ID NO 98
<211> LENGTH: 5
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = K or G or Q or S or N
<220> FEATURE:
<221> NAME/KEY: VARIANT
<222> LOCATION: 2
<223> OTHER INFORMATION: Xaa = Q or L or P or A or V or T or R or W or K
      or G or Y
<220> FEATURE:
<221> NAME/KEY: VARIANT
<222> LOCATION: 3
<223> OTHER INFORMATION: Xaa = D or S or E or N
<220> FEATURE:
<221> NAME/KEY: VARIANT
<222> LOCATION: 4
<223> OTHER INFORMATION: Xaa = S or F or Y or L or F or Q or M
<220> FEATURE:
<221> NAME/KEY: VARIANT
<222> LOCATION: 5
<223> OTHER INFORMATION: Xaa = D or E or N or A or L or F or H or Q

<400> SEQUENCE: 98

Xaa Xaa Xaa Xaa Xaa
1               5

<210> SEQ ID NO 99
<211> LENGTH: 30
<212> TYPE: PRT
<213> ORGANISM: Artificial Sequence
<220> FEATURE:
<223> OTHER INFORMATION: Synthetic Construct

<400> SEQUENCE: 99

Gly Cys Asn Ile Met Leu Pro Phe Trp Gly Cys Gly Gln Ser Phe Glu
1               5                   10                  15

Cys Leu Ala Gly Cys Val Cys Gln Tyr Tyr Gln Ser Cys Gly
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Synthetic Construct

<400> SEQUENCE: 100

Gly Cys Asn Ile Met Leu Pro Phe Trp Gly Cys Gly Leu Asp Tyr Asp
1               5                   10                  15

Cys Leu Ala Gly Cys Val Cys Gln Tyr Tyr Gln Ser Cys Gly
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Synthetic Construct

<400> SEQUENCE: 101

Gly Cys Asn Ile Met Leu Pro Phe Trp Gly Cys Gly Pro Asp Leu Gln
1               5                   10                  15

Cys Leu Ala Gly Cys Val Cys Gln Tyr Tyr Gln Ser Cys Gly
            20                  25                  30

<210> SEQ ID NO 102
```

```
<211> LENGTH: 30
<212> TYPE: PRT
<213> ORGANISM: Artificial Sequence
<220> FEATURE:
<223> OTHER INFORMATION: Synthetic Construct

<400> SEQUENCE: 102

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Synthetic Construct

<400> SEQUENCE: 103

Gly Cys Asn Ile Met Leu Pro Phe Trp Gly Cys Gly Arg Asp Phe Glu
1               5                   10                  15

Cys Leu Gln Gln Cys Ile Cys Gln Tyr Tyr Gln Ser Cys Gly
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetic Construct

<400> SEQUENCE: 104

Gly Cys Asn Ile Met Leu Pro Phe Trp Gly Cys Gly Arg Asp Phe Glu
1               5                   10                  15

Cys Val Glu Arg Cys Ile Cys Gln Tyr Tyr Gln Ser Cys Gly
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Synthetic Construct

<400> SEQUENCE: 105

Gly Cys Asn Ile Met Leu Pro Phe Trp Gly Cys Gly Arg Asp Phe Glu
1               5                   10                  15

Cys Met Ser Asp Cys Ile Cys Gln Tyr Tyr Gln Ser Cys Gly
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Synthetic Construct

<400> SEQUENCE: 106

Gly Cys Asn Ile Met Leu Pro Phe Trp Gly Cys Gly Arg Asp Phe Glu
1               5                   10                  15

Cys Met Asn Gln Cys Ile Cys Gln Tyr Tyr Gln Ser Cys Gly
            20                  25                  30
```

```
<210> SEQ ID NO 107
<211> LENGTH: 30
<212> TYPE: PRT
<213> ORGANISM: Artificial Sequence
<220> FEATURE:
<223> OTHER INFORMATION: Synthetic Construct

<400> SEQUENCE: 107

Gly Cys Asn Ile Met Leu Pro Phe Trp Gly Cys Gly Arg Asp Phe Glu
1               5                   10                  15

Cys Met Gln Thr Cys Ile Cys Gln Tyr Tyr Gln Ser Cys Gly
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetic Construct

<400> SEQUENCE: 108

Gly Cys Asn Ile Met Leu Pro Phe Trp Gly Cys Gly Arg Asp Phe Glu
1               5                   10                  15

Cys Val Tyr Gln Cys Ile Cys Gln Tyr Tyr Gln Ser Cys Gly
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Synthetic Construct

<400> SEQUENCE: 109

Gly Cys Asn Ile Met Leu Pro Phe Trp Gly Cys Gly Arg Asp Phe Glu
1               5                   10                  15

Cys Phe Ile Asn Cys Ile Cys Gln Tyr Tyr Gln Ser Cys Gly
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Synthetic Construct

<400> SEQUENCE: 110

Gly Cys Asn Ile Met Leu Pro Phe Trp Gly Cys Gly Arg Asp Phe Glu
1               5                   10                  15

Cys Val Ser Gln Cys Ile Cys Gln Tyr Tyr Gln Ser Cys Gly
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetic Construct

<400> SEQUENCE: 111

Gly Cys Asn Ile Met Leu Pro Phe Trp Gly Cys Gly Arg Asp Phe Glu
1               5                   10                  15

Cys Val Thr Glu Cys Ile Cys Gln Tyr Tyr Gln Ser Cys Gly
            20                  25                  30
```

<210> SEQ ID NO 112
<211> LENGTH: 30
<212> TYPE: PRT
<213> ORGANISM: Artificial Sequence
<220> FEATURE:
<223> OTHER INFORMATION: Synthetic Construct

<400> SEQUENCE: 112

Gly Cys Asn Ile Met Leu Pro Phe Trp Gly Cys Gly Arg Asp Phe Glu
1               5                   10                  15

Cys Phe Tyr Glu Cys Ile Cys Gln Tyr Tyr Gln Ser Cys Gly
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Synthetic Construct

<400> SEQUENCE: 113

Gly Cys Asn Ile Met Leu Pro Phe Trp Gly Cys Gly Arg Asp Phe Glu
1               5                   10                  15

Cys Met Glu Gln Cys Ile Cys Gln Tyr Tyr Gln Ser Cys Gly
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Synthetic Construct

<400> SEQUENCE: 114

Gly Cys Asn Ile Met Leu Pro Phe Trp Gly Cys Gly Arg Asp Phe Glu
1               5                   10                  15

Cys Val Tyr Arg Cys Ile Cys Gln Tyr Tyr Gln Ser Cys Gly
            20                  25                  30

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = K or P or Q or R
<220> FEATURE:
<221> NAME/KEY: VARIANT
<222> LOCATION: 2
<223> OTHER INFORMATION: Xaa = K or T or L or D
<220> FEATURE:
<221> NAME/KEY: VARIANT
<222> LOCATION: 3
<223> OTHER INFORMATION: Xaa = W or T or M or L
<220> FEATURE:
<221> NAME/KEY: VARIANT
<222> LOCATION: 4
<223> OTHER INFORMATION: Xaa = Q or R or D
<220> FEATURE:
<221> NAME/KEY: VARIANT
<222> LOCATION: 5
<223> OTHER INFORMATION: Xaa = W or F or P or V
<220> FEATURE:
<221> NAME/KEY: VARIANT
<222> LOCATION: 6
<223> OTHER INFORMATION: Xaa = W or K or F

```
<220> FEATURE:
<221> NAME/KEY: VARIANT
<222> LOCATION: 7
<223> OTHER INFORMATION: Xaa = Y or Q or W
<220> FEATURE:
<221> NAME/KEY: VARIANT
<222> LOCATION: 8
<223> OTHER INFORMATION: Xaa = M or Y or G or D

<400> SEQUENCE: 115

Xaa Xaa Xaa Xaa Xaa Xaa Xaa Xaa
1               5

<210> SEQ ID NO 116

<400> SEQUENCE: 116

000

<210> SEQ ID NO 117
<211> LENGTH: 5
<212> TYPE: PRT
<213> ORGANISM: Artificial Sequence
<220> FEATURE:
<223> OTHER INFORMATION: Synthetic Construct

<400> SEQUENCE: 117

Gly Glu Asn Phe Leu
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic Construct

<400> SEQUENCE: 118

Gly Pro Asp Ile Asp
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Construct

<400> SEQUENCE: 119

Gly Arg Asp Met Asp
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic Construct

<400> SEQUENCE: 120

Glu Met Asp Phe Asp
1               5

<210> SEQ ID NO 121
<211> LENGTH: 5
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 1
<223> OTHER INFORMATION: Xaa = K or G or D or A or E
<220> FEATURE:
<221> NAME/KEY: VARIANT
<222> LOCATION: 2
<223> OTHER INFORMATION: Xaa = Q or E or R or V or P or D or M or G or N
      or L or A or F
<220> FEATURE:
<221> NAME/KEY: VARIANT
<222> LOCATION: 3
<223> OTHER INFORMATION: Xaa = D or N or Y or S
<220> FEATURE:
<221> NAME/KEY: VARIANT
<222> LOCATION: 4
<223> OTHER INFORMATION: Xaa = S or F or L or I or M or Y or V or N or E
<220> FEATURE:
<221> NAME/KEY: VARIANT
<222> LOCATION: 5
<223> OTHER INFORMATION: Xaa = D or L or Q or S or E or T or L or A or N

<400> SEQUENCE: 121

Xaa Xaa Xaa Xaa Xaa
1               5

<210> SEQ ID NO 122
<211> LENGTH: 30
<212> TYPE: PRT
<213> ORGANISM: Artificial Sequence
<220> FEATURE:
<223> OTHER INFORMATION: Synthetic Construct

<400> SEQUENCE: 122

Gly Cys Asp Val Met Gln Pro Tyr Trp Gly Cys Gly Glu Asn Phe Leu
1               5                   10                  15

Cys Leu Ala Gly Cys Val Cys His Trp Tyr Asn Ser Cys Gly
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Synthetic Construct

<400> SEQUENCE: 123

Gly Cys Asp Val Met Gln Pro Tyr Trp Gly Cys Gly Pro Asp Ile Asp
1               5                   10                  15

Cys Leu Ala Gly Cys Val Cys His Trp Tyr Asn Ser Cys Gly
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Synthetic Construct

<400> SEQUENCE: 124

Gly Cys Asp Val Met Gln Pro Tyr Trp Gly Cys Gly Arg Asp Met Asp
1               5                   10                  15

Cys Leu Ala Gly Cys Val Cys His Trp Tyr Asn Ser Cys Gly
            20                  25                  30

<210> SEQ ID NO 125
<211> LENGTH: 30
```

<212> TYPE: PRT
<213> ORGANISM: Artificial Sequence
<220> FEATURE:
<223> OTHER INFORMATION: Synthetic Construct

<400> SEQUENCE: 125

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Synthetic Construct

<400> SEQUENCE: 126

Gly Cys Asp Val Met Gln Pro Tyr Trp Gly Cys Gly Glu Ser Leu Ser
1               5                   10                  15

Cys Leu Ala Gly Cys Val Cys His Trp Tyr Asn Ser Cys Gly
            20                  25                  30

<210> SEQ ID NO 127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 127

Asp Val Met Lys Pro Met Trp Gly
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Asp Val Leu Asp Pro Thr Trp Gly
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic Construct

<400> SEQUENCE: 129

Asp Val Leu Gln Pro Leu Trp Gly
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = M or L

```
<220> FEATURE:
<221> NAME/KEY: VARIANT
<222> LOCATION: 4
<223> OTHER INFORMATION: Xaa = Q or K or D
<220> FEATURE:
<221> NAME/KEY: VARIANT
<222> LOCATION: 6
<223> OTHER INFORMATION: Xaa = Y or M or T or L

<400> SEQUENCE: 130

Asp Val Xaa Xaa Pro Xaa Trp Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Synthetic Construct

<400> SEQUENCE: 131

Gln Trp Tyr Asn Ser
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic Construct

<400> SEQUENCE: 132

Leu Trp Tyr Asn Ser
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic Construct

<400> SEQUENCE: 133

Arg Trp Tyr Asn Ser
1               5

<210> SEQ ID NO 134
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = H or L or Q or R

<400> SEQUENCE: 134

Xaa Trp Tyr Asn Ser
1               5

<210> SEQ ID NO 135
<211> LENGTH: 30
<212> TYPE: PRT
<213> ORGANISM: Artificial Sequence
<220> FEATURE:
<223> OTHER INFORMATION: Synthetic Construct

<400> SEQUENCE: 135
```

```
Gly Cys Asp Val Met Lys Pro Met Trp Gly Cys Lys Gln Asp Ser Asp
1               5                   10                  15

Cys Leu Ala Gly Cys Val Cys Gln Trp Tyr Asn Ser Cys Gly
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Synthetic Construct

<400> SEQUENCE: 136

Gly Cys Asp Val Leu Asp Pro Thr Trp Gly Cys Lys Gln Asp Ser Asp
1               5                   10                  15

Cys Leu Ala Gly Cys Val Cys Leu Trp Tyr Asn Ser Cys Gly
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Synthetic Construct

<400> SEQUENCE: 137

Gly Cys Asp Val Leu Gln Pro Leu Trp Gly Cys Lys Gln Asp Ser Asp
1               5                   10                  15

Cys Leu Ala Gly Cys Val Cys Arg Trp Tyr Asn Ser Cys Gly
            20                  25                  30

<210> SEQ ID NO 138

<400> SEQUENCE: 138

000

<210> SEQ ID NO 139
<211> LENGTH: 30
<212> TYPE: PRT
<213> ORGANISM: Artificial Sequence
<220> FEATURE:
<223> OTHER INFORMATION: Synthetic Construct

<400> SEQUENCE: 139

Gly Cys Asp Val Met Gln Pro Tyr Trp Gly Cys Gly Pro Asp Ile Asp
1               5                   10                  15

Cys Phe Val Arg Cys Leu Cys His Trp Tyr Asn Ser Cys Gly
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Synthetic Construct

<400> SEQUENCE: 140

Gly Cys Asp Val Met Gln Pro Tyr Trp Gly Cys Gly Pro Asp Ile Asp
1               5                   10                  15

Cys Leu Ser Asn Cys Ile Cys His Trp Tyr Asn Ser Cys Gly
            20                  25                  30
```

-continued

```
<210> SEQ ID NO 141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 141

Asn Ile Met Leu Pro Tyr Trp Gly
1               5

<210> SEQ ID NO 142
<211> LENGTH: 30
<212> TYPE: PRT
<213> ORGANISM: Artificial Sequence
<220> FEATURE:
<223> OTHER INFORMATION: Synthetic Construct

<400> SEQUENCE: 142

Gly Cys Asn Ile Met Leu Pro Tyr Trp Gly Cys Gly Arg Asp Phe Glu
1               5                   10                  15

Cys Met Glu Gln Cys Ile Cys Gln Tyr Tyr Gln Ser Cys Gly
            20                  25                  30

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = norleucine

<400> SEQUENCE: 143

Asn Ile Xaa Leu Pro Tyr Trp Gly
1               5

<210> SEQ ID NO 144
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 144

Gly Cys Asn Ile Xaa Leu Pro Phe Trp Gly Cys Gly Arg Asp Phe Glu
1               5                   10                  15

Cys Met Ser Asp Cys Ile Cys Gln Tyr Tyr Gln Ser Cys Gly
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 145
```

```
Gly Cys Asn Ile Xaa Leu Pro Phe Trp Gly Cys Gly Arg Asp Phe Glu
1               5                   10                  15
Cys Val Ser Gln Cys Ile Cys Tyr Tyr Gln Ser Cys Gly
            20              25                  30

<210> SEQ ID NO 146
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 146

Gly Cys Asn Ile Xaa Leu Pro Tyr Trp Gly Cys Gly Arg Asp Phe Glu
1               5                   10                  15
Cys Met Glu Gln Cys Ile Cys Gln Tyr Tyr Gln Ser Cys Gly
            20              25                  30

<210> SEQ ID NO 147
<211> LENGTH: 8
<212> TYPE: PRT
<213> ORGANISM: Artificial Sequence
<220> FEATURE:
<223> OTHER INFORMATION: Synthetic Construct

<400> SEQUENCE: 147

Arg Thr Asn Arg Val Lys Gly Gly
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Construct

<400> SEQUENCE: 148

Val Asn Arg Val Arg Gly
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149

Met Asn His Val Lys Ala Arg Arg
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Construct

<400> SEQUENCE: 150

Arg Ser Val Asn Lys Ile
1               5
```

<210> SEQ ID NO 151
<211> LENGTH: 6
<212> TYPE: PRT
<213> ORGANISM: Artificial Sequence
<220> FEATURE:
<223> OTHER INFORMATION: Synthetic Construct

<400> SEQUENCE: 151

Val Asn Lys Ile Lys Gly
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic Construct

<400> SEQUENCE: 152

Arg Asn Ser Ile Lys Arg
1               5

<210> SEQ ID NO 153
<211> LENGTH: 8
<212> TYPE: PRT
<213> ORGANISM: Artificial Sequence
<220> FEATURE:
<223> OTHER INFORMATION: Synthetic Construct

<400> SEQUENCE: 153

Val Ser Asn Arg Val Asn Lys Gly
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic Construct

<400> SEQUENCE: 154

Arg Gly Asn Ile Ile Lys
1               5

<210> SEQ ID NO 155
<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Arg Ser Gly Asn Thr Ile Arg Lys Arg Glu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Ala Ser Ser Asn Ser Ile Arg Gln Gly Trp
1               5                   10

<210> SEQ ID NO 157

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 157

Arg Ser Asn Arg Ile Arg
1               5

<210> SEQ ID NO 158
<211> LENGTH: 10
<212> TYPE: PRT
<213> ORGANISM: Artificial Sequence
<220> FEATURE:
<223> OTHER INFORMATION: Synthetic Construct

<400> SEQUENCE: 158

Arg Ser Asn Lys Leu Arg Glu Ala Arg Gly
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct

<400> SEQUENCE: 159

Val Asn Ser Val Lys Arg
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic Construct

<400> SEQUENCE: 160

Gly Ser Asn Lys Ile Arg Pro Arg
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic Construct

<400> SEQUENCE: 161

Asn Arg Ile Arg Asn Ser
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic Construct

<400> SEQUENCE: 162

Ser Arg Asn Ser Ile Lys
1               5

<210> SEQ ID NO 163
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 163

Ser Asn Tyr Val Lys Arg
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic Construct

<400> SEQUENCE: 164

Arg Ala Asn Arg Val Ser Gly Arg
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic Construct

<400> SEQUENCE: 165

Ser Asn Arg Val Lys Val Arg Ala
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic Construct

<400> SEQUENCE: 166

Glu Asn Arg Thr Lys Gly
1               5

<210> SEQ ID NO 167
<211> LENGTH: 6
<212> TYPE: PRT
<213> ORGANISM: Artificial Sequence
<220> FEATURE:
<223> OTHER INFORMATION: Synthetic Construct

<400> SEQUENCE: 167

Gly Asn Lys Ile Arg Ala
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Ala Asn Arg Val Lys Arg Thr Ser
1               5

<210> SEQ ID NO 169
<211> LENGTH: 5
<212> TYPE: PRT
```

<213> ORGANISM: Artificial Sequence
<220> FEATURE:
<223> OTHER INFORMATION: Synthetic Construct

<400> SEQUENCE: 169

Ser Gly Gly Arg Asp
1               5

<210> SEQ ID NO 170
<211> LENGTH: 5
<212> TYPE: PRT
<213> ORGANISM: Artificial Sequence
<220> FEATURE:
<223> OTHER INFORMATION: Synthetic Construct

<400> SEQUENCE: 170

Gly Ser Ser Arg Asn
1               5

<210> SEQ ID NO 171
<211> LENGTH: 5
<212> TYPE: PRT
<213> ORGANISM: Artificial Sequence
<220> FEATURE:
<223> OTHER INFORMATION: Synthetic Construct

<400> SEQUENCE: 171

Gly Val Glu Gly Arg
1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct

<400> SEQUENCE: 172

Ser Val Gly His Gly
1               5

<210> SEQ ID NO 173
<211> LENGTH: 5
<212> TYPE: PRT
<213> ORGANISM: Artificial Sequence
<220> FEATURE:
<223> OTHER INFORMATION: Synthetic Construct

<400> SEQUENCE: 173

Asn Glu Ser Arg Gly
1               5

<210> SEQ ID NO 174
<211> LENGTH: 5
<212> TYPE: PRT
<213> ORGANISM: Artificial Sequence
<220> FEATURE:
<223> OTHER INFORMATION: Synthetic Construct

<400> SEQUENCE: 174

Gly Gly Pro Gly Gly
1               5

<210> SEQ ID NO 175
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 175

Gly Pro Lys Ser Asn
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic Construct

<400> SEQUENCE: 176

Tyr Gly His Gly Asp
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic Construct

<400> SEQUENCE: 177

Gly Ser Arg Gln Asp
1               5

<210> SEQ ID NO 178
<211> LENGTH: 5
<212> TYPE: PRT
<213> ORGANISM: Artificial Sequence
<220> FEATURE:
<223> OTHER INFORMATION: Synthetic Construct

<400> SEQUENCE: 178

Ser Arg Gly Val Asn
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic Construct

<400> SEQUENCE: 179

Gly Pro Asn Asp Phe
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic Construct

<400> SEQUENCE: 180

Gly Arg Gly Asp Tyr
1               5

<210> SEQ ID NO 181
<211> LENGTH: 5
<212> TYPE: PRT
<213> ORGANISM: Artificial Sequence
<220> FEATURE:
```

```
<223> OTHER INFORMATION: Synthetic Construct

<400> SEQUENCE: 181

Ala Ser Gly Ser Ser
1               5

<210> SEQ ID NO 182
<211> LENGTH: 5
<212> TYPE: PRT
<213> ORGANISM: Artificial Sequence
<220> FEATURE:
<223> OTHER INFORMATION: Synthetic Construct

<400> SEQUENCE: 182

Ser Pro Gly Gly Arg
1               5

<210> SEQ ID NO 183
<211> LENGTH: 5
<212> TYPE: PRT
<213> ORGANISM: Artificial Sequence
<220> FEATURE:
<223> OTHER INFORMATION: Synthetic Construct

<400> SEQUENCE: 183

Gly Phe Arg Gly Thr
1               5

<210> SEQ ID NO 184
<211> LENGTH: 5
<212> TYPE: PRT
<213> ORGANISM: Artificial Sequence
<220> FEATURE:
<223> OTHER INFORMATION: Synthetic Construct

<400> SEQUENCE: 184

Arg Asp Arg Val Gly
1               5

<210> SEQ ID NO 185
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = V or R or N or S or E or G
<220> FEATURE:
<221> NAME/KEY: VARIANT
<222> LOCATION: 2
<223> OTHER INFORMATION: Xaa = N or S or G or R
<220> FEATURE:
<221> NAME/KEY: VARIANT
<222> LOCATION: 3
<223> OTHER INFORMATION: Xaa = R or V or K or S or N or I or Y
<220> FEATURE:
<221> NAME/KEY: VARIANT
<222> LOCATION: 4
<223> OTHER INFORMATION: Xaa = V or N or I or R or S or T
<220> FEATURE:
<221> NAME/KEY: VARIANT
<222> LOCATION: 5
<223> OTHER INFORMATION: Xaa = R or K or I or N
<220> FEATURE:
<221> NAME/KEY: VARIANT
<222> LOCATION: 6
<223> OTHER INFORMATION: Xaa = G or I or R or K or S or A

<400> SEQUENCE: 185
```

```
Xaa Xaa Xaa Xaa Xaa Xaa
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or R or M or V or G or S
<220> FEATURE:
<221> NAME/KEY: VARIANT
<222> LOCATION: 2
<223> OTHER INFORMATION: Xaa = N or T or S or A
<220> FEATURE:
<221> NAME/KEY: VARIANT
<222> LOCATION: 3
<223> OTHER INFORMATION: Xaa = R or N or H
<220> FEATURE:
<221> NAME/KEY: VARIANT
<222> LOCATION: 4
<223> OTHER INFORMATION: Xaa = V or R or K
<220> FEATURE:
<221> NAME/KEY: VARIANT
<222> LOCATION: 5
<223> OTHER INFORMATION: Xaa = K or V or I
<220> FEATURE:
<221> NAME/KEY: VARIANT
<222> LOCATION: 6
<223> OTHER INFORMATION: Xaa = R or K or A or N or S or V
<220> FEATURE:
<221> NAME/KEY: VARIANT
<222> LOCATION: 7
<223> OTHER INFORMATION: Xaa = T or G or R or K or P
<220> FEATURE:
<221> NAME/KEY: VARIANT
<222> LOCATION: 8
<223> OTHER INFORMATION: Xaa = S or G or R or A

<400> SEQUENCE: 186

Xaa Xaa Xaa Xaa Xaa Xaa Xaa Xaa
1               5

<210> SEQ ID NO 187
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = R or A or Q
<220> FEATURE:
<221> NAME/KEY: VARIANT
<222> LOCATION: 2
<223> OTHER INFORMATION: Xaa = S or A
<220> FEATURE:
<221> NAME/KEY: VARIANT
<222> LOCATION: 3
<223> OTHER INFORMATION: Xaa = G or S or N or I
<220> FEATURE:
<221> NAME/KEY: VARIANT
<222> LOCATION: 4
<223> OTHER INFORMATION: Xaa = N or K
<220> FEATURE:
<221> NAME/KEY: VARIANT
<222> LOCATION: 5
<223> OTHER INFORMATION: Xaa = T or S or L or R
<220> FEATURE:
<221> NAME/KEY: VARIANT
<222> LOCATION: 6
```

```
<223> OTHER INFORMATION: Xaa = I or R or V
<220> FEATURE:
<221> NAME/KEY: VARIANT
<222> LOCATION: 7
<223> OTHER INFORMATION: Xaa = R or E or K
<220> FEATURE:
<221> NAME/KEY: VARIANT
<222> LOCATION: 8
<223> OTHER INFORMATION: Xaa = K or Q or A or R
<220> FEATURE:
<221> NAME/KEY: VARIANT
<222> LOCATION: 9
<223> OTHER INFORMATION: Xaa = R or G or Q
<220> FEATURE:
<221> NAME/KEY: VARIANT
<222> LOCATION: 10
<223> OTHER INFORMATION: Xaa = E or W or G or R

<400> SEQUENCE: 187

Xaa Xaa Xaa Xaa Xaa Xaa Xaa Xaa Xaa Xaa
1               5                   10

<210> SEQ ID NO 188
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or S or N or Y or A or R
<220> FEATURE:
<221> NAME/KEY: VARIANT
<222> LOCATION: 2
<223> OTHER INFORMATION: Xaa = P or G or S or V or E or R or F or D
<220> FEATURE:
<221> NAME/KEY: VARIANT
<222> LOCATION: 3
<223> OTHER INFORMATION: Xaa = N or G or S or E or P or K or H or R
<220> FEATURE:
<221> NAME/KEY: VARIANT
<222> LOCATION: 4
<223> OTHER INFORMATION: Xaa = G or R or H or S or Q or V or D
<220> FEATURE:
<221> NAME/KEY: VARIANT
<222> LOCATION: 5
<223> OTHER INFORMATION: Xaa = F or D or N or R or G or Y or S or T

<400> SEQUENCE: 188

Xaa Xaa Xaa Xaa Xaa
1               5

<210> SEQ ID NO 189
<211> LENGTH: 30
<212> TYPE: PRT
<213> ORGANISM: Artificial Sequence
<220> FEATURE:
<223> OTHER INFORMATION: Synthetic Construct

<400> SEQUENCE: 189

Gly Cys Arg Thr Asn Arg Val Lys Gly Gly Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 190
<211> LENGTH: 28
<212> TYPE: PRT
<213> ORGANISM: Artificial Sequence
<220> FEATURE:
<223> OTHER INFORMATION: Synthetic Construct
```

```
<400> SEQUENCE: 190

Gly Cys Val Asn Arg Val Arg Gly Cys Lys Gln Asp Ser Asp Cys Leu
1               5                   10                  15

Ala Gly Cys Val Cys Ser Gly Gly Arg Asp Cys Gly
            20                  25

<210> SEQ ID NO 191
<211> LENGTH: 30
<212> TYPE: PRT
<213> ORGANISM: Artificial Sequence
<220> FEATURE:
<223> OTHER INFORMATION: Synthetic Construct

<400> SEQUENCE: 191

Gly Cys Met Asn His Val Lys Ala Arg Arg Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 192
<211> LENGTH: 28
<212> TYPE: PRT
<213> ORGANISM: Artificial Sequence
<220> FEATURE:
<223> OTHER INFORMATION: Synthetic Construct

<400> SEQUENCE: 192

Gly Cys Arg Ser Val Asn Lys Ile Cys Lys Gln Asp Ser Asp Cys Leu
1               5                   10                  15

Ala Gly Cys Val Cys Gly Ser Ser Arg Asn Cys Gly
            20                  25

<210> SEQ ID NO 193
<211> LENGTH: 28
<212> TYPE: PRT
<213> ORGANISM: Artificial Sequence
<220> FEATURE:
<223> OTHER INFORMATION: Synthetic Construct

<400> SEQUENCE: 193

Gly Cys Val Asn Lys Ile Lys Gly Cys Lys Gln Asp Ser Asp Cys Leu
1               5                   10                  15

Ala Gly Cys Val Cys Gly Val Glu Gly Arg Cys Gly
            20                  25

<210> SEQ ID NO 194
<211> LENGTH: 28
<212> TYPE: PRT
<213> ORGANISM: Artificial Sequence
<220> FEATURE:
<223> OTHER INFORMATION: Synthetic Construct

<400> SEQUENCE: 194

Gly Cys Arg Asn Ser Ile Lys Arg Cys Lys Gln Asn Ser Asp Cys Leu
1               5                   10                  15

Ala Gly Cys Val Cys Ser Val Gly His Gly Cys Gly
            20                  25

<210> SEQ ID NO 195
<211> LENGTH: 30
<212> TYPE: PRT
<213> ORGANISM: Artificial Sequence
<220> FEATURE:
```

<223> OTHER INFORMATION: Synthetic Construct

<400> SEQUENCE: 195

Gly Cys Val Ser Asn Arg Val Asn Lys Gly Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 196
<211> LENGTH: 28
<212> TYPE: PRT
<213> ORGANISM: Artificial Sequence
<220> FEATURE:
<223> OTHER INFORMATION: Synthetic Construct

<400> SEQUENCE: 196

Gly Cys Arg Gly Asn Ile Ile Lys Cys Lys Gln Asp Ser Asp Cys Leu
1               5                   10                  15

Ala Gly Cys Val Cys Asn Glu Ser Arg Gly Cys Gly
            20                  25

<210> SEQ ID NO 197
<211> LENGTH: 32
<212> TYPE: PRT
<213> ORGANISM: Artificial Sequence
<220> FEATURE:
<223> OTHER INFORMATION: Synthetic Construct

<400> SEQUENCE: 197

Gly Cys Arg Ser Gly Asn Thr Ile Arg Lys Arg Glu Cys Lys Gln Asp
1               5                   10                  15

Ser Asp Cys Leu Ala Gly Cys Val Cys Gly Pro Gly Gly Cys Gly
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Synthetic Construct

<400> SEQUENCE: 198

Gly Cys Ala Ser Ser Asn Ser Ile Arg Gln Gly Trp Cys Lys Gln Asp
1               5                   10                  15

Ser Asp Cys Leu Ala Gly Cys Val Cys Gly Pro Lys Ser Asn Cys Gly
            20                  25                  30

<210> SEQ ID NO 199
<211> LENGTH: 28
<212> TYPE: PRT
<213> ORGANISM: Artificial Sequence
<220> FEATURE:
<223> OTHER INFORMATION: Synthetic Construct

<400> SEQUENCE: 199

Gly Cys Arg Ser Asn Arg Ile Arg Cys Lys Gln Asp Ser Asp Cys Leu
1               5                   10                  15

Ala Gly Cys Val Cys Tyr Gly His Gly Asp Cys Gly
            20                  25

<210> SEQ ID NO 200
<211> LENGTH: 32
<212> TYPE: PRT
<213> ORGANISM: Artificial Sequence

```
<220> FEATURE:
<223> OTHER INFORMATION: Synthetic Construct

<400> SEQUENCE: 200

Gly Cys Arg Ser Asn Lys Leu Arg Glu Ala Arg Gly Cys Lys Gln Asp
1               5                   10                  15

Ser Asp Cys Leu Ala Gly Cys Val Cys Gly Ser Arg Gln Asp Cys Gly
                20                  25                  30

<210> SEQ ID NO 201
<211> LENGTH: 28
<212> TYPE: PRT
<213> ORGANISM: Artificial Sequence
<220> FEATURE:
<223> OTHER INFORMATION: Synthetic Construct

<400> SEQUENCE: 201

Gly Cys Val Asn Ser Val Lys Arg Cys Lys Gln Asp Ser Asp Cys Leu
1               5                   10                  15

Ala Gly Cys Val Cys Ser Arg Gly Val Asn Cys Gly
                20                  25

<210> SEQ ID NO 202
<211> LENGTH: 30
<212> TYPE: PRT
<213> ORGANISM: Artificial Sequence
<220> FEATURE:
<223> OTHER INFORMATION: Synthetic Construct

<400> SEQUENCE: 202

Gly Cys Gly Ser Asn Lys Ile Arg Pro Arg Cys Lys Gln Asp Ser Asp
1               5                   10                  15

Cys Leu Ala Gly Cys Val Cys Gly Pro Asn Asp Phe Cys Gly
                20                  25                  30

<210> SEQ ID NO 203
<211> LENGTH: 28
<212> TYPE: PRT
<213> ORGANISM: Artificial Sequence
<220> FEATURE:
<223> OTHER INFORMATION: Synthetic Construct

<400> SEQUENCE: 203

Gly Cys Asn Arg Ile Arg Asn Ser Cys Lys Gln Asp Ser Asp Cys Leu
1               5                   10                  15

Ala Gly Cys Val Cys Gly Arg Gly Asp Tyr Cys Gly
                20                  25

<210> SEQ ID NO 204
<211> LENGTH: 28
<212> TYPE: PRT
<213> ORGANISM: Artificial Sequence
<220> FEATURE:
<223> OTHER INFORMATION: Synthetic Construct

<400> SEQUENCE: 204

Gly Cys Ser Arg Asn Ser Ile Lys Cys Lys Gln Asp Ser Asp Cys Leu
1               5                   10                  15

Ala Gly Cys Val Cys Ala Ser Gly Ser Ser Cys Gly
                20                  25

<210> SEQ ID NO 205
<211> LENGTH: 28
<212> TYPE: PRT
```

<213> ORGANISM: Artificial Sequence
<220> FEATURE:
<223> OTHER INFORMATION: Synthetic Construct

<400> SEQUENCE: 205

Gly Cys Ser Asn Tyr Val Lys Arg Cys Lys Gln Asp Ser Asp Cys Leu
1               5                   10                  15

Ala Gly Cys Val Cys Ser Pro Gly Gly Arg Cys Gly
            20                  25

<210> SEQ ID NO 206
<211> LENGTH: 30
<212> TYPE: PRT
<213> ORGANISM: Artificial Sequence
<220> FEATURE:
<223> OTHER INFORMATION: Synthetic Construct

<400> SEQUENCE: 206

Gly Cys Arg Ala Asn Arg Val Ser Gly Arg Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Synthetic Construct

<400> SEQUENCE: 207

Gly Cys Ser Asn Arg Val Lys Val Arg Ala Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 208
<211> LENGTH: 28
<212> TYPE: PRT
<213> ORGANISM: Artificial Sequence
<220> FEATURE:
<223> OTHER INFORMATION: Synthetic Construct

<400> SEQUENCE: 208

Gly Cys Glu Asn Arg Thr Lys Gly Cys Lys Gln Asp Ser Asp Cys Leu
1               5                   10                  15

Ala Gly Cys Val Cys Gly Phe Arg Gly Thr Cys Gly
            20                  25

<210> SEQ ID NO 209
<211> LENGTH: 28
<212> TYPE: PRT
<213> ORGANISM: Artificial Sequence
<220> FEATURE:
<223> OTHER INFORMATION: Synthetic Construct

<400> SEQUENCE: 209

Gly Cys Gly Asn Lys Ile Arg Ala Cys Lys Gln Asp Ser Asp Cys Leu
1               5                   10                  15

Ala Gly Cys Val Cys Arg Asp Arg Val Gly Cys Gly
            20                  25

<210> SEQ ID NO 210
<211> LENGTH: 30

```
<212> TYPE: PRT
<213> ORGANISM: Artificial Sequence
<220> FEATURE:
<223> OTHER INFORMATION: Synthetic Construct

<400> SEQUENCE: 210

Gly Cys Ala Asn Arg Val Lys Arg Thr Ser Cys Lys Gln Asp Ser Asp
1               5                   10                  15

Cys Leu Ala Gly Cys Val Cys Gly Pro Asn Gly Phe Cys Gly
            20                  25                  30

<210> SEQ ID NO 211
<211> LENGTH: 5
<212> TYPE: PRT
<213> ORGANISM: Artificial Sequence
<220> FEATURE:
<223> OTHER INFORMATION: Synthetic Construct

<400> SEQUENCE: 211

Gly Glu Ser Leu Ser
1               5

<210> SEQ ID NO 212
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = 3,4-difluoro-L-phenylalanine,
      3,4-dichloro-L-phenylalanine, 4-chloro-L-phenylalanine,
      3-F,4-Cl-L-phenylalanine, 2-pyridone(NH para)-L-alanine,
      pyridone(NH meta)-L-alanine, or sulfotyrosine

<400> SEQUENCE: 212

Asn Ile Met Leu Pro Xaa Trp Gly
1               5

<210> SEQ ID NO 213
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = 1-Naphthyl alanine, 2-Naphthyl alanine,
      or 2-chloroindole

<400> SEQUENCE: 213

Asn Ile Met Leu Pro Phe Xaa Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = norleucine

<400> SEQUENCE: 214

Asp Val Xaa Gln Pro Tyr Trp Gly
```

<210> SEQ ID NO 215
<211> LENGTH: 30
<212> TYPE: PRT
<213> ORGANISM: Artificial Sequence
<220> FEATURE:
<223> OTHER INFORMATION: Synthetic Construct

<400> SEQUENCE: 215

Gly Cys Asn Ile Met Leu Pro Tyr Trp Gly Cys Gly Gln Ser Phe Glu
1               5                   10                  15

Cys Leu Ala Gly Cys Val Cys Gln Tyr Tyr Gln Ser Cys Gly
            20                  25                  30

<210> SEQ ID NO 216
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 30
<223> OTHER INFORMATION: glycine can be capped with C(=O)-oxetane-3yl

<400> SEQUENCE: 216

Gly Cys Asn Ile Met Leu Pro Tyr Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 217
<211> LENGTH: 28
<212> TYPE: PRT
<213> ORGANISM: Artificial Sequence
<220> FEATURE:
<223> OTHER INFORMATION: Synthetic Construct

<400> SEQUENCE: 217

Cys Asn Ile Met Leu Pro Tyr Trp Gly Cys Gly Arg Asp Phe Glu Cys
1               5                   10                  15

Leu Ala Gly Cys Val Cys Gln Tyr Tyr Gln Ser Cys
            20                  25

<210> SEQ ID NO 218
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 218

Gly Cys Asn Ile Xaa Leu Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 219
<211> LENGTH: 30
<212> TYPE: PRT
<213> ORGANISM: Artificial Sequence

```
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = 1-naphthylalanine or 2-naphthylalanine

<400> SEQUENCE: 219

Gly Cys Asn Ile Met Leu Pro Phe Xaa Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 220
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = 3-fluorotyrosine or 4-fluorophenylalanine

<400> SEQUENCE: 220

Gln Tyr Xaa Gln Ser
1               5

<210> SEQ ID NO 221
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = PEG6-propargylglycine

<400> SEQUENCE: 221

Xaa Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Synthetic Construct

<400> SEQUENCE: 222

Gly Cys Asn Ile Met Leu Pro Tyr Trp Gly Cys Gly Arg Asp Phe Glu
1               5                   10                  15

Cys Met Asn Gln Cys Ile Cys Gln Tyr Tyr Gln Ser Cys Gly
            20                  25                  30

<210> SEQ ID NO 223
<211> LENGTH: 30
<212> TYPE: PRT
<213> ORGANISM: Artificial Sequence
<220> FEATURE:
<223> OTHER INFORMATION: Synthetic Construct

<400> SEQUENCE: 223

Gly Cys Asn Ile Met Leu Pro Tyr Trp Gly Cys Gly Arg Asp Phe Glu
```

```
                1               5                   10                  15
Cys Phe Tyr Glu Cys Ile Cys Gln Tyr Tyr Gln Ser Cys Gly
                20                  25                  30

<210> SEQ ID NO 224
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 224

Gly Cys Asp Val Xaa Gln Pro Tyr Trp Gly Cys Gly Pro Asp Ile Asp
1               5                   10                  15

Cys Leu Ser Asn Cys Ile Cys His Trp Tyr Asn Ser Cys Gly
                20                  25                  30

<210> SEQ ID NO 225
<211> LENGTH: 10
<212> TYPE: PRT
<213> ORGANISM: Artificial Sequence
<220> FEATURE:
<223> OTHER INFORMATION: Synthetic Construct

<400> SEQUENCE: 225

Glu Thr Asp Trp Tyr Pro His Gln Ile Asp
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Synthetic Construct

<400> SEQUENCE: 226

Gly Glu Thr Val Phe Glu Gln Phe Leu Trp
1               5                   10

<210> SEQ ID NO 227
<211> LENGTH: 6
<212> TYPE: PRT
<213> ORGANISM: Artificial Sequence
<220> FEATURE:
<223> OTHER INFORMATION: Synthetic Construct

<400> SEQUENCE: 227

His Met Met Tyr Asp Tyr
1               5

<210> SEQ ID NO 228
<211> LENGTH: 8
<212> TYPE: PRT
<213> ORGANISM: Artificial Sequence
<220> FEATURE:
<223> OTHER INFORMATION: Synthetic Construct

<400> SEQUENCE: 228

Lys Lys Trp Gln Trp Trp Tyr Met
1               5

<210> SEQ ID NO 229
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 229

Pro Ala Ile Gln Asn Trp Lys Glu His Pro
1               5                   10

<210> SEQ ID NO 230
<211> LENGTH: 8
<212> TYPE: PRT
<213> ORGANISM: Artificial Sequence
<220> FEATURE:
<223> OTHER INFORMATION: Synthetic Construct

<400> SEQUENCE: 230

Gln Leu Met His Pro Phe Trp Gly
1               5

<210> SEQ ID NO 231
<211> LENGTH: 6
<212> TYPE: PRT
<213> ORGANISM: Artificial Sequence
<220> FEATURE:
<223> OTHER INFORMATION: Synthetic Construct

<400> SEQUENCE: 231

His Met Met Tyr Asp Tyr
1               5

<210> SEQ ID NO 232
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E or G or P or Q or R or T or V
<220> FEATURE:
<221> NAME/KEY: VARIANT
<222> LOCATION: 2
<223> OTHER INFORMATION: Xaa = T or E or A or D
<220> FEATURE:
<221> NAME/KEY: VARIANT
<222> LOCATION: 3
<223> OTHER INFORMATION: Xaa = D or T or I or P
<220> FEATURE:
<221> NAME/KEY: VARIANT
<222> LOCATION: 4
<223> OTHER INFORMATION: Xaa = W or V or Q or T or W
<220> FEATURE:
<221> NAME/KEY: VARIANT
<222> LOCATION: 5
<223> OTHER INFORMATION: Xaa = Y or F or N or E or P or K
<220> FEATURE:
<221> NAME/KEY: VARIANT
<222> LOCATION: 6
<223> OTHER INFORMATION: Xaa = P or E or W or N or P
<220> FEATURE:
<221> NAME/KEY: VARIANT
<222> LOCATION: 7
<223> OTHER INFORMATION: Xaa = H or Q or K or W or H
<220> FEATURE:
<221> NAME/KEY: VARIANT
<222> LOCATION: 8
<223> OTHER INFORMATION: Xaa = Q or F or E or A or D or W
<220> FEATURE:
<221> NAME/KEY: VARIANT
<222> LOCATION: 9
```

```
<223> OTHER INFORMATION: Xaa = I or L or H
<220> FEATURE:
<221> NAME/KEY: VARIANT
<222> LOCATION: 10
<223> OTHER INFORMATION: Xaa = D or W or P or Y or T or M or N

<400> SEQUENCE: 232

Xaa Xaa Xaa Xaa Xaa Xaa Xaa Xaa Xaa Xaa
1               5                   10

<210> SEQ ID NO 233
<211> LENGTH: 5
<212> TYPE: PRT
<213> ORGANISM: Artificial Sequence
<220> FEATURE:
<223> OTHER INFORMATION: Synthetic Construct

<400> SEQUENCE: 233

Gly Pro Asn Gly Phe
1               5

<210> SEQ ID NO 234
<211> LENGTH: 5
<212> TYPE: PRT
<213> ORGANISM: Artificial Sequence
<220> FEATURE:
<223> OTHER INFORMATION: Synthetic Construct

<400> SEQUENCE: 234

Gly Pro Asn Gly Phe
1               5

<210> SEQ ID NO 235
<211> LENGTH: 5
<212> TYPE: PRT
<213> ORGANISM: Artificial Sequence
<220> FEATURE:
<223> OTHER INFORMATION: Synthetic Construct

<400> SEQUENCE: 235

Glu Met Tyr Asp Ala
1               5

<210> SEQ ID NO 236
<211> LENGTH: 5
<212> TYPE: PRT
<213> ORGANISM: Artificial Sequence
<220> FEATURE:
<223> OTHER INFORMATION: Synthetic Construct

<400> SEQUENCE: 236

Tyr Pro Trp Thr Glu
1               5

<210> SEQ ID NO 237
<211> LENGTH: 6
<212> TYPE: PRT
<213> ORGANISM: Artificial Sequence
<220> FEATURE:
<223> OTHER INFORMATION: Synthetic Construct

<400> SEQUENCE: 237

Ser Trp Trp Pro Ser Leu
1               5

<210> SEQ ID NO 238
<211> LENGTH: 5
```

<212> TYPE: PRT
<213> ORGANISM: Artificial Sequence
<220> FEATURE:
<223> OTHER INFORMATION: Synthetic Construct

<400> SEQUENCE: 238

His Trp Tyr Arg Ser
1               5

<210> SEQ ID NO 239
<211> LENGTH: 32
<212> TYPE: PRT
<213> ORGANISM: Artificial Sequence
<220> FEATURE:
<223> OTHER INFORMATION: Synthetic Construct

<400> SEQUENCE: 239

Gly Cys Glu Thr Asp Trp Tyr Pro His Gln Ile Asp Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Synthetic Construct

<400> SEQUENCE: 240

Gly Cys Gly Glu Thr Val Phe Glu Gln Phe Leu Trp Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 241
<211> LENGTH: 28
<212> TYPE: PRT
<213> ORGANISM: Artificial Sequence
<220> FEATURE:
<223> OTHER INFORMATION: Synthetic Construct

<400> SEQUENCE: 241

Gly Cys His Met Met Tyr Asp Tyr Cys Lys Gln Asp Ser Asp Cys Leu
1               5                   10                  15

Ala Gly Cys Val Cys Glu Met Tyr Asp Ala Cys Gly
            20                  25

<210> SEQ ID NO 242
<211> LENGTH: 30
<212> TYPE: PRT
<213> ORGANISM: Artificial Sequence
<220> FEATURE:
<223> OTHER INFORMATION: Synthetic Construct

<400> SEQUENCE: 242

Gly Cys Lys Lys Trp Gln Trp Trp Tyr Met Cys Lys Gln Asp Ser Asp
1               5                   10                  15

Cys Leu Ala Gly Cys Val Cys Tyr Pro Trp Thr Glu Cys Gly
            20                  25                  30

<210> SEQ ID NO 243
<211> LENGTH: 33
<212> TYPE: PRT
<213> ORGANISM: Artificial Sequence

```
<220> FEATURE:
<223> OTHER INFORMATION: Synthetic Construct

<400> SEQUENCE: 243

Gly Cys Pro Ala Ile Gln Asn Trp Lys Glu His Pro Cys Lys Gln Asp
1               5                   10                  15

Ser Asp Cys Leu Ala Gly Cys Val Cys Ser Trp Trp Pro Ser Leu Cys
            20                  25                  30

Gly

<210> SEQ ID NO 244
<211> LENGTH: 30
<212> TYPE: PRT
<213> ORGANISM: Artificial Sequence
<220> FEATURE:
<223> OTHER INFORMATION: Synthetic Construct

<400> SEQUENCE: 244

Gly Cys Gln Leu Met His Pro Phe Trp Gly Cys Lys Gln Asp Ser Asp
1               5                   10                  15

Cys Leu Ala Gly Cys Val Cys His Trp Tyr Arg Ser Cys Gly
            20                  25                  30

<210> SEQ ID NO 245
<211> LENGTH: 8
<212> TYPE: PRT
<213> ORGANISM: Artificial Sequence
<220> FEATURE:
<223> OTHER INFORMATION: Synthetic Construct

<400> SEQUENCE: 245

His Leu Phe Glu Pro Leu Trp Gly
1               5

<210> SEQ ID NO 246
<211> LENGTH: 8
<212> TYPE: PRT
<213> ORGANISM: Artificial Sequence
<220> FEATURE:
<223> OTHER INFORMATION: Synthetic Construct

<400> SEQUENCE: 246

Gln Val Met Arg Pro Phe Trp Gly
1               5

<210> SEQ ID NO 247
<211> LENGTH: 8
<212> TYPE: PRT
<213> ORGANISM: Artificial Sequence
<220> FEATURE:
<223> OTHER INFORMATION: Synthetic Construct

<400> SEQUENCE: 247

Gln Val Met Gln Pro Ala Trp Gly
1               5

<210> SEQ ID NO 248
<211> LENGTH: 8
<212> TYPE: PRT
<213> ORGANISM: Artificial Sequence
<220> FEATURE:
<223> OTHER INFORMATION: Synthetic Construct

<400> SEQUENCE: 248

His Arg Leu Gln Pro Leu Trp Gly
```

```
<210> SEQ ID NO 249
<211> LENGTH: 8
<212> TYPE: PRT
<213> ORGANISM: Artificial Sequence
<220> FEATURE:
<223> OTHER INFORMATION: Synthetic Construct

<400> SEQUENCE: 249

Glu Leu Leu Gln Pro Ser Trp Gly
1               5

<210> SEQ ID NO 250
<211> LENGTH: 8
<212> TYPE: PRT
<213> ORGANISM: Artificial Sequence
<220> FEATURE:
<223> OTHER INFORMATION: Synthetic Construct

<400> SEQUENCE: 250

Asn Val Leu Leu Pro Leu Trp Gly
1               5

<210> SEQ ID NO 251
<211> LENGTH: 8
<212> TYPE: PRT
<213> ORGANISM: Artificial Sequence
<220> FEATURE:
<223> OTHER INFORMATION: Synthetic Construct

<400> SEQUENCE: 251

Asp Leu Met Gln Pro Leu Trp Gly
1               5

<210> SEQ ID NO 252
<211> LENGTH: 8
<212> TYPE: PRT
<213> ORGANISM: Artificial Sequence
<220> FEATURE:
<223> OTHER INFORMATION: Synthetic Construct

<400> SEQUENCE: 252

Asn Pro Met Leu Pro Leu Trp Gly
1               5

<210> SEQ ID NO 253
<211> LENGTH: 8
<212> TYPE: PRT
<213> ORGANISM: Artificial Sequence
<220> FEATURE:
<223> OTHER INFORMATION: Synthetic Construct

<400> SEQUENCE: 253

Gln Val Leu Gln Pro Ser Trp Gly
1               5

<210> SEQ ID NO 254
<211> LENGTH: 8
<212> TYPE: PRT
<213> ORGANISM: Artificial Sequence
<220> FEATURE:
<223> OTHER INFORMATION: Synthetic Construct

<400> SEQUENCE: 254

Gln Leu Leu Glu Pro Met Trp Gly
1               5
```

<210> SEQ ID NO 255
<211> LENGTH: 8
<212> TYPE: PRT
<213> ORGANISM: Artificial Sequence
<220> FEATURE:
<223> OTHER INFORMATION: Synthetic Construct

<400> SEQUENCE: 255

Lys Leu Leu Gln Pro Met Trp Gly
1               5

<210> SEQ ID NO 256
<211> LENGTH: 8
<212> TYPE: PRT
<213> ORGANISM: Artificial Sequence
<220> FEATURE:
<223> OTHER INFORMATION: Synthetic Construct

<400> SEQUENCE: 256

Asp Arg Met Gln Pro Tyr Trp Gly
1               5

<210> SEQ ID NO 257
<211> LENGTH: 8
<212> TYPE: PRT
<213> ORGANISM: Artificial Sequence
<220> FEATURE:
<223> OTHER INFORMATION: Synthetic Construct

<400> SEQUENCE: 257

Lys Ile Met Gln Pro Leu Trp Gly
1               5

<210> SEQ ID NO 258
<211> LENGTH: 8
<212> TYPE: PRT
<213> ORGANISM: Artificial Sequence
<220> FEATURE:
<223> OTHER INFORMATION: Synthetic Construct

<400> SEQUENCE: 258

Asn Leu Met His Pro Phe Trp Gly
1               5

<210> SEQ ID NO 259
<211> LENGTH: 8
<212> TYPE: PRT
<213> ORGANISM: Artificial Sequence
<220> FEATURE:
<223> OTHER INFORMATION: Synthetic Construct

<400> SEQUENCE: 259

Ala Leu Leu Gln Pro Leu Trp Gly
1               5

<210> SEQ ID NO 260
<211> LENGTH: 8
<212> TYPE: PRT
<213> ORGANISM: Artificial Sequence
<220> FEATURE:
<223> OTHER INFORMATION: Synthetic Construct

<400> SEQUENCE: 260

Arg Leu Leu Glu Pro Ser Trp Gly
1               5

<210> SEQ ID NO 261
<211> LENGTH: 8
<212> TYPE: PRT
<213> ORGANISM: Artificial Sequence
<220> FEATURE:
<223> OTHER INFORMATION: Synthetic Construct

<400> SEQUENCE: 261

His Leu Leu Leu Pro Leu Trp Gly
1               5

<210> SEQ ID NO 262
<211> LENGTH: 5
<212> TYPE: PRT
<213> ORGANISM: Artificial Sequence
<220> FEATURE:
<223> OTHER INFORMATION: Synthetic Construct

<400> SEQUENCE: 262

Gln Trp Tyr Lys Ser
1               5

<210> SEQ ID NO 263
<211> LENGTH: 5
<212> TYPE: PRT
<213> ORGANISM: Artificial Sequence
<220> FEATURE:
<223> OTHER INFORMATION: Synthetic Construct

<400> SEQUENCE: 263

Leu Trp Tyr Asp Ser
1               5

<210> SEQ ID NO 264
<211> LENGTH: 5
<212> TYPE: PRT
<213> ORGANISM: Artificial Sequence
<220> FEATURE:
<223> OTHER INFORMATION: Synthetic Construct

<400> SEQUENCE: 264

Gln Trp Tyr Gln Ser
1               5

<210> SEQ ID NO 265
<211> LENGTH: 30
<212> TYPE: PRT
<213> ORGANISM: Artificial Sequence
<220> FEATURE:
<223> OTHER INFORMATION: Synthetic Construct

<400> SEQUENCE: 265

Gly Cys His Leu Phe Glu Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Synthetic Construct

<400> SEQUENCE: 266

Gly Cys Gln Val Met Arg Pro Phe Trp Gly Cys Lys Gln Asp Ser Asp

```
                1               5                  10                  15
Cys Leu Ala Gly Cys Val Cys His Trp Tyr Gln Ser Cys Gly
                20                  25                  30

<210> SEQ ID NO 267
<211> LENGTH: 30
<212> TYPE: PRT
<213> ORGANISM: Artificial Sequence
<220> FEATURE:
<223> OTHER INFORMATION: Synthetic Construct

<400> SEQUENCE: 267

Gly Cys Gln Val Met Gln Pro Ala Trp Gly Cys Lys Gln Asp Ser Asp
1               5                   10                  15

Cys Leu Ala Gly Cys Val Cys His Trp Tyr Gln Ser Cys Gly
                20                  25                  30

<210> SEQ ID NO 268
<211> LENGTH: 30
<212> TYPE: PRT
<213> ORGANISM: Artificial Sequence
<220> FEATURE:
<223> OTHER INFORMATION: Synthetic Construct

<400> SEQUENCE: 268

Gly Cys His Arg Leu Gln Pro Leu Trp Gly Cys Lys Gln Asp Ser Asp
1               5                   10                  15

Cys Leu Ala Gly Cys Val Cys His Trp Tyr Gln Ser Cys Gly
                20                  25                  30

<210> SEQ ID NO 269
<211> LENGTH: 30
<212> TYPE: PRT
<213> ORGANISM: Artificial Sequence
<220> FEATURE:
<223> OTHER INFORMATION: Synthetic Construct

<400> SEQUENCE: 269

Gly Cys Glu Leu Leu Gln Pro Ser Trp Gly Cys Lys Gln Asp Ser Asp
1               5                   10                  15

Cys Leu Ala Gly Cys Val Cys His Trp Tyr Gln Ser Cys Gly
                20                  25                  30

<210> SEQ ID NO 270
<211> LENGTH: 30
<212> TYPE: PRT
<213> ORGANISM: Artificial Sequence
<220> FEATURE:
<223> OTHER INFORMATION: Synthetic Construct

<400> SEQUENCE: 270

Gly Cys Asn Pro Met Leu Pro Phe Trp Gly Cys Lys Gln Asp Ser Asp
1               5                   10                  15

Cys Leu Ala Gly Cys Val Cys His Trp Tyr Gln Ser Cys Gly
                20                  25                  30

<210> SEQ ID NO 271
<211> LENGTH: 30
<212> TYPE: PRT
<213> ORGANISM: Artificial Sequence
<220> FEATURE:
<223> OTHER INFORMATION: Synthetic Construct

<400> SEQUENCE: 271
```

Gly Cys Asn Val Leu Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 272
<211> LENGTH: 30
<212> TYPE: PRT
<213> ORGANISM: Artificial Sequence
<220> FEATURE:
<223> OTHER INFORMATION: Synthetic Construct

<400> SEQUENCE: 272

Gly Cys Asp Ile Met Gln Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 273
<211> LENGTH: 30
<212> TYPE: PRT
<213> ORGANISM: Artificial Sequence
<220> FEATURE:
<223> OTHER INFORMATION: Synthetic Construct

<400> SEQUENCE: 273

Gly Cys Asp Leu Met Gln Pro Leu Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 274
<211> LENGTH: 5
<212> TYPE: PRT
<213> ORGANISM: Artificial Sequence
<220> FEATURE:
<223> OTHER INFORMATION: Synthetic Construct

<400> SEQUENCE: 274

Gln Met Phe Asn Ser
1               5

<210> SEQ ID NO 275
<211> LENGTH: 30
<212> TYPE: PRT
<213> ORGANISM: Artificial Sequence
<220> FEATURE:
<223> OTHER INFORMATION: Synthetic Construct

<400> SEQUENCE: 275

Gly Cys Gln Val Leu Gln Pro Ser Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 276
<211> LENGTH: 30
<212> TYPE: PRT
<213> ORGANISM: Artificial Sequence
<220> FEATURE:
<223> OTHER INFORMATION: Synthetic Construct

<400> SEQUENCE: 276

Gly Cys Gln Leu Met Gln Pro Phe Trp Gly Cys Lys Gln Asp Ser Asp
1               5                   10                  15

```
Cys Leu Ala Gly Cys Val Cys Arg Trp Tyr Asn Ser Cys Gly
            20                  25                  30

<210> SEQ ID NO 277
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = norleucine

<400> SEQUENCE: 277

Asn Ile Xaa Leu Pro Phe Trp Gly
1               5

<210> SEQ ID NO 278
<211> LENGTH: 30
<212> TYPE: PRT
<213> ORGANISM: Artificial Sequence
<220> FEATURE:
<223> OTHER INFORMATION: Synthetic Construct

<400> SEQUENCE: 278

Gly Cys Gln Leu Met Gln Pro Phe Trp Gly Cys Lys Gln Asp Ser Asp
1               5                   10                  15

Cys Leu Ala Gly Cys Val Cys Arg Trp Tyr His Ser Cys Gly
            20                  25                  30

<210> SEQ ID NO 279
<211> LENGTH: 30
<212> TYPE: PRT
<213> ORGANISM: Artificial Sequence
<220> FEATURE:
<223> OTHER INFORMATION: Synthetic Construct

<400> SEQUENCE: 279

Gly Cys Gln Leu Leu Glu Pro Met Trp Gly Cys Lys Gln Asp Ser Asp
1               5                   10                  15

Cys Leu Ala Gly Cys Val Cys His Trp Tyr Asn Ser Cys Gly
            20                  25                  30

<210> SEQ ID NO 280
<211> LENGTH: 30
<212> TYPE: PRT
<213> ORGANISM: Artificial Sequence
<220> FEATURE:
<223> OTHER INFORMATION: Synthetic Construct

<400> SEQUENCE: 280

Gly Cys Lys Leu Leu Gln Pro Met Trp Gly Cys Lys Gln Asp Ser Asp
1               5                   10                  15

Cys Leu Ala Gly Cys Val Cys Arg Trp Tyr Gln Ser Cys Gly
            20                  25                  30

<210> SEQ ID NO 281
<211> LENGTH: 30
<212> TYPE: PRT
<213> ORGANISM: Artificial Sequence
<220> FEATURE:
<223> OTHER INFORMATION: Synthetic Construct

<400> SEQUENCE: 281
```

Gly Cys Asp Arg Met Gln Pro Tyr Trp Gly Cys Lys Gln Asp Ser Asp
1               5                   10                  15

Cys Leu Ala Gly Cys Val Cys Gln Trp Tyr Lys Ser Cys Gly
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Synthetic Construct

<400> SEQUENCE: 282

Gly Cys Lys Ile Met Gln Pro Leu Trp Gly Cys Lys Gln Asp Ser Asp
1               5                   10                  15

Cys Leu Ala Gly Cys Val Cys Leu Trp Tyr Asp Ser Cys Gly
            20                  25                  30

<210> SEQ ID NO 283
<211> LENGTH: 30
<212> TYPE: PRT
<213> ORGANISM: Artificial Sequence
<220> FEATURE:
<223> OTHER INFORMATION: Synthetic Construct

<400> SEQUENCE: 283

Gly Cys Asn Leu Met His Pro Phe Trp Gly Cys Lys Gln Asp Ser Asp
1               5                   10                  15

Cys Leu Ala Gly Cys Val Cys His Trp Tyr Gln Ser Cys Gly
            20                  25                  30

<210> SEQ ID NO 284
<211> LENGTH: 30
<212> TYPE: PRT
<213> ORGANISM: Artificial Sequence
<220> FEATURE:
<223> OTHER INFORMATION: Synthetic Construct

<400> SEQUENCE: 284

Gly Cys Ala Leu Leu Gln Pro Leu Trp Gly Cys Lys Gln Asp Ser Asp
1               5                   10                  15

Cys Leu Ala Gly Cys Val Cys Arg Trp Tyr Asn Ser Cys Gly
            20                  25                  30

<210> SEQ ID NO 285
<211> LENGTH: 30
<212> TYPE: PRT
<213> ORGANISM: Artificial Sequence
<220> FEATURE:
<223> OTHER INFORMATION: Synthetic Construct

<400> SEQUENCE: 285

Gly Cys Arg Leu Leu Glu Pro Ser Trp Gly Cys Lys Gln Asp Ser Asp
1               5                   10                  15

Cys Leu Ala Gly Cys Val Cys Gln Trp Tyr Gln Ser Cys Gly
            20                  25                  30

<210> SEQ ID NO 286
<211> LENGTH: 30
<212> TYPE: PRT
<213> ORGANISM: Artificial Sequence
<220> FEATURE:
<223> OTHER INFORMATION: Synthetic Construct

<400> SEQUENCE: 286

```
Gly Cys His Leu Leu Pro Leu Trp Gly Cys Lys Gln Asp Ser Asp
1               5                   10                  15

Cys Leu Ala Gly Cys Val Cys Arg Trp Tyr His Ser Cys Gly
            20                  25              30
```

<210> SEQ ID NO 287
<211> LENGTH: 10
<212> TYPE: PRT
<213> ORGANISM: Artificial Sequence
<220> FEATURE:
<223> OTHER INFORMATION: Synthetic Construct

<400> SEQUENCE: 287

```
Asp Asp Pro Ser Phe Asp Trp Ser Val Tyr
1               5                   10
```

<210> SEQ ID NO 288
<211> LENGTH: 10
<212> TYPE: PRT
<213> ORGANISM: Artificial Sequence
<220> FEATURE:
<223> OTHER INFORMATION: Synthetic Construct

<400> SEQUENCE: 288

```
Trp Asp Pro Thr Phe Asn Trp Ala Leu Tyr
1               5                   10
```

<210> SEQ ID NO 289
<211> LENGTH: 10
<212> TYPE: PRT
<213> ORGANISM: Artificial Sequence
<220> FEATURE:
<223> OTHER INFORMATION: Synthetic Construct

<400> SEQUENCE: 289

```
Gln Asp Pro Thr Leu Asn Trp Ala Thr Tyr
1               5                   10
```

<210> SEQ ID NO 290
<211> LENGTH: 10
<212> TYPE: PRT
<213> ORGANISM: Artificial Sequence
<220> FEATURE:
<223> OTHER INFORMATION: Synthetic Construct

<400> SEQUENCE: 290

```
Glu Asp Pro Thr Val Asp Trp Ala Gln Tyr
1               5                   10
```

<210> SEQ ID NO 291
<211> LENGTH: 10
<212> TYPE: PRT
<213> ORGANISM: Artificial Sequence
<220> FEATURE:
<223> OTHER INFORMATION: Synthetic Construct

<400> SEQUENCE: 291

```
Lys Asp Thr Thr Phe Asn Trp Gly Leu Phe
1               5                   10
```

<210> SEQ ID NO 292
<211> LENGTH: 5
<212> TYPE: PRT
<213> ORGANISM: Artificial Sequence
<220> FEATURE:
<223> OTHER INFORMATION: Synthetic Construct -continued

<400> SEQUENCE: 292

Arg Met Tyr Asp Ser
1               5

<210> SEQ ID NO 293
<211> LENGTH: 32
<212> TYPE: PRT
<213> ORGANISM: Artificial Sequence
<220> FEATURE:
<223> OTHER INFORMATION: Synthetic Construct

<400> SEQUENCE: 293

Gly Cys Asp Asp Pro Ser Phe Asp Trp Ser Val Tyr Cys Lys Gln Asp
1               5                   10                  15

Ser Asp Cys Leu Ala Gly Cys Val Cys Arg Met Tyr Asp Ser Cys Gly
                20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Synthetic Construct

<400> SEQUENCE: 294

Gly Cys Trp Asp Pro Thr Phe Asn Trp Ala Leu Tyr Cys Lys Gln Asp
1               5                   10                  15

Ser Asp Cys Leu Ala Gly Cys Val Cys Gln Met Tyr Asp Ser Cys Gly
                20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Synthetic Construct

<400> SEQUENCE: 295

Gly Cys Gln Asp Pro Thr Leu Asn Trp Ala Thr Tyr Cys Lys Gln Asp
1               5                   10                  15

Ser Asp Cys Leu Ala Gly Cys Val Cys Gln Met Tyr Gln Ser Cys Gly
                20                  25                  30

<210> SEQ ID NO 296
<211> LENGTH: 32
<212> TYPE: PRT
<213> ORGANISM: Artificial Sequence
<220> FEATURE:
<223> OTHER INFORMATION: Synthetic Construct

<400> SEQUENCE: 296

Gly Cys Glu Asp Pro Thr Val Asp Trp Ala Gln Tyr Cys Lys Gln Asp
1               5                   10                  15

Ser Asp Cys Leu Ala Gly Cys Val Cys Gln Met Tyr Gln Ser Cys Gly
                20                  25                  30

<210> SEQ ID NO 297
<211> LENGTH: 32
<212> TYPE: PRT
<213> ORGANISM: Artificial Sequence
<220> FEATURE:
<223> OTHER INFORMATION: Synthetic Construct

<400> SEQUENCE: 297

Gly Cys Lys Asp Thr Thr Phe Asn Trp Gly Leu Phe Cys Lys Gln Asp
1               5                   10                  15

Ser Asp Cys Leu Ala Gly Cys Val Cys Gln Leu Tyr Gln Ser Cys Gly
                20                  25                  30

<210> SEQ ID NO 298
<211> LENGTH: 5
<212> TYPE: PRT
<213> ORGANISM: Artificial Sequence
<220> FEATURE:
<223> OTHER INFORMATION: Synthetic Construct

<400> SEQUENCE: 298

Gly Pro Glu Leu Asn
1               5

<210> SEQ ID NO 299
<211> LENGTH: 5
<212> TYPE: PRT
<213> ORGANISM: Artificial Sequence
<220> FEATURE:
<223> OTHER INFORMATION: Synthetic Construct

<400> SEQUENCE: 299

Gln Ala Asp Tyr Ala
1               5

<210> SEQ ID NO 300
<211> LENGTH: 5
<212> TYPE: PRT
<213> ORGANISM: Artificial Sequence
<220> FEATURE:
<223> OTHER INFORMATION: Synthetic Construct

<400> SEQUENCE: 300

Gly Val Asp Tyr Leu
1               5

<210> SEQ ID NO 301
<211> LENGTH: 5
<212> TYPE: PRT
<213> ORGANISM: Artificial Sequence
<220> FEATURE:
<223> OTHER INFORMATION: Synthetic Construct

<400> SEQUENCE: 301

Gly Thr Asn Phe Leu
1               5

<210> SEQ ID NO 302
<211> LENGTH: 5
<212> TYPE: PRT
<213> ORGANISM: Artificial Sequence
<220> FEATURE:
<223> OTHER INFORMATION: Synthetic Construct

<400> SEQUENCE: 302

Ser Arg Asp Phe Asp
1               5

<210> SEQ ID NO 303
<211> LENGTH: 5
<212> TYPE: PRT
<213> ORGANISM: Artificial Sequence
<220> FEATURE:
<223> OTHER INFORMATION: Synthetic Construct

<400> SEQUENCE: 303

Asn Arg Asp Phe Leu
1               5

<210> SEQ ID NO 304
<211> LENGTH: 5
<212> TYPE: PRT
<213> ORGANISM: Artificial Sequence
<220> FEATURE:
<223> OTHER INFORMATION: Synthetic Construct

<400> SEQUENCE: 304

Gly Trp Asp Gln Phe
1               5

<210> SEQ ID NO 305
<211> LENGTH: 5
<212> TYPE: PRT
<213> ORGANISM: Artificial Sequence
<220> FEATURE:
<223> OTHER INFORMATION: Synthetic Construct

<400> SEQUENCE: 305

Gly Lys Asp Phe His
1               5

<210> SEQ ID NO 306
<211> LENGTH: 5
<212> TYPE: PRT
<213> ORGANISM: Artificial Sequence
<220> FEATURE:
<223> OTHER INFORMATION: Synthetic Construct

<400> SEQUENCE: 306

Ser Gly Asp Phe Ala
1               5

<210> SEQ ID NO 307
<211> LENGTH: 5
<212> TYPE: PRT
<213> ORGANISM: Artificial Sequence
<220> FEATURE:
<223> OTHER INFORMATION: Synthetic Construct

<400> SEQUENCE: 307

Gly Lys Glu Leu Asn
1               5

<210> SEQ ID NO 308
<211> LENGTH: 5
<212> TYPE: PRT
<213> ORGANISM: Artificial Sequence
<220> FEATURE:
<223> OTHER INFORMATION: Synthetic Construct

<400> SEQUENCE: 308

Gly Trp Ser Met Asp
1               5

<210> SEQ ID NO 309
<211> LENGTH: 5
<212> TYPE: PRT
<213> ORGANISM: Artificial Sequence
<220> FEATURE:
<223> OTHER INFORMATION: Synthetic Construct

<400> SEQUENCE: 309

Gly Tyr Asp Leu Gln
1               5

<210> SEQ ID NO 310
<211> LENGTH: 30
<212> TYPE: PRT
<213> ORGANISM: Artificial Sequence
<220> FEATURE:
<223> OTHER INFORMATION: Synthetic Construct

<400> SEQUENCE: 310

Gly Cys Asn Ile Met Leu Pro Phe Trp Gly Cys Gly Pro Glu Leu Asn
1               5                   10                  15

Cys Leu Ala Gly Cys Val Cys Gln Tyr Tyr Gln Ser Cys Gly
            20                  25                  30

<210> SEQ ID NO 311
<211> LENGTH: 30
<212> TYPE: PRT
<213> ORGANISM: Artificial Sequence
<220> FEATURE:
<223> OTHER INFORMATION: Synthetic Construct

<400> SEQUENCE: 311

Gly Cys Asn Ile Met Leu Pro Phe Trp Gly Cys Gln Ala Asp Tyr Ala
1               5                   10                  15

Cys Leu Ala Gly Cys Val Cys Gln Tyr Tyr Gln Ser Cys Gly
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: Synthetic Construct

<400> SEQUENCE: 312

Gly Cys Asn Ile Met Leu Pro Phe Trp Gly Cys Gly Val Asp Tyr Leu
1               5                   10                  15

Cys Leu Ala Gly Cys Val Cys Gln Tyr Tyr Gln Ser Cys Gly
            20                  25                  30

<210> SEQ ID NO 313
<211> LENGTH: 30
<212> TYPE: PRT
<213> ORGANISM: Artificial Sequence
<220> FEATURE:
<223> OTHER INFORMATION: Synthetic Construct

<400> SEQUENCE: 313

Gly Cys Asn Ile Met Leu Pro Phe Trp Gly Cys Gly Thr Asn Phe Leu
1               5                   10                  15

Cys Leu Ala Gly Cys Val Cys Gln Tyr Tyr Gln Ser Cys Gly
            20                  25                  30

<210> SEQ ID NO 314
<211> LENGTH: 30
<212> TYPE: PRT
<213> ORGANISM: Artificial Sequence
<220> FEATURE:
<223> OTHER INFORMATION: Synthetic Construct

<400> SEQUENCE: 314

Gly Cys Asn Ile Met Leu Pro Phe Trp Gly Cys Ser Arg Asp Phe Asp
1               5                   10                  15

Cys Leu Ala Gly Cys Val Cys Gln Tyr Tyr Gln Ser Cys Gly
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Synthetic Construct

<400> SEQUENCE: 315

Gly Cys Asn Ile Met Leu Pro Phe Trp Gly Cys Asn Arg Asp Phe Leu
1               5                   10                  15

Cys Leu Ala Gly Cys Val Cys Gln Tyr Tyr Gln Ser Cys Gly
            20                  25                  30

<210> SEQ ID NO 316
<211> LENGTH: 30
<212> TYPE: PRT
<213> ORGANISM: Artificial Sequence
<220> FEATURE:
<223> OTHER INFORMATION: Synthetic Construct

<400> SEQUENCE: 316

Gly Cys Asn Ile Met Leu Pro Phe Trp Gly Cys Gly Trp Asp Gln Phe
1               5                   10                  15

Cys Leu Ala Gly Cys Val Cys Gln Tyr Tyr Gln Ser Cys Gly
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: Synthetic Construct

<400> SEQUENCE: 317

Gly Cys Asn Ile Met Leu Pro Phe Trp Gly Cys Gly Lys Asp Phe His
1               5                   10                  15

Cys Leu Ala Gly Cys Val Cys Gln Tyr Tyr Gln Ser Cys Gly
            20                  25                  30

<210> SEQ ID NO 318
<211> LENGTH: 30
<212> TYPE: PRT
<213> ORGANISM: Artificial Sequence
<220> FEATURE:
<223> OTHER INFORMATION: Synthetic Construct

<400> SEQUENCE: 318

Gly Cys Asn Ile Met Leu Pro Phe Trp Gly Cys Ser Gly Asp Phe Ala
1               5                   10                  15

Cys Leu Ala Gly Cys Val Cys Gln Tyr Tyr Gln Ser Cys Gly
            20                  25                  30

<210> SEQ ID NO 319
<211> LENGTH: 30
<212> TYPE: PRT
<213> ORGANISM: Artificial Sequence
<220> FEATURE:
<223> OTHER INFORMATION: Synthetic Construct

<400> SEQUENCE: 319

```
Gly Cys Asn Ile Met Leu Pro Phe Trp Gly Cys Gly Lys Glu Leu Asn
1               5                   10                  15

Cys Leu Ala Gly Cys Val Cys Gln Tyr Tyr Gln Ser Cys Gly
            20                  25                  30

<210> SEQ ID NO 320
<211> LENGTH: 30
<212> TYPE: PRT
<213> ORGANISM: Artificial Sequence
<220> FEATURE:
<223> OTHER INFORMATION: Synthetic Construct

<400> SEQUENCE: 320

Gly Cys Asn Ile Met Leu Pro Phe Trp Gly Cys Gly Trp Ser Met Asp
1               5                   10                  15

Cys Leu Ala Gly Cys Val Cys Gln Tyr Tyr Gln Ser Cys Gly
            20                  25                  30

<210> SEQ ID NO 321
<211> LENGTH: 30
<212> TYPE: PRT
<213> ORGANISM: Artificial Sequence
<220> FEATURE:
<223> OTHER INFORMATION: Synthetic Construct

<400> SEQUENCE: 321

Gly Cys Asn Ile Met Leu Pro Phe Trp Gly Cys Gly Tyr Asp Leu Gln
1               5                   10                  15

Cys Leu Ala Gly Cys Val Cys Gln Tyr Tyr Gln Ser Cys Gly
            20                  25                  30

<210> SEQ ID NO 322
<211> LENGTH: 5
<212> TYPE: PRT
<213> ORGANISM: Artificial Sequence
<220> FEATURE:
<223> OTHER INFORMATION: Synthetic Construct

<400> SEQUENCE: 322

Gly Arg Asp Leu Gln
1               5

<210> SEQ ID NO 323
<211> LENGTH: 5
<212> TYPE: PRT
<213> ORGANISM: Artificial Sequence
<220> FEATURE:
<223> OTHER INFORMATION: Synthetic Construct

<400> SEQUENCE: 323

Gly Val Asp Leu Ser
1               5

<210> SEQ ID NO 324
<211> LENGTH: 5
<212> TYPE: PRT
<213> ORGANISM: Artificial Sequence
<220> FEATURE:
<223> OTHER INFORMATION: Synthetic Construct

<400> SEQUENCE: 324

Gly Asp Asp Leu Glu
1               5
```

```
<210> SEQ ID NO 325
<211> LENGTH: 5
<212> TYPE: PRT
<213> ORGANISM: Artificial Sequence
<220> FEATURE:
<223> OTHER INFORMATION: Synthetic Construct

<400> SEQUENCE: 325

Gly Val Asp Met Thr
1               5

<210> SEQ ID NO 326
<211> LENGTH: 5
<212> TYPE: PRT
<213> ORGANISM: Artificial Sequence
<220> FEATURE:
<223> OTHER INFORMATION: Synthetic Construct

<400> SEQUENCE: 326

Gly Met Asp Ile Glu
1               5

<210> SEQ ID NO 327
<211> LENGTH: 5
<212> TYPE: PRT
<213> ORGANISM: Artificial Sequence
<220> FEATURE:
<223> OTHER INFORMATION: Synthetic Construct

<400> SEQUENCE: 327

Asp Gly Asp Tyr Gln
1               5

<210> SEQ ID NO 328
<211> LENGTH: 5
<212> TYPE: PRT
<213> ORGANISM: Artificial Sequence
<220> FEATURE:
<223> OTHER INFORMATION: Synthetic Construct

<400> SEQUENCE: 328

Gly Asn Asp Val Ser
1               5

<210> SEQ ID NO 329
<211> LENGTH: 5
<212> TYPE: PRT
<213> ORGANISM: Artificial Sequence
<220> FEATURE:
<223> OTHER INFORMATION: Synthetic Construct

<400> SEQUENCE: 329

Ala Gly Asp Glu Leu
1               5

<210> SEQ ID NO 330
<211> LENGTH: 5
<212> TYPE: PRT
<213> ORGANISM: Artificial Sequence
<220> FEATURE:
<223> OTHER INFORMATION: Synthetic Construct

<400> SEQUENCE: 330

Gly Leu Asp Glu Glu
1               5

<210> SEQ ID NO 331
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 331

Asp Gly Asp Phe Asp
1               5

<210> SEQ ID NO 332
<211> LENGTH: 5
<212> TYPE: PRT
<213> ORGANISM: Artificial Sequence
<220> FEATURE:
<223> OTHER INFORMATION: Synthetic Construct

<400> SEQUENCE: 332

Ala Gly Asp Phe Glu
1               5

<210> SEQ ID NO 333
<211> LENGTH: 5
<212> TYPE: PRT
<213> ORGANISM: Artificial Sequence
<220> FEATURE:
<223> OTHER INFORMATION: Synthetic Construct

<400> SEQUENCE: 333

Gly Asn Ser Phe Glu
1               5

<210> SEQ ID NO 334
<211> LENGTH: 5
<212> TYPE: PRT
<213> ORGANISM: Artificial Sequence
<220> FEATURE:
<223> OTHER INFORMATION: Synthetic Construct

<400> SEQUENCE: 334

Gly Gln Asp Leu Thr
1               5

<210> SEQ ID NO 335
<211> LENGTH: 5
<212> TYPE: PRT
<213> ORGANISM: Artificial Sequence
<220> FEATURE:
<223> OTHER INFORMATION: Synthetic Construct

<400> SEQUENCE: 335

Gly Glu Asn Leu Ala
1               5

<210> SEQ ID NO 336
<211> LENGTH: 5
<212> TYPE: PRT
<213> ORGANISM: Artificial Sequence
<220> FEATURE:
<223> OTHER INFORMATION: Synthetic Construct

<400> SEQUENCE: 336

Gly Gln Asp Tyr Asn
1               5

<210> SEQ ID NO 337
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 337

Gly Ala Asp Leu Ser
1               5

<210> SEQ ID NO 338
<211> LENGTH: 5
<212> TYPE: PRT
<213> ORGANISM: Artificial Sequence
<220> FEATURE:
<223> OTHER INFORMATION: Synthetic Construct

<400> SEQUENCE: 338

Gly Phe Asp Met Asp
1               5

<210> SEQ ID NO 339
<211> LENGTH: 5
<212> TYPE: PRT
<213> ORGANISM: Artificial Sequence
<220> FEATURE:
<223> OTHER INFORMATION: Synthetic Construct

<400> SEQUENCE: 339

Asp Leu Asn Tyr Glu
1               5

<210> SEQ ID NO 340
<211> LENGTH: 30
<212> TYPE: PRT
<213> ORGANISM: Artificial Sequence
<220> FEATURE:
<223> OTHER INFORMATION: Synthetic Construct

<400> SEQUENCE: 340

Gly Cys Asp Val Met Gln Pro Tyr Trp Gly Cys Gly Arg Asp Leu Gln
1               5                   10                  15

Cys Leu Ala Gly Cys Val Cys His Trp Tyr Asn Ser Cys Gly
            20                  25                  30

<210> SEQ ID NO 341
<211> LENGTH: 30
<212> TYPE: PRT
<213> ORGANISM: Artificial Sequence
<220> FEATURE:
<223> OTHER INFORMATION: Synthetic Construct

<400> SEQUENCE: 341

Gly Cys Asp Val Met Gln Pro Tyr Trp Gly Cys Gly Val Asp Leu Ser
1               5                   10                  15

Cys Leu Ala Gly Cys Val Cys His Trp Tyr Asn Ser Cys Gly
            20                  25                  30

<210> SEQ ID NO 342
<211> LENGTH: 30
<212> TYPE: PRT
<213> ORGANISM: Artificial Sequence
<220> FEATURE:
<223> OTHER INFORMATION: Synthetic Construct

<400> SEQUENCE: 342

Gly Cys Asp Val Met Gln Pro Tyr Trp Gly Cys Gly Asp Asp Leu Glu
```

```
                1               5                  10                  15
Cys Leu Ala Gly Cys Val Cys His Trp Tyr Asn Ser Cys Gly
                20                  25                  30
```

<210> SEQ ID NO 343
<211> LENGTH: 30
<212> TYPE: PRT
<213> ORGANISM: Artificial Sequence
<220> FEATURE:
<223> OTHER INFORMATION: Synthetic Construct

<400> SEQUENCE: 343

```
Gly Cys Asp Val Met Gln Pro Tyr Trp Gly Cys Gly Val Asp Met Thr
1               5                   10                  15
Cys Leu Ala Gly Cys Val Cys His Trp Tyr Asn Ser Cys Gly
                20                  25                  30
```

<210> SEQ ID NO 344
<211> LENGTH: 30
<212> TYPE: PRT
<213> ORGANISM: Artificial Sequence
<220> FEATURE:
<223> OTHER INFORMATION: Synthetic Construct

<400> SEQUENCE: 344

```
Gly Cys Asp Val Met Gln Pro Tyr Trp Gly Cys Gly Met Asp Ile Glu
1               5                   10                  15
Cys Leu Ala Gly Cys Val Cys His Trp Tyr Asn Ser Cys Gly
                20                  25                  30
```

<210> SEQ ID NO 345
<211> LENGTH: 30
<212> TYPE: PRT
<213> ORGANISM: Artificial Sequence
<220> FEATURE:
<223> OTHER INFORMATION: Synthetic Construct

<400> SEQUENCE: 345

```
Gly Cys Asp Val Met Gln Pro Tyr Trp Gly Cys Asp Gly Asp Tyr Gln
1               5                   10                  15
Cys Leu Ala Gly Cys Val Cys His Trp Tyr Asn Ser Cys Gly
                20                  25                  30
```

<210> SEQ ID NO 346
<211> LENGTH: 30
<212> TYPE: PRT
<213> ORGANISM: Artificial Sequence
<220> FEATURE:
<223> OTHER INFORMATION: Synthetic Construct

<400> SEQUENCE: 346

```
Gly Cys Asp Val Met Gln Pro Tyr Trp Gly Cys Gly Asn Asp Val Ser
1               5                   10                  15
Cys Leu Ala Gly Cys Val Cys His Trp Tyr Asn Ser Cys Gly
                20                  25                  30
```

<210> SEQ ID NO 347
<211> LENGTH: 30
<212> TYPE: PRT
<213> ORGANISM: Artificial Sequence
<220> FEATURE:
<223> OTHER INFORMATION: Synthetic Construct

<400> SEQUENCE: 347

```
Gly Cys Asp Val Met Gln Pro Tyr Trp Gly Cys Ala Gly Asp Glu Leu
1               5                   10                  15

Cys Leu Ala Gly Cys Val Cys His Trp Tyr Asn Ser Cys Gly
            20                  25                  30
```

<210> SEQ ID NO 348
<211> LENGTH: 30
<212> TYPE: PRT
<213> ORGANISM: Artificial Sequence
<220> FEATURE:
<223> OTHER INFORMATION: Synthetic Construct

<400> SEQUENCE: 348

```
Gly Cys Asp Val Met Gln Pro Tyr Trp Gly Cys Gly Leu Asp Glu Glu
1               5                   10                  15

Cys Leu Ala Gly Cys Val Cys His Trp Tyr Asn Ser Cys Gly
            20                  25                  30
```

<210> SEQ ID NO 349
<211> LENGTH: 30
<212> TYPE: PRT
<213> ORGANISM: Artificial Sequence
<220> FEATURE:
<223> OTHER INFORMATION: Synthetic Construct

<400> SEQUENCE: 349

```
Gly Cys Asp Val Met Gln Pro Tyr Trp Gly Cys Asp Gly Asp Phe Asp
1               5                   10                  15

Cys Leu Ala Gly Cys Val Cys His Trp Tyr Asn Ser Cys Gly
            20                  25                  30
```

<210> SEQ ID NO 350
<211> LENGTH: 30
<212> TYPE: PRT
<213> ORGANISM: Artificial Sequence
<220> FEATURE:
<223> OTHER INFORMATION: Synthetic Construct

<400> SEQUENCE: 350

```
Gly Cys Asp Val Met Gln Pro Tyr Trp Gly Cys Ala Gly Asp Phe Glu
1               5                   10                  15

Cys Leu Ala Gly Cys Val Cys His Trp Tyr Asn Ser Cys Gly
            20                  25                  30
```

<210> SEQ ID NO 351
<211> LENGTH: 30
<212> TYPE: PRT
<213> ORGANISM: Artificial Sequence
<220> FEATURE:
<223> OTHER INFORMATION: Synthetic Construct

<400> SEQUENCE: 351

```
Gly Cys Asp Val Met Gln Pro Tyr Trp Gly Cys Gly Asn Ser Phe Glu
1               5                   10                  15

Cys Leu Ala Gly Cys Val Cys His Trp Tyr Asn Ser Cys Gly
            20                  25                  30
```

<210> SEQ ID NO 352
<211> LENGTH: 30
<212> TYPE: PRT
<213> ORGANISM: Artificial Sequence
<220> FEATURE:
<223> OTHER INFORMATION: Synthetic Construct

<400> SEQUENCE: 352

Gly Cys Asp Val Met Gln Pro Tyr Trp Gly Cys Gly Gln Asp Leu Thr
1               5                   10                  15

Cys Leu Ala Gly Cys Val Cys His Trp Tyr Asn Ser Cys Gly
            20                  25                  30

<210> SEQ ID NO 353
<211> LENGTH: 30
<212> TYPE: PRT
<213> ORGANISM: Artificial Sequence
<220> FEATURE:
<223> OTHER INFORMATION: Synthetic Construct

<400> SEQUENCE: 353

Gly Cys Asp Val Met Gln Pro Tyr Trp Gly Cys Gly Glu Asn Leu Ala
1               5                   10                  15

Cys Leu Ala Gly Cys Val Cys His Trp Tyr Asn Ser Cys Gly
            20                  25                  30

<210> SEQ ID NO 354
<211> LENGTH: 30
<212> TYPE: PRT
<213> ORGANISM: Artificial Sequence
<220> FEATURE:
<223> OTHER INFORMATION: Synthetic Construct

<400> SEQUENCE: 354

Gly Cys Asp Val Met Gln Pro Tyr Trp Gly Cys Gly Gln Asp Tyr Asn
1               5                   10                  15

Cys Leu Ala Gly Cys Val Cys His Trp Tyr Asn Ser Cys Gly
            20                  25                  30

<210> SEQ ID NO 355
<211> LENGTH: 30
<212> TYPE: PRT
<213> ORGANISM: Artificial Sequence
<220> FEATURE:
<223> OTHER INFORMATION: Synthetic Construct

<400> SEQUENCE: 355

Gly Cys Asp Val Met Gln Pro Tyr Trp Gly Cys Gly Ala Asp Leu Ser
1               5                   10                  15

Cys Leu Ala Gly Cys Val Cys His Trp Tyr Asn Ser Cys Gly
            20                  25                  30

<210> SEQ ID NO 356
<211> LENGTH: 30
<212> TYPE: PRT
<213> ORGANISM: Artificial Sequence
<220> FEATURE:
<223> OTHER INFORMATION: Synthetic Construct

<400> SEQUENCE: 356

Gly Cys Asp Val Met Gln Pro Tyr Trp Gly Cys Gly Phe Asp Met Asp
1               5                   10                  15

Cys Leu Ala Gly Cys Val Cys His Trp Tyr Asn Ser Cys Gly
            20                  25                  30

<210> SEQ ID NO 357
<211> LENGTH: 30
<212> TYPE: PRT
<213> ORGANISM: Artificial Sequence
<220> FEATURE:
<223> OTHER INFORMATION: Synthetic Construct

<400> SEQUENCE: 357

Gly Cys Asp Val Met Gln Pro Tyr Trp Gly Cys Asp Leu Asn Tyr Glu
1               5                   10                  15

Cys Leu Ala Gly Cys Val Cys His Trp Tyr Asn Ser Cys Gly
            20                  25                  30

<210> SEQ ID NO 358
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q or H or E or N or D
<220> FEATURE:
<221> NAME/KEY: VARIANT
<222> LOCATION: 2
<223> OTHER INFORMATION: Xaa = L or V or R or P or I
<220> FEATURE:
<221> NAME/KEY: VARIANT
<222> LOCATION: 3
<223> OTHER INFORMATION: Xaa = M or F or L
<220> FEATURE:
<221> NAME/KEY: VARIANT
<222> LOCATION: 4
<223> OTHER INFORMATION: Xaa = Q or E or R or L
<220> FEATURE:
<221> NAME/KEY: VARIANT
<222> LOCATION: 6
<223> OTHER INFORMATION: Xaa = F or A or L or S

<400> SEQUENCE: 358

Xaa Xaa Xaa Xaa Pro Xaa Trp Gly
1               5

<210> SEQ ID NO 359
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = R or H
<220> FEATURE:
<221> NAME/KEY: VARIANT
<222> LOCATION: 4
<223> OTHER INFORMATION: Xaa = N or Q or H

<400> SEQUENCE: 359

Xaa Trp Tyr Xaa Ser
1               5

<210> SEQ ID NO 360
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = H or L or R or Q
<220> FEATURE:
<221> NAME/KEY: VARIANT
<222> LOCATION: 2
<223> OTHER INFORMATION: Xaa = W or F or Y
<220> FEATURE:
<221> NAME/KEY: VARIANT

```
<222> LOCATION: 4
<223> OTHER INFORMATION: Xaa = Q or N or K or H or D or E

<400> SEQUENCE: 360

Xaa Xaa Tyr Xaa Ser
1               5

<210> SEQ ID NO 361
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine

<400> SEQUENCE: 361

Xaa Cys Asn Ile Met Leu Pro Tyr Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 362
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = sulfotyrosine, 3,4-difluoro-L-
      phenylalanine, 3,4-dichloro-L-phenylalanine, 4-chloro-L-
      phenylalanine, 3-F,4-Cl-L-phenylalanine, 2-pyridone(NH para)-L-
      alanine, or pyridone(NH meta)-L-alanine

<400> SEQUENCE: 362

Gly Cys Asn Ile Met Leu Pro Xaa Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 363
<211> LENGTH: 30
<212> TYPE: PRT
<213> ORGANISM: Artificial Sequence
<220> FEATURE:
<223> OTHER INFORMATION: Synthetic Construct

<400> SEQUENCE: 363

Gly Cys Asn Ile Met Leu Pro Tyr Trp Gly Cys Gly Arg Asp Phe Glu
1               5                   10                  15

Cys Met Ser Asp Cys Ile Cys Gln Tyr Tyr Gln Ser Cys Gly
            20                  25                  30

<210> SEQ ID NO 364
<211> LENGTH: 30
<212> TYPE: PRT
<213> ORGANISM: Artificial Sequence
<220> FEATURE:
<223> OTHER INFORMATION: Synthetic Construct

<400> SEQUENCE: 364

Gly Cys Asn Ile Met Leu Pro Tyr Trp Gly Cys Gly Arg Asp Phe Glu
1               5                   10                  15
```

Cys Met Ser Asp Cys Ile Cys Gln Tyr Tyr Gln Ser Cys Gly
            20                  25                  30

<210> SEQ ID NO 365
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 365

Gly Cys Asn Ile Xaa Leu Pro Tyr Trp Gly Cys Gly Arg Asp Phe Glu
1               5                   10                  15

Cys Met Ser Asp Cys Ile Cys Gln Tyr Tyr Gln Ser Cys Gly
            20                  25                  30

<210> SEQ ID NO 366
<211> LENGTH: 32
<212> TYPE: PRT
<213> ORGANISM: Artificial Sequence
<220> FEATURE:
<223> OTHER INFORMATION: Synthetic Construct

<400> SEQUENCE: 366

Gly Cys Gln Ala Ile Asn Arg Val Lys Arg Gln Arg Cys Lys Gln Asp
1               5                   10                  15

Ser Asp Cys Leu Ala Gly Cys Val Cys Gly Pro Asn Gly Phe Cys Gly
            20                  25                  30

<210> SEQ ID NO 367
<211> LENGTH: 10
<212> TYPE: PRT
<213> ORGANISM: Artificial Sequence
<220> FEATURE:
<223> OTHER INFORMATION: Synthetic Construct

<400> SEQUENCE: 367

Gln Ala Ile Asn Arg Val Lys Arg Gln Arg
1               5                   10

<210> SEQ ID NO 368
<211> LENGTH: 8
<212> TYPE: PRT
<213> ORGANISM: Artificial Sequence
<220> FEATURE:
<223> OTHER INFORMATION: Synthetic Construct

<400> SEQUENCE: 368

Asn Pro Met Leu Pro Phe Trp Gly
1               5

<210> SEQ ID NO 369
<211> LENGTH: 33
<212> TYPE: PRT
<213> ORGANISM: Artificial Sequence
<220> FEATURE:
<223> OTHER INFORMATION: Synthetic Construct

<400> SEQUENCE: 369

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Pro Leu
            20                  25                  30

Ile

<210> SEQ ID NO 370
<211> LENGTH: 33
<212> TYPE: PRT
<213> ORGANISM: Artificial Sequence
<220> FEATURE:
<223> OTHER INFORMATION: Synthetic Construct

<400> SEQUENCE: 370

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Asn Tyr
            20                  25                  30

Gln

<210> SEQ ID NO 371
<211> LENGTH: 33
<212> TYPE: PRT
<213> ORGANISM: Artificial Sequence
<220> FEATURE:
<223> OTHER INFORMATION: Synthetic Construct

<400> SEQUENCE: 371

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Pro Leu
            20                  25                  30

Gln

<210> SEQ ID NO 372
<211> LENGTH: 33
<212> TYPE: PRT
<213> ORGANISM: Artificial Sequence
<220> FEATURE:
<223> OTHER INFORMATION: Synthetic Construct

<400> SEQUENCE: 372

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Thr Phe
            20                  25                  30

Gln

<210> SEQ ID NO 373
<211> LENGTH: 33
<212> TYPE: PRT
<213> ORGANISM: Artificial Sequence
<220> FEATURE:
<223> OTHER INFORMATION: Synthetic Construct

<400> SEQUENCE: 373

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Asp Leu
            20                  25                  30

Val

<210> SEQ ID NO 374

<211> LENGTH: 33
<212> TYPE: PRT
<213> ORGANISM: Artificial Sequence
<220> FEATURE:
<223> OTHER INFORMATION: Synthetic Construct

<400> SEQUENCE: 374

Gly Cys Asn Ile Met Leu Pro Phe Trp Gly Cys Gly Arg Asp Phe Glu
1               5                   10                  15
Cys Leu Ala Gly Cys Val Cys Gln Tyr Tyr Gln Ser Cys Gly Glu His
            20                  25                  30
Lys

<210> SEQ ID NO 375
<211> LENGTH: 33
<212> TYPE: PRT
<213> ORGANISM: Artificial Sequence
<220> FEATURE:
<223> OTHER INFORMATION: Synthetic Construct

<400> SEQUENCE: 375

Gly Cys Asn Ile Met Leu Pro Phe Trp Gly Cys Gly Arg Asp Phe Glu
1               5                   10                  15
Cys Leu Ala Gly Cys Val Cys Gln Tyr Tyr Gln Ser Cys Gly Tyr Leu
            20                  25                  30
Ser

<210> SEQ ID NO 376
<211> LENGTH: 33
<212> TYPE: PRT
<213> ORGANISM: Artificial Sequence
<220> FEATURE:
<223> OTHER INFORMATION: Synthetic Construct

<400> SEQUENCE: 376

Gly Cys Asn Ile Met Leu Pro Phe Trp Gly Cys Gly Arg Asp Phe Glu
1               5                   10                  15
Cys Leu Ala Gly Cys Val Cys Gln Tyr Tyr Gln Ser Cys Gly Trp Asp
            20                  25                  30
Tyr

<210> SEQ ID NO 377
<211> LENGTH: 33
<212> TYPE: PRT
<213> ORGANISM: Artificial Sequence
<220> FEATURE:
<223> OTHER INFORMATION: Synthetic Construct

<400> SEQUENCE: 377

Gly Cys Asn Ile Met Leu Pro Phe Trp Gly Cys Gly Arg Asp Phe Glu
1               5                   10                  15
Cys Leu Ala Gly Cys Val Cys Gln Tyr Tyr Gln Ser Cys Gly Trp Pro
            20                  25                  30
His

<210> SEQ ID NO 378
<211> LENGTH: 33
<212> TYPE: PRT
<213> ORGANISM: Artificial Sequence
<220> FEATURE:
<223> OTHER INFORMATION: Synthetic Construct

<400> SEQUENCE: 378

-continued

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Pro His
            20                  25                  30

Gln

<210> SEQ ID NO 379
<211> LENGTH: 32
<212> TYPE: PRT
<213> ORGANISM: Artificial Sequence
<220> FEATURE:
<223> OTHER INFORMATION: Synthetic Construct

<400> SEQUENCE: 379

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Phe His
            20                  25                  30

<210> SEQ ID NO 380
<211> LENGTH: 32
<212> TYPE: PRT
<213> ORGANISM: Artificial Sequence
<220> FEATURE:
<223> OTHER INFORMATION: Synthetic Construct

<400> SEQUENCE: 380

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Ile Ala
            20                  25                  30

<210> SEQ ID NO 381
<211> LENGTH: 32
<212> TYPE: PRT
<213> ORGANISM: Artificial Sequence
<220> FEATURE:
<223> OTHER INFORMATION: Synthetic Construct

<400> SEQUENCE: 381

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Gly Ser
            20                  25                  30

<210> SEQ ID NO 382
<211> LENGTH: 32
<212> TYPE: PRT
<213> ORGANISM: Artificial Sequence
<220> FEATURE:
<223> OTHER INFORMATION: Synthetic Construct

<400> SEQUENCE: 382

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Thr Arg
            20                  25                  30

<210> SEQ ID NO 383
<211> LENGTH: 32
<212> TYPE: PRT
<213> ORGANISM: Artificial Sequence
<220> FEATURE:

<223> OTHER INFORMATION: Synthetic Construct

<400> SEQUENCE: 383

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Val His
            20                  25                  30

<210> SEQ ID NO 384
<211> LENGTH: 32
<212> TYPE: PRT
<213> ORGANISM: Artificial Sequence
<220> FEATURE:
<223> OTHER INFORMATION: Synthetic Construct

<400> SEQUENCE: 384

Gly Cys Asn Ile Met Leu Pro Phe Trp Gly Cys Gly Arg Asp Phe Glu
1               5                   10                  15

Cys Leu Ala Gly Cys Val Cys Gln Tyr Tyr Gln Ser Cys Gly Leu Ser
            20                  25                  30

<210> SEQ ID NO 385
<211> LENGTH: 8
<212> TYPE: PRT
<213> ORGANISM: Artificial Sequence
<220> FEATURE:
<223> OTHER INFORMATION: Synthetic Construct

<400> SEQUENCE: 385

Asp Val Leu Gln Pro Tyr Trp Gly
1               5

<210> SEQ ID NO 386
<211> LENGTH: 30
<212> TYPE: PRT
<213> ORGANISM: Artificial Sequence
<220> FEATURE:
<223> OTHER INFORMATION: Synthetic Construct

<400> SEQUENCE: 386

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly
            20                  25                  30

<210> SEQ ID NO 387
<211> LENGTH: 32
<212> TYPE: PRT
<213> ORGANISM: Artificial Sequence
<220> FEATURE:
<223> OTHER INFORMATION: Synthetic Construct

<400> SEQUENCE: 387

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Arg Thr
            20                  25                  30

<210> SEQ ID NO 388
<211> LENGTH: 32
<212> TYPE: PRT
<213> ORGANISM: Artificial Sequence
<220> FEATURE:
<223> OTHER INFORMATION: Synthetic Construct

<400> SEQUENCE: 388

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Trp Lys
            20                  25                  30

<210> SEQ ID NO 389
<211> LENGTH: 32
<212> TYPE: PRT
<213> ORGANISM: Artificial Sequence
<220> FEATURE:
<223> OTHER INFORMATION: Synthetic Construct

<400> SEQUENCE: 389

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Pro Leu
            20                  25                  30

<210> SEQ ID NO 390
<211> LENGTH: 32
<212> TYPE: PRT
<213> ORGANISM: Artificial Sequence
<220> FEATURE:
<223> OTHER INFORMATION: Synthetic Construct

<400> SEQUENCE: 390

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Asp Glu
            20                  25                  30

<210> SEQ ID NO 391
<211> LENGTH: 32
<212> TYPE: PRT
<213> ORGANISM: Artificial Sequence
<220> FEATURE:
<223> OTHER INFORMATION: Synthetic Construct

<400> SEQUENCE: 391

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Gln Phe
            20                  25                  30

<210> SEQ ID NO 392
<211> LENGTH: 32
<212> TYPE: PRT
<213> ORGANISM: Artificial Sequence
<220> FEATURE:
<223> OTHER INFORMATION: Synthetic Construct

<400> SEQUENCE: 392

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Glu Gln
            20                  25                  30

<210> SEQ ID NO 393
<211> LENGTH: 32
<212> TYPE: PRT
<213> ORGANISM: Artificial Sequence
<220> FEATURE:
<223> OTHER INFORMATION: Synthetic Construct

<400> SEQUENCE: 393

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Pro Thr
            20                  25                  30

<210> SEQ ID NO 394
<211> LENGTH: 32
<212> TYPE: PRT
<213> ORGANISM: Artificial Sequence
<220> FEATURE:
<223> OTHER INFORMATION: Synthetic Construct

<400> SEQUENCE: 394

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Arg Leu
            20                  25                  30

<210> SEQ ID NO 395
<211> LENGTH: 32
<212> TYPE: PRT
<213> ORGANISM: Artificial Sequence
<220> FEATURE:
<223> OTHER INFORMATION: Synthetic Construct

<400> SEQUENCE: 395

Gly Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Gly Ser Leu
            20                  25                  30

<210> SEQ ID NO 396
<211> LENGTH: 8
<212> TYPE: PRT
<213> ORGANISM: Artificial Sequence
<220> FEATURE:
<223> OTHER INFORMATION: Synthetic Construct

<400> SEQUENCE: 396

Asn Ile Leu Leu Pro Phe Trp Gly
1               5

<210> SEQ ID NO 397
<211> LENGTH: 8
<212> TYPE: PRT
<213> ORGANISM: Artificial Sequence
<220> FEATURE:
<223> OTHER INFORMATION: Synthetic Construct

<400> SEQUENCE: 397

Asn Ile Leu Leu Pro Tyr Trp Gly
1               5

<210> SEQ ID NO 398
<211> LENGTH: 8
<212> TYPE: PRT
<213> ORGANISM: Artificial Sequence
<220> FEATURE:
<223> OTHER INFORMATION: Synthetic Construct

<400> SEQUENCE: 398

Asn Ile Met Ser Pro Phe Trp Gly
1               5

<210> SEQ ID NO 399
<211> LENGTH: 8
<212> TYPE: PRT
<213> ORGANISM: Artificial Sequence
<220> FEATURE:
<223> OTHER INFORMATION: Synthetic Construct

<400> SEQUENCE: 399

Asn Ile Met Thr Pro Phe Trp Gly
1               5

<210> SEQ ID NO 400
<211> LENGTH: 8
<212> TYPE: PRT
<213> ORGANISM: Artificial Sequence
<220> FEATURE:
<223> OTHER INFORMATION: Synthetic Construct

<400> SEQUENCE: 400

Asn Ile Met Gln Pro Phe Trp Gly
1               5

<210> SEQ ID NO 401
<211> LENGTH: 8
<212> TYPE: PRT
<213> ORGANISM: Artificial Sequence
<220> FEATURE:
<223> OTHER INFORMATION: Synthetic Construct

<400> SEQUENCE: 401

Asn Ile Met Asn Pro Phe Trp Gly
1               5

<210> SEQ ID NO 402
<211> LENGTH: 8
<212> TYPE: PRT
<213> ORGANISM: Artificial Sequence
<220> FEATURE:
<223> OTHER INFORMATION: Synthetic Construct

<400> SEQUENCE: 402

Asn Ile Met Glu Pro Phe Trp Gly
1               5

<210> SEQ ID NO 403
<211> LENGTH: 8
<212> TYPE: PRT
<213> ORGANISM: Artificial Sequence
<220> FEATURE:
<223> OTHER INFORMATION: Synthetic Construct

<400> SEQUENCE: 403

Asn Ile Met Asp Pro Phe Trp Gly
1               5

<210> SEQ ID NO 404
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = benzyl-L-proline, 4-fluoro-benzyl-L-
      proline, 3-OH-L-proline, 3-fluoro-L-proline, or
      trifluoromethyl-benzyl-L-proline

```
<400> SEQUENCE: 404

Asn Ile Met Leu Xaa Phe Trp Gly
1               5

<210> SEQ ID NO 405
<211> LENGTH: 30
<212> TYPE: PRT
<213> ORGANISM: Artificial Sequence
<220> FEATURE:
<223> OTHER INFORMATION: Synthetic Construct

<400> SEQUENCE: 405

Gly Cys Asn Ile Leu Leu Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 406
<211> LENGTH: 30
<212> TYPE: PRT
<213> ORGANISM: Artificial Sequence
<220> FEATURE:
<223> OTHER INFORMATION: Synthetic Construct

<400> SEQUENCE: 406

Gly Cys Asn Ile Leu Leu Pro Tyr Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 407
<211> LENGTH: 30
<212> TYPE: PRT
<213> ORGANISM: Artificial Sequence
<220> FEATURE:
<223> OTHER INFORMATION: Synthetic Construct

<400> SEQUENCE: 407

Gly Cys Asn Ile Met Ser Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 408
<211> LENGTH: 30
<212> TYPE: PRT
<213> ORGANISM: Artificial Sequence
<220> FEATURE:
<223> OTHER INFORMATION: Synthetic Construct

<400> SEQUENCE: 408

Gly Cys Asn Ile Met Thr Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 409
<211> LENGTH: 30
<212> TYPE: PRT
<213> ORGANISM: Artificial Sequence
<220> FEATURE:
<223> OTHER INFORMATION: Synthetic Construct

<400> SEQUENCE: 409
```

-continued

Gly Cys Asn Ile Met Gln Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 410
<211> LENGTH: 30
<212> TYPE: PRT
<213> ORGANISM: Artificial Sequence
<220> FEATURE:
<223> OTHER INFORMATION: Synthetic Construct

<400> SEQUENCE: 410

Gly Cys Asn Ile Met Asn Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 411
<211> LENGTH: 30
<212> TYPE: PRT
<213> ORGANISM: Artificial Sequence
<220> FEATURE:
<223> OTHER INFORMATION: Synthetic Construct

<400> SEQUENCE: 411

Gly Cys Asn Ile Met Glu Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 412
<211> LENGTH: 30
<212> TYPE: PRT
<213> ORGANISM: Artificial Sequence
<220> FEATURE:
<223> OTHER INFORMATION: Synthetic Construct

<400> SEQUENCE: 412

Gly Cys Asn Ile Met Asp Pro Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 413
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = benzyl-L-proline, 4-fluoro-benzyl-L-
      proline, 3-OH-L-proline, 3-fluoro-L-proline, or trifluoromethyl-
      benzyl-L-proline

<400> SEQUENCE: 413

Gly Cys Asn Ile Met Leu Xaa Phe Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 414

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 414

Asn Ile Met Leu Pro Ser Trp Gly
1               5

<210> SEQ ID NO 415
<211> LENGTH: 30
<212> TYPE: PRT
<213> ORGANISM: Artificial Sequence
<220> FEATURE:
<223> OTHER INFORMATION: Synthetic Construct

<400> SEQUENCE: 415

Gly Cys Asn Ile Met Leu Pro Ser Trp Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 416
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = N-methyl indole, N-ethyl indole,
      N-isopropyl indole, or 5-aza-indole

<400> SEQUENCE: 416

Asn Ile Met Leu Pro Tyr Xaa Gly
1               5

<210> SEQ ID NO 417
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = N-methyl indole, N-ethyl indole, N-
      isopropyl indole, or 5-aza-indole

<400> SEQUENCE: 417

Gly Cys Asn Ile Met Leu Pro Tyr Xaa Gly Cys Gly Arg Asp Phe Glu
1               5                   10                  15

Cys Leu Ala Gly Cys Val Cys Gln Tyr Tyr Gln Ser Cys Gly
            20                  25                  30

<210> SEQ ID NO 418
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = 4-methyl-L-phenylalanine, 2-naphthyl-L-
      alanine, 2-quinolyl-Alanine, or 4-biphenyl-L-alanine
<220> FEATURE:
```

```
<221> NAME/KEY: VARIANT
<222> LOCATION: 4
<223> OTHER INFORMATION: Xaa = 3-(3-quinolinyl)-L-alanine, 3-(2-
      quinolinyl)-L-alanine, 3-(2-quinoxalinyl)-L-alanine, or 4-methyl-
      2-pyridyl-alanine
<220> FEATURE:
<221> NAME/KEY: VARIANT
<222> LOCATION: 4
<223> OTHER INFORMATION: Xaa = 4-ethyl-2-pyridyl-L-alanine,
      benzothiazole-L-alanine, or benzothiophene-L-alanine, or 3-
      isoquinolinyl-L-alanine

<400> SEQUENCE: 418

Gly Arg Asp Xaa Glu
1               5

<210> SEQ ID NO 419
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa = 4-methyl-L-phenylalanine, 2-naphthyl-L-
      alanine, 2-quinolyl-Alanine, or 4-biphenyl-L-alanine
<220> FEATURE:
<221> NAME/KEY: VARIANT
<222> LOCATION: 15
<223> OTHER INFORMATION: Xaa = 3-(3-quinolinyl)-L-alanine, 3-(2-
      quinolinyl)-L-alanine, 3-(2-quinoxalinyl)-L-alanine, or 4-methyl-
      2-pyridyl-alanine
<220> FEATURE:
<221> NAME/KEY: VARIANT
<222> LOCATION: 15
<223> OTHER INFORMATION: Xaa = 4-ethyl-2-pyridyl-L-alanine,
      benzothiazole-L-alanine, benzothiophene-L-alanine, or 3-
      isoquinolinyl-L-alanine

<400> SEQUENCE: 419

Gly Cys Asn Ile Met Leu Pro Tyr Trp Gly Cys Gly Arg Asp Xaa
1               5                   10                  15

Cys Leu Ala Gly Cys Val Cys Gln Tyr Tyr Gln Ser Cys Gly
            20                  25                  30

<210> SEQ ID NO 420
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 18
<223> OTHER INFORMATION: Xaa = t-butyl-L-alanine, cyclobutyl-L-alanine,
      cyclopentyl-L-alanine, or 5,5,5-Trifluoro-L-leucine

<400> SEQUENCE: 420

Gly Cys Asn Ile Met Leu Pro Tyr Trp Gly Cys Gly Arg Asp Phe Glu
1               5                   10                  15

Cys Xaa Ala Gly Cys Val Cys Gln Tyr Tyr Gln Ser Cys Gly
            20                  25                  30

<210> SEQ ID NO 421
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 421

Gly Cys Asn Ile Met Leu Pro Phe Trp Gly Cys Gly Arg Asp Phe Glu
1               5                   10                  15

Cys Leu Ser Gly Cys Val Cys Gln Tyr Tyr Gln Ser Cys Gly
            20                  25                  30

<210> SEQ ID NO 422
<211> LENGTH: 30
<212> TYPE: PRT
<213> ORGANISM: Artificial Sequence
<220> FEATURE:
<223> OTHER INFORMATION: Synthetic Construct

<400> SEQUENCE: 422

Gly Cys Asn Ile Met Leu Pro Phe Trp Gly Cys Gly Arg Asp Phe Glu
1               5                   10                  15

Cys Leu Thr Gly Cys Val Cys Gln Tyr Tyr Gln Ser Cys Gly
            20                  25                  30

<210> SEQ ID NO 423
<211> LENGTH: 30
<212> TYPE: PRT
<213> ORGANISM: Artificial Sequence
<220> FEATURE:
<223> OTHER INFORMATION: Synthetic Construct

<400> SEQUENCE: 423

Gly Cys Asn Ile Met Leu Pro Phe Trp Gly Cys Gly Arg Asp Phe Glu
1               5                   10                  15

Cys Leu Glu Gly Cys Val Cys Gln Tyr Tyr Gln Ser Cys Gly
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: Synthetic Construct

<400> SEQUENCE: 424

Gly Cys Asn Ile Met Leu Pro Tyr Trp Gly Cys Gly Arg Asp Phe Glu
1               5                   10                  15

Cys Leu Ala Gly Cys Leu Cys Gln Tyr Tyr Gln Ser Cys Gly
            20                  25                  30

<210> SEQ ID NO 425
<211> LENGTH: 30
<212> TYPE: PRT
<213> ORGANISM: Artificial Sequence
<220> FEATURE:
<223> OTHER INFORMATION: Synthetic Construct

<400> SEQUENCE: 425

Gly Cys Asn Ile Met Leu Pro Tyr Trp Gly Cys Gly Arg Asp Phe Glu
1               5                   10                  15

Cys Leu Ala Gly Cys Ile Cys Gln Tyr Tyr Gln Ser Cys Gly
            20                  25                  30

<210> SEQ ID NO 426
<211> LENGTH: 30
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 22
<223> OTHER INFORMATION: Xaa = t-butyl-L-glycine (also known as L-
      tert-Leucine), t-butyl-L-alanine, L-cyclopentylglycine, or
      cyclopentyl-L-alanine
<220> FEATURE:
<221> NAME/KEY: VARIANT
<222> LOCATION: 22
<223> OTHER INFORMATION: Xaa = L-cyclobutyl-L-glycine, cyclobutyl-
      L-alanine, or 5,5,5-Trifluoro-L-leucine

<400> SEQUENCE: 426

Gly Cys Asn Ile Met Leu Pro Tyr Trp Gly Cys Gly Arg Asp Phe Glu
1               5                   10                  15

Cys Leu Ala Gly Cys Xaa Cys Gln Tyr Tyr Gln Ser Cys Gly
            20                  25                  30

<210> SEQ ID NO 427
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = 2-pyridone, 3,4-hydroxy phenylalanine,
      3,4-fluoro phenylalanine, or 3-Fluoro,4-OH phenylalanine

<400> SEQUENCE: 427

Gln Xaa Tyr Gln Ser
1               5

<210> SEQ ID NO 428
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 25
<223> OTHER INFORMATION: Xaa = 2-pyridone, 3,4-hydroxy phenylalanine,
      3,4-fluoro phenylalanine, or 3-Fluoro,4-OH phenylalanine

<400> SEQUENCE: 428

Gly Cys Asn Ile Met Leu Pro Tyr Trp Gly Cys Gly Arg Asp Phe Glu
1               5                   10                  15

Cys Leu Ala Gly Cys Val Cys Gln Xaa Tyr Gln Ser Cys Gly
            20                  25                  30

<210> SEQ ID NO 429
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = 2-Chloro Tyrosine, 2-Methyl Tyrosine,
      2-Ethyl Tyrosine, or 1-naphthol alanine

<400> SEQUENCE: 429

Gln Tyr Xaa Gln Ser
1               5

<210> SEQ ID NO 430
```

```
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 26
<223> OTHER INFORMATION: Xaa = 2-Chloro Tyrosine, 2-Methyl Tyrosine,
      2-Ethyl Tyrosine, or 1-naphthol alanine

<400> SEQUENCE: 430

Gly Cys Asn Ile Met Leu Pro Tyr Trp Gly Cys Gly Arg Asp Phe Glu
1               5                   10                  15

Cys Leu Ala Gly Cys Val Cys Gln Tyr Xaa Gln Ser Cys Gly
            20                  25                  30

<210> SEQ ID NO 431
<211> LENGTH: 30
<212> TYPE: PRT
<213> ORGANISM: Artificial Sequence
<220> FEATURE:
<223> OTHER INFORMATION: Synthetic Construct

<400> SEQUENCE: 431

Gly Cys Asn Ile Met Leu Pro Tyr Trp Gly Cys Gly Arg Asp Phe Glu
1               5                   10                  15

Cys Leu Ala Gly Cys Val Cys Gln Tyr Tyr Gln Ser Cys Ser
            20                  25                  30

<210> SEQ ID NO 432
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 30
<223> OTHER INFORMATION: Xaa = D-serine, L-beta-homoserine, L-beta-
      alanine, N-alpha-methyl Glycine, glycine amide, or glycine ester
      of glycerol
<220> FEATURE:
<221> NAME/KEY: VARIANT
<222> LOCATION: 30
<223> OTHER INFORMATION: Xaa = glycine ester of  glycol, glycine ester
      of oxetane-3-yl alcohol, or glycine morpholine amide

<400> SEQUENCE: 432

Gly Cys Asn Ile Met Leu Pro Tyr Trp Gly Cys Gly Arg Asp Phe Glu
1               5                   10                  15

Cys Leu Ala Gly Cys Val Cys Gln Tyr Tyr Gln Ser Cys Xaa
            20                  25                  30

<210> SEQ ID NO 433
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = norleucine

<400> SEQUENCE: 433

Asn Ile Xaa Gln Pro Tyr Trp Gly
1               5
```

```
<210> SEQ ID NO 434
<211> LENGTH: 8
<212> TYPE: PRT
<213> ORGANISM: Artificial Sequence
<220> FEATURE:
<223> OTHER INFORMATION: Synthetic Construct

<400> SEQUENCE: 434

Asn Ile Leu Gln Pro Tyr Trp Gly
1               5

<210> SEQ ID NO 435
<211> LENGTH: 30
<212> TYPE: PRT
<213> ORGANISM: Artificial Sequence
<220> FEATURE:
<223> OTHER INFORMATION: Synthetic Construct

<400> SEQUENCE: 435

Gly Cys Asn Ile Leu Leu Pro Tyr Trp Gly Cys Gly Arg Asp Phe Glu
1               5                   10                  15

Cys Met Glu Gln Cys Ile Cys Gln Tyr Tyr Gln Ser Cys Gly
            20                  25                  30

<210> SEQ ID NO 436
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 436

Gly Cys Asn Ile Xaa Gln Pro Tyr Trp Gly Cys Gly Arg Asp Phe Glu
1               5                   10                  15

Cys Met Glu Gln Cys Ile Cys Gln Tyr Tyr Gln Ser Cys Gly
            20                  25                  30

<210> SEQ ID NO 437
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 18
<223> OTHER INFORMATION: Xaa = norleucine or cyclobutyl-L-alanine

<400> SEQUENCE: 437

Gly Cys Asn Ile Xaa Leu Pro Tyr Trp Gly Cys Gly Arg Asp Phe Glu
1               5                   10                  15

Cys Xaa Glu Gln Cys Ile Cys Gln Tyr Tyr Gln Ser Cys Gly
            20                  25                  30

<210> SEQ ID NO 438
<211> LENGTH: 30
<212> TYPE: PRT
<213> ORGANISM: Artificial Sequence
<220> FEATURE:
```

<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 438

Gly Cys Asn Ile Xaa Leu Pro Tyr Trp Gly Cys Gly Arg Asp Phe Glu
1               5                   10                  15

Cys Leu Glu Gln Cys Ile Cys Gln Tyr Tyr Gln Ser Cys Gly
            20                  25                  30

<210> SEQ ID NO 439
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 18
<223> OTHER INFORMATION: Xaa = cyclobutyl-L-alanine
<220> FEATURE:
<221> NAME/KEY: VARIANT
<222> LOCATION: 22
<223> OTHER INFORMATION: Xaa = cyclobutyl-L-glycine, cyclobutyl-L-
      alanine or norleucine

<400> SEQUENCE: 439

Gly Cys Asn Ile Xaa Leu Pro Tyr Trp Gly Cys Gly Arg Asp Phe Glu
1               5                   10                  15

Cys Xaa Glu Gln Cys Xaa Cys Gln Tyr Tyr Gln Ser Cys Gly
            20                  25                  30

<210> SEQ ID NO 440
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 18
<223> OTHER INFORMATION: Xaa = cyclobutyl-L-alanine
<220> FEATURE:
<221> NAME/KEY: VARIANT
<222> LOCATION: 22
<223> OTHER INFORMATION: Xaa = cyclobutyl-L-glycine or cyclobutyl-L-
      alanine

<400> SEQUENCE: 440

Gly Cys Asn Ile Xaa Gln Pro Tyr Trp Gly Cys Gly Arg Asp Phe Glu
1               5                   10                  15

Cys Xaa Glu Gln Cys Xaa Cys Gln Tyr Tyr Gln Ser Cys Gly
            20                  25                  30

<210> SEQ ID NO 441
<211> LENGTH: 30
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 18
<223> OTHER INFORMATION: Xaa = cyclobutyl-L-alanine or t-butyl-L-alanine

<400> SEQUENCE: 441

Gly Cys Asn Ile Leu Leu Pro Tyr Trp Gly Cys Gly Arg Asp Phe Glu
1               5                   10                  15
Cys Xaa Glu Gln Cys Ile Cys Gln Tyr Tyr Gln Ser Cys Gly
            20                  25                  30

<210> SEQ ID NO 442
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 22
<223> OTHER INFORMATION: Xaa = cyclobutyl-L-glycine or cyclobutyl-L-
      alanine

<400> SEQUENCE: 442

Gly Cys Asn Ile Leu Leu Pro Tyr Trp Gly Cys Gly Arg Asp Phe Glu
1               5                   10                  15
Cys Met Glu Gln Cys Xaa Cys Gln Tyr Tyr Gln Ser Cys Gly
            20                  25                  30

<210> SEQ ID NO 443
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 30
<223> OTHER INFORMATION: Xaa = glycine amide

<400> SEQUENCE: 443

Xaa Cys Asn Ile Xaa Leu Pro Tyr Trp Gly Cys Gly Arg Asp Phe Glu
1               5                   10                  15
Cys Met Glu Gln Cys Ile Cys Gln Tyr Tyr Gln Ser Cys Xaa
            20                  25                  30

<210> SEQ ID NO 444
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 30
<223> OTHER INFORMATION: Xaa = glycine amide

<400> SEQUENCE: 444
```

```
Xaa Cys Asn Ile Leu Leu Pro Tyr Trp Gly Cys Gly Arg Asp Phe Glu
1               5                   10                  15

Cys Met Glu Gln Cys Ile Cys Gln Tyr Tyr Gln Ser Cys Xaa
            20                  25                  30

<210> SEQ ID NO 445
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 30
<223> OTHER INFORMATION: Xaa = glycine amide

<400> SEQUENCE: 445

Xaa Cys Asn Ile Leu Gln Pro Tyr Trp Gly Cys Gly Arg Asp Phe Glu
1               5                   10                  15

Cys Met Glu Gln Cys Ile Cys Gln Tyr Tyr Gln Ser Cys Xaa
            20                  25                  30

<210> SEQ ID NO 446
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 30
<223> OTHER INFORMATION: Xaa = glycine amide

<400> SEQUENCE: 446

Xaa Cys Asn Ile Leu Gln Pro Tyr Trp Gly Cys Gly Arg Asp Phe Glu
1               5                   10                  15

Cys Leu Glu Gln Cys Ile Cys Gln Tyr Tyr Gln Ser Cys Xaa
            20                  25                  30

<210> SEQ ID NO 447
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 18
<223> OTHER INFORMATION: Xaa = cyclobutyl-L-alanine or t-butyl-L-alanine

<400> SEQUENCE: 447

Gly Cys Asp Val Leu Gln Pro Tyr Trp Gly Cys Gly Pro Asp Ile Asp
1               5                   10                  15

Cys Xaa Ser Asn Cys Ile Cys His Trp Tyr Asn Ser Cys Gly
            20                  25                  30

<210> SEQ ID NO 448
<211> LENGTH: 30
<212> TYPE: PRT
```

<213> ORGANISM: Artificial Sequence
<220> FEATURE:
<223> OTHER INFORMATION: Synthetic Construct
<220> FEATURE:
<221> NAME/KEY: VARIANT
<222> LOCATION: 22
<223> OTHER INFORMATION: Xaa = cyclobutyl-L-glycine

<400> SEQUENCE: 448

Gly Cys Asp Val Leu Gln Pro Tyr Trp Gly Cys Gly Pro Asp Ile Asp
1               5                   10                  15

Cys Leu Ser Asn Cys Xaa Cys His Trp Tyr Asn Ser Cys Gly
            20                  25                  30

<210> SEQ ID NO 449
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 18
<223> OTHER INFORMATION: Xaa = cyclobutyl-L-alanine
<220> FEATURE:
<221> NAME/KEY: VARIANT
<222> LOCATION: 22
<223> OTHER INFORMATION: Xaa = cyclobutyl-L-glycine or cyclobutyl-L-
      alanine

<400> SEQUENCE: 449

Gly Cys Asp Val Xaa Gln Pro Tyr Trp Gly Cys Gly Pro Asp Ile Asp
1               5                   10                  15

Cys Xaa Ser Asn Cys Xaa Cys His Trp Tyr Asn Ser Cys Gly
            20                  25                  30

<210> SEQ ID NO 450
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 18
<223> OTHER INFORMATION: Xaa = cyclobutyl-L-alanine
<220> FEATURE:
<221> NAME/KEY: VARIANT
<222> LOCATION: 22
<223> OTHER INFORMATION: Xaa = cyclobutyl-L-glycine or cyclobutyl-L-
      alanine

<400> SEQUENCE: 450

Gly Cys Asp Val Leu Gln Pro Tyr Trp Gly Cys Gly Pro Asp Ile Asp
1               5                   10                  15

Cys Xaa Ser Asn Cys Xaa Cys His Trp Tyr Asn Ser Cys Gly
            20                  25                  30

<210> SEQ ID NO 451
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 1
<223> OTHER INFORMATION: Xaa = acetylglycine
<220> FEATURE:
<221> NAME/KEY: VARIANT
<222> LOCATION: 18
<223> OTHER INFORMATION: Xaa = cyclobutyl-L-alanine
<220> FEATURE:
<221> NAME/KEY: VARIANT
<222> LOCATION: 22
<223> OTHER INFORMATION: Xaa = cyclobutyl-L-glycine or cyclobutyl-L-
      alanine
<220> FEATURE:
<221> NAME/KEY: VARIANT
<222> LOCATION: 30
<223> OTHER INFORMATION: Xaa = glycine amide

<400> SEQUENCE: 451

Xaa Cys Asp Val Leu Gln Pro Tyr Trp Gly Cys Gly Pro Asp Ile Asp
1               5                   10                  15

Cys Xaa Ser Asn Cys Xaa Cys His Trp Tyr Asn Ser Cys Xaa
            20                  25                  30

<210> SEQ ID NO 452
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 30
<223> OTHER INFORMATION: Xaa = glycine amide

<400> SEQUENCE: 452

Xaa Cys Asp Val Xaa Gln Pro Tyr Trp Gly Cys Gly Pro Asp Ile Asp
1               5                   10                  15

Cys Leu Ser Asn Cys Ile Cys His Trp Tyr Asn Ser Cys Xaa
            20                  25                  30

<210> SEQ ID NO 453
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = acetylglycine
<220> FEATURE:
<221> NAME/KEY: VARIANT
<222> LOCATION: 30
<223> OTHER INFORMATION: Xaa = glycine amide

<400> SEQUENCE: 453

Xaa Cys Asp Val Leu Gln Pro Tyr Trp Gly Cys Gly Pro Asp Ile Asp
1               5                   10                  15

Cys Leu Ser Asn Cys Ile Cys His Trp Tyr Asn Ser Cys Xaa
            20                  25                  30

<210> SEQ ID NO 454
<211> LENGTH: 8
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = M or L
<220> FEATURE:
<221> NAME/KEY: VARIANT
<222> LOCATION: 4
<223> OTHER INFORMATION: Xaa = L or S or T or Q or N or E or D
<220> FEATURE:
<221> NAME/KEY: VARIANT
<222> LOCATION: 6
<223> OTHER INFORMATION: Xaa = F or Y or S

<400> SEQUENCE: 454

Asn Ile Xaa Xaa Pro Xaa Trp Gly
 1               5

<210> SEQ ID NO 455
<211> LENGTH: 32
<212> TYPE: PRT
<213> ORGANISM: Artificial Sequence
<220> FEATURE:
<223> OTHER INFORMATION: Synthetic Construct

<400> SEQUENCE: 455

Gly Cys Asn Ile Met Leu Pro Phe Trp Gly Cys Lys Gln Asp Phe Asp
 1               5                  10                  15

Cys Leu Ala Gly Cys Ile Cys Gln Tyr Tyr Gln Ser Cys Gly Phe His
             20                  25                  30

<210> SEQ ID NO 456
<211> LENGTH: 32
<212> TYPE: PRT
<213> ORGANISM: Artificial Sequence
<220> FEATURE:
<223> OTHER INFORMATION: Synthetic Construct

<400> SEQUENCE: 456

Gly Cys Asp Val Met Gln Pro Tyr Trp Gly Cys Glu Met Asp Phe Asp
 1               5                  10                  15

Cys Leu Ala Gly Cys Val Cys His Trp Tyr Asn Ser Cys Gly Ser Leu
             20                  25                  30

<210> SEQ ID NO 457
<211> LENGTH: 32
<212> TYPE: PRT
<213> ORGANISM: Artificial Sequence
<220> FEATURE:
<223> OTHER INFORMATION: Synthetic Construct

<400> SEQUENCE: 457

Gly Cys Asn Ile Met Leu Pro Phe Trp Gly Cys Lys Gln Asp Phe Asp
 1               5                  10                  15

Cys Leu Ala Gly Cys Ile Cys Gln Tyr Tyr Gln Ser Cys Gly Gly Glu
             20                  25                  30

<210> SEQ ID NO 458
<211> LENGTH: 32
<212> TYPE: PRT
<213> ORGANISM: Artificial Sequence
<220> FEATURE:
<223> OTHER INFORMATION: Synthetic Construct

<400> SEQUENCE: 458
```

```
Gly Cys Asn Ile Met Leu Pro Phe Trp Gly Cys Lys Gln Asp Ser Asp
1               5                   10                  15

Cys Leu Val Gly Cys Ile Cys Gln Tyr Tyr Gln Ser Cys Gly Ser Ile
            20                  25                  30
```

<210> SEQ ID NO 459
<211> LENGTH: 32
<212> TYPE: PRT
<213> ORGANISM: Artificial Sequence
<220> FEATURE:
<223> OTHER INFORMATION: Synthetic Construct

<400> SEQUENCE: 459

```
Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Gly Arg
            20                  25                  30
```

<210> SEQ ID NO 460
<211> LENGTH: 32
<212> TYPE: PRT
<213> ORGANISM: Artificial Sequence
<220> FEATURE:
<223> OTHER INFORMATION: Synthetic Construct

<400> SEQUENCE: 460

```
Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Arg Pro
            20                  25                  30
```

<210> SEQ ID NO 461
<211> LENGTH: 32
<212> TYPE: PRT
<213> ORGANISM: Artificial Sequence
<220> FEATURE:
<223> OTHER INFORMATION: Synthetic Construct

<400> SEQUENCE: 461

```
Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Gln Tyr
            20                  25                  30
```

<210> SEQ ID NO 462
<211> LENGTH: 32
<212> TYPE: PRT
<213> ORGANISM: Artificial Sequence
<220> FEATURE:
<223> OTHER INFORMATION: Synthetic Construct

<400> SEQUENCE: 462

```
Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Glu Asn
            20                  25                  30
```

<210> SEQ ID NO 463
<211> LENGTH: 32
<212> TYPE: PRT
<213> ORGANISM: Artificial Sequence
<220> FEATURE:
<223> OTHER INFORMATION: Synthetic Construct -continued

<400> SEQUENCE: 463

Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Asp Thr
            20                  25                  30

<210> SEQ ID NO 464
<211> LENGTH: 32
<212> TYPE: PRT
<213> ORGANISM: Artificial Sequence
<220> FEATURE:
<223> OTHER INFORMATION: Synthetic Construct

<400> SEQUENCE: 464

Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Gln His
            20                  25                  30

<210> SEQ ID NO 465
<211> LENGTH: 32
<212> TYPE: PRT
<213> ORGANISM: Artificial Sequence
<220> FEATURE:
<223> OTHER INFORMATION: Synthetic Construct

<400> SEQUENCE: 465

Gly Cys Asn Ile Met Leu Pro Phe Trp Gly Cys Lys Gln Asp Ser Asp
1               5                   10                  15

Cys Leu Ala Gly Cys Ile Cys Gln Tyr Tyr Gln Ser Cys Gly Gln Asn
            20                  25                  30

<210> SEQ ID NO 466
<211> LENGTH: 32
<212> TYPE: PRT
<213> ORGANISM: Artificial Sequence
<220> FEATURE:
<223> OTHER INFORMATION: Synthetic Construct

<400> SEQUENCE: 466

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Glu Glu
            20                  25                  30

<210> SEQ ID NO 467
<211> LENGTH: 32
<212> TYPE: PRT
<213> ORGANISM: Artificial Sequence
<220> FEATURE:
<223> OTHER INFORMATION: Synthetic Construct

<400> SEQUENCE: 467

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Asp Asp
            20                  25                  30

<210> SEQ ID NO 468
<211> LENGTH: 32
<212> TYPE: PRT
<213> ORGANISM: Artificial Sequence
<220> FEATURE:
<223> OTHER INFORMATION: Synthetic Construct

<400> SEQUENCE: 468

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Asp Gly
            20                  25                  30

<210> SEQ ID NO 469
<211> LENGTH: 32
<212> TYPE: PRT
<213> ORGANISM: Artificial Sequence
<220> FEATURE:
<223> OTHER INFORMATION: Synthetic Construct

<400> SEQUENCE: 469

Gly Cys Asn Ile Met Leu Pro Phe Trp Gly Cys Lys Gln Asp Phe Asp
1               5                   10                  15

Cys Leu Ala Gly Cys Val Cys Gln Tyr Tyr Gln Ser Cys Gly Leu Glu
            20                  25                  30

<210> SEQ ID NO 470
<211> LENGTH: 32
<212> TYPE: PRT
<213> ORGANISM: Artificial Sequence
<220> FEATURE:
<223> OTHER INFORMATION: Synthetic Construct

<400> SEQUENCE: 470

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Thr Asp
            20                  25                  30

<210> SEQ ID NO 471
<211> LENGTH: 32
<212> TYPE: PRT
<213> ORGANISM: Artificial Sequence
<220> FEATURE:
<223> OTHER INFORMATION: Synthetic Construct

<400> SEQUENCE: 471

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Ser Glu
            20                  25                  30

<210> SEQ ID NO 472
<211> LENGTH: 32
<212> TYPE: PRT
<213> ORGANISM: Artificial Sequence
<220> FEATURE:
<223> OTHER INFORMATION: Synthetic Construct

<400> SEQUENCE: 472

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Pro Glu
            20                  25                  30

<210> SEQ ID NO 473
<211> LENGTH: 32
<212> TYPE: PRT
<213> ORGANISM: Artificial Sequence
<220> FEATURE:

<223> OTHER INFORMATION: Synthetic Construct

<400> SEQUENCE: 473

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Thr Asn
            20                  25                  30

<210> SEQ ID NO 474
<211> LENGTH: 32
<212> TYPE: PRT
<213> ORGANISM: Artificial Sequence
<220> FEATURE:
<223> OTHER INFORMATION: Synthetic Construct

<400> SEQUENCE: 474

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Pro His
            20                  25                  30

<210> SEQ ID NO 475
<211> LENGTH: 32
<212> TYPE: PRT
<213> ORGANISM: Artificial Sequence
<220> FEATURE:
<223> OTHER INFORMATION: Synthetic Construct

<400> SEQUENCE: 475

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Met Asp
            20                  25                  30

<210> SEQ ID NO 476
<211> LENGTH: 32
<212> TYPE: PRT
<213> ORGANISM: Artificial Sequence
<220> FEATURE:
<223> OTHER INFORMATION: Synthetic Construct

<400> SEQUENCE: 476

Gly Cys Asn Ile Met Leu Pro Phe Trp Gly Cys Lys Gln Asp Ser Asp
1               5                   10                  15

Cys Leu Ala Gly Cys Val Cys Gln Tyr Tyr Gln Ser Cys Gly Ser Asp
            20                  25                  30

<210> SEQ ID NO 477
<211> LENGTH: 32
<212> TYPE: PRT
<213> ORGANISM: Artificial Sequence
<220> FEATURE:
<223> OTHER INFORMATION: Synthetic Construct

<400> SEQUENCE: 477

Gly Cys Asn Ile Met Leu Pro Phe Trp Gly Cys Gly Gln Ser Phe Glu
1               5                   10                  15

Cys Leu Ala Gly Cys Ile Cys Gln Tyr Tyr Gln Ser Cys Gly Ile Ala
            20                  25                  30

<210> SEQ ID NO 478
<211> LENGTH: 32
<212> TYPE: PRT
<213> ORGANISM: Artificial Sequence -continued

```
<220> FEATURE:
<223> OTHER INFORMATION: Synthetic Construct

<400> SEQUENCE: 478

Gly Cys Asn Ile Met Leu Pro Phe Trp Gly Cys Gly Gln Ser Phe Glu
1               5                   10                  15

Cys Leu Ala Gly Cys Ile Cys Gln Tyr Tyr Gln Ser Cys Gly Gly Ser
            20                  25                  30

<210> SEQ ID NO 479
<211> LENGTH: 32
<212> TYPE: PRT
<213> ORGANISM: Artificial Sequence
<220> FEATURE:
<223> OTHER INFORMATION: Synthetic Construct

<400> SEQUENCE: 479

Gly Cys Asn Ile Met Leu Pro Phe Trp Gly Cys Gly Gln Ser Phe Glu
1               5                   10                  15

Cys Leu Ala Gly Cys Ile Cys Gln Tyr Tyr Gln Ser Cys Gly Thr Arg
            20                  25                  30

<210> SEQ ID NO 480
<211> LENGTH: 32
<212> TYPE: PRT
<213> ORGANISM: Artificial Sequence
<220> FEATURE:
<223> OTHER INFORMATION: Synthetic Construct

<400> SEQUENCE: 480

Gly Cys Asn Ile Met Leu Pro Phe Trp Gly Cys Gly Gln Ser Phe Glu
1               5                   10                  15

Cys Leu Ala Gly Cys Ile Cys Gln Tyr Tyr Gln Ser Cys Gly Val His
            20                  25                  30

<210> SEQ ID NO 481
<211> LENGTH: 32
<212> TYPE: PRT
<213> ORGANISM: Artificial Sequence
<220> FEATURE:
<223> OTHER INFORMATION: Synthetic Construct

<400> SEQUENCE: 481

Gly Cys Asp Val Met Gln Pro Tyr Trp Gly Cys Lys Gln Asp Phe Asp
1               5                   10                  15

Cys Leu Ala Gly Cys Val Cys His Trp Tyr Asn Ser Cys Gly Pro Ser
            20                  25                  30

<210> SEQ ID NO 482
<211> LENGTH: 32
<212> TYPE: PRT
<213> ORGANISM: Artificial Sequence
<220> FEATURE:
<223> OTHER INFORMATION: Synthetic Construct

<400> SEQUENCE: 482

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Phe Ser
            20                  25                  30

<210> SEQ ID NO 483
<211> LENGTH: 32
<212> TYPE: PRT
```

<213> ORGANISM: Artificial Sequence
<220> FEATURE:
<223> OTHER INFORMATION: Synthetic Construct

<400> SEQUENCE: 483

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Gly Lys
            20                  25                  30

<210> SEQ ID NO 484
<211> LENGTH: 32
<212> TYPE: PRT
<213> ORGANISM: Artificial Sequence
<220> FEATURE:
<223> OTHER INFORMATION: Synthetic Construct

<400> SEQUENCE: 484

Gly Cys Asp Val Met Gln Pro Tyr Trp Gly Cys Lys Gln Asp Phe Asp
1               5                   10                  15

Cys Leu Ala Gly Cys Ile Cys His Trp Tyr Asn Ser Cys Gly Tyr Leu
            20                  25                  30

<210> SEQ ID NO 485
<211> LENGTH: 32
<212> TYPE: PRT
<213> ORGANISM: Artificial Sequence
<220> FEATURE:
<223> OTHER INFORMATION: Synthetic Construct

<400> SEQUENCE: 485

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Asp Leu
            20                  25                  30

<210> SEQ ID NO 486
<211> LENGTH: 32
<212> TYPE: PRT
<213> ORGANISM: Artificial Sequence
<220> FEATURE:
<223> OTHER INFORMATION: Synthetic Construct

<400> SEQUENCE: 486

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Glu Lys
            20                  25                  30

<210> SEQ ID NO 487
<211> LENGTH: 32
<212> TYPE: PRT
<213> ORGANISM: Artificial Sequence
<220> FEATURE:
<223> OTHER INFORMATION: Synthetic Construct

<400> SEQUENCE: 487

Gly Cys Asp Val Met Gln Pro Tyr Trp Gly Cys Lys Gln Asp Ser Asp
1               5                   10                  15

Cys Leu Ala Gly Cys Ile Cys His Trp Tyr Asn Ser Cys Gly Thr Asp
            20                  25                  30

<210> SEQ ID NO 488
<211> LENGTH: 32

```
<212> TYPE: PRT
<213> ORGANISM: Artificial Sequence
<220> FEATURE:
<223> OTHER INFORMATION: Synthetic Construct

<400> SEQUENCE: 488

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Gln Val
            20                  25                  30

<210> SEQ ID NO 489
<211> LENGTH: 32
<212> TYPE: PRT
<213> ORGANISM: Artificial Sequence
<220> FEATURE:
<223> OTHER INFORMATION: Synthetic Construct

<400> SEQUENCE: 489

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Arg Leu
            20                  25                  30

<210> SEQ ID NO 490
<211> LENGTH: 32
<212> TYPE: PRT
<213> ORGANISM: Artificial Sequence
<220> FEATURE:
<223> OTHER INFORMATION: Synthetic Construct

<400> SEQUENCE: 490

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Tyr Ala
            20                  25                  30

<210> SEQ ID NO 491
<211> LENGTH: 32
<212> TYPE: PRT
<213> ORGANISM: Artificial Sequence
<220> FEATURE:
<223> OTHER INFORMATION: Synthetic Construct

<400> SEQUENCE: 491

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Ala Ser
            20                  25                  30

<210> SEQ ID NO 492
<211> LENGTH: 32
<212> TYPE: PRT
<213> ORGANISM: Artificial Sequence
<220> FEATURE:
<223> OTHER INFORMATION: Synthetic Construct

<400> SEQUENCE: 492

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Ser Arg
            20                  25                  30

<210> SEQ ID NO 493
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 493

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Pro Thr
            20                  25                  30

<210> SEQ ID NO 494
<211> LENGTH: 32
<212> TYPE: PRT
<213> ORGANISM: Artificial Sequence
<220> FEATURE:
<223> OTHER INFORMATION: Synthetic Construct

<400> SEQUENCE: 494

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Trp Asp
            20                  25                  30

<210> SEQ ID NO 495
<211> LENGTH: 32
<212> TYPE: PRT
<213> ORGANISM: Artificial Sequence
<220> FEATURE:
<223> OTHER INFORMATION: Synthetic Construct

<400> SEQUENCE: 495

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Ser Met
            20                  25                  30

<210> SEQ ID NO 496
<211> LENGTH: 32
<212> TYPE: PRT
<213> ORGANISM: Artificial Sequence
<220> FEATURE:
<223> OTHER INFORMATION: Synthetic Construct

<400> SEQUENCE: 496

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Thr Arg
            20                  25                  30

<210> SEQ ID NO 497
<211> LENGTH: 32
<212> TYPE: PRT
<213> ORGANISM: Artificial Sequence
<220> FEATURE:
<223> OTHER INFORMATION: Synthetic Construct

<400> SEQUENCE: 497

Gly Cys Asp Val Met Gln Pro Tyr Trp Gly Cys Lys Gln Asp Ser Asp
1               5                   10                  15

Cys Leu Ala Gly Cys Val Cys His Trp Tyr Asn Ser Cys Gly Glu Asn
            20                  25                  30
```

```
<210> SEQ ID NO 498
<211> LENGTH: 32
<212> TYPE: PRT
<213> ORGANISM: Artificial Sequence
<220> FEATURE:
<223> OTHER INFORMATION: Synthetic Construct

<400> SEQUENCE: 498
```

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Asn Asn
            20                  25                  30

```
<210> SEQ ID NO 499
<211> LENGTH: 32
<212> TYPE: PRT
<213> ORGANISM: Artificial Sequence
<220> FEATURE:
<223> OTHER INFORMATION: Synthetic Construct

<400> SEQUENCE: 499
```

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Pro Glu
            20                  25                  30

```
<210> SEQ ID NO 500
<211> LENGTH: 32
<212> TYPE: PRT
<213> ORGANISM: Artificial Sequence
<220> FEATURE:
<223> OTHER INFORMATION: Synthetic Construct

<400> SEQUENCE: 500
```

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Gly Ile
            20                  25                  30

```
<210> SEQ ID NO 501
<211> LENGTH: 32
<212> TYPE: PRT
<213> ORGANISM: Artificial Sequence
<220> FEATURE:
<223> OTHER INFORMATION: Synthetic Construct

<400> SEQUENCE: 501
```

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Val Glu
            20                  25                  30

```
<210> SEQ ID NO 502
<211> LENGTH: 32
<212> TYPE: PRT
<213> ORGANISM: Artificial Sequence
<220> FEATURE:
<223> OTHER INFORMATION: Synthetic Construct

<400> SEQUENCE: 502
```

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Pro Leu
            20                  25                  30

<210> SEQ ID NO 503
<211> LENGTH: 32
<212> TYPE: PRT
<213> ORGANISM: Artificial Sequence
<220> FEATURE:
<223> OTHER INFORMATION: Synthetic Construct

<400> SEQUENCE: 503

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Pro Leu
            20                  25                  30

<210> SEQ ID NO 504
<211> LENGTH: 32
<212> TYPE: PRT
<213> ORGANISM: Artificial Sequence
<220> FEATURE:
<223> OTHER INFORMATION: Synthetic Construct

<400> SEQUENCE: 504

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Arg Pro
            20                  25                  30

<210> SEQ ID NO 505
<211> LENGTH: 32
<212> TYPE: PRT
<213> ORGANISM: Artificial Sequence
<220> FEATURE:
<223> OTHER INFORMATION: Synthetic Construct

<400> SEQUENCE: 505

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Asn Asp
            20                  25                  30

<210> SEQ ID NO 506
<211> LENGTH: 32
<212> TYPE: PRT
<213> ORGANISM: Artificial Sequence
<220> FEATURE:
<223> OTHER INFORMATION: Synthetic Construct

<400> SEQUENCE: 506

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Leu Gln
            20                  25                  30

<210> SEQ ID NO 507
<211> LENGTH: 32
<212> TYPE: PRT
<213> ORGANISM: Artificial Sequence
<220> FEATURE:
<223> OTHER INFORMATION: Synthetic Construct

<400> SEQUENCE: 507

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Asp Glu
            20                  25                  30

<210> SEQ ID NO 508
<211> LENGTH: 32
<212> TYPE: PRT
<213> ORGANISM: Artificial Sequence
<220> FEATURE:
<223> OTHER INFORMATION: Synthetic Construct

<400> SEQUENCE: 508

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Arg Thr
            20                  25                  30

<210> SEQ ID NO 509
<211> LENGTH: 32
<212> TYPE: PRT
<213> ORGANISM: Artificial Sequence
<220> FEATURE:
<223> OTHER INFORMATION: Synthetic Construct

<400> SEQUENCE: 509

Gly Cys Asp Val Met Gln Pro Tyr Trp Gly Cys Glu Ile Asp Phe Asp
1               5                   10                  15

Cys Leu Ala Gly Cys Val Cys His Trp Tyr Asn Ser Cys Gly Gln Val
            20                  25                  30

<210> SEQ ID NO 510
<211> LENGTH: 32
<212> TYPE: PRT
<213> ORGANISM: Artificial Sequence
<220> FEATURE:
<223> OTHER INFORMATION: Synthetic Construct

<400> SEQUENCE: 510

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Gly Ile
            20                  25                  30

<210> SEQ ID NO 511
<211> LENGTH: 32
<212> TYPE: PRT
<213> ORGANISM: Artificial Sequence
<220> FEATURE:
<223> OTHER INFORMATION: Synthetic Construct

<400> SEQUENCE: 511

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Tyr Met
            20                  25                  30

<210> SEQ ID NO 512
<211> LENGTH: 32
<212> TYPE: PRT
<213> ORGANISM: Artificial Sequence
<220> FEATURE:
<223> OTHER INFORMATION: Synthetic Construct

<400> SEQUENCE: 512

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Gly Gln 20                  25                  30

<210> SEQ ID NO 513
<211> LENGTH: 32
<212> TYPE: PRT
<213> ORGANISM: Artificial Sequence
<220> FEATURE:
<223> OTHER INFORMATION: Synthetic Construct

<400> SEQUENCE: 513

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Thr Pro
            20                  25                  30

<210> SEQ ID NO 514
<211> LENGTH: 32
<212> TYPE: PRT
<213> ORGANISM: Artificial Sequence
<220> FEATURE:
<223> OTHER INFORMATION: Synthetic Construct

<400> SEQUENCE: 514

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Val Asn
            20                  25                  30

<210> SEQ ID NO 515
<211> LENGTH: 32
<212> TYPE: PRT
<213> ORGANISM: Artificial Sequence
<220> FEATURE:
<223> OTHER INFORMATION: Synthetic Construct

<400> SEQUENCE: 515

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Phe Asn
            20                  25                  30

<210> SEQ ID NO 516
<211> LENGTH: 32
<212> TYPE: PRT
<213> ORGANISM: Artificial Sequence
<220> FEATURE:
<223> OTHER INFORMATION: Synthetic Construct

<400> SEQUENCE: 516

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Glu Pro
            20                  25                  30

<210> SEQ ID NO 517
<211> LENGTH: 32
<212> TYPE: PRT
<213> ORGANISM: Artificial Sequence
<220> FEATURE:
<223> OTHER INFORMATION: Synthetic Construct

<400> SEQUENCE: 517

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Asn Ser
            20                  25                  30

<210> SEQ ID NO 518
<211> LENGTH: 32
<212> TYPE: PRT
<213> ORGANISM: Artificial Sequence
<220> FEATURE:
<223> OTHER INFORMATION: Synthetic Construct

<400> SEQUENCE: 518

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Ser Thr
            20                  25                  30

<210> SEQ ID NO 519
<211> LENGTH: 32
<212> TYPE: PRT
<213> ORGANISM: Artificial Sequence
<220> FEATURE:
<223> OTHER INFORMATION: Synthetic Construct

<400> SEQUENCE: 519

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Arg Tyr
            20                  25                  30

<210> SEQ ID NO 520
<211> LENGTH: 32
<212> TYPE: PRT
<213> ORGANISM: Artificial Sequence
<220> FEATURE:
<223> OTHER INFORMATION: Synthetic Construct

<400> SEQUENCE: 520

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Phe Ser
            20                  25                  30

<210> SEQ ID NO 521
<211> LENGTH: 32
<212> TYPE: PRT
<213> ORGANISM: Artificial Sequence
<220> FEATURE:
<223> OTHER INFORMATION: Synthetic Construct

<400> SEQUENCE: 521

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Gln Val
            20                  25                  30

<210> SEQ ID NO 522
<211> LENGTH: 32
<212> TYPE: PRT
<213> ORGANISM: Artificial Sequence
<220> FEATURE:
<223> OTHER INFORMATION: Synthetic Construct

<400> SEQUENCE: 522

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Tyr Ala
            20                  25                  30

<210> SEQ ID NO 523
<211> LENGTH: 32
<212> TYPE: PRT
<213> ORGANISM: Artificial Sequence
<220> FEATURE:
<223> OTHER INFORMATION: Synthetic Construct

<400> SEQUENCE: 523

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Ser Arg
            20                  25                  30

<210> SEQ ID NO 524
<211> LENGTH: 32
<212> TYPE: PRT
<213> ORGANISM: Artificial Sequence
<220> FEATURE:
<223> OTHER INFORMATION: Synthetic Construct

<400> SEQUENCE: 524

Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Pro Thr
            20                  25                  30

<210> SEQ ID NO 525
<211> LENGTH: 32
<212> TYPE: PRT
<213> ORGANISM: Artificial Sequence
<220> FEATURE:
<223> OTHER INFORMATION: Synthetic Construct

<400> SEQUENCE: 525

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Ser Met
            20                  25                  30

<210> SEQ ID NO 526
<211> LENGTH: 32
<212> TYPE: PRT
<213> ORGANISM: Artificial Sequence
<220> FEATURE:
<223> OTHER INFORMATION: Synthetic Construct

<400> SEQUENCE: 526

Gly Cys Asp Val Met Gln Pro Tyr Trp Gly Cys Glu Met Asp Phe Asp
1               5                   10                  15

Cys Leu Ala Gly Cys Val Cys His Trp Tyr Asn Ser Cys Gly Gly Ile
            20                  25                  30

<210> SEQ ID NO 527
<211> LENGTH: 32
<212> TYPE: PRT
<213> ORGANISM: Artificial Sequence
<220> FEATURE:
<223> OTHER INFORMATION: Synthetic Construct

<400> SEQUENCE: 527

Gly Cys Asp Val Met Gln Pro Tyr Trp Gly Cys Glu Met Asp Phe Asp

```
                1               5                  10                  15
Cys Leu Ala Gly Cys Ile Cys His Trp Tyr Asn Ser Cys Gly Thr Ser
            20                  25                  30
```

<210> SEQ ID NO 528
<211> LENGTH: 32
<212> TYPE: PRT
<213> ORGANISM: Artificial Sequence
<220> FEATURE:
<223> OTHER INFORMATION: Synthetic Construct

<400> SEQUENCE: 528

```
Gly Cys Asp Val Met Gln Pro Tyr Trp Gly Cys Glu Met Asp Phe Asp
1               5                   10                  15
Cys Leu Ala Gly Cys Ile Cys His Trp Tyr Asn Ser Cys Gly Leu Gln
            20                  25                  30
```

<210> SEQ ID NO 529
<211> LENGTH: 32
<212> TYPE: PRT
<213> ORGANISM: Artificial Sequence
<220> FEATURE:
<223> OTHER INFORMATION: Synthetic Construct

<400> SEQUENCE: 529

```
Gly Cys Asp Val Met Gln Pro Tyr Trp Gly Cys Glu Met Asp Phe Asp
1               5                   10                  15
Cys Leu Val Gly Cys Val Cys His Trp Tyr Asn Ser Cys Gly Asp Glu
            20                  25                  30
```

<210> SEQ ID NO 530
<211> LENGTH: 32
<212> TYPE: PRT
<213> ORGANISM: Artificial Sequence
<220> FEATURE:
<223> OTHER INFORMATION: Synthetic Construct

<400> SEQUENCE: 530

```
Gly Cys Asp Val Met Gln Pro Tyr Trp Gly Cys Glu Met Asp Phe Asp
1               5                   10                  15
Cys Leu Ala Gly Cys Val Cys His Trp Tyr Asn Ser Cys Gly Asp Leu
            20                  25                  30
```

<210> SEQ ID NO 531
<211> LENGTH: 32
<212> TYPE: PRT
<213> ORGANISM: Artificial Sequence
<220> FEATURE:
<223> OTHER INFORMATION: Synthetic Construct

<400> SEQUENCE: 531

```
Gly Cys Asp Val Met Gln Pro Tyr Trp Gly Cys Glu Met Asp Phe Asp
1               5                   10                  15
Cys Leu Ala Gly Cys Val Cys His Trp Tyr Asn Ser Cys Gly Gln Phe
            20                  25                  30
```

<210> SEQ ID NO 532
<211> LENGTH: 32
<212> TYPE: PRT
<213> ORGANISM: Artificial Sequence
<220> FEATURE:
<223> OTHER INFORMATION: Synthetic Construct

<400> SEQUENCE: 532

```
Gly Cys Asp Val Met Gln Pro Tyr Trp Gly Cys Glu Met Asp Phe Asp
1               5                   10                  15

Cys Leu Ala Gly Cys Ile Cys His Trp Tyr Asn Ser Cys Gly Trp Lys
            20                  25                  30
```

<210> SEQ ID NO 533
<211> LENGTH: 32
<212> TYPE: PRT
<213> ORGANISM: Artificial Sequence
<220> FEATURE:
<223> OTHER INFORMATION: Synthetic Construct

<400> SEQUENCE: 533

```
Gly Cys Asn Ile Met Leu Pro Phe Trp Gly Cys Gly Gln Ser Phe Glu
1               5                   10                  15

Cys Leu Ala Gly Cys Ile Cys Gln Tyr Tyr Gln Ser Cys Gly Leu Ser
            20                  25                  30
```

<210> SEQ ID NO 534
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = D or E
<220> FEATURE:
<221> NAME/KEY: VARIANT
<222> LOCATION: 20
<223> OTHER INFORMATION: Xaa = N, K, or ornithine

<400> SEQUENCE: 534

```
Gly Cys Asp Val Xaa Gln Pro Tyr Trp Gly Cys Gly Pro Asp Ile Xaa
1               5                   10                  15

Cys Leu Ser Xaa Cys Ile Cys His Trp Tyr Asn Ser Cys Gly
            20                  25                  30
```

<210> SEQ ID NO 535
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = N, K, or ornithine
<220> FEATURE:
<221> NAME/KEY: VARIANT
<222> LOCATION: 20
<223> OTHER INFORMATION: Xaa = D or E

<400> SEQUENCE: 535

```
Gly Cys Asp Val Xaa Gln Pro Tyr Trp Gly Cys Gly Pro Asp Ile Xaa
1               5                   10                  15

Cys Leu Ser Xaa Cys Ile Cys His Trp Tyr Asn Ser Cys Gly
            20                  25                  30
```

-continued

```
<210> SEQ ID NO 536
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 536

Gly Cys Asp Val Xaa Gln Pro Tyr Trp Gly Cys Gly Pro Asp Ile Asp
1               5                   10                  15

Cys Leu Ser Lys Cys Ile Cys His Trp Tyr Asn Ser Cys Gly
            20                  25                  30

<210> SEQ ID NO 537
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = ornithine

<400> SEQUENCE: 537

Gly Cys Asp Val Xaa Gln Pro Tyr Trp Gly Cys Gly Pro Asp Ile Asp
1               5                   10                  15

Cys Leu Ser Xaa Cys Ile Cys His Trp Tyr Asn Ser Cys Gly
            20                  25                  30

<210> SEQ ID NO 538
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = D or E
<220> FEATURE:
<221> NAME/KEY: VARIANT
<222> LOCATION: 20
<223> OTHER INFORMATION: Xaa = N, K, or ornithine

<400> SEQUENCE: 538

Gly Cys Asn Ile Xaa Leu Pro Tyr Trp Gly Cys Gly Arg Asp Phe Xaa
1               5                   10                  15

Cys Met Glu Xaa Cys Ile Cys Gln Tyr Tyr Gln Ser Cys Gly
            20                  25                  30

<210> SEQ ID NO 539
<211> LENGTH: 30
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 5
<223> OTHER INFORMATION: Xaa = norleucine
<220> FEATURE:
<221>

```
<212> TYPE: PRT
<213> ORGANISM: Artificial Sequence
<220> FEATURE:
<223> OTHER INFORMATION: Synthetic Construct

<400> SEQUENCE: 542

Gly Cys Asn Ile Met Leu Pro Tyr Trp Gly Cys Gly Arg Asp Phe Glu
1               5                   10                  15

Cys Leu Ala Lys Cys Val Cys Gln Tyr Tyr Gln Ser Cys Gly
            20                  25                  30

<210> SEQ ID NO 543
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 543

Gly Cys Asn Ile Xaa Leu Pro Tyr Trp Gly Cys Gly Arg Asp Phe Glu
1               5                   10                  15

Cys Met Glu Lys Cys Ile Cys Gln Tyr Tyr Gln Ser Cys Gly
            20                  25                  30

<210> SEQ ID NO 544
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = ornithine

<400> SEQUENCE: 544

Gly Cys Asn Ile Xaa Leu Pro Tyr Trp Gly Cys Gly Arg Asp Phe Glu
1               5                   10                  15

Cys Met Glu Xaa Cys Ile Cys Gln Tyr Tyr Gln Ser Cys Gly
            20                  25                  30

<210> SEQ ID NO 545
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 545

Gly Cys Asn Ile Xaa Leu Pro Phe Trp Gly Cys Gly Arg Asp Phe Glu
1               5                   10                  15

Cys Val Ser Lys Cys Ile Cys Gln Tyr Tyr Gln Ser Cys Gly
            20                  25                  30

<210> SEQ ID NO 546
```

```
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = ornithine

<400> SEQUENCE: 546

Gly Cys Asn Ile Xaa Leu Pro Phe Trp Gly Cys Gly Arg Asp Phe Glu
1               5                   10                  15

Cys Val Ser Xaa Cys Ile Cys Gln Tyr Tyr Gln Ser Cys Gly
            20                  25                  30

<210> SEQ ID NO 547
<211> LENGTH: 30
<212> TYPE: PRT
<213> ORGANISM: Artificial Sequence
<220> FEATURE:
<223> OTHER INFORMATION: Synthetic Construct

<400> SEQUENCE: 547

Gly Cys Asn Ile Leu Leu Pro Phe Trp Gly Cys Gly Arg Asp Phe Glu
1               5                   10                  15

Cys Val Ser Gln Cys Ile Cys Gln Tyr Tyr Gln Ser Cys Gly
            20                  25                  30

<210> SEQ ID NO 548
<211> LENGTH: 30
<212> TYPE: PRT
<213> ORGANISM: Artificial Sequence
<220> FEATURE:
<223> OTHER INFORMATION: Synthetic Construct

<400> SEQUENCE: 548

Gly Cys Asn Ile Leu Gln Pro Phe Trp Gly Cys Gly Arg Asp Phe Glu
1               5                   10                  15

Cys Val Ser Gln Cys Ile Cys Gln Tyr Tyr Gln Ser Cys Gly
            20                  25                  30

<210> SEQ ID NO 549
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = D or E

<400> SEQUENCE: 549

Gly Cys Asp Val Xaa Gln Pro Tyr Trp Gly Cys Gly Pro Asp Ile Lys
1               5                   10                  15

Cys Leu Ser Xaa Cys Ile Cys His Trp Tyr Asn Ser Cys Gly
            20                  25                  30
```

```
<210> SEQ ID NO 550
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 550

Gly Cys Asp Val Xaa Gln Pro Tyr Trp Gly Cys Gly Pro Asp Ile Lys
1               5                   10                  15

Cys Leu Ser Asp Cys Ile Cys His Trp Tyr Asn Ser Cys Gly
            20                  25                  30

<210> SEQ ID NO 551
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 551

Gly Cys Asp Val Xaa Gln Pro Tyr Trp Gly Cys Gly Pro Asp Ile Lys
1               5                   10                  15

Cys Leu Ser Glu Cys Ile Cys His Trp Tyr Asn Ser Cys Gly
            20                  25                  30

<210> SEQ ID NO 552
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine
<220> FEATURE:
<221> NAME/KEY: VARIANT
<222> LOCATION: 20
<223> OTHER INFORMATION: Xaa = D or E

<400> SEQUENCE: 552

Gly Cys Asp Val Xaa Gln Pro Tyr Trp Gly Cys Gly Pro Asp Ile Xaa
1               5                   10                  15

Cys Leu Ser Xaa Cys Ile Cys His Trp Tyr Asn Ser Cys Gly
            20                  25                  30

<210> SEQ ID NO 553
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
```

```
<221> NAME/KEY: VARIANT
<222> LOCATION: 16
<223> OTHER INFORMATION: Xaa = ornithine

<400> SEQUENCE: 553

Gly Cys Asp Val Xaa Gln Pro Tyr Trp Gly Cys Gly Pro Asp Ile Xaa
1               5                   10                  15

Cys Leu Ser Asp Cys Ile Cys His Trp Tyr Asn Ser Cys Gly
            20                  25                  30

<210> SEQ ID NO 554
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine

<400> SEQUENCE: 554

Gly Cys Asp Val Xaa Gln Pro Tyr Trp Gly Cys Gly Pro Asp Ile Xaa
1               5                   10                  15

Cys Leu Ser Glu Cys Ile Cys His Trp Tyr Asn Ser Cys Gly
            20                  25                  30

<210> SEQ ID NO 555
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = D or E

<400> SEQUENCE: 555

Gly Cys Asn Ile Xaa Leu Pro Tyr Trp Gly Cys Gly Arg Asp Phe Lys
1               5                   10                  15

Cys Met Glu Xaa Cys Ile Cys Gln Tyr Tyr Gln Ser Cys Gly
            20                  25                  30

<210> SEQ ID NO 556
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 556

Gly Cys Asn Ile Xaa Leu Pro Tyr Trp Gly Cys Gly Arg Asp Phe Lys
1               5                   10                  15

Cys Met Glu Asp Cys Ile Cys Gln Tyr Tyr Gln Ser Cys Gly
            20                  25                  30
```

<210> SEQ ID NO 557
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine

<400> SEQUENCE: 557

Gly Cys Asn Ile Xaa Leu Pro Tyr Trp Gly Cys Gly Arg Asp Phe Lys
1               5                   10                  15

Cys Met Glu Glu Cys Ile Cys Gln Tyr Tyr Gln Ser Cys Gly
            20                  25                  30

<210> SEQ ID NO 558
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine
<220> FEATURE:
<221> NAME/KEY: VARIANT
<222> LOCATION: 20
<223> OTHER INFORMATION: Xaa = D or E

<400> SEQUENCE: 558

Gly Cys Asn Ile Xaa Leu Pro Tyr Trp Gly Cys Gly Arg Asp Phe Xaa
1               5                   10                  15

Cys Met Glu Xaa Cys Ile Cys Gln Tyr Tyr Gln Ser Cys Gly
            20                  25                  30

<210> SEQ ID NO 559
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine

<400> SEQUENCE: 559

Gly Cys Asn Ile Xaa Leu Pro Tyr Trp Gly Cys Gly Arg Asp Phe Xaa
1               5                   10                  15

Cys Met Glu Asp Cys Ile Cys Gln Tyr Tyr Gln Ser Cys Gly
            20                  25                  30

<210> SEQ ID NO 560
<211> LENGTH: 30
<212> TYPE: PRT
<213> ORGANISM: Artificial Sequence
<220> FEATURE:

```
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine

<400> SEQUENCE: 560

Gly Cys Asn Ile Xaa Leu Pro Tyr Trp Gly Cys Gly Arg Asp Phe Xaa
1               5                   10                  15
Cys Met Glu Glu Cys Ile Cys Gln Tyr Tyr Gln Ser Cys Gly
            20                  25                  30

<210> SEQ ID NO 561
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 20
<223> OTHER INFORMATION: Xaa = D or E

<400> SEQUENCE: 561

Gly Cys Asn Ile Xaa Leu Pro Phe Trp Gly Cys Gly Arg Asp Phe Lys
1               5                   10                  15
Cys Val Ser Xaa Cys Ile Cys Gln Tyr Tyr Gln Ser Cys Gly
            20                  25                  30

<210> SEQ ID NO 562
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = norleucine

<400> SEQUENCE: 562

Cys Asn Ile Xaa Leu Pro Phe Trp Gly Cys Gly Arg Asp Phe Lys Cys
1               5                   10                  15
Val Ser Asp Cys Ile Cys Gln Tyr Tyr Gln Ser Cys Gly
            20                  25

<210> SEQ ID NO 563
<211> LENGTH: 29
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = norleucine

<400> SEQUENCE: 563

Cys Asn Ile Xaa Leu Pro Phe Trp Gly Cys Gly Arg Asp Phe Lys Cys
1               5                   10                  15
```

```
Val Ser Glu Cys Ile Cys Gln Tyr Tyr Gln Ser Cys Gly
        20                  25

<210> SEQ ID NO 564
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine
<220> FEATURE:
<221> NAME/KEY: VARIANT
<222> LOCATION: 20
<223> OTHER INFORMATION: Xaa = D or E

<400> SEQUENCE: 564

Gly Cys Asn Ile Xaa Leu Pro Phe Trp Gly Cys Gly Arg Asp Phe Xaa
1               5                   10                  15

Cys Val Ser Xaa Cys Ile Cys Gln Tyr Tyr Gln Ser Cys Gly
            20                  25                  30

<210> SEQ ID NO 565
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine

<400> SEQUENCE: 565

Gly Cys Asn Ile Xaa Leu Pro Phe Trp Gly Cys Gly Arg Asp Phe Xaa
1               5                   10                  15

Cys Val Ser Asp Cys Ile Cys Gln Tyr Tyr Gln Ser Cys Gly
            20                  25                  30

<210> SEQ ID NO 566
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = norleucine
<220> FEATURE:
<221> NAME/KEY: VARIANT
<222> LOCATION: 16
<223> OTHER INFORMATION: Xaa = ornithine

<400> SEQUENCE: 566

Gly Cys Asn Ile Xaa Leu Pro Phe Trp Gly Cys Gly Arg Asp Phe Xaa
1               5                   10                  15

Cys Val Ser Glu Cys Ile Cys Gln Tyr Tyr Gln Ser Cys Gly
            20                  25                  30
```

```
<210> SEQ ID NO 567
<211> LENGTH: 5
<212> TYPE: PRT
<213> ORGANISM: Artificial Sequence
<220> FEATURE:
<223> OTHER INFORMATION: Synthetic Construct

<400> SEQUENCE: 567

Arg Trp Tyr Glu Ser
1               5

<210> SEQ ID NO 568
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 20
<223> OTHER INFORMATION: Xaa = ornithine

<400> SEQUENCE: 568

Gly Cys Asn Ile Met Leu Pro Tyr Trp Gly Cys Gly Arg Asp Phe Glu
1               5                   10                  15

Cys Leu Ala Xaa Cys Val Cys Gln Tyr Tyr Gln Ser Cys Gly
            20                  25                  30
```

CYSTINE KNOT SCAFFOLD PLATFORM

CROSS REFERENCE TO RELATED APPLICATIONS

This application claims the priority benefit of U.S. Provisional Application Ser. No. 62/219,063, filed Sep. 15, 2015, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392026800SEQLIST.txt, date recorded: Sep. 15, 2016, size: 178 KB).

BACKGROUND OF THE INVENTION

The design and engineering of novel proteins from alternative protein scaffolds has been an emerging field in the last decade with a broad spectrum of applications ranging from structure biology and imaging tools to therapeutic reagents that are currently being tested in the clinic (HK Binz et al., Nat Biotechnol 23, 1257-1268, 2005; HK Binz and A Pluckthun, Curr Opin Biotechnol 16, 459-469, 2005; SS Sidhu and S Koide, Curr Opin Struct Biol 17, 481-487, 2007; A Skerra, Curr Opin Biotechnol 18, 295-304, 2007; C Gronwall and S Stahl, J Biotechnol 140, 254-269, 2009; T Wurch et al., Trends Biotechnol 30, 575-582, 2012; S Banta et al., Annu Rev Biomed Eng 15, 93-113, 2013).

Desirable physical properties of potential alternative scaffold molecules include high thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase α-helix propensity, engineering of salt bridges, alteration of the surface charge of the protein, directed evolution, and composition of consensus sequences (Lehmann and Wyss, Cur Open Biotechnology 12, 371-375, 2001).

Cystine-knot peptides come from a wide range of sources and exhibit diverse pharmacological activities. They are roughly 30-50 amino acids in length and contain six conserved cysteine residues which form three disulfide bonds. One of the disulfides penetrates the macrocycle which is formed by the two other disulfides and their interconnecting backbones, thereby yielding a characteristic knotted topology with multiple loops exposed on the surface. The loops are defined as the amino acid regions which flank the six conserved cysteine residues and are highly variable in nature. Furthermore, the unique arrangement of the disulfide bonds renders cystine-knot peptides highly stable to thermal, proteolytic and chemical degradation.

Thus, there is a need to develop small, stable, artificial antibody-like molecules for a variety of therapeutic and diagnostic applications, such as ocular diseases and disorders. The present invention meets this and other needs.

BRIEF SUMMARY OF THE INVENTION

In certain embodiments, provided herein is a non-naturally occurring cystine knot peptide (CKP) that binds to vascular endothelial growth factor A (VEGF-A), wherein the CKP comprises the cystine scaffold structure:

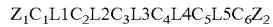

$$Z_1C_1L1C_2L2C_3L3C_4L4C_5L5C_6Z_2$$

wherein:

$Z_1$ and $Z_2$ are any amino acid;

L1 is Loop 1 and has a structure selected from the group consisting of: $X_1X_2X_3X_4X_5X_6$ (SEQ ID NO: 2), $X_1X_2X_3X_4X_5X_6X_7$ (SEQ ID NO: 3), $X_1X_2X_3X_4X_5X_6X_7X_8$ (SEQ ID NO: 4), $X_1X_2X_3X_4X_5X_6X_7X_8X_9$ (SEQ ID NO: 5), and $X_1X_2X_3X_4X_5X_6X_7X_8X_9X_{10}$ (SEQ ID NO: 6), wherein each of $X_1$-$X_{10}$ is any amino acid;

L2 is Loop 2 and has the structure: $X_1X_2X_3X_4X_5$ (SEQ ID NO: 7), wherein each of $X_1$-$X_5$ is any amino acid or an unnatural amino acid;

L3 is Loop 3 and has the structure: $X_1X_2X_3$, wherein each of $X_1$-$X_3$ is any amino acid or an unnatural amino acid;

L4 is Loop 4 and has the structure: $X_1$, wherein $X_1$ is any amino acid or an unnatural amino acid;

L5 is Loop 5 and has the structure: $X_1X_2X_3X_4X_5$ (SEQ ID NO: 7), wherein each of $X_1$-$X_5$ is any amino acid or an unnatural amino acid;

wherein the unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine; and wherein the CKP binds to VEGF-A with an affinity of 500 pM or better.

In certain embodiments according to (or as applied to) any of the embodiments above, the non-naturally occurring (CKP) that binds to VEGF-A has an altered disulfide bond connectivity—with reference to a wild-type Ecballium elaterium trypsin inhibitor EETI-II protein having the amino acid sequence set forth in SEQ ID NO: 1; wherein the altered disulfide bond connectivity is C1-C4, C2-C3 and C5-C6.

In certain embodiments according to (or as applied to) any of the embodiments above, the unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine,-L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments according to (or as applied to) any of the embodiments above, $Z_1$ and/or $Z_2$ is more than one amino acid, or an unnatural amino acid. In certain embodiments, $Z_2$ is two amino acids. In certain embodiments, $Z_2$ is three amino acids.

In certain embodiments according to (or as applied to) any of the embodiments above, $Z_1$ and/or $Z_2$ is G.

In certain embodiments according to (or as applied to) any of the embodiments above, in L1, $X_3$ is not I; $X_5$ is not M; and/or $X_6$ is not R. In certain embodiments according to (or as applied to) any of the embodiments above, in L1: $X_1$ is an amino acid selected from P, Q, R, T, V, D, N, K, L, and X; $X_2$ is an amino acid selected from T, D, L, V, I, R, P, N and X; $X_3$ is an amino acid selected from T, P, M, L, S, F, R, and X; $X_4$ is an amino acid selected from R, T, Q, D, W, L, E, S, K, and X; $X_5$ is an amino acid selected from F, P, V, E, K, L, I, and X; $X_6$ is an amino acid selected from K, N, F, P, L, Y, T, D, M, and X; $X_7$ is an amino acid selected from Q, W, H and/X; and/or $X_8$ is an amino acid selected from Y, A, G, D, E, W, S, and X, wherein X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine. In certain embodiments according to (or as applied to) any of the embodiments above, in L1: $X_9$ is an amino acid selected from L, I, V, D, E and X, wherein X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine. In certain embodiments according to (or as applied to) any of the embodiments above, in L1: $X_{10}$ is an amino acid selected from Y, T, M, N, F, and X, wherein X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments according to (or as applied to) any of the embodiments above, in L5, each of $X_1$-$X_5$ is any amino acid with the exception that $X_2$ is not proline (P). In certain embodiments according to (or as applied to) any of the embodiments above, in L5, each of $X_1$-$X_5$ is any amino acid with the exception that $X_4$ is not glycine (G). In certain embodiments according to (or as applied to) any of the embodiments above, in L5: $X_1$ is an amino acid selected from G, Q, H, R, L, and Q; $X_2$ is an amino acid selected from P, M, W, Y, F, L, and H; $X_3$ is an amino acid selected from N, F, H, and Y; $X_4$ is an amino acid selected from G, Q, D, N, K, H, E, and S; and/or $X_5$ is an amino acid selected from F, S, and T.

In certain embodiments according to (or as applied to) any of the embodiments above, L1 has the structure $X_1X_2X_3X_4X_5X_6X_7X_8$ (SEQ ID NO: 4), wherein: $X_1$ is an amino acid selected from P, Q, and R; $X_2$ is an amino acid selected from T, L, and D; $X_3$ is an amino acid selected from T, M and L; $X_4$ is an amino acid selected from R, Q, and D; $X_5$ is an amino acid selected from F, P, and V; $X_6$ is an amino acid selected from K and F; $X_7$ is an amino acid selected from Q and W; and $X_8$ is an amino acid selected from Y, G, and D. In certain embodiments according to (or as applied to) any of the embodiments above, L1 has the structure $X_1X_2X_3X_4X_5X_6X_7X_8X_9X_{10}$ (SEQ ID NO: 6), wherein: $X_1$ is an amino acid selected from Q, R, T and V; $X_2$ is an amino acid selected from T and D; $X_3$ is P; $X_4$ is an amino acid selected from T and W; $X_5$ is an amino acid selected from F, E, P, and K; $X_6$ is an amino acid selected from N and P; $X_7$ is an amino acid selected from W and H; $X_8$ is an amino acid selected from A, D, E, and W; $X_9$ is an amino acid selected from L and I; and $X_{10}$ is an amino acid selected from Y, T, M and N.

In certain embodiments according to (or as applied to) any of the embodiments above, in L5: $X_1$ is an amino acid selected from G, H, and Q; $X_2$ is an amino acid selected from P, M, W, and Y; $X_3$ is an amino acid selected from N and Y; $X_4$ is an amino acid selected from G, Q, and S; and $X_5$ is an amino acid selected from F and S.

In certain embodiments according to (or as applied to) any of the embodiments above, L1 has the structure $X_1X_2X_3X_4X_5X_6X_7X_8$ (SEQ ID NO: 4), wherein: $X_1$ is an amino acid selected from D, Q, N, and K; $X_2$ is an amino acid selected from V, I, R, L, and P; $X_3$ is an amino acid selected from L, S, M, T, and F; $X_4$ is an amino acid selected from Q, L, and E; $X_5$ is P; $X_6$ is an amino acid selected from F, L, and Y; $X_7$ is W; and $X_8$ is G.

In certain embodiments according to (or as applied to) any of the embodiments above, in L5: $X_3$ is Y; $X_5$ is S; and $X_1$, $X_2$ and $X_4$ are each any amino acid, with the exception that $X_1$ is not G, $X_2$ is not P, $X_4$ is not G, and/or $X_5$ is not F. In certain embodiments according to (or as applied to) any of the embodiments above, in L5: $X_1$ is an amino acid selected from H, L, R, and Q; $X_2$ is an amino acid selected from W, F, and Y; $X_3$ is Y; $X_4$ is an amino acid selected from Q, N, K, H, and E; and $X_5$ is S.

In certain embodiments according to (or as applied to) any of the embodiments above, L1 has the structure $X_1X_2X_3X_4X_5X_6X_7X_8X_9X_{10}$ (SEQ ID NO: 6), wherein: $X_1$ is an amino acid selected from K, Q, L, and R; $X_2$ is an amino acid selected from N and D; $X_3$ is an amino acid selected from P and L; $X_4$ is an amino acid selected from L, T, S and K; $X_5$ is an amino acid selected from F, V, I, and L; $X_6$ is an amino acid selected from N and D; $X_7$ is W; $X_8$ is an amino acid selected from A and S; $X_9$ is an amino acid selected from L, V, E and D; and $X_{10}$ is an amino acid selected from Y and F.

In certain embodiments according to (or as applied to) any of the embodiments above, in L5: $X_1$ is Q; $X_2$ is an amino acid selected from L, F, M, and H; $X_3$ is an amino acid selected from F, Y, and H; $X_4$ is an amino acid selected from D, Q, N, and K; and $X_5$ is an amino acid selected from S and T.

In certain embodiments according to (or as applied to) any of the embodiments above, in L2, $X_1$ is K, $X_2$ is Q, $X_3$ is D, $X_4$ is S, and $X_5$ is D.

In certain embodiments according to (or as applied to) any of the embodiments above, L1 has the structure $X_1X_2X_3X_4X_5X_6X_7X_8$ (SEQ ID NO: 4), wherein: $X_5$ is P; $X_7$ is W; $X_8$ is G; and wherein $X_1$, $X_2$, $X_3$, $X_4$ and $X_6$ are each any amino acid, with the exception that $X_1$ is not P, $X_2$ is not R, $X_3$ is not I, and/or $X_6$ is not R. In certain embodiments according to (or as applied to) any of the embodiments above, L1 has the structure $X_1X_2X_3X_4X_5X_6X_7X_8$ (SEQ ID NO: 4), wherein: $X_1$ is an amino acid selected from N and D; $X_2$ is an amino acid selected from I and V; $X_3$ is an amino acid selected from M and L; $X_4$ is an amino acid selected from L, Q, D and K; $X_5$ is P; $X_6$ is an amino acid selected from F, Y, T, L, and M; $X_7$ is W; and $X_8$ is G.

In certain embodiments according to (or as applied to) any of the embodiments above, in L5: $X_1$ is an amino acid selected from Q, H, L, and R; $X_2$ is an amino acid selected from Y and W; $X_3$ is Y; $X_4$ is an amino acid selected from Q and N; and $X_5$ is S. In certain embodiments according to (or as applied to) any of the embodiments above, in L5: $X_3$ is Y; $X_5$ is S; and $X_1$, $X_2$, and $X_4$ are each any amino acid, with the exception that: $X_1$ is not G, $X_2$ is not P, and/or $X_4$ is not G.

In certain embodiments according to (or as applied to) any of the embodiments above, in L2: $X_1$ is an amino acid selected from G or E; $X_2$ is an amino acid selected from Q, L, P, R, E, and M; $X_3$ is an amino acid selected from S, D, and N; $X_4$ is an amino acid selected from F, Y, L, M, and I; and/or $X_5$ is an amino acid selected from E, D, Q, L, and S.

In certain embodiments according to (or as applied to) any of the embodiments above, in L3, $X_1$ is L, $X_2$ is A, and $X_3$ is G.

In certain embodiments according to (or as applied to) any of the embodiments above, in L4, $X_1$ is V or F.

In certain embodiments according to (or as applied to) any of the embodiments above, in L5, each of $X_1$-$X_5$ is any amino acid with the exception that $X_2$ is not proline (P).

In certain embodiments according to (or as applied to) any of the embodiments above, in L5, each of $X_1$-$X_5$ is any amino acid with the exception that $X_4$ is not glycine (G).

In certain embodiments according to (or as applied to) any of the embodiments above, in L5: $X_1$ is any amino acid except G; $X_2$ is any amino acid except P; $X_3$ is any amino acid except N; $X_4$ is any amino acid except G; and/or $X_5$ is any amino acid except F.

In certain embodiments according to (or as applied to) any of the embodiments above, L1 has the structure $X_1X_2X_3X_4X_5X_6X_7X_8$ (SEQ ID NO: 4), wherein $X_1$ is an amino acid selected from N, D, and X; $X_2$ is an amino acid selected from I, V, and X; $X_3$ is M or X; $X_4$ is an amino acid selected from L, Q, and X; $X_5$ is P or X; $X_6$ is F, Y, or X; $X_7$ is W or X; and $X_8$ is G or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments according to (or as applied to) any of the embodiments above, in L3, each of $X_1$-$X_3$ is any amino acid or unnatural amino acid with the exception that $X_1$ is not Leucine (L), $X_2$ is not Alanine (A), and $X_3$ is not glycine (G), wherein the unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine. In certain embodiments according to (or as applied to) any of the embodiments above, in L3: $X_1$ is an amino acid selected from M, F, L V, and X; $X_2$ is an amino acid selected from S, N, Q, I, Y, E, V, T, and X; $X_3$ is an amino acid selected from D, Q, T, N, E, R, and X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, in L4, $X_1$ is any amino acid except V or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine. In certain embodiments according to (or as applied to) any of the embodiments above, in L4, $X_1$ is I, L, or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, in L5: $X_3$ is Y or X; $X_5$ is S or X; and $X_1$, $X_2$, and $X_4$ are each any amino acid or X, with the exception that $X_1$ is not G, $X_2$ is not P, and/or $X_4$ is not G, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine. In certain embodiments according to (or as applied to) any of the embodiments above, in L5, each of $X_1$-$X_5$ is any amino acid with the exception that $X_2$ is not proline (P). In certain embodiments according to (or as applied to) any of the embodiments above, in L5, each of $X_1$-$X_5$ is any amino acid with the exception that $X_4$ is not glycine (G). In certain embodiments according to (or as applied to) any of the embodiments above, in L5: $X_1$ is an amino acid selected from Q, H, and X; $X_2$ is an amino acid selected from Y, W, and X; $X_3$ is Y or X; $X_4$ is an amino acid selected from Q, N, or X; $X_5$ is S or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, X is and unnatural amino acid is selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments according to (or as applied to) any of the embodiments above, in L2: $X_1$ is G or X; $X_2$ is R, P, or X; $X_3$ is D or X; $X_4$ is F, I, or X; and $X_5$ is E, D, or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, and L-4-fluorophenylalanine.

In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECLQQCICQYYQSCG (SEQ ID NO: 103). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECVERCICQYYQSCG (SEQ ID NO: 104). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECMSDCICQYYQSCG (SEQ ID NO: 105). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECMNQCICQYYQSCG (SEQ ID NO: 106). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECMQTCICQYYQSCG (SEQ ID NO: 107). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECVYQCICQYYQSCG (SEQ ID NO: 108). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECFINCICQYYQSCG (SEQ ID NO: 109). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECVSQCICQYYQSCG (SEQ ID NO: 110). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECVTECICQYYQSCG (SEQ ID NO: 111). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECFYECICQYYQSCG (SEQ ID NO: 112). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECMEQCICQYYQSCG (SEQ ID NO: 113). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPFWGCGRDFECVYRCICQYYQSCG (SEQ ID NO: 114). In certain embodiments according to (or as applied to) any of the embodiments above, the non-naturally occurring cystine knot peptide (CKP) that binds to vascular endothelial growth factor A (VEGF-A) comprises the amino acid sequence GCDVMQPYWGCGPDIDCFVRCLCHWYNSCG (SEQ ID NO: 139). In certain embodiments according to (or as applied to) any of the embodiments above, the non-naturally occurring cystine knot peptide (CKP) that binds to vascular endothelial growth factor A (VEGF-A) comprises the amino acid sequence GCDVMQPYWGCGPDIDCLSNCICHWYNSCG (SEQ ID NO: 140). In certain embodiments according to (or as applied to) any of the embodiments above, the non-naturally occurring cystine knot peptide (CKP) that binds to vascular endothelial growth factor A (VEGF-A) comprises the amino acid sequence GCNIMLPYWGCGRDFECMEQCICQYYQSCG (SEQ ID NO: 142). In certain embodiments according to (or as applied to) any of the embodiments above, the non-naturally occurring cystine knot peptide (CKP) that binds to vascular endothelial growth factor A (VEGF-A) comprises the amino acid sequence GCNIXLPFWGCGRDFECMSDCICQYYQSCG (SEQ ID NO: 144), wherein X is norleucine (Nle). In certain embodiments according to (or as applied to) any of the embodiments above, the non-naturally occurring cystine knot peptide (CKP) that binds to vascular endothelial growth factor A (VEGF-A) comprises the amino acid sequence GCNIXLPFWGCGRDFECVSQCICQYYQSCG (SEQ ID NO: 145), wherein X is norleucine (Nle). In certain embodiments according to (or as applied to) any of the embodiments above, the non-naturally occurring cystine knot peptide (CKP) that binds to vascular endothelial growth factor A (VEGF-A) comprises the amino acid sequence GCNIXLPYWGCGRDFECMEQCICQYYQSCG (SEQ ID NO: 146), wherein X is norleucine (Nle).

In certain embodiments according to (or as applied to) any of the embodiments above, the non-naturally occurring cystine knot peptide (CKP) that binds to vascular endothelial growth factor A (VEGF-A) comprises the amino acid sequence GCDVXQPYWGCGPDIDCLSNCICHWYNSCG (SEQ ID NO: 224), wherein X is norleucine.

In certain embodiments, provided is a non-naturally occurring cystine knot peptide (CKP) comprising the amino acid selected from the group consisting of: GCNIMLPFWGCGRDFECMEQCICQYYQSCG (SEQ ID NO: 113), GCNIMLPFWGCGRDFECVYRCICQYYQSCG (SEQ ID NO: 114), GCDVMQPYWGCGPDIDCFVRCLCHWYNSCG (SEQ ID NO: 139), GCDVMQPYWGCGPDIDCLSNCICHWYNSCG (SEQ ID NO: 140), GCNIMLPYWGCGRDFECMEQCICQYYQSCG (SEQ ID NO: 142), GCNIXLPFWGCGRDFECMSDCICQYYQSCG (SEQ ID NO: 144), wherein X is norleucine (Nle), GCNIXLPFWGCGRDFECVSQCICQYYQSCG (SEQ ID NO: 145), wherein X is norleucine (Nle), GCNIXLPYWGCGRDFECMEQCICQYYQSCG (SEQ ID NO: 146), wherein X is norleucine (Nle), and GCDVXQPYWGCGPDIDCLSNCICHWYNSCG (SEQ ID NO: 224), wherein X is norleucine. In certain embodiments according to (or as applied to) any of the embodiments above, the CKP comprises the amino acid sequence set forth in GCNIMLPFWGCGRDFECMEQCICQYYQSCG (SEQ ID NO: 113). In certain embodiments according to (or as applied to) any of the embodiments above, the CKP comprises the amino acid sequence set forth in GCNIMLPFWGCGRDFECVYRCICQYYQSCG (SEQ ID NO: 114). In certain embodiments according to (or as applied to) any of the embodiments above, the CKP comprises the amino acid sequence set forth in GCDVMQPYWGCGPDIDCFVRCLCHWYNSCG (SEQ ID NO: 139). In certain embodiments according to (or as applied to) any of the embodiments above, the CKP comprises the amino acid sequence set forth in GCDVMQPYWGCGPDIDCLSNCICHWYNSCG (SEQ ID NO: 140). In certain embodiments according to (or as applied to) any of the embodiments above, the CKP comprises the amino acid sequence set forth in GCNIMLPYWGCGRDFECMEQCICQYYQSCG (SEQ ID NO: 142). In certain embodiments according to (or as applied to) any of the embodiments above, the CKP comprises the amino acid sequence set forth in GCNIXLPFWGCGRDFECMSDCICQYYQSCG (SEQ ID NO: 144), wherein X is norleucine (Nle). In certain embodiments according to (or as applied to) any of the embodiments above, the CKP comprises the amino acid sequence set forth in GCNIXLPFWGCGRDFECVSQCICQYYQSCG (SEQ ID NO: 145), wherein X is norleucine (Nle).

In certain embodiments according to (or as applied to) any of the embodiments above, the CKP comprises the amino acid sequence set forth in GCNIXLPYWGCGRDFECMEQCICQYYQSCG (SEQ ID NO: 146), wherein X is norleucine (Nle). In certain embodiments according to (or as applied to) any of the embodiments above, the CKP comprises the amino acid sequence set forth in GCDVXQPYWGCGPDIDCLSNCICHWYNSCG (SEQ ID NO: 224), wherein X is norleucine. In certain embodiments according to (or as applied to) any of the embodiments above, the CKP binds VEGF-A.

In certain embodiments, provided is a non-naturally occurring cystine knot peptide (CKP) comprising the amino acid selected from the group consisting of: GCDVX$_1$QPYWGCGPDI-D/E-CLS-N/K/X$_2$-CICHWYNSCG (SEQ ID NO: 534), GCDVX$_1$QPYWGCGPDI-N/K/X$_2$-CLS-D/E-CICHWYNSCG (SEQ ID NO: 535), GCNIX$_1$LPYWGCGRDF-D/E-CME-N/K/X$_2$-CICQYYQSCG (SEQ ID NO: 538), GCNIX$_1$LPYWGCGRDF-N/K/X$_2$-CME-D/E-CICQYYQSCG (SEQ ID NO: 539), GCNIX$_1$LPFWGCGRDF-D/E-CVS-N/K/X$_2$-CICQYYQSCG (SEQ ID NO: 540), and GCNIX$_1$LPFWGCGRDF-N/K/X$_2$-CVS-D/E-CICQYYQSCG (SEQ ID NO: 541), wherein X$_1$ is norleucine and X$_2$ is ornithine. In certain embodiments according to (or as applied to) any of the embodiments above, the CKP comprises the amino acid sequence set forth in GCDVX$_1$QPYWGCGPDI-D/E-CLS-N/K/X$_2$-CICHWYNSCG (SEQ ID NO: 534), wherein X$_1$ is norleucine and X$_2$ is ornithine. In certain embodiments according to (or as applied to) any of the embodiments above, the CKP comprises the amino acid sequence set forth in GCDVXQPYWGCGPDIDCLSKCICHWYNSCG (SEQ ID NO: 536), wherein X is norleucine. In certain embodiments according to (or as applied to) any of the embodiments above, the CKP comprises the amino acid sequence set forth in GCDVX$_1$QPYWGCGPDIDCLSX$_2$CICHWYNSCG (SEQ ID NO: 537), wherein X$_1$ is norleucine and X$_2$ is ornithine. In certain embodiments according to (or as applied to) any of the embodiments above, the CKP comprises the amino acid sequence set forth in GCDVX$_1$QPYWGCGPDI-N/K/X$_2$-CLS-D/E-CICHWYNSCG (SEQ ID NO: 535), wherein X$_1$ is norleucine and X$_2$ is ornithine. In certain embodiments according to (or as applied to) any of the embodiments above, the CKP comprises the amino acid sequence set forth in GCNIX$_1$LPYWGCGRDF-D/E-CME-N/K/X$_2$-CICQYYQSCG (SEQ ID NO: 538), wherein X$_1$ is norleucine and X$_2$ is ornithine. In certain embodiments according to (or as applied to) any of the embodiments above, the CKP comprises the amino acid sequence set forth in GCNIXLPYWGCGRDFECMEKCICQYYQSCG (SEQ ID NO: 543), wherein X is norleucine. In certain embodiments according to (or as applied to) any of the embodiments above, the CKP comprises the amino acid sequence set forth in GCNIX$_1$LPYWGCGRDFECMEX$_2$CICQYYQSCG (SEQ ID NO: 544), wherein X$_1$ is norleucine and X$_2$ is ornithine. In certain embodiments according to (or as applied to) any of the embodiments above, the CKP comprises the amino acid sequence set forth in GCNIX$_1$LPYWGCGRDF-N/K/X$_2$-CME-D/E-CICQYYQSCG (SEQ ID NO: 539), wherein X$_1$ is norleucine and X$_2$ is ornithine. In certain embodiments according to (or as applied to) any of the embodiments above, the CKP comprises the amino acid sequence set forth in GCNIX$_1$LPFWGCGRDF-D/E-CVS-N/K/X$_2$-CICQYY- QSCG (SEQ ID NO: 540), wherein $X_1$ is norleucine and $X_2$ is ornithine. In certain embodiments according to (or as applied to) any of the embodiments above, the CKP comprises the amino acid sequence set forth in GCNIXLPF-WGCGRDFECVSKCICQYYQSCG (SEQ ID NO: 545), wherein X is norleucine. In certain embodiments according to (or as applied to) any of the embodiments above, the CKP comprises the amino acid sequence set forth in GCNIX$_1$LPFWGCGRDFECVSX$_2$CICQYYQSCG (SEQ ID NO: 546), wherein $X_1$ is norleucine and $X_2$ is ornithine. In certain embodiments according to (or as applied to) any of the embodiments above, the CKP comprises the amino acid sequence set forth in GCNIX$_1$LPFWGCGRDF-N/K/X$_2$-CVS-D/E-CICQYYQSCG (SEQ ID NO: 541), wherein $X_1$ is norleucine and $X_2$ is ornithine. In certain embodiments according to (or as applied to) any of the embodiments above, the CKP binds VEGF-A.

In certain embodiments according to (or as applied to) any of the embodiments above, provided is a non-naturally occurring cystine knot peptide (CKP) that binds to VEGF-A, wherein the CKP comprises the cystine scaffold structure:

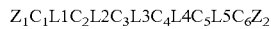

wherein:

$Z_1$ and $Z_2$ are any amino acid;

L1 is Loop 1 and has a structure selected from the group consisting of: $X_1X_2X_3X_4X_5X_6X_7X_8$, $X_1X_2X_3X_4X_5X_6X_7X_8X_9$, and $X_1X_2X_3X_4X_5X_6X_7X_8X_9X_{10}$, wherein each of $X_1$-$X_{10}$ is any amino acid;

L2 is Loop 2 and has the structure: $X_1X_2X_3X_4X_5$, wherein each of $X_1$-$X_5$ is any amino acid;

L3 is Loop 3 and has the structure: $X_1X_2X_3$ wherein each of $X_1$-$X_3$ is any amino acid;

L4 is Loop 4 and has the structure: $X_1$, wherein $X_1$ is any amino acid;

L5 is Loop 5 and has the structure: $X_1X_2X_3X_4X_5$, wherein each of $X_1$-$X_5$ is any amino acid;

wherein the CKP has an altered disulfide bond connectivity with reference to a wild-type Ecballium elaterium trypsin inhibitor EETI-II protein having the amino acid sequence set forth in SEQ ID NO: 1; wherein the altered disulfide bond connectivity is C1-C4, C2-C3 and C5-C6; and wherein the CKP has a percent alpha helix content of at least 20%.

In certain embodiments according to (or as applied to) any of the embodiments above, $Z_1$ and $Z_2$ are any amino acid, more than one amino acid, or an unnatural amino acid. In certain embodiments according to (or as applied to) any of the embodiments above, each of $X_1$-$X_{10}$ in L1 is any amino acid or an unnatural amino acid. In certain embodiments according to (or as applied to) any of the embodiments above, each of $X_1$-$X_5$ in L2 is any amino acid or an unnatural amino acid. In certain embodiments according to (or as applied to) any of the embodiments above, each of $X_1$-$X_3$ in L3 is any amino acid or an unnatural amino acid. In certain embodiments according to (or as applied to) any of the embodiments above, $X_1$ in L4 is any amino acid or an unnatural amino acid. In certain embodiments according to (or as applied to) any of the embodiments above, each of $X_1$-$X_5$ in L5 is any amino acid or an unnatural amino acid. In certain embodiments, the unnatural amino acid is selected from the group consisting of: L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments according to (or as applied to) any of the embodiments above, the non-naturally occurring (CKP) that binds to VEGF-A binds to VEGF-A with an affinity of 500 pM or less. In certain embodiments according to (or as applied to) any of the embodiments above, the binding affinity is determined via surface plasmon resonance.

In certain embodiments according to (or as applied to) any of the embodiments above, $Z_1$ and/or $Z_2$ is more than one amino acid, or an unnatural amino acid. In certain embodiments, $Z_2$ is two amino acids. In certain embodiments, $Z_2$ is three amino acids. In certain embodiments according to (or as applied to) any of the embodiments above, in L5, each of $X_1$-$X_5$ is any amino acid with the exception that $X_2$ is not proline (P). In certain embodiments according to (or as applied to) any of the embodiments above, in L5, each of $X_1$-$X_5$ is any amino acid with the exception that $X_4$ is not glycine (G).

In certain embodiments according to (or as applied to) any of the embodiments above, the C-terminal carboxyl group of the non-naturally occurring (CKP) that binds to VEGF-A is modified (such as capped). In certain embodiments according to (or as applied to) any of the embodiments above, the N-terminal amine group of the non-naturally occurring (CKP) that binds to VEGF-A is modified (such as capped). In certain embodiments according to (or as applied to) any of the embodiments above, the C-terminal carboxyl group of the non-naturally occurring (CKP) that binds to VEGF-A is capped and the N-terminal amine group of the non-naturally occurring (CKP) that binds to VEGF-A is modified (such as capped).

In certain embodiments according to (or as applied to) any of the embodiments above, the C-terminal carboxyl group of the non-naturally occurring (CKP) that binds to VEGF-A is amidated. In certain embodiments according to (or as applied to) any of the embodiments above, the N-terminal amine group of the non-naturally occurring (CKP) that binds to VEGF-A is acetylated. In certain embodiments according to (or as applied to) any of the embodiments above, the C-terminal carboxyl group of the non-naturally occurring (CKP) that binds to VEGF-A is amidated and the N-terminal amine group of the non-naturally occurring (CKP) that binds to VEGF-A is acetylated.

In certain embodiments according to (or as applied to) any of the embodiments above, the non-naturally occurring (CKP) that binds to VEGF-A inhibits VEGF-A activity. In certain embodiments according to (or as applied to) any of the embodiments above, CKP inhibits VEGF-A activity with and $IC_{50}$ between about 0.5 nM and about 1.0 nM. In certain embodiments according to (or as applied to) any of the embodiments above, the non-naturally occurring EETI-II scaffold protein binds human VEGF-A, mouse VEGF-A, and rat VEGF-A.

In certain embodiments according to (or as applied to) any of the embodiments above, the non-naturally occurring CKP competes with the antibody G6.31 for binding to VEGF-A. In certain embodiments according to (or as applied to) any of the embodiments above, provided is a non-naturally occurring CKP that competes with the non-naturally occurring (CKP) that binds to VEGF-A of any one of embodiments above for binding to VEGF-A.

In certain embodiments according to (or as applied to) any of the embodiments above, non-naturally occurring CKP that binds to an epitope on VEGF-A comprising at least one of the amino acid residues selected from the group consisting of: V14, V15, F17, D19, Y21, Q22, Y25, I46, K48, N62, D63, L66, M81, I83, K84, P85, H86, G88, Q89, I91, C104, R105, and P106.

In certain embodiments according to (or as applied to) any of the embodiments above, the residues are selected from the group consisting of: K48, N62, and D63. In certain embodiments according to (or as applied to) any of the embodiments above, the residues are selected from the group consisting of: Y21, Y25, and P106. In certain embodiments according to (or as applied to) any of the embodiments above, the residues are selected from the group consisting of: H86 and Q89. In certain embodiments according to (or as applied to) any of the embodiments above, the residues are selected from the group consisting of: M81, D19, and Q22. In certain embodiments according to (or as applied to) any of the embodiments above, the residues are selected from the group consisting of: F17, M81, and I91. In certain embodiments according to (or as applied to) any of the embodiments above, the residues are selected from the group consisting of: V14, F17, D19, Q22, M81, and I91. In certain embodiments according to (or as applied to) any of the embodiments above, the residues are selected from the group consisting of: Y25.

In certain embodiments according to (or as applied to) any of the embodiments above, the non-naturally occurring CKP that binds to VEGF-A is conjugated to a therapeutic agent. In certain embodiments according to (or as applied to) any of the embodiments above, the non-naturally occurring CKP that binds to VEGF-A is conjugated to a label. In certain embodiments according to (or as applied to) any of the embodiments above, the label is selected from the group consisting of a radioisotope, a fluorescent dye, and an enzyme.

In certain embodiments according to (or as applied to) any of the embodiments above, provided is an isolated nucleic acid encoding the non-naturally occurring (CKP) that binds to VEGF-A of any one of embodiments above. Also provided is an expression vector encoding the nucleic acid molecule of any one of the embodiments above. Also provided is a cell comprising the expression vector of any one of the embodiments above. Also provided is a method of producing the non-naturally occurring (CKP) that binds to VEGF-A of any one of embodiments above, comprising culturing the cell of any one of the embodiments above, and recovering the non-naturally occurring (CKP) that binds to VEGF-A from the cell culture.

Also provided is a method of producing the non-naturally occurring (CKP) that binds to VEGF-A of any one of embodiments above, comprising chemically synthesizing the non-naturally occurring (CKP) that binds to VEGF-A.

Provided herein is a composition comprising the non-naturally occurring (CKP) that binds to VEGF-A of any one of the embodiments above and a pharmaceutically acceptable carrier. In certain embodiments according to (or as applied to) any of the embodiments above, the composition comprises one or more additional compounds. In certain embodiments according to (or as applied to) any of the embodiments above, the additional compound binds to a second biological molecule selected from the group consisting of interleukin-6 (IL-6); interleukin-6 receptor (IL-6R); PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk such as complement pathway components C2, factor B, factor H, CFHR3, C3b, C5, C5a, C3a, HtrA1, ARMS2, TIMP3, HLA, interleukin-8 (IL-8), CX3CR1, TLR3, TLR4, CETP, LIPC, COL10A1, and TNFRSF10A. In certain embodiments according to (or as applied to) any of the embodiments above, the additional compound is a non-naturally occurring CKP. In certain embodiments according to (or as applied to) any of the embodiments above, the additional compound is an antibody or antigen-binding fragment thereof.

Provided herein is a method of treating an ocular disease characterized by angiogenesis and/or vascular permeability or leakage in a subject, comprising administering an effective amount of the non-naturally occurring (CKP) that binds to VEGF-A of any one of embodiments above to the subject. In certain embodiments according to (or as applied to) any of the embodiments above, the method further comprises administering one or more additional compounds. In certain embodiments according to (or as applied to) any of the embodiments above, the non-naturally occurring CKP that binds to VEGF-A is administered simultaneously with the additional compound(s). In certain embodiments according to (or as applied to) any of the embodiments above, the non-naturally occurring CKP that binds to VEGF-A is administered before or after the additional compound(s). In certain embodiments according to (or as applied to) any of the embodiments above, the additional compound binds to a second biological molecule selected from the group consisting of interleukin-6 (IL-6); interleukin-6 receptor (IL-6R); PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk such as complement pathway components C2, factor B, factor H, CFHR3, C3b, C5, C5a, C3a, HtrA1, ARMS2, TIMP3, HLA, interleukin-8 (IL-8), CX3CR1, TLR3, TLR4, CETP, LIPC, COL10A1, and TNFRSF10A. In certain embodiments according to (or as applied to) any of the embodiments above, the additional compound is a non-naturally occurring CKP. In certain embodiments according to (or as applied to) any of the embodiments above, the additional compound is an antibody or antigen-binding fragment thereof. In certain embodiments according to (or as applied to) any of the embodiments above, the ocular disease is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including Central Retinal Vein Occlusion (CRVO) and branched retinal vein occlusion (BRVO), corneal neovascularization, retinal neovascularization, and retinopathy of prematurity (ROP).

In certain embodiments according to (or as applied to) any of the embodiments above, the non-naturally occurring (CKP) that binds to VEGF-A or the composition is administered to the subject via an implantable device. In certain embodiments according to (or as applied to) any of the embodiments above, the implantable device selected from the group consisting of: an ocular insert, a slow-release depot, an ocular plug/reservoir, an non-biodegradable ocular implant or a biodegradable ocular implant.

In certain embodiments according to (or as applied to) any of the embodiments above, provided is a composition comprising the non-naturally occurring (CKP) that binds to VEGF-A of any one of embodiments above for use in treating an ocular disease characterized by angiogenesis and/or vascular permeability or leakage in a subject. In certain embodiments according to (or as applied to) any of the embodiments above, the ocular disease is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including Central Retinal Vein Occlusion (CRVO) and branched retinal vein occlusion (BRVO), corneal neovascularization, retinal neovascularization, and retinopathy of prematurity (ROP). In certain embodiments according to (or as applied to) any of the embodiments above, the composition is administered to the subject via an implantable device. In certain embodiments according to (or as applied to) any of the embodiments above, the implantable device selected from the group consisting of: an ocular insert, a slow-release depot, an ocular plug/reservoir, an non-biodegradable ocular implant or a biodegradable ocular implant.

In certain embodiments according to (or as applied to) any of the embodiments above, provided is a composition comprising the non-naturally occurring (CKP) that binds to VEGF-A of any one of embodiments above for use in treating an ocular disease characterized by angiogenesis and/or vascular permeability or leakage in a subject. In certain embodiments according to (or as applied to) any of the embodiments above, the ocular disease is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including Central Retinal Vein Occlusion (CRVO) and branched retinal vein occlusion (BRVO), corneal neovascularization, retinal neovascularization, and retinopathy of prematurity (ROP). In certain embodiments according to (or as applied to) any of the embodiments above, the medicament is administered to the subject via an implantable device. In certain embodiments according to (or as applied to) any of the embodiments above, the implantable device selected from the group consisting of: an ocular insert, a slow-release depot, an ocular plug/reservoir, an non-biodegradable ocular implant or a biodegradable ocular implant.

In certain embodiments according to (or as applied to) any of the embodiments above, the non-naturally occurring (CKP) that binds to VEGF-A is formulated for long acting delivery.

Provided herein is a formulation comprising the non-naturally occurring (CKP) that binds to VEGF-A of any of embodiments above and PLGA. In certain embodiments according to (or as applied to) any of the embodiments above, the PLGA is a PLGA rod.

Also provided herein is a non-naturally occurring cystine knot peptide (CKP) that binds to human low density lipoprotein receptor-related protein 6 (LRP6), wherein the CKP comprises the cystine scaffold structure:

$$Z_1C_1L1C_2L2C_3L3C_4L4C_5L5C_6Z_2;$$

wherein:
$Z_1$ and $Z_2$ are any amino acid;
L1 is Loop 1 and has a structure selected from the group consisting of: $X_1X_2X_3X_4X_5X_6$, $X_1X_2X_3X_4X_5X_6X_7$, $X_1X_2X_3X_4X_5X_6X_7X_8$, $X_1X_2X_3X_4X_5X_6X_7X_8X_9$, and $X_1X_2X_3X_4X_5X_6X_7X_8X_9X_{10}$, wherein each of $X_1$-$X_{10}$ is any amino acid;
L2 is Loop 2 and has the structure: $X_1X_2X_3X_4X_5$, wherein each of $X_1$-$X_5$ is any amino acid;
L3 is Loop 3 and has the structure: $X_1X_2X_3$ wherein each of $X_1$-$X_3$ is any amino acid;
L4 is Loop 4 and has the structure: $X_1$, wherein $X_1$ is any amino acid; and
L5 is Loop 5 and has the structure: $X_1X_2X_3X_4X_5$, wherein each of $X_1$-$X_5$ is any amino acid.

In certain embodiments according to (or as applied to) any of the embodiments above, $Z_1$ and/or $Z_2$ is more than one amino acid, or an unnatural amino acid. In certain embodiments, $Z_2$ is two amino acids. In certain embodiments, $Z_2$ is three amino acids.

In certain embodiments according to (or as applied to) any of the embodiments above, $Z_1$ and/or $Z_2$ is G.

In certain embodiments according to (or as applied to) any of the embodiments above, in L1: $X_1$ is an amino acid selected from R, V, M, A, G, N, S, and E; $X_2$ is an amino acid selected from T, N, S, G, R, and A; $X_3$ is an amino acid selected from N, R, H, V, K, S, G, I, and Y; $X_4$ is an amino acid selected from R, V, N, I, K, S, and T; $X_5$ is an amino acid selected from V, R, K, I, T, S, L, and N; and $X_6$ is an amino acid selected from K, G, A, I, R, N, S, and V. In certain embodiments according to (or as applied to) any of the embodiments above, in L1: $X_7$ is an amino acid selected from G, R, K, E, P, and T. In certain embodiments according to (or as applied to) any of the embodiments above, in L1: $X_8$ is an amino acid selected from G, R, K, Q, A, and S. In certain embodiments according to (or as applied to) any of the embodiments above, in L1: $X_9$ is an amino acid selected from R or G. In certain embodiments according to (or as applied to) any of the embodiments above, in L1: $X_{10}$ is an amino acid selected from E, W, and G.

In certain embodiments according to (or as applied to) any of the embodiments above, in L5: $X_1$ is an amino acid selected from G, S, N, Y, A, and R; $X_2$ is an amino acid selected from P, G, S, V, E, R, F, and D; $X_3$ is an amino acid selected from N, G, S, E, P, K, H, and R; $X_4$ is an amino acid selected from G, R, H, S, Q, V, and D; and $X_5$ is an amino acid selected from F, D, N, R, G, Y, S, and T.

In certain embodiments according to (or as applied to) any of the embodiments above, in L2, $X_1$ is K, $X_2$ is Q, $X_3$ is D, $X_4$ is S, and $X_5$ is D. In certain embodiments according to (or as applied to) any of the embodiments above, in L3, $X_1$ is L, X₂ is A, and X₃ is G. In certain embodiments according to (or as applied to) any of the embodiments above, in L4, X₁ is V.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A depicts the co-crystal structure of VEGF_CKP9.54.90 in complex with VEGF-A. FIG. 6B depicts the co-crystal structure of VEGF_CKP9.54.90 in complex with VEGF-A rotated 90° relative to FIG. 6A.

FIG. 13 provides the results of experiments that were performed to determine the IC₅₀ values of VEGF-binding CKP variants.

FIG. 14A provides the amino acid sequences of VEGF_CKP9 (also referred to as E9), VEGF_CKP9.54 (also referred to as EM54), and VEGF_CKP9.63 (also referred to as EM63). FIG. 14B depicts the structure of VEGF_CKP9.54. FIG. 14C depicts the structure of VEGF_CKP9.63.

FIG. 14D provides a portion of the co-crystal structure of VEGF_CKP9.63 in complex with VEGF-A superimposed on the co-crystal structure of VEGF_CKP9.54 in complex with VEGF-A. FIG. 14D shows that residue at position 8 within loop 1 of VEGF_CKP9.63 could form a hydrogen bond with the side chain of Gln22 of VEGF-A.

DETAILED DESCRIPTION OF THE INVENTION

Figure 1:
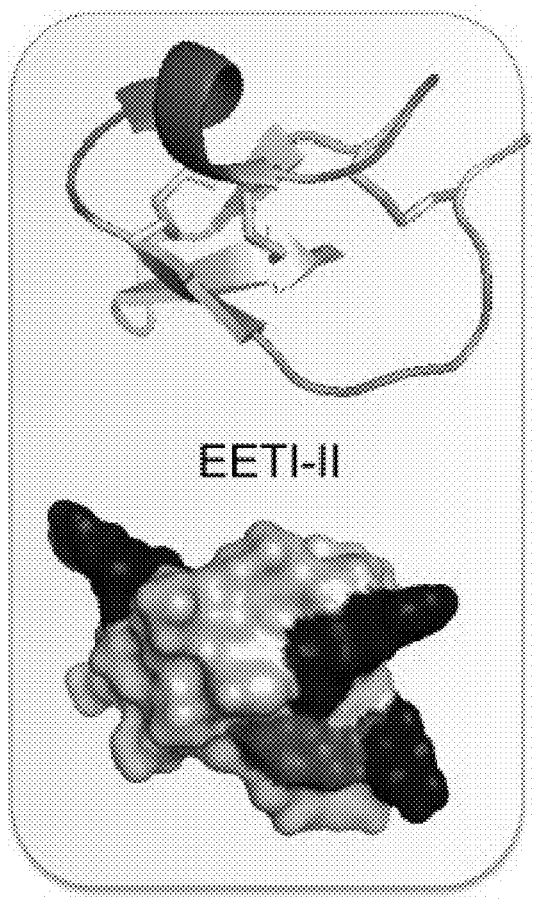
FIG. 1 depicts the structure of the EETI-II cystine knot protein.

Provided are non-naturally occurring cystine knot peptides (CKPs) that specifically bind human VEGF-A. Such non-naturally occurring CKPs demonstrate one or more of the following characteristics: inhibition of VEGF-A activity with and IC₅₀ between less than about 0.5 nM and less than about 1.0 nM; binding to human VEGF-A, mouse VEGF-A, and rat VEGF-A; resistance to trypsin digestion; a disulfide bond connectivity of C1-C4, C2-C3, and C5-C6; an alpha helix content of at least about at least about 15% to least about 50%; binding to an epitope on VEGF-A that is different from the epitope bound by antibody G6.31, binding to an epitope on VEGF-A that is different from the epitope bound by bevacizumab, and/or binding to an epitope on VEGF-A that is different from the epitope bound by Flt-1.

Also provided are chimeric molecules and conjugates comprising non-naturally occurring cystine knot peptides that bind VEGF-A, nucleic acids encoding non-naturally occurring CKPs that bind VEGF-A, and compositions (such as pharmaceutical compositions). Also provided are methods of using non-naturally occurring CKPs that bind VEGF-A for treating ocular diseases and/or disorders (such as ocular vascular proliferative diseases and/or disorders) resulting from abnormal (such as excessive) angiogenesis and/or abnormal vascular permeability. Also provided are uses of non-naturally occurring CKPs that bind VEGF-A in the manufacture of a medicament for the treatment of ocular disease or disorders.

In a related aspect, non-naturally occurring CKPs that bind human low density lipoprotein receptor-related protein 6 (LRP6) are also provided.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3$^{rd}$ edition, John Wiley & Sons, Hoboken, N.J., 2008; Sambrook, J. et al., "Molecular Cloning: A Laboratory Manual," 3$^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4$^{th}$ edition, John Wiley & Sons, Somerset, N J, 2000; and the series "Methods in Enzymology," Academic Press, San Diego, Calif.

Definitions

As used herein "non-naturally occurring" means, e.g., a polypeptide comprising an amino acid sequence that is not found in nature, or, e.g., a nucleic acid comprising a nucleotide sequence that is not found in nature. A "non-naturally occurring cystine knot peptide" or "non-naturally occurring CKP" (or a nucleic acid encoding the same) provided herein does not have the amino acid sequence of a wild type EETI-II protein, i.e., GCPRILMRCKQDSDCLAGCVCG-PNGFCG (SEQ ID NO: 1), wherein Loop 1 (L1) is the amino acid sequence PRILMR (SEQ ID NO: 92), Loop 2 (L2) is the amino acid sequence KQDSD (SEQ ID NO: 93), Loop 3 (L3) is the amino acid sequence LAG, Loop 4 (L4) is the amino acid V, and Loop 5 (L5) is the amino acid sequence GPNGF (SEQ ID NO: 15). A non-naturally occurring CKP provided herein can be produced by genetic engineering methods or by chemical synthesis methods. Thus, a non-naturally occurring CKP described herein may be recombinant, i.e., produced by a cell, or nucleic acid, or vector, that has been modified by the introduction of a heterologous nucleic acid or the alteration of a native nucleic acid to a form not native to that cell, or that the cell is derived from a cell so modified. Alternatively, a non-naturally occurring CKP described herein can be produced via chemical peptide synthesis.

As used herein, the term "cystine-knot peptide" or "CKP" refers to a peptide between 26-50 amino acids in length, which contain six conserved cysteine residues that form three disulfide bonds. One of the disulfides penetrates the macrocycle which is formed by the two other disulfides and their interconnecting backbones, thereby yielding a characteristic knotted topology with multiple loops exposed on the surface. The loops are defined as the amino acid regions which flank the six conserved cysteine residues and are highly variable in nature.

As used herein, an "amino acid alteration" refers to the addition, deletion, or substitution of at least one amino acid in, e.g., a peptide sequence (such as in the WT EETI-II peptide sequence to generate a non-naturally occurring CKP, or in a non-naturally occurring CKP to generate another non-naturally occurring CKP).

An "isolated" non-naturally occurring CKP or composition is one which has been identified and separated and/or recovered from a component of its natural environment. Contaminant components of its natural environment are materials which would interfere with diagnostic or therapeutic uses for the non-naturally occurring CKP, and can include enzymes, hormones, and other proteinaceous or nonproteinaceous solutes. In preferred embodiments, the non-naturally occurring CKP or composition will be purified (1) to greater than 95% by weight of non-naturally occurring CKP as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated non-naturally occurring CKP includes the CKP in situ within recombinant cells since at least one component of the CKP's natural environment will not be present. An isolated non-naturally occurring CKP will be prepared by at least one purification step.

"Percent (%) amino acid sequence identity" or "homology" with respect to the polypeptide sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

As used herein the term "epitope" refers to a protein determinant capable of being specifically bound by a non-naturally occurring CKP provided herein. An epitope can comprise between about 3-10 amino acids in a spatial conformation, which is unique to the epitope. These amino acids can be linear within the protein (i.e., consecutive in the amino acid sequence) or they can be positioned in different parts of the protein (i.e., non-consecutive in the amino acid sequence). Methods of determining the spatial conformation of amino acids within a protein, or at the interface of two proteins, are known in the art, and include, for example, x-ray crystallography and 2-dimensional nuclear magnetic resonance.

The terms "disulfide bonding pattern (DBP)," "disulfide bond connectivity," and "disulfide linkage pattern" refers to the linking pattern of the cysteines relative to the WT EETI-II protein. The WT EETI-II protein comprises six conserved cysteine residues (numbered 1-6) that form three disulfide bonds with connectivities C1-C4, C2-05, and C3-C6. The disulfide bonding pattern is topologically constant, meaning the disulfide bonds can only be changed by unlinking one or more disulfides such as using redox conditions.

A "subject," "patient," or an "individual" for purposes of treatment refers to any animal classified as a mammal, including humans, domestic and farm animals, and zoo, sports, or pet animals, such as dogs, horses, cats, cows, etc. Preferably, the mammal is human.

An "effective amount" of a non-naturally occurring CKP (or a composition comprising such a non-naturally occurring CKP) as disclosed herein is an amount sufficient to carry out a specifically stated purpose. An "effective amount" can be determined empirically and by known methods relating to the stated purpose.

The term "therapeutically effective amount" refers to an amount of a non-naturally occurring CKP or composition as disclosed herein, effective to "treat" a disease or disorder in a mammal (such as a human patient). In the case of ocular disease or ocular disorder (such as an ocular vascular proliferative disease or ocular disorder characterized by excessive angiogenesis), the therapeutically effective amount of a non-naturally occurring CKP that binds VEGF-A described herein (or a composition comprising such a non-naturally occurring VEGF-A-binding CKP) refers to the amount to reduce, stop or prevent at least one symptom of the ocular disease, such as a symptom or disorder of an ocular disease described in further detail elsewhere herein. For example, an effective amount would be considered as the amount sufficient to reduce or prevent a symptom of the ocular disease or ocular disorder (such as an ocular vascular proliferative disease or ocular disorder characterized by excessive angiogenesis), for example a complete or partial resolution and/or maintenance of the ocular disease as measured by optical coherence tomography (OCT) or an increase and/or maintenance in best corrected visual acuity (such as greater than 5 letters as assessed by EDTRS eye chart), or a reduction in the size of the neovascularization or neovascular permeability as assessed by fundus fluorescence angiography. An effective amount used herein would also include an amount sufficient to prevent or delay the development of, e.g., macular edema, enhanced permeability (such as retinal vascular permeability), size of CNV lesion, and vision loss. An effective amount as used herein would also include an amount sufficient to prevent or delay the development of a symptom of the ocular disease, alter the course of a symptom disease (for example but not limited to, slow the progression of a symptom of the ocular disease), or reverse a symptom of the disease.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the ocular disease, diminishing the extent of the ocular disease, stabilizing the ocular disease (e.g., preventing or delaying the worsening of the disease), preventing or delaying the spread of the disease (such as to surrounding ocular tissues), preventing or delaying the recurrence of the ocular disease, delay or slowing the progression of the ocular disease, ameliorating the disease state, providing a remission or resolution (partial or total) of the ocular disease, decreasing the dose of one or more other medications required to treat the ocular disease, delaying the progression of the ocular disease, increasing or improving the quality of life, and/or preventing or delaying vision loss. Also encompassed by "treatment" is a reduction of pathological consequence of an ocular disease (such as, for example, vision loss). The methods provided herein contemplate any one or more of these aspects of treatment.

A "disorder" is any condition that would benefit from treatment with a non-naturally occurring CKP that binds VEGF-A described herein. Non-limiting examples of VEGF-A-related disorders to be treated herein include ocular diseases and disorders (such as ocular vascular proliferative diseases or ocular disorders characterized by excessive angiogenesis), as described elsewhere herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as a target ligand). The term thus refers to the use of the materials, compositions, and methods provided herein for qualitative and quantitative determinations. In general, the particular technique used for detection is not critical for practice of the invention.

For example, "detecting" according to the invention may include: observing the presence or absence of a target ligand (including, but not limited to, a human low density lipoprotein receptor-related protein 6 (LRP6) polypeptide or a human vascular endothelial growth factor A (VEGF-A) polypeptide); a change in the levels of a target ligand; and/or a change in biological function/activity of a target ligand. In certain embodiments, "detecting" may include detecting levels of a target ligand (e.g., polypeptide levels of a human LRP6 or a human VEGF-A). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the non-naturally occurring CKP. The label may itself be detectable by itself (e.g., radioisotope labels or fluorescent labels) or, in the case of an enzymatic label, may catalyze chemical alteration of a substrate compound or composition which is detectable.

With regard to the binding of a non-naturally occurring CKP to a target ligand, the term "specific binding" or "specifically binds to" or is "specific for" a particular target ligand means that binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In certain embodiments, the extent of binding of the non-naturally occurring CKP to a "non-target" ligand will be less than about 10% of the binding of the non-naturally occurring CKP to its target ligand (such as LRP6 or VEGF-A) as determined by, e.g., fluorescence activated cell sorting (FACS) analysis or radioimmunoprecipitation (RIA). In certain embodiments, a non-naturally occurring CKP of the present disclosure specifically binds to a target ligand (such as human low density lipoprotein receptor-related protein 6 (LRP6) or human vascular endothelial growth factor A (VEGF-A)) with a dissociation constant (Kd) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM; measured at a temperature of about 4° C., 25° C., 37° C., or 45° C.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Non-Naturally Occurring Cystine Knot Peptides (CKPs) that Bind Human Vascular Endothelial Growth Factor A (VEGF-A)

In certain embodiments, provided herein is a non-naturally occurring cystine knot peptide (CKP) that binds to vascular endothelial growth factor A (VEGF-A), wherein the CKP comprises the following cystine scaffold structure (i.e., scaffold structure I):

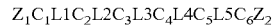

$$Z_1C_1L1C_2L2C_3L3C_4L4C_5L5C_6Z_2 \quad (I)$$

wherein:
  $Z_1$ and $Z_2$ are any amino acid;
  L1 is Loop 1 and has a structure selected from the group consisting of: $X_1X_2X_3X_4X_5X_6X_7X_8$,
    $X_1X_2X_3X_4X_5X_6X_7X_8X_9$, and
    $X_1X_2X_3X_4X_5X_6X_7X_8X_9X_{10}$, wherein each of $X_1$-$X_{10}$ is any amino acid;
  L2 is Loop 2 and has the structure: $X_1X_2X_3X_4X_5$, wherein each of $X_1$-$X_5$ is any amino acid or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

L3 is Loop 3 and has the structure: $X_1X_2X_3$ wherein each of $X_1$-$X_3$ is any amino acid or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

L4 is Loop 4 and has the structure: $X_1$, wherein $X_1$ is any amino acid or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluorobenzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide;

L5 is Loop 5 and has the structure: $X_1X_2X_3X_4X_5$, wherein each of $X_1$-$X_5$ is any amino acid or an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide; and wherein the CKP binds to VEGF-A with an affinity of 500 pM or less.

In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

In certain embodiments, the non-naturally occurring cystine knot peptide (CKP) that binds to VEGF-A has an altered disulfide bond connectivity—with reference to a wild-type *Ecballium elaterium* trypsin inhibitor EETI-II protein having the amino acid sequence set forth in SEQ ID NO: 1; wherein the altered disulfide bond connectivity is C1-C4, C2-C3 and C5-C6.

In certain embodiments, $Z_1$ and/or $Z_2$ of the non-naturally occurring cystine knot peptide (CKP) that binds to VEGF-A is G. In certain embodiments, $Z_1$ and/or $Z_2$ comprise more than one amino acid. In certain embodiments, $Z_1$ and/or $Z_2$ comprise 4 amino acids. In certain embodiments, $Z_1$ and/or $Z_2$ comprise 5 amino acids. In certain embodiments, $Z_1$ and/or $Z_2$ is an unnatural amino acid. In certain embodiments, the unnatural amino acid is N-acetylglycine or glycine amide. In certain embodiments, the non-naturally occurring cystine knot peptide (CKP) that binds to VEGF-A comprises an L1 wherein $X_3$ is not I; wherein $X_5$ is not M; and/or wherein $X_6$ is not R. In certain embodiments, the non-naturally occurring cystine knot peptide (CKP) that binds to VEGF-A comprises an L1 wherein $X_1$ is an amino acid selected from P, Q, R, T, V, D, N, K, L, and X; wherein $X_2$ is an amino acid selected from T, D, L, V, I, R, P, N and X; wherein $X_3$ is an amino acid selected from T, P, M, L, S, F, R, and X; wherein $X_4$ is an amino acid selected from R, T, Q, D, W, L, E, S, K, and X; wherein $X_5$ is an amino acid selected from F, P, V, E, K, L, I, and X; wherein $X_6$ is an amino acid selected from K, N, F, P, L, Y, T, D, M, and X; wherein $X_7$ is an amino acid selected from Q, W, H and/X; and/or wherein $X_8$ is an amino acid selected from Y, A, G, D, E, W, S, and X, wherein X is and unnatural amino acid is selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L1 wherein $X_9$ is an amino acid selected from L, I, V, D, E and X, wherein X is and unnatural amino acid is selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L- alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L1 wherein $X_{10}$ is an amino acid selected from Y, T, M, N, F, and X, wherein X is and unnatural amino acid is selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments, the non-naturally occurring cystine knot peptide (CKP) that binds to VEGF-A comprises an L5 wherein each of $X_1$-$X_5$ is any amino acid or an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone (NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide; with the exception that $X_2$ is not proline (P).

In certain embodiments, the non-naturally occurring cystine knot peptide (CKP) that binds to VEGF-A comprises an L5 wherein each of $X_1$-$X_5$ is any amino acid or an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone (NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide, with the exception that $X_4$ is not glycine (G). In certain embodiments, the non-naturally occurring cystine knot peptide (CKP) that binds to VEGF-A comprises an L5 wherein $X_1$ is an amino acid selected from G, Q, H, R, L, and Q; wherein $X_2$ is an amino acid selected from P, M, W, Y, F, L, and H; wherein $X_3$ is an amino acid selected from N, F, H, and Y; wherein $X_4$ is an amino acid selected from G, Q, D, N, K, H, E, and S; and/or wherein $X_5$ is an amino acid selected from F, S, and T. In certain embodiments, the non-naturally occurring cystine knot peptide (CKP) that binds to VEGF-A comprises an L2 wherein $X_1$ is K, $X_2$ is Q, $X_3$ is D, $X_4$ is S, and $X_5$ is D. In certain embodiments, the non-naturally occurring cystine knot peptide (CKP) that binds to VEGF-A comprises an L3 wherein $X_1$ is L, $X_2$ is A, and $X_3$ is G. In certain embodiments, the non-naturally occurring cystine knot peptide (CKP) that binds to VEGF-A comprises an L4 wherein $X_1$ is V or F.

In certain embodiments, the non-naturally occurring cystine knot peptide (CKP) that binds to VEGF-A comprises an L1 comprising the structure $X_1X_2X_3X_4X_5X_6X_7X_8$, wherein: $X_1$ is an amino acid selected from P, Q, and R; $X_2$ is an amino acid selected from T, L, and D; $X_3$ is an amino acid selected from T, M and L; $X_4$ is an amino acid selected from R, Q, and D; $X_5$ is an amino acid selected from F, P, and V; $X_6$ is an amino acid selected from K and F; $X_7$ is an amino acid selected from Q and W; and $X_8$ is an amino acid selected from Y, G, and D. In certain embodiments, the non-naturally occurring cystine knot peptide (CKP) that binds to VEGF-A comprises an L1 comprising the structure $X_1X_2X_3X_4X_5X_6X_7X_8X_9X_{10}$, wherein $X_1$ is an amino acid selected from Q, R, T and V; $X_2$ is an amino acid selected from T and D; $X_3$ is P; $X_4$ is an amino acid selected from T and W; $X_5$ is an amino acid selected from F, E, P, and K; $X_6$ is an amino acid selected from N and P; $X_7$ is an amino acid selected from W and H; $X_8$ is an amino acid selected from A, D, E, and W; $X_9$ is an amino acid selected from L and I; and $X_{10}$ is an amino acid selected from Y, T, M and N. In certain embodiments, the non-naturally occurring cystine knot peptide (CKP) that binds to VEGF-A comprises an L5 wherein $X_1$ is an amino acid selected from G, H, and Q; $X_2$ is an amino acid selected from P, M, W, and Y; $X_3$ is an amino acid selected from N and Y; $X_4$ is an amino acid selected from G, Q, and S; and $X_5$ is an amino acid selected from F and S. In certain embodiments, the non-naturally occurring cystine knot peptide (CKP) that binds to VEGF-A comprises an L2 wherein $X_1$ is K, $X_2$ is Q, $X_3$ is D, $X_4$ is S, and $X_5$ is D. In certain embodiments, the non-naturally occurring cystine knot peptide (CKP) that binds to VEGF-A comprises an L3 wherein $X_1$ is L, $X_2$ is A, and $X_3$ is G. In certain embodiments, the non-naturally occurring cystine knot peptide (CKP) that binds to VEGF-A comprises an L4 wherein $X_1$ is V or F.

In certain embodiments, the non-naturally occurring cystine knot peptide (CKP) that binds to VEGF-A comprises an L1 having the structure $X_1X_2X_3X_4X_5X_6X_7X_8$, wherein: $X_1$ is an amino acid selected from D, Q, N, and K; $X_2$ is an amino acid selected from V, I, R, L, and P; $X_3$ is an amino acid selected from L, S, M, T, and F; $X_4$ is an amino acid selected from Q, L, and E; $X_5$ is P; $X_6$ is an amino acid selected from F, L, and Y; $X_7$ is W; and $X_8$ is G. In certain embodiments, the non-naturally occurring cystine knot peptide (CKP) that binds to VEGF-A comprises an L5 wherein $X_3$ is Y; $X_5$ is S; and wherein $X_1$, $X_2$ and $X_4$ are each any amino acid, with the exception that $X_1$ is not G, $X_2$ is not P, $X_4$ is not G, and/or $X_5$ is not F. In certain embodiments, the non-naturally occurring cystine knot peptide (CKP) that binds to VEGF-A comprises an L5 wherein $X_1$ is an amino acid selected from H, L, R, and Q; $X_2$ is an amino acid selected from W, F, and Y; $X_3$ is Y; $X_4$ is an amino acid selected from Q, N, K, H, and E; and $X_5$ is S. In certain embodiments, the non-naturally occurring cystine knot peptide (CKP) that binds to VEGF-A comprises an L2 wherein $X_1$ is K, $X_2$ is Q, $X_3$ is D, $X_4$ is S, and $X_5$ is D. In certain embodiments, the non-naturally occurring cystine knot peptide (CKP) that binds to VEGF-A comprises an L3 wherein $X_1$ is L, $X_2$ is A, and $X_3$ is G. In certain embodiments, the non-naturally occurring cystine knot peptide (CKP) that binds to VEGF-A comprises an L4 wherein $X_1$ is V or F.

In certain embodiments, the non-naturally occurring cystine knot peptide (CKP) that binds to VEGF-A comprises an L1 comprising the structure $X_1X_2X_3X_4X_5X_6X_7X_8X_9X_{10}$, wherein $X_1$ is an amino acid selected from K, Q, L, and R; $X_2$ is an amino acid selected from N and D; $X_3$ is an amino acid selected from P and L; $X_4$ is an amino acid selected from L, T, S and K; $X_5$ is an amino acid selected from F, V, I, and L; $X_6$ is an amino acid selected from N and D; $X_7$ is W; $X_8$ is an amino acid selected from A and S; $X_9$ is an amino acid selected from L, V, E and D; and $X_{10}$ is an amino acid selected from Y and F. In certain embodiments, the non-naturally occurring cystine knot peptide (CKP) that binds to VEGF-A comprises an L5 wherein $X_1$ is Q; $X_2$ is an amino acid selected from L, F, M, and H; $X_3$ is an amino acid selected from F, Y, and H; $X_4$ is an amino acid selected from D, Q, N, and K; and $X_5$ is an amino acid selected from S and T. In certain embodiments, the non-naturally occurring cystine knot peptide (CKP) that binds to VEGF-A comprises an L2 wherein $X_1$ is K, $X_2$ is Q, $X_3$ is D, $X_4$ is S, and $X_5$ is D. In certain embodiments, the non-naturally occurring cystine knot peptide (CKP) that binds to VEGF-A comprises an L3 wherein $X_1$ is L, $X_2$ is A, and $X_3$ is G. In certain embodiments, the non-naturally occurring cystine knot peptide (CKP) that binds to VEGF-A comprises an L4 wherein $X_1$ is V or F.

In certain embodiments, the non-naturally occurring cystine knot peptide (CKP) that binds to VEGF-A comprises an L1 comprising the structure $X_1X_2X_3X_4X_5X_6X_7X_8$, wherein: $X_5$ is P; $X_7$ is W; $X_8$ is G; and wherein $X_1$, $X_2$, $X_3$, $X_4$ and $X_6$ are each any amino acid, with the exception that $X_1$ is not P, $X_2$ is not R, $X_3$ is not I, and/or $X_6$ is not R. In certain embodiments, the non-naturally occurring cystine knot peptide (CKP) that binds to VEGF-A comprises an L1 comprising the structure $X_1X_2X_3X_4X_5X_6X_7X_8$, wherein $X_1$ is an amino acid selected from N and D; $X_2$ is an amino acid selected from I and V; $X_3$ is an amino acid selected from M and L; $X_4$ is an amino acid selected from L, Q, D and K; $X_5$ is P; $X_6$ is an amino acid selected from F, Y, T, L, and M; $X_7$ is W; and $X_8$ is G. In the non-naturally occurring cystine knot peptide (CKP) that binds to VEGF-A comprises an L5 wherein $X_1$ is an amino acid selected from Q, H, L, and R; $X_2$ is an amino acid selected from Y and W; $X_3$ is Y; $X_4$ is an amino acid selected from Q and N; and $X_5$ is S. In certain embodiments, the non-naturally occurring cystine knot peptide (CKP) that binds to VEGF-A comprises an L5 wherein $X_3$ is Y; $X_5$ is 5; and wherein $X_1$, $X_2$, and $X_4$ are each any amino acid, with the exception that $X_1$ is not G, $X_2$ is not P, and/or $X_4$ is not G. In certain embodiments, the non-naturally occurring cystine knot peptide (CKP) that binds to VEGF-A comprises an L2 wherein $X_1$ is an amino acid selected from G or E; $X_2$ is an amino acid selected from Q, L, P, R, E, and M; $X_3$ is an amino acid selected from S, D, and N; $X_4$ is an amino acid selected from F, Y, L, M, and I; and/or $X_5$ is an amino acid selected from E, D, Q, L, and S. In certain embodiments, the non-naturally occurring cystine knot peptide (CKP) that binds to VEGF-A comprises an L3 wherein $X_1$ is L, $X_2$ is A, and $X_3$ is G. In certain embodiments, the non-naturally occurring cystine knot peptide (CKP) that binds to VEGF-A comprises an L4 wherein $X_1$ is V or F.

In certain embodiments, the non-naturally occurring cystine knot peptide (CKP) that binds to VEGF-A comprises an L5, wherein each of $X_1$-$X_5$ is any amino acid with the exception that $X_2$ is not proline (P). In certain embodiments, the non-naturally occurring cystine knot peptide (CKP) that binds to VEGF-A comprises an L5, wherein each of $X_1$-$X_5$ is any amino acid with the exception that $X_4$ is not glycine (G). In certain embodiments, the non-naturally occurring cystine knot peptide (CKP) that binds to VEGF-A comprises an L5, wherein $X_1$ is any amino acid except G; $X_2$ is any amino acid except P; $X_3$ is any amino acid except N; $X_4$ is any amino acid except G; and/or $X_5$ is any amino acid except F.

In certain embodiments, the non-naturally occurring cystine knot peptide (CKP) that binds to VEGF-A comprises an L1 comprising the structure $X_1X_2X_3X_4X_5X_6X_7X_8$, wherein $X_1$ is an amino acid selected from N, D, and X; $X_2$ is an amino acid selected from I, V, and X; $X_3$ is M or X; $X_4$ is an amino acid selected from L, Q, and X; $X_5$ is P or X; $X_6$ is F, Y, or X; $X_7$ is W or X; and $X_8$ is G or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L3 wherein each of $X_1$-$X_3$ is any amino acid or an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide, with the exception that $X_1$ is not Leucine (L), $X_2$ is not Alanine (A), and $X_3$ is not glycine (G), wherein the unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L3 wherein $X_1$ is an amino acid selected from M, F, L V, and X; $X_2$ is an amino acid selected from S, N, Q, I, Y, E, V, T, and X; and $X_3$ is an amino acid selected from D, Q, T, N, E, R, and X, wherein X is an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L4 wherein $X_1$ is any amino acid except V, or an unnatural amino acid selected from the group consisting of L-propargylglycine-$PEG_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L- alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L4 wherein $X_1$ is I, L, or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L5 wherein $X_3$ is Y or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide; $X_5$ is S or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone (NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide; and wherein $X_1$, $X_2$, and $X_4$ are each any amino acid or an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide, with the exception that $X_1$ is not G, $X_2$ is not P, and/or $X_4$ is not G. In certain embodiments, the non-naturally occurring cystine knot peptide (CKP) that binds to VEGF-A comprises an L5, wherein each of $X_1$-$X_5$ is any amino acid with the exception that $X_2$ is not proline (P). In certain embodiments, the non-naturally occurring cystine knot peptide (CKP) that binds to VEGF-A comprises an L5 wherein each of $X_1$-$X_5$ is any amino acid with the exception that $X_4$ is not glycine (G). In certain embodiments, the non-naturally occurring cystine knot peptide (CKP) that binds to VEGF-A comprises an L5 wherein $X_1$ is an amino acid selected from Q, H, and X; $X_2$ is an amino acid selected from Y, W, and X; $X_3$ is Y or X; $X_4$ is an amino acid selected from Q, N, or X; $X_5$ is S or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluorobenzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide. In certain embodiments, the non-naturally occurring cystine knot peptide (CKP) that binds to VEGF-A comprises an L2 wherein $X_1$ is G or X; $X_2$ is R, P, or X; $X_3$ is D or X; $X_4$ is F, I, or X; and $X_5$ is E, D, or X, wherein X is an unnatural amino acid selected from the group consisting of L-propargylglycine-PEG$_6$-, L-sulfotyrosine, L-norleucine, L-1-naphthylalanine, L-2-naphthylalanine, L-2-chlorotryptophan, L-3-fluorotyrosine, L-4-fluorophenylalanine, gamma-benzyl-L-proline, gamma-(4-fluoro-benzyl)-L-proline, 4-OH-L-proline, 4-fluoro-L-proline, 4-[4-(trifluoromethyl)-benzyl]-L-proline, 3,4-difluoro-L-phenylalanine, 3,4-dichloro-L-phenylalanine, 4-chloro-L-phenylalanine, 3-F,4-Cl-L-phenylalanine, 2-pyridone(NH para)-L-alanine, pyridone(NH meta)-L-alanine, 3-(1-N-methyl indole)-L-alanine, 3-(1-N-ethyl indole)-L-alanine, 3-(1-N-isopropyl indole)-L-alanine, 3-(5-aza-indole)-L-alanine, 4-methyl-L-phenylalanine, 2-naphthyl-L-alanine, L-4,4'-biphenylalanine, 3-(3-quinolinyl)-L-alanine, 3-(2-quinolinyl)-L-alanine, 3-(2-quinoxalinyl)-L-alanine, 4-methyl-2-pyridyl-alanine, 4-ethyl-2-pyridyl-L-alanine, benzothiazole-L-alanine, benzothiophene-L-alanine, 3-isoquinolinyl-L-alanine, t-butyl-L-alanine (also known as L-Nepentyl glycine), 3-cyclobutyl-L-alanine, cyclopentyl-L-alanine, 5,5,5-Trifluoro-L-leucine, t-butyl-L-glycine (also known as L-tert-Leucine), L-cyclopentylglycine, L-cyclobutylglycine, 3,4-hydroxy-L-phenylalanine, 3,4-fluoro-L-phenylalanine, 3-fluoro,4-OH-L-phenylalanine, 2-chloro-L-tyrosine, 2-methyl-L-tyrosine, 2-ethyl-L-tyrosine, 4-(naphthalen-1-ol)-L-alanine, D-serine, L-beta-homoserine, L-beta-alanine, N-alpha-methyl glycine, glycine amide, glycine ester of glycerol, glycine ester of glycol, glycine ester of oxetane-3-yl, and glycine morpholine amide.

In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

Also provided herein is a non-naturally occurring cystine knot peptide (CKP) that binds to VEGF-A, wherein the CKP comprises the cystine scaffold structure provided below (i.e., scaffold structure I):

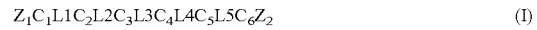

$$Z_1C_1L1C_2L2C_3L3C_4L4C_5L5C_6Z_2 \quad (I)$$

wherein:

$Z_1$ and $Z_2$ are any amino acid;

L1 is Loop 1 and has a structure selected from the group consisting of: $X_1X_2X_3X_4X_5X_6X_7X_8$, $X_1X_2X_3X_4X_5X_6X_7X_8X_9$, and $X_1X_2X_3X_4X_5X_6X_7X_8X_9X_{10}$, wherein each of $X_1$-$X_{10}$ is any amino acid;

L2 is Loop 2 and has the structure: $X_1X_2X_3X_4X_5$, wherein each of $X_1$-$X_5$ is any amino acid;

L3 is Loop 3 and has the structure: $X_1X_2X_3$ wherein each of $X_1$-$X_3$ is any amino acid;

L4 is Loop 4 and has the structure: $X_1$, wherein $X_1$ is any amino acid;

L5 is Loop 5 and has the structure: $X_1X_2X_3X_4X_5$, wherein each of $X_1$-$X_5$ is any amino acid; wherein the CKP has an altered disulfide bond connectivity with reference to a wild-type *Ecballium elaterium* trypsin inhibitor EETI-II protein having the amino acid sequence set forth in SEQ ID NO: 1; wherein the altered disulfide bond connectivity is C1-C4, C2-C3 and C5-C6; and wherein the CKP has a percent alpha helix content of at least about 15%, at least about 20%, at least about 25%, at least about 30%, at least about 35%, at least about 40%, at least about 45%, or at least about 50%, including any range in between these values.

In certain embodiments, the non-naturally occurring CKP binds to VEGF-A with an affinity of about 500 pM or less.

In certain embodiments, the binding affinity of the non-naturally occurring CKP to VEGF-A is determined via, e.g., surface plasmon resonance or other assays detailed in the Examples below.

In certain embodiments, $Z_1$ and/or $Z_2$ of the non-naturally occurring cystine knot peptide (CKP) that binds to VEGF-A is G. In certain embodiments, $Z_1$ and/or $Z_2$ comprise more than one amino acid. In certain embodiments, $Z_1$ and/or $Z_2$ comprise 4 amino acids. In certain embodiments, $Z_1$ and/or $Z_2$ comprise 5 amino acids. In certain embodiments, $Z_1$ and/or $Z_2$ is an unnatural amino acid. In certain embodiments, the unnatural amino acid is N-acetylglycine or glycine amide.

In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

In certain embodiments, the non-naturally occurring CKP that binds VEGF-A comprises an L5 wherein each of $X_1$-$X_5$ is any amino acid with the exception that $X_2$ is not proline (P). In certain embodiments, the non-naturally occurring CKP that binds VEGF-A comprises an L5, each of $X_1$-$X_5$ is any amino acid with the exception that $X_4$ is not glycine (G). In certain embodiments, the non-naturally occurring CKP that binds VEGF-A inhibits VEGF-A activity with and $IC_{50}$ of about 0.5 nM to about 1.0 nM. In certain embodiments, the degree of inhibition is determined via a cellular $IC_{50}$ assay, as described in further detail in the Examples below.

In certain embodiments, the non-naturally occurring CKP that binds VEGF-A comprises an L1 comprising the amino acid sequence HMMYDY (SEQ ID NO: 231) or K/P/Q/R-K/T/L/D-W/T/M/L-Q/R/D-W/F/P/V-W/K/F-Y/Q/W-M/Y/G/D (SEQ ID NO: 115) or E/G/P/Q/R/T/V-T/E/A/D-D/T/I/P-W/V/Q/T/W-Y/F/N/E/P/K-P/E/W/N/P-H/Q/K/W/H-Q/F/E/A/D/W-I/L/H-D/W/P/Y/T/M/N (SEQ ID NO: 232), with reference to scaffold structure I above. In certain embodiments, the non-naturally occurring CKP that binds VEGF-A further comprises an L2 comprising the amino acid sequence KQDSD (SEQ ID NO: 93). In certain embodiments, the non-naturally occurring CKP that binds VEGF-A further comprises an L3 comprising the amino acid sequence LAG. In certain embodiments, the non-naturally occurring CKP that binds VEGF-A comprises an L4 comprising V or F. In certain embodiments, the non-naturally occurring CKP that binds VEGF-A comprises an L5 comprising the amino acid sequence G/E/Y/Q/H-P/M/W/Y-N/Y/W-G/D/T/Q/R/S-F/A/E/S (SEQ ID NO: 20) or SWWPSL (SEQ ID NO: 237).

In certain embodiments, the non-naturally occurring CKP that binds VEGF-A comprises an L1 comprising an amino acid sequence selected from the group consisting of SEQ ID NOs: 8-14 and 225-230, with reference to scaffold structure I above. In certain embodiments, the non-naturally occurring CKP that binds VEGF-A further comprises an L2 comprising the amino acid sequence KQDSD (SEQ ID NO: 93). In certain embodiments, the non-naturally occurring CKP that binds VEGF-A further comprises an L3 comprising the amino acid sequence LAG. In certain embodiments, the non-naturally occurring CKP that binds VEGF-A comprises an L4 comprising V or F. In certain embodiments, the non-naturally occurring CKP that binds VEGF-A further comprises an L5 comprising an amino acid sequence selected from the group consisting of SEQ ID NOs 15-18 and 233-238). The amino acid sequences of SEQ ID NOs 8-18, 225-230, and 233-238 are provided in Table 1 below.

TABLE 1

| | |
|---|---|
| ETDWYPHQID | (SEQ ID NO: 225) |
| GETVFEQFLW | (SEQ ID NO: 226) |
| HMMYDY | (SEQ ID NO: 227) |
| KKWQWWYM | (SEQ ID NO: 228) |
| PAIQNWKEHP | (SEQ ID NO: 229) |
| PTTRFKQY | (SEQ ID NO: 8) |
| QDPTFNWALY | (SEQ ID NO: 9) |
| QLMHPFWG | (SEQ ID NO: 230) |
| QLMQPFWG | (SEQ ID NO: 10) |
| RDLDVKWD | (SEQ ID NO: 11) |
| RTPWEPHDIT | (SEQ ID NO: 12) |
| TTPWPPHEIM | (SEQ ID NO: 13) |
| VTPWKPHWIN | (SEQ ID NO: 14) |
| GPNGF | (SEQ ID NO: 233) |
| GPNGF | (SEQ ID NO: 234) |
| EMYDA | (SEQ ID NO: 235) |
| YPWTE | (SEQ ID NO: 236) |
| SWWPSL | (SEQ ID NO: 237) |
| GPNGF | (SEQ ID NO: 15) |
| QMYQS | (SEQ ID NO: 16) |
| HWYRS | (SEQ ID NO: 238) |
| HWYQS | (SEQ ID NO: 17) |
| QYYSS | (SEQ ID NO: 18) |
| GPNGF | (SEQ ID NO: 19) |

In certain embodiments, the non-naturally occurring VEGF-A binding CKP comprises the amino acid sequence on any one of SEQ ID NOs: 21-17 and 239-244. The amino acid sequences of SEQ ID NOs: 21-17 and 239-244 are provided in Table 2 below.

TABLE 2

| | |
|---|---|
| GCETDWYPHQIDCKQDSDCLAGCVCGPNGFCG | (SEQ ID NO: 239) |
| GCGETVFEQFLWCKQDSDCLAGCVCGPNGFCG | (SEQ ID NO: 240) |
| GCHMMYDYCKQDSDCLAGCVCEMYDACG | (SEQ ID NO: 241) |
| GCKKWQWWYMCKQDSDCLAGCVCYPWTECG | (SEQ ID NO: 242) |
| GCPAIQNWKEHPCKQDSDCLAGCVCSWWPSLCG | (SEQ ID NO: 243) |
| GCPTTRFKQYCKQDSDCLAGCVCGPNGFCG | (SEQ ID NO: 21) |
| GCQDPTFNWALYCKQDSDCLAGCVCQMYQSCG | (SEQ ID NO: 22) |
| GCQLMHPFWGCKQDSDCLAGCVCHWYRSCG | (SEQ ID NO: 244) |
| GCQLMQPFWGCKQDSDCLAGCVCHWYQSCG | (SEQ ID NO: 23) |
| GCRDLDVKWDCKQDSDCLAGCFCQYYSSCG | (SEQ ID NO: 24) |
| GCRTPWEPHDITCKQDSDCLAGCVCGPNGFCG | (SEQ ID NO: 25) |

TABLE 2-continued

```
GCTTPWPPHEIMCKQDSDCLAGCVCGPNGFCG    (SEQ ID NO: 26)
GCVTPWKPHWINCKQDSDCLAGCVCGPNGFCG    (SEQ ID NO: 27)
```

In certain embodiments, the non-naturally occurring VEGF-A binding CKP comprises an L1 comprising the amino acid sequence Q/H/E/N/D-L/V/R/P/I-M/F/L-Q/E/R/L-P-F/A/L/S-W-G (SEQ ID NO: 358), with reference to scaffold structure I above. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. IN certain embodiments the non-naturally occurring VEGF-A binding CKP further comprises an L5 comprising the amino acid sequence HWYQS (SEQ ID NO: 17).

In certain embodiments, the non-naturally occurring VEGF-A binding CKP comprises an L1 comprising an amino acid sequence selected from the group consisting of SEQ ID NOs 33, 36, and 245-253, with reference to scaffold structure I. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence HWYQS (SEQ ID NO: 17). The amino acid sequences of SEQ ID NOs 33, 36, and 245-253 are provided in Table 3 below:

TABLE 3

```
HLFEPLWG    (SEQ ID NO: 245)
QVMRPFWG    (SEQ ID NO: 246)
QVMQPAWG    (SEQ ID NO: 247)
HRLQPLWG    (SEQ ID NO: 248)
ELLQPSWG    (SEQ ID NO: 249)
NPMLPFWG    (SEQ ID NO: 368)
NVLLPLWG    (SEQ ID NO: 250)
DIMQPLWG    (SEQ ID NO: 36)
DLMQPLWG    (SEQ ID NO: 251)
NPMLPLWG    (SEQ ID NO: 252)
QVLQPSWG    (SEQ ID NO: 253)
```

In certain embodiments, the non-naturally occurring VEGF-A binding CKP comprises the amino acid sequence on any one of SEQ ID NOs: 265-275. The amino acid sequences of SEQ ID NOs: 265-275 are provided in Table 4 below.

TABLE 4

```
GCHLFEPLWGCKQDSDCLAGCVCHWYQSCG    (SEQ ID NO: 265)
GCQVMRPFWGCKQDSDCLAGCVCHWYQSCG    (SEQ ID NO: 266)
GCQVMQPAWGCKQDSDCLAGCVCHWYQSCG    (SEQ ID NO: 267)
GCHRLQPLWGCKQDSDCLAGCVCHWYQSCG    (SEQ ID NO: 268)
GCELLQPSWGCKQDSDCLAGCVCHWYQSCG    (SEQ ID NO: 269)
GCNPMLPFWGCKQDSDCLAGCVCHWYQSCG    (SEQ ID NO: 270)
GCNVLLPLWGCKQDSDCLAGCVCHWYQSCG    (SEQ ID NO: 271)
GCDIMQPLWGCKQDSDCLAGCVCHWYQSCG    (SEQ ID NO: 272)
GCDLMQPLWGCKQDSDCLAGCVCHWYQSCG    (SEQ ID NO: 273)
GCNPMLPLWGCKQDSDCLAGCVCHWYQSCG    (SEQ ID NO: 58)
GCQVLQPSWGCKQDSDCLAGCVCHWYQSCG    (SEQ ID NO: 275)
```

In certain embodiments, the non-naturally occurring VEGF-A binding CKP further comprises an L1 comprising the amino acid sequence QLMQPFWG (SEQ ID NO: 10), with reference to scaffold structure I. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments, the non-naturally occurring VEGF-A binding CKP comprises an L5 comprising the amino acid sequence R/H-W-Y-N/Q/H-S(SEQ ID NO: 359).

In certain embodiments, the non-naturally occurring VEGF-A binding CKP further comprises an L1 comprising the amino acid sequence QLMQPFWG (SEQ ID NO: 10), with reference to scaffold structure I above. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments, the non-naturally occurring VEGF-A binding CKP comprises an L5 comprising an amino acid sequence selected from the group consisting of HWYQS (SEQ ID NO: 17), RWYHS (SEQ ID NO: 43), and RWYNS (SEQ ID NO: 133).

In certain embodiments, the non-naturally occurring VEGF-A binding CKP comprises an amino acid sequence selected from the group consisting of SEQ ID NOs: 23, 276, and 278. SEQ ID NOs 23, 276, and 278 are provided in Table 5 below.

TABLE 5

```
GCQLMQPFWGCKQDSDCLAGCVCRWYNSCG    (SEQ ID NO: 276)
GCQLMQPFWGCKQDSDCLAGCVCHWYQSCG    (SEQ ID NO: 23)
GCQLMQPFWGCKQDSDCLAGCVCRWYHSCG    (SEQ ID NO: 278)
```

In certain embodiments, the non-naturally occurring VEGF-A binding CKP comprises an L1 comprising the amino acid sequence Q/D/K/N/A/R/H-L/V/I/R/P/V/-M/L/S/

T/F-Q/E/L/H-P-F/L/M/Y/S-W-G (SEQ ID NO: 40), with reference to scaffold structure I. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence H/L/R/Q/-W/F/Y-Y-Q/N/K/H/D/E-S (SEQ ID NO: 360).

In certain embodiments, the non-naturally occurring VEGF-A binding CKP comprises an L1 comprising an amino acid sequence selected from the group consisting of SEQ ID NOs: 28-39 and 254-261, with reference to scaffold structure I. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising an amino acid sequence selected from the group consisting of SEQ ID NOs: 17, 41-46, 133, 262-264, and 567. The amino acid sequences of SEQ ID NOs: 17, 28-39, 41-46, 133, 254-264, and 567 are provided in Table 6 below:

TABLE 6

| | | | |
|---|---|---|---|
| DVLQPFWG | (SEQ ID NO: 28) | HWYQS | (SEQ ID NO: 17) |
| QISQPFWG | (SEQ ID NO: 29) | HFYNS | (SEQ ID NO: 41) |
| DRMQPLWG | (SEQ ID NO: 30) | LWYKS | (SEQ ID NO: 42) |
| QLLEPMWG | (SEQ ID NO: 254) | HWYNS | (SEQ ID NO: 46) |
| KLLQPMWG | (SEQ ID NO: 255) | QWYKS | (SEQ ID NO: 262) |
| DRMQPYWG | (SEQ ID NO: 256) | RWYHS | (SEQ ID NO: 43) |
| NLMLPFWG | (SEQ ID NO: 31) | RWYQS | (SEQ ID NO: 44) |
| QRTQPFWG | (SEQ ID NO: 32) | LWYDS | (SEQ ID NO: 263) |
| KIMQPLWG | (SEQ ID NO: 257) | QYYQS | (SEQ ID NO: 45) |
| NLMHPFWG | (SEQ ID NO: 258) | RWYNS | (SEQ ID NO: 133) |
| NIMLPFWG | (SEQ ID NO: 33) | QWYQS | (SEQ ID NO: 264) |
| DPMQPFWG | (SEQ ID NO: 34) | NPMLPLWG | (SEQ ID NO: 38) |
| DVMQPYWG | (SEQ ID NO: 35) | KLFEPLWG | (SEQ ID NO: 39) |
| DIMQPLWG | (SEQ ID NO: 36) | RWYES | (SEQ ID NO: 567) |
| ALLQPLWG | (SEQ ID NO: 259) | | |
| QLLQPLWG | (SEQ ID NO: 37) | | |
| RLLEPSWG | (SEQ ID NO: 260) | | |
| HLLLPLWG | (SEQ ID NO: 261) | | |

In certain embodiments, the non-naturally occurring VEGF-A binding CKP comprises an amino acid sequence selected from the group consisting of SEQ ID NOs: 47-59 and 279-286. The amino acid sequences of SEQ ID NOs: 47-59 and 279-286 are provided in Table 7 below.

TABLE 7

| | |
|---|---|
| GCDVLQPFWGCKQDSDCLAGCVCHWYQSCG | (SEQ ID NO: 47) |
| GCQISQPFWGCKQDSDCLAGCVCHFYNSCG | (SEQ ID NO: 48) |
| GCDRMQPLWGCKQDSDCLAGCVCLWYKSCG | (SEQ ID NO: 49) |
| GCQLLEPMWGCKQDSDCLAGCVCHWYNSCG | (SEQ ID NO: 279) |
| GCKLLQPMWGCKQDSDCLAGCVCRWYQSCG | (SEQ ID NO: 280) |
| GCDRMQPYWGCKQDSDCLAGCVCQWYKSCG | (SEQ ID NO: 281) |
| GCNLMLPFWGCKQDSDCLAGCVCRWYHSCG | (SEQ ID NO: 50) |
| GCQRTQPFWGCKQDSDCLAGCVCRWYQSCG | (SEQ ID NO: 51) |
| GCKIMQPLWGCKQDSDCLAGCVCLWYDSCG | (SEQ ID NO: 282) |
| GCNLMHPFWGCKQDSDCLAGCVCHWYQSCG | (SEQ ID NO: 283) |
| GCNIMLPFWGCKQDSDCLAGCVCQYYQSCG | (SEQ ID NO: 52) |
| GCNPMLPFWGCKQDSDCLAGCVCHWYQSCG | (SEQ ID NO: 53) |
| GCDPMQPFWGCKQDSDCLAGCVCRWYQSCG | (SEQ ID NO: 54) |
| GCDVMQPYWGCKQDSDCLAGCVCHWYNSCG | (SEQ ID NO: 55) |
| GCDIMQPLWGCKQDSDCLAGCVCHWYQSCG | (SEQ ID NO: 56) |
| GCALLQPLWGCKQDSDCLAGCVCRWYNSCG | (SEQ ID NO: 284) |
| GCQLLQPLWGCKQDSDCLAGCVCRWYQSCG | (SEQ ID NO: 57) |
| GCRLLEPSWGCKQDSDCLAGCVCQWYQSCG | (SEQ ID NO: 285) |
| GCHLLLPLWGCKQDSDCLAGCVCRWYHSCG | (SEQ ID NO: 286) |
| GCNPMLPLWGCKQDSDCLAGCVCHWYQSCG | (SEQ ID NO: 58) |
| GCKLFEPLWGCKQDSDCLAGCVCRWYESCG | (SEQ ID NO: 59) |

In certain embodiments, the non-naturally occurring VEGF-A binding CKP comprises an L1 comprising the amino acid sequence Q/D/K/W/E/L/R-D/N-P/R/L/T-T/S/L/K-F/V/L/I-N/D-W-A/S/G-L/V/E/T/Q/D-F/Y(SEQ ID NO: 70), with reference to scaffold structure I. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence Q/R-M/L/F/H-Y/F/H-D/Q/N/K-S/T (SEQ ID NO: 80).

In certain embodiments, the non-naturally occurring VEGF-A binding CKP comprises an L1 comprising an amino acid sequence selected from the group consisting of SEQ ID NOs: 60-69 and 287-291. In certain embodiments the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising an amino acid sequence selected from the group consisting of SEQ ID NOs: 16, 71-79, 274, and 292. The amino acid sequences of SEQ ID NOs: 16, 60-69, 71-79, 274, and 287-292 are provided in Table 8 below.

TABLE 8

| | |
|---|---|
| DDPSFDWSVY (SEQ ID NO: 287) | RMYDS (SEQ ID NO: 292) |
| KNPLFNWALY (SEQ ID NO: 60) | QLFDS (SEQ ID NO: 71) |
| QDPTVNWAVY (SEQ ID NO: 61) | QFYQS (SEQ ID NO: 72) |
| QDPTFNWAEY (SEQ ID NO: 62) | QLYQS (SEQ ID NO: 73) |
| WDPTFNWALY (SEQ ID NO: 288) | QMYDS (SEQ ID NO: 76) |
| QDPTLNWATY (SEQ ID NO: 289) | QMYQS (SEQ ID NO: 16) |
| EDPTVDWAQY (SEQ ID NO: 290) | QMHQS (SEQ ID NO: 74) |
| QDPSLNWADY (SEQ ID NO: 63) | QMYNS (SEQ ID NO: 75) |
| LDRTLNWALY (SEQ ID NO: 64) | QLYQS (SEQ ID NO: 73) |
| LDPSFNWSLY (SEQ ID NO: 65) | QHYKT (SEQ ID NO: 77) |
| RDLTINWALF (SEQ ID NO: 66) | QLFNS (SEQ ID NO: 78) |
| KDTTFNWGLF (SEQ ID NO: 291) | QLYNS (SEQ ID NO: 79) |
| LDPTVNWALF (SEQ ID NO: 67) | QMFNS (SEQ ID NO: 274) |
| QDPKLNWAVY (SEQ ID NO: 68) | |
| LDPSFDWALY (SEQ ID NO: 69) | |

In certain embodiments, the non-naturally occurring VEGF-A binding CKP comprises an amino acid sequence selected from the group consisting of SEQ ID NOs: 81-91 and 293-297. The amino acid sequences of SEQ ID NOs: 81-91 and 293-297 are provided in Table 9 below.

TABLE 9

| |
|---|
| GCDDPSFDWSVYCKQDSDCLAGCVCRMYDSCG (SEQ ID NO: 293) |
| GCKNPLFNWALYCKQDSDCLAGCVCQLFDSCG (SEQ ID NO: 81) |
| GCQDPTVNWAVYCKQDSDCLAGCVCQFYQSCG (SEQ ID NO: 82) |
| GCQDPTFNWAEYCKQDSDCLAGCVCQLYQSCG (SEQ ID NO: 83) |
| GCWDPTFNWALYCKQDSDCLAGCVCQMYDSCG (SEQ ID NO: 294) |
| GCQDPTFNWAEYCKQDSDCLAGCVCQMYQSCG (SEQ ID NO: 84) |
| GCQDPSLNWADYCKQDSDCLAGCVCQMHQSCG (SEQ ID NO: 85) |
| GCQDPTLNWATYCKQDSDCLAGCVCQMYQSCG (SEQ ID NO: 295) |
| GCEDPTVDWAQYCKQDSDCLAGCVCQMYQSCG (SEQ ID NO: 296) |
| GCLDRTLNWALYCKQDSDCLAGCVCQMYNSCG (SEQ ID NO: 86) |
| GCLDPSFNWSLYCKQDSDCLAGCVCQMYDSCG (SEQ ID NO: 87) |
| GCRDLTINWALFCKQDSDCLAGCVCQMFNSCG (SEQ ID NO: 88) |
| GCKDTTFNWGLFCKQDSDCLAGCVCQLYQSCG (SEQ ID NO: 297) |
| GCLDPTVNWALFCKQDSDCLAGCVCQHYKTCG (SEQ ID NO: 89) |
| GCQDPKLNWAVYCKQDSDCLAGCVCQLFNSCG (SEQ ID NO: 90) |
| GCLDPSFDWALYCKQDSDCLAGCVCQLYNSCG (SEQ ID NO: 91) |

In certain embodiments, the non-naturally occurring VEGF-A binding CKP comprises an L1 comprising the amino acid sequence NIMLPFWG (SEQ ID NO: 33), with reference to scaffold structure I. In certain embodiments, the non-naturally occurring VEGF-A binding CKP further comprises an L2 comprising the amino acid sequence K/G/Q/S/N-Q/L/P/A/V/T/R/W/K/G/Y-D/S/E/N-S/F/Y/L/F/Q/M-D/E/N/A/L/F/H/Q (SEQ ID NO: 98). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence QYYQS (SEQ ID NO: 45).

In certain embodiments, the non-naturally occurring VEGF-A binding CKP comprises an L1 comprising the amino acid sequence NIMLPFWG (SEQ ID NO: 33), with reference to scaffold structure I. In certain embodiments, the non-naturally occurring VEGF-A binding CKP further comprises an L2 comprising an amino acid sequence selected from the group consisting of SEQ ID NOs: 94-97 and 298-309. In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence QYYQS (SEQ ID NO: 45). The amino acid sequences of SEQ ID NOs: 94-97 and 298-309 are provided in Table 10 below.

TABLE 10

| | |
|---|---|
| GQSFE (SEQ ID NO: 94) | GWDQF (SEQ ID NO: 304) |
| GLDYD (SEQ ID NO: 95) | GKDFH (SEQ ID NO: 305) |
| GPELN (SEQ ID NO: 298) | GPDLQ (SEQ ID NO: 96) |
| QADYA (SEQ ID NO: 299) | SGDFA (SEQ ID NO: 306) |
| GVDYL (SEQ ID NO: 300) | GKELN (SEQ ID NO: 307) |
| GTNFL (SEQ ID NO: 301) | GWSMD (SEQ ID NO: 308) |
| SRDFD (SEQ ID NO: 302) | GYDLQ (SEQ ID NO: 309) |
| NRDFL (SEQ ID NO: 303) | GRDFE (SEQ ID NO: 97) |

In certain embodiments, the non-naturally occurring VEGF-A binding CKP comprises an amino acid sequence selected from the group consisting of SEQ ID NOs: 99-102 and 310-321. The amino acid sequences of SEQ ID NOs: 99-102 and 310-321 are provided in Table 11 below.

TABLE 11

| |
|---|
| GCNIMLPFWGCGQSFECLAGCVCQYYQSCG (SEQ ID NO: 99) |
| GCNIMLPFWGCGLDYDCLAGCVCQYYQSCG (SEQ ID NO: 100) |
| GCNIMLPFWGCGPELNCLAGCVCQYYQSCG (SEQ ID NO: 310) |
| GCNIMLPFWGCQADYACLAGCVCQYYQSCG (SEQ ID NO: 311) |
| GCNIMLPFWGCGVDYLCLAGCVCQYYQSCG (SEQ ID NO: 312) |
| GCNIMLPFWGCGTNFLCLAGCVCQYYQSCG (SEQ ID NO: 313) |

TABLE 11-continued

GCNIMLPFWGCSRDFDCLAGCVCQYYQSCG (SEQ ID NO: 314)

GCNIMLPFWGCNRDFLCLAGCVCQYYQSCG (SEQ ID NO: 315)

GCNIMLPFWGCWDQFCLAGCVCQYYQSCG (SEQ ID NO: 316)

GCNIMLPFWGCKDFHCLAGCVCQYYQSCG (SEQ ID NO: 317)

GCNIMLPFWGCGPDLQCLAGCVCQYYQSCG (SEQ ID NO: 101)

GCNIMLPFWGCSGDFACLAGCVCQYYQSCG (SEQ ID NO: 318)

GCNIMLPFWGCGKELNCLAGCVCQYYQSCG (SEQ ID NO: 319)

GCNIMLPFWGCGWSMDCLAGCVCQYYQSCG (SEQ ID NO: 320)

GCNIMLPFWGCGYDLQCLAGCVCQYYQSCG (SEQ ID NO: 321)

GCNIMLPFWGCGRDFECLAGCVCQYYQSCG (SEQ ID NO: 102)

In certain embodiments, the non-naturally occurring VEGF-A binding CKP comprises an L1 comprising the amino acid sequence N-I-M/L-L/S/T/Q/N/E/D-P-F/Y/S-WG (SEQ ID NO: 454), with reference to scaffold structure I. In certain embodiments, the non-naturally occurring VEGF-A binding CKP comprises an L1 comprising the amino acid sequence NIMLPFWG (SEQ ID NO: 33), with reference to scaffold structure I. In certain embodiments, the non-naturally occurring VEGF-A binding CKP further comprises an L2 comprising the amino acid sequence GRDFE (SEQ ID NO: 97). In certain embodiments the non-naturally occurring VEGF-A binding CKP further comprises an L3 comprising the amino acid sequence L/V/M/F-A/Q/E/S/N/Y/I/T-G/Q/R/D/T/N/E. In certain embodiments the non-naturally occurring VEGF-A binding CKP further comprises an L4 comprising the amino acid V or I. In certain embodiments the non-naturally occurring VEGF-A binding CKP further comprises an L5 comprising the amino acid sequence QYYQS (SEQ ID NO: 45).

In certain embodiments, the non-naturally occurring VEGF-A binding CKP comprises an L1 comprising the amino acid sequence selected from the group consisting of NIMLPFWG (SEQ ID NO: 33), NILLPFWG (SEQ ID NO: 396), NILLPYWG (SEQ ID NO: 397), NIMSPFWG (SEQ ID NO: 398), NIMTPFWG (SEQ ID NO: 399), NIMQPFWG (SEQ ID NO: 400), NIMNPFWG (SEQ ID NO: 401), NIMEPFWG (SEQ ID NO: 402), NIMDPFWG (SEQ ID NO: 403), NIMLPSWG (SEQ ID NO: 414), and NIMLPYWG (SEQ ID NO: 141) with reference to scaffold structure I. In certain embodiments, the non-naturally occurring VEGF-A binding CKP comprises an L1 comprising the amino acid sequence NIMLPFWG (SEQ ID NO: 33), with reference to scaffold structure V or I. In certain embodiments, the non-naturally occurring VEGF-A binding CKP further comprises an L2 comprising the amino acid sequence GRDFE (SEQ ID NO: 97). In certain embodiments the non-naturally occurring VEGF-A binding CKP further comprises an L3 comprising an amino acid sequence selected from the group consisting of: LQQ, VER, MSD, MNQ, MQT, VYQ, FIN, VSQ, VTE, FYE, MEQ, and VYR. In certain embodiments the non-naturally occurring VEGF-A binding CKP further comprises an L4 comprising the amino acid I. In certain embodiments the non-naturally occurring VEGF-A binding CKP further comprises an L5 comprising the amino acid sequence QYYQS (SEQ ID NO: 45).

In certain embodiments, the non-naturally occurring VEGF-A binding CKP comprises an amino acid sequence selected from the group consisting of SEQ ID NO: 103-114. The amino acid sequences of SEQ ID NOs: 103-114 are provided in Table 12 below.

TABLE 12

| |
|---|
| GCNIMLPFWGCGRDFECLQQCICQYYQSCG (SEQ ID NO: 103) |
| GCNIMLPFWGCGRDFECVERCICQYYQSCG (SEQ ID NO: 104) |
| GCNIMLPFWGCGRDFECMSDCICQYYQSCG (SEQ ID NO: 105) |
| GCNIMLPFWGCGRDFECMNQCICQYYQSCG (SEQ ID NO: 106) |
| GCNIMLPFWGCGRDFECMQTCICQYYQSCG (SEQ ID NO: 107) |
| GCNIMLPFWGCGRDFECVYQCICQYYQSCG (SEQ ID NO: 108) |
| GCNIMLPFWGCGRDFECFINCICQYYQSCG (SEQ ID NO: 109) |
| GCNIMLPFWGCGRDFECVSQCICQYYQSCG (SEQ ID NO: 110) |
| GCNIMLPFWGCGRDFECVTECICQYYQSCG (SEQ ID NO: 111) |
| GCNIMLPFWGCGRDFECFYECICQYYQSCG (SEQ ID NO: 112) |
| GCNIMLPFWGCGRDFECMEQCICQYYQSCG (SEQ ID NO: 113) |
| GCNIMLPFWGCGRDFECVYRCICQYYQSCG (SEQ ID NO: 114) |
| GCDVLQPYWGCGPDIDCLSNCICHWYNSCG (SEQ ID NO: 386) |
| GCNILLPFWGCGRDFECLAGCVCQYYQSCG (SEQ ID NO: 405) |
| GCNILLPYWGCGRDFECLAGCVCQYYQSCG (SEQ ID NO: 406) |
| GCNIMSPFWGCGRDFECLAGCVCQYYQSCG (SEQ ID NO: 407) |
| GCNIMTPFWGCGRDFECLAGCVCQYYQSCG (SEQ ID NO: 408) |
| GCNIMQPFWGCGRDFECLAGCVCQYYQSCG (SEQ ID NO: 409) |
| GCNIMNPFWGCGRDFECLAGCVCQYYQSCG (SEQ ID NO: 410) |
| GCNIMEPFWGCGRDFECLAGCVCQYYQSCG (SEQ ID NO: 411) |
| GCNIMDPFWGCGRDFECLAGCVCQYYQSCG (SEQ ID NO: 412) |
| GCNIMLPSWGCGRDFECLAGCVCQYYQSCG (SEQ ID NO: 415) |
| GCNIMLPFWGCGRDFECLSGCVCQYYQSCG (SEQ ID NO: 421) |
| GCNIMLPFWGCGRDFECLTGCVCQYYQSCG (SEQ ID NO: 422) |
| GCNIMLPFWGCGRDFECLEGCVCQYYQSCG (SEQ ID NO: 423) |
| GCNIMLPYWGCGRDFECLAGCLCQYYQSCG (SEQ ID NO: 424) |
| GCNIMLPYWGCGRDFECLAGCICQYYQSCG (SEQ ID NO: 425) |
| GCNIMLPYWGCGRDFECLAGCVCQYYQSCS (SEQ ID NO: 431) |
| GCNILLPYWGCGRDFECMEQCICQYYQSCG (SEQ ID NO: 435) |

In certain embodiments, the non-naturally occurring VEGF-A binding CKP comprises an L1 comprising the amino acid sequence DVMQPYWG (SEQ ID NO: 35), with reference to scaffold structure I. In certain embodiments, the non-naturally occurring VEGF-A binding CKP further comprises an L2 comprising the amino acid sequence K/G/D/A/E-Q/E/R/V/P/D/M/G/N/L/A/F-D/N/Y/S-S/F/L/I/M/Y/V/N/E-D/L/Q/S/E/T/L/A/N (SEQ ID NO: 121). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence HWYNS (SEQ ID NO: 46).

In certain embodiments, the non-naturally occurring VEGF-A binding CKP comprises an L1 comprising the amino acid sequence DVMQPYWG (SEQ ID NO: 35), with reference to scaffold structure I. In certain embodiments, the non-naturally occurring VEGF-A binding CKP further comprises an L2 comprising an amino acid sequence selected from the group consisting of SEQ ID NOs: 117-120, 211, and 322-339. In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence HWYNS (SEQ ID NO: 46). The amino acid sequences of SEQ ID NOs: 117-120, 211, and 322-339 are provided in Table 13 below.

TABLE 13

| | |
|---|---|
| GENFL (SEQ ID NO: 117) | DGDFD (SEQ ID NO: 331) |
| GRDLQ (SEQ ID NO: 322) | AGDFE (SEQ ID NO: 332) |
| GVDLS (SEQ ID NO: 323) | EMDFD (SEQ ID NO: 120) |
| GPDID (SEQ ID NO: 118) | GNSFE (SEQ ID NO: 333) |
| GDDLE (SEQ ID NO: 324) | GQDLT (SEQ ID NO: 334) |
| GVDMT (SEQ ID NO: 325) | GENLA (SEQ ID NO: 335) |
| GMDIE (SEQ ID NO: 326) | GQDYN (SEQ ID NO: 336) |
| DGDYQ (SEQ ID NO: 327) | GADLS (SEQ ID NO: 337) |
| GNDVS (SEQ ID NO: 328) | GFDMD (SEQ ID NO: 338) |
| GRDMD (SEQ ID NO: 119) | GESLS (SEQ ID NO: 211) |
| AGDEL (SEQ ID NO: 329) | DLNYE (SEQ ID NO: 339) |
| GLDEE (SEQ ID NO: 330) | |

In certain embodiments, the non-naturally occurring VEGF-A binding CKP comprises an amino acid sequence selected from the group consisting of SEQ ID NOs: 122-126 and 340-357. The amino acid sequences of SEQ ID NOs: SEQ ID NOs: 122-126 and 340-357 are provided in Table 14 below.

TABLE 14

| |
|---|
| GCDVMQPYWGCGENFLCLAGCVCHWYNSCG (SEQ ID NO: 122) |
| GCDVMQPYWGCGRDLQCLAGCVCHWYNSCG (SEQ ID NO: 340) |
| GCDVMQPYWGCGVDLSCLAGCVCHWYNSCG (SEQ ID NO: 341) |
| GCDVMQPYWGCGPDIDCLAGCVCHWYNSCG (SEQ ID NO: 123) |
| GCDVMQPYWGCGDDLECLAGCVCHWYNSCG (SEQ ID NO: 342) |
| GCDVMQPYWGCGVDMTCLAGCVCHWYNSCG (SEQ ID NO: 343) |
| GCDVMQPYWGCGMDIECLAGCVCHWYNSCG (SEQ ID NO: 344) |
| GCDVMQPYWGCDGDYQCLAGCVCHWYNSCG (SEQ ID NO: 345) |
| GCDVMQPYWGCGNDVSCLAGCVCHWYNSCG (SEQ ID NO: 346) |

TABLE 14-continued

| |
|---|
| GCDVMQPYWGCGRDMDCLAGCVCHWYNSCG (SEQ ID NO: 124) |
| GCDVMQPYWGCAGDELCLAGCVCHWYNSCG (SEQ ID NO: 347) |
| GCDVMQPYWGCGLDEECLAGCVCHWYNSCG (SEQ ID NO: 348) |
| GCDVMQPYWGCDGDFDCLAGCVCHWYNSCG (SEQ ID NO: 349) |
| GCDVMQPYWGCAGDFECLAGCVCHWYNSCG (SEQ ID NO: 350) |
| GCDVMQPYWGCEMDFDCLAGCVCHWYNSCG (SEQ ID NO: 125) |
| GCDVMQPYWGCGNSFECLAGCVCHWYNSCG (SEQ ID NO: 351) |
| GCDVMQPYWGCGQDLTCLAGCVCHWYNSCG (SEQ ID NO: 352) |
| GCDVMQPYWGCGENLACLAGCVCHWYNSCG (SEQ ID NO: 353) |
| GCDVMQPYWGCGQDYNCLAGCVCHWYNSCG (SEQ ID NO: 354) |
| GCDVMQPYWGCGADLSCLAGCVCHWYNSCG (SEQ ID NO: 355) |
| GCDVMQPYWGCGFDMDCLAGCVCHWYNSCG (SEQ ID NO: 356) |
| GCDVMQPYWGCGESLSCLAGCVCHWYNSCG (SEQ ID NO: 126) |
| GCDVMQPYWGCDLNYECLAGCVCHWYNSCG (SEQ ID NO: 357) |

In certain embodiments, the non-naturally occurring VEGF-A binding CKP comprises an L1 comprising the amino acid sequence D-V-M/L-Q/K/D-P-Y/M/T/L-W-G (SEQ ID NO: 130), with reference to scaffold structure I. In certain embodiments, the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising the amino acid sequence H/L/Q/R-W-Y-N-S (SEQ ID NO: 134).

In certain embodiments, the non-naturally occurring VEGF-A binding CKP comprises an L1 comprising an amino acid sequence selected from SEQ ID NOs: 127-129, with reference to scaffold structure I. In certain embodiments, the non-naturally occurring VEGF-A binding CKP further comprises an L2 comprising the amino acid sequence KQDSD (SEQ ID NO: 93). In certain embodiments the non-naturally occurring VEGF-A binding CKP further comprises an L3 comprising the amino acid sequence LAG. In certain embodiments the non-naturally occurring VEGF-A binding CKP further comprises an L4 comprising the amino acid V. In certain embodiments the non-naturally occurring VEGF-A binding CKP further comprises an L5 comprising an amino acid sequence selected from the group consisting of SEQ ID NOs: 131-133. The amino acid sequences of SEQ ID NOs: 127-129 and 131-133 are provided in Table 15 below:

TABLE 15

| | |
|---|---|
| DVMKPMWG (SEQ ID NO: 127) | QWYNS (SEQ ID NO: 131) |
| DVLDPTWG (SEQ ID NO: 128) | LWYNS (SEQ ID NO: 132) |
| DVLQPLWG (SEQ ID NO: 129) | RWYNS (SEQ ID NO: 133) |

In certain embodiments, the non-naturally occurring VEGF-A binding CKP comprises an amino acid sequence selected from the group consisting of SEQ ID NOs: 135-137. The amino acid sequences of SEQ ID NOs: 135-127 are provided in Table 16 below:

TABLE 16

GCDVMKPMWGCKQDSDCLAGCVCQWYNSCG (SEQ ID NO: 135)

GCDVLDPTWGCKQDSDCLAGCVCLWYNSCG (SEQ ID NO: 136)

GCDVLQPLWGCKQDSDCLAGCVCRWYNSCG (SEQ ID NO: 137)

In certain embodiments, the non-naturally occurring VEGF-A binding CKP comprises an L1 comprising the amino acid sequence DVMQPYWG (SEQ ID NO: 35), with reference to scaffold structure I. In certain embodiments, the non-naturally occurring VEGF-A binding CKP further comprises an L2 comprising the amino acid sequence GPDID (SEQ ID NO: 118). In certain embodiments the non-naturally occurring VEGF-A binding CKP further comprises an L3 comprising the amino acid sequence L/F-A/V/S-G/R/N. In certain embodiments the non-naturally occurring VEGF-A binding CKP further comprises an L4 comprising an amino acid selected from V, I, and L. In certain embodiments the non-naturally occurring VEGF-A binding CKP further comprises an L5 comprising the amino acid sequence HWYNS (SEQ ID NO: 46).

In certain embodiments, the non-naturally occurring VEGF-A binding CKP comprises an L1 comprising the amino acid sequence DVMQPYWG (SEQ ID NO: 35), with reference to scaffold structure I. In certain embodiments, the non-naturally occurring VEGF-A binding CKP further comprises an L2 comprising the amino acid sequence GPDID (SEQ ID NO: 118). In certain embodiments the non-naturally occurring VEGF-A binding CKP further comprises an L3 comprising an amino acid sequence FVR and LSN. In certain embodiments the non-naturally occurring VEGF-A binding CKP further comprises an L4 comprising an amino acid selected from V, I, and L. In certain embodiments the non-naturally occurring VEGF-A binding CKP further comprises an L5 comprising the amino acid sequence HWYNS (SEQ ID NO: 46).

In certain embodiments, the non-naturally occurring VEGF-A binding CKP comprises the amino acid sequence GCDVMQPYWGCGPDIDCFVRCLCHWYNSCG (SEQ ID NO: 139). In certain embodiments, the non-naturally occurring VEGF-A binding CKP comprises the amino acid sequence GCDVMQPYWGCGPDIDCLSNCICHWYNSCG (SEQ ID NO: 140).

In certain embodiments, the non-naturally occurring VEGF-A binding CKP comprises an L1, L2, L3, L4 and/or L5 of any one of the non-naturally occurring VEGF-A binding CKPs disclosed herein. Thus, in certain embodiments, the non-naturally occurring VEGF-A binding CKP comprises an L1 comprising an amino acid sequence selected from the group consisting of SEQ ID NOs: 8-14, 28-39, 60-69, 127-129, 141, 225-230, 245-261, 287-291, 396-403, and 414 with reference to scaffold structure I. In certain embodiments, the non-naturally occurring VEGF-A binding CKP further comprises an L2 comprising an amino acid sequence selected from the group consisting of SEQ ID NOs: 93-97, 117-120, 211, 298-309, and 322-339. In certain embodiments, the non-naturally occurring VEGF-A binding CKP further comprises an L3 comprising an amino acid sequence selected from the group consisting of LAG, LQQ, VER, MSD, MNQ, MQT, VYQ, FIN, VSQ, VTE, FYE, MEQ, and VYR, FVR and LSN. In certain embodiments, the non-naturally occurring VEGF-A binding CKP further comprises an L4 comprising the amino acid V, F, I, or L. In certain embodiments, the non-naturally occurring VEGF-A binding CKP further comprises an L5 comprising an amino acid sequence selected from the group consisting of SEQ ID NOs: 15-18, 41-46, 71-79, 131-133, 233-238, 262-264, and 292. In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

In certain embodiments, at least one amino acid is deleted from a VEGF-A binding CKP provided herein. In certain embodiments, at least one amino acid is deleted from the N-terminus. In certain embodiments, at least one amino acid is deleted from the C-terminus. In certain embodiments, at least one amino acid is deleted from the N-terminus and the C-terminus. In certain embodiments, at least one internal amino acid is deleted. In certain embodiments, the non-naturally occurring VEGF-A binding CKP comprises the amino acid sequence CNIMLPYWGCGRDFECLAGCVCQYYQSC (SEQ ID NO: 217). In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

In certain embodiments, the non-naturally occurring VEGF-A binding CKP comprises at least one amino acid addition. In certain embodiments, at least one amino acid is added to the N-terminus. In certain embodiments, at least one amino acid is added to the C-terminus. In certain embodiments, at least one amino acid is added to the N-terminus and the C-terminus.

In certain embodiments, two amino acids are added to the N-terminus of a non-naturally occurring VEGF-A binding CKP provided herein. In certain embodiments, two amino acids are added to the N-terminus of the non-naturally occurring VEGF-A binding CKP set forth in GCNIMLPF- WGCGRDFECLAGCVCQYYQSCG (SEQ ID NO: 102). In certain embodiments, the two amino acids added to the N-terminus of SEQ ID NO: 102 are F/I/G/T/V/L-H/A/S/R. In certain embodiments, the two amino acids added to the N-terminus of SEQ ID NO: 102 are selected from the group consisting of: FH, IA, GS, TR, VH, and LS. In certain embodiments, the non-naturally occurring VEGF-A binding CKP comprises an amino acid sequence set forth in GCNIMLPFWGCGRDFECLAGCVCQYYQSCGFH (SEQ ID NO: 379). In certain embodiments, the non-naturally occurring VEGF-A binding CKP comprises an amino acid sequence set forth in GCNIMLPFWGCGRDFECLAGCVCQYYQSCGIA (SEQ ID NO: 380). In certain embodiments, the non-naturally occurring VEGF-A binding CKP comprises an amino acid sequence set forth in GCNIMLPFWGCGRDFECLAGCVCQYYQSCGGS (SEQ ID NO: 381). In certain embodiments, the non-naturally occurring VEGF-A binding CKP comprises an amino acid sequence set forth in GCNIMLPFWGCGRDFECLAGCVCQYYQSCGTR (SEQ ID NO: 382). In certain embodiments, the non-naturally occurring VEGF-A binding CKP comprises an amino acid sequence set forth in GCNIMLPFWGCGRDFECLAGCVCQYYQSCGVH (SEQ ID NO: 383). In certain embodiments, the non-naturally occurring VEGF-A binding CKP comprises an amino acid sequence set forth in GCNIMLPFWGCGRDFECLAGCVCQYYQSCGLS (SEQ ID NO: 384).

In certain embodiments, two amino acids are added to the N-terminus of the non-naturally occurring VEGF-A binding CKP set forth in GCDVLQPYWGCGPDIDCLSNCICHWYNSCG (SEQ ID NO: 386). In certain embodiments, the two amino acids added to the N-terminus of SEQ ID NO: 102 are R/W/P/D/Q/E/S-T/K/E/F/Q/L/S. In certain embodiments, the two amino acids added to the N-terminus of SEQ ID NO: 102 are selected from the group consisting of: RT, WK, PL, DE, QF, EQ, PT, RL, and SL. In certain embodiments, the non-naturally occurring VEGF-A binding CKP comprises an amino acid sequence set forth in GCDVLQPYWGCGPDIDCLSNCICHWYNSCGRT (SEQ ID NO: 387). In certain embodiments, the non-naturally occurring VEGF-A binding CKP comprises an amino acid sequence set forth in GCDVLQPYWGCGPDIDCLSNCICHWYNSCGWK (SEQ ID NO: 388). In certain embodiments, the non-naturally occurring VEGF-A binding CKP comprises an amino acid sequence set forth in GCDVLQPYWGCGPDIDCLSNCICHWYNSCGPL (SEQ ID NO: 389). In certain embodiments, the non-naturally occurring VEGF-A binding CKP comprises an amino acid sequence set forth in GCDVLQPYWGCGPDIDCLSNCICHWYNSCGDE (SEQ ID NO: 390). In certain embodiments, the non-naturally occurring VEGF-A binding CKP comprises an amino acid sequence set forth in GCDVLQPYWGCGPDIDCLSNCICHWYNSCGQF (SEQ ID NO: 391). In certain embodiments, the non-naturally occurring VEGF-A binding CKP comprises an amino acid sequence set forth in GCDVLQPYWGCGPDIDCLSNCICHWYNSCGEQ (SEQ ID NO: 392). In certain embodiments, the non-naturally occurring VEGF-A binding CKP comprises an amino acid sequence set forth in GCDVLQPYWGCGPDIDCLSNCICHWYNSCGPT (SEQ ID NO: 393). In certain embodiments, the non-naturally occurring VEGF-A binding CKP comprises an amino acid sequence set forth in GCDVLQPYWGCGPDIDCLSNCICHWYNSCGRL (SEQ ID NO: 394). In certain embodiments, the non-naturally occurring VEGF-A binding CKP comprises an amino acid sequence set forth in GCDVLQPYWGCGPDIDCLSNCICHWYNSCGSL (SEQ ID NO: 395).

In certain embodiments, three amino acids are added to the N-terminus of a non-naturally occurring VEGF-A binding CKP provided herein. In certain embodiments, two amino acids are added to the N-terminus of the non-naturally occurring VEGF-A binding CKP set forth in GCNIMLPFWGCGRDFECLAGCVCQYYQSCG (SEQ ID NO: 102). In certain embodiments, the three amino acids added to the N-terminus of SEQ ID NO: 102 are P/N/T/D/E/Y/W-L/Y/F/H/D/P-I/Q/V/K/S/Y/H. In certain embodiments, the three amino acids added to the N-terminus of SEQ ID NO: 102 are selected from the group consisting of: PLI, NYQ, PLQ, TFQ, DLV, EHK, YLS, WDY, WPH, and PHQ. In certain embodiments, the non-naturally occurring VEGF-A binding CKP comprises an amino acid sequence set forth in GCNIMLPFWGCGRDFECLAGCVCQYYQSCGPLI (SEQ ID NO: 369). In certain embodiments, the non-naturally occurring VEGF-A binding CKP comprises an amino acid sequence set forth in GCNIMLPFWGCGRDFECLAGCVCQYYQSCGNYQ (SEQ ID NO: 370). In certain embodiments, the non-naturally occurring VEGF-A binding CKP comprises an amino acid sequence set forth in GCNIMLPFWGCGRDFECLAGCVCQYYQSCGPLQ (SEQ ID NO: 371). In certain embodiments, the non-naturally occurring VEGF-A binding CKP comprises an amino acid sequence set forth in GCNIMLPFWGCGRDFECLAGCVCQYYQSCGTFQ (SEQ ID NO: 372). In certain embodiments, the non-naturally occurring VEGF-A binding CKP comprises an amino acid sequence set forth in GCNIMLPFWGCGRDFECLAGCVCQYYQSCGDLV (SEQ ID NO: 373). In certain embodiments, the non-naturally occurring VEGF-A binding CKP comprises an amino acid sequence set forth in GCNIMLPFWGCGRDFECLAGCVCQYYQSCGEHK (SEQ ID NO: 374). In certain embodiments, the non-naturally occurring VEGF-A binding CKP comprises an amino acid sequence set forth in GCNIMLPFWGCGRDFECLAGCVCQYYQSCGYLS (SEQ ID NO: 375). In certain embodiments, the non-naturally occurring VEGF-A binding CKP comprises an amino acid sequence set forth in GCNIMLPFWGCGRDFECLAGCVCQYYQSCGWDY (SEQ ID NO: 376). In certain embodiments, the non-naturally occurring VEGF-A binding CKP comprises an amino acid sequence set forth in GCNIMLPFWGCGRDFECLAGCVCQYYQSCGWPH (SEQ ID NO: 377). In certain embodiments, the non-naturally occurring VEGF-A binding CKP comprises an amino acid sequence set forth in GCNIMLPFWGCGRDFECLAGCVCQYYQSCGPHQ (SEQ ID NO: 378).

In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

In certain embodiments, the non-naturally occurring VEGF-A-binding CKP is a variant of a non-naturally occurring VEGF-A-binding CKP described herein. In certain embodiments, such a variant comprises at least 1, at least 2, at least 3, at least 4, at least 5, at least 6, at least 7, at least 8, at least 9, or at least 10 amino acid substitutions in one or more of the sequences set forth in SEQ ID NOs: 8-14, 28-39, 60-69, 127-129, 141, 225-230, 245-261, 287-291, 396-403, and 414; SEQ ID NOs: 93-97, 117-120, 211, 298-309, and 322-339; amino acid sequences LAG, LQQ, VER, MSD, MNQ, MQT, VYQ, FIN, VSQ, VTE, FYE, MEQ, and VYR, FVR and LSN; and/or 15-18, 41-46, 71-79, 131-133, 233-238, 262-264, and 292. In certain embodiments, the amino acid substitution(s) are conservative amino acid substitution(s). In certain embodiments, the amino acid substitutions do not substantially reduce the ability of the non-naturally occurring VEGF-A-binding CKP to bind human VEGF-A. For example, conservative alterations (e.g., conservative substitutions as provided herein) that do not substantially reduce VEGF-A binding affinity may be made. The binding affinity of a variant of a non-naturally occurring VEGF-A-binding CKP can be assessed using a method described in the Examples below.

Conservative substitutions are shown in Table 17 below under the heading of "conservative substitutions." More substantial changes are provided in Table 17 under the heading of "exemplary substitutions," and as further described below in reference to amino acid side chain classes. Amino acid substitutions may be introduced into a variant of a non-naturally occurring VEGF-A-binding CKP and the products screened for a desired activity, e.g., retained/improved VEGF-A binding.

TABLE 17

Conservative Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class.

An exemplary substitutional variant is an affinity matured non-naturally occurring VEGF-A-binding CKP, which may be conveniently generated, e.g., using phage display based affinity maturation techniques such as those described herein. Briefly, one or more residues in L1, L2, L3, L4, and/or L5 is altered (i.e., added, deleted, or substituted) and the variant VEGF-A-binding CKP is displayed on phage and screened for VEGF-A binding affinity. In certain embodiments of affinity maturation, diversity is introduced into the variable genes chosen for maturation by any of a variety of methods (e.g., error-prone PCR, loop shuffling, or oligonucleotide-directed mutagenesis). A secondary library is then created. The library is then screened to identify any non-naturally occurring CKP variants with the desired affinity for VEGF-A. In certain embodiments, introducing diversity involves loop-directed approaches, in which several residues in L1, L2, L3, L4, and/or L5 (e.g., about 5, about 4-6, or about 6-10 residues at a time) are randomized. L1, L2, L3, L4, and/or L5 residues involved in binding a target ligand may be identified, e.g., using alanine scanning mutagenesis or modeling.

In certain embodiments, the non-naturally occurring VEGF-A binding CKP comprises the amino acid sequence GCNIMLPYWGCGQSFECLAGCVCQYYQSCG (SEQ ID NO: 215).

In certain embodiments, the non-naturally occurring VEGF-A binding CKP comprises the amino acid sequence GCNIMLPYWGCGRDFECLAGCVCQYYQSCG (SEQ ID NO: 216).

In certain embodiments, the non-naturally occurring VEGF-A binding CKP comprises the amino acid sequence GCNIMLPYWGCGRDFECLAKCVCQYYQSCG (SEQ ID NO: 542).

In certain embodiments, the non-naturally occurring VEGF-A binding CKP comprises the amino acid sequence GCNIMLPYWGCGRDFECMSDCICQYYQSCG (SEQ ID NO: 363).

In certain embodiments, the non-naturally occurring VEGF-A binding CKP comprises the amino acid sequence GCNIMLPYWGCGRDFECMSDCICQYYQSCG (SEQ ID NO: 364).

In certain embodiments, the non-naturally occurring VEGF-A binding CKP comprises the amino acid sequence GCNIMLPYWGCGRDFECMNQCICQYYQSCG (SEQ ID NO: 222).

In certain embodiments, the non-naturally occurring VEGF-A binding CKP comprises the amino acid sequence GCNIMLPYWGCGRDFECFYECICQYYQSCG (SEQ ID NO: 223).

In certain embodiments, the non-naturally occurring VEGF-A binding CKP comprises the amino acid sequence GCNIMLPYWGCGRDFECMEQCICQYYQSCG (SEQ ID NO: 142).

In certain embodiments, the non-naturally occurring VEGF-A binding CKP comprises the amino acid sequence GCNILLPFWGCGRDFECLAGCVCQYYQSCG (SEQ ID NO: 405).

In certain embodiments, the non-naturally occurring VEGF-A binding CKP comprises the amino acid sequence GCNILLPYWGCGRDFECLAGCVCQYYQSCG (SEQ ID NO: 406).

In certain embodiments, the non-naturally occurring VEGF-A binding CKP comprises the amino acid sequence GCNIMSPFWGCGRDFECLAGCVCQYYQSCG (SEQ ID NO: 407).

In certain embodiments, the non-naturally occurring VEGF-A binding CKP comprises the amino acid sequence GCNIMTPFWGCGRDFECLAGCVCQYYQSCG (SEQ ID NO: 408).

In certain embodiments, the non-naturally occurring VEGF-A binding CKP comprises the amino acid sequence GCNIMQPFWGCGRDFECLAGCVCQYYQSCG (SEQ ID NO: 409).

In certain embodiments, the non-naturally occurring VEGF-A binding CKP comprises the amino acid sequence GCNIMNPFWGCGRDFECLAGCVCQYYQSCG (SEQ ID NO: 410).

In certain embodiments, the non-naturally occurring VEGF-A binding CKP comprises the amino acid sequence GCNIMEPFWGCGRDFECLAGCVCQYYQSCG (SEQ ID NO: 411).

In certain embodiments, the non-naturally occurring VEGF-A binding CKP comprises the amino acid sequence GCNIMDPFWGCGRDFECLAGCVCQYYQSCG (SEQ ID NO: 412).

In certain embodiments, the non-naturally occurring VEGF-A binding CKP comprises the amino acid sequence GCNIMLPSWGCGRDFECLAGCVCQYYQSCG (SEQ ID NO: 415).

In certain embodiments, the non-naturally occurring VEGF-A binding CKP comprises the amino acid sequence GCNIMLPFWGCGRDFECLSGCVCQYYQSCG (SEQ ID NO: 421).

In certain embodiments, the non-naturally occurring VEGF-A binding CKP comprises the amino acid sequence GCNIMLPFWGCGRDFECLTGCVCQYYQSCG (SEQ ID NO: 422).

In certain embodiments, the non-naturally occurring VEGF-A binding CKP comprises the amino acid sequence GCNIMLPFWGCGRDFECLEGCVCQYYQSCG (SEQ ID NO: 423).

In certain embodiments, the non-naturally occurring VEGF-A binding CKP comprises the amino acid sequence GCNIMLPYWGCGRDFECLAGCLCQYYQSCG (SEQ ID NO: 424).

In certain embodiments, the non-naturally occurring VEGF-A binding CKP comprises the amino acid sequence GCNIMLPYWGCGRDFECLAGCICQYYQSCG (SEQ ID NO: 425).

In certain embodiments, the non-naturally occurring VEGF-A binding CKP comprises the amino acid sequence GCNIMLPYWGCGRDFECLAGCVCQYYQSCS (SEQ ID NO: 431).

In certain embodiments, the non-naturally occurring VEGF-A binding CKP comprises the amino acid sequence GCNILLPYWGCGRDFECMEQCICQYYQSCG (SEQ ID NO: 435).

In certain embodiments, the non-naturally occurring VEGF-A binding CKP comprises the amino acid sequence GCDVLQPYWGCGPDIDCLSNCICHWYNSCG (SEQ ID NO: 386).

In certain embodiments, the non-naturally occurring VEGF-A binding CKP comprises the amino acid sequence GCNILLPFWGCGRDFECVSQCICQYYQSCG (SEQ ID NO: 547).

In certain embodiments, the non-naturally occurring VEGF-A binding CKP comprises the amino acid sequence GCNILQPFWGCGRDFECVSQCICQYYQSCG (SEQ ID NO: 548).

In certain embodiments, one or more amino acids in the sequence of a non-naturally occurring VEGF-A binding CKP provided herein are substituted with unnatural amino acids. In certain embodiments, the one or more amino acids are substituted with the same unnatural amino acid. In certain embodiments, the one or more amino acids are each substituted with a different unnatural amino acid. In certain embodiments, the non-naturally occurring VEGF-A binding CKP comprises an unnatural amino acid at any amino acid position in L1, L2, L3, L4, and/or L5, with respect to scaffold structure I.

In certain embodiments, the non-naturally occurring VEGF-A binding CKP comprises the amino acid sequence GCNIMLPYWGCGRDFECLAGCVCQYYQSCG (SEQ ID NO: 216), wherein the N-terminal glycine is capped with C(=O)-oxetane-3yl.

In certain embodiments, the non-naturally occurring VEGF-A binding CKP comprises the amino acid sequence GCNIMLPYWGCGRDFECLAXCVCQYYQSCG (SEQ ID NO: 568, wherein X is ornithine.

In certain embodiments, the non-naturally occurring VEGF-A binding CKP comprises the amino acid sequence XCNIMLPYWGCGRDFECLAGCVCQYYQSCG (SEQ ID NO: 361), wherein X is N-acetylglycine.

In certain embodiments, the non-naturally occurring VEGF-A binding CKP comprises the amino acid sequence GCNIMLPXWGCGRDFECLAGCVCQYYQSCG (SEQ ID NO: 362), wherein X is sulfotyrosine. In certain embodiments, the non-naturally occurring VEGF-A binding CKP comprises the amino acid sequence GCNIMLPXWGCGRDFECLAGCVCQYYQSCG (SEQ ID NO: 362), wherein X is 3,4-difluoro-L-phenylalanine. In certain embodiments, the non-naturally occurring VEGF-A binding CKP comprises the amino acid sequence GCNIMLPXWGCGRDFECLAGCVCQYYQSCG (SEQ ID NO: 362), wherein X is 3,4-dichloro-L-phenylalanine. In certain embodiments, the non-naturally occurring VEGF-A-binding CKP comprises the amino acid sequence GCNIMLPXWGCGRDFECLAGCVCQYYQSCG (SEQ ID NO: 362), wherein X is 4-chloro-L-phenylalanine. In certain embodiments, the non-naturally occurring VEGF-A binding CKP comprises the amino acid sequence GCNIMLPXWGCGRDFECLAGCVCQYYQSCG (SEQ ID NO: 362), wherein X is 3-F,4-Cl-L-phenylalanine. In certain embodiments, the non-naturally occurring VEGF-A binding CKP comprises the amino acid sequence GCNIMLPXWGCGRDFECLAGCVCQYYQSCG (SEQ ID NO: 362), wherein X is 2-pyridone (NH para)-L-alanine. In certain embodiments, the non-naturally occurring VEGF-A binding CKP comprises the amino acid sequence GCNIMLPXWGCGRDFECLAGCVCQYYQSCG (SEQ ID NO: 362), wherein X is pyridone (NH meta)-L-alanine.

In certain embodiments, the non-naturally occurring VEGF-A binding CKP comprises the amino acid sequence GCNIXLPFWGCGRDFECLAGCVCQYYQSCG (SEQ ID NO: 218), wherein X is norleucine.

In certain embodiments, the non-naturally occurring VEGF-A binding CKP comprises the amino acid sequence GCNIMLPFXGCGRDFECLAGCVCQYYQSCG (SEQ ID NO: 219), wherein X is 1-naphthylalanine.

In certain embodiments, the non-naturally occurring VEGF-A binding CKP comprises the amino acid sequence GCNIMLPFXGCGRDFECLAGCVCQYYQSCG (SEQ ID NO: 219), wherein X is 2-naphthylalanine.

In certain embodiments, the non-naturally occurring VEGF-A binding CKP comprises the amino acid sequence XCNIMLPFWGCGRDFECLAGCVCQYYQSCG (SEQ ID NO: 221), wherein X is PEG6-propargylglycine.

In certain embodiments, the non-naturally occurring VEGF-A binding CKP comprises the amino acid sequence GCNIXLPYWGCGRDFECMSDCICQYYQSCG (SEQ ID NO: 365), wherein X is norleucine.

In certain embodiments, the non-naturally occurring VEGF-A binding CKP comprises the amino acid sequence GCNIXLPFWGCGRDFECMSDCICQYYQSCG (SEQ ID NO: 144), wherein X is norleucine.

In certain embodiments, the non-naturally occurring VEGF-A binding CKP comprises the amino acid sequence GCNIXLPFWGCGRDFECVSQCICQYYQSCG (SEQ ID NO: 145), wherein X is norleucine.

In certain embodiments, the non-naturally occurring VEGF-A binding CKP comprises the amino acid sequence GCNIX$_1$LPFWGCGRDF-D/E-CVS-N/K/X$_2$CICQYY-QSCG (SEQ ID NO: 540) wherein X$_1$ is norleucine and X$_2$ is ornithine. In certain embodiments, the non-naturally occurring VEGF-A binding CKP comprises the amino acid sequence GCNIXLPFWGCGRDFECVSKCICQYYQSCG (SEQ ID NO: 545) wherein X is norleucine. In certain embodiments, the non-naturally occurring VEGF-A binding CKP comprises the amino acid sequence GCNIX$_1$LPFWGCGRDFECVSX$_2$CICQYYQSCG (SEQ ID NO: 546) wherein X$_1$ is norleucine and X$_2$ is ornithine. In certain embodiments, the non-naturally occurring VEGF-A binding CKP comprises the amino acid sequence GCNIX$_1$LPFWGCGRDF-N/K/X$_2$-CVS-DIE-CICQYY-QSCG (SEQ ID NO: 541), wherein X$_1$ is norleucine and X$_2$ is ornithine.

In certain embodiments, the non-naturally occurring VEGF-A binding CKP comprises the amino acid sequence GCNIXLPFWGCGRDFKCVS-D/E-CICQYYQSCG (SEQ ID NO: 561, herein X is norleucine. In certain embodiments, the non-naturally occurring VEGF-A binding CKP comprises the amino acid sequence CNIXLPFWGCGRD-FKCVSDCICQYYQSCG (SEQ ID NO: 562, herein X is norleucine. In certain embodiments, the non-naturally occurring VEGF-A binding CKP comprises the amino acid sequence CNIXLPFWGCGRDFKCVSECICQYYQSCG (SEQ ID NO: 563, herein X is norleucine. In certain embodiments, the non-naturally occurring VEGF-A binding CKP comprises the amino acid sequence GCNIX1LPFWGCGRDFX2CVS-DIE-CICQYYQSCG (SEQ ID NO: 564, herein X1 is norleucine and X2 is ornithine. In certain embodiments, the non-naturally occurring VEGF-A binding CKP comprises the amino acid sequence GCNIX1LPFWGCGRDFX2CVSDCICQYYQSCG (SEQ ID NO: 565, herein X1 is norleucine and X2 is ornithine. In certain embodiments, the non-naturally occurring VEGF-A binding CKP comprises the amino acid sequence GCNIX1LPFWGCGRDFX2CVSECICQYYQSCG (SEQ ID NO: 566, herein X1 is norleucine and X2 is ornithine.

In certain embodiments, the non-naturally occurring VEGF-A binding CKP comprises the amino acid sequence GCNIXLPYWGCGRDFECMEQCICQYYQSCG (SEQ ID NO: 146), wherein X is norleucine.

In certain embodiments, the non-naturally occurring VEGF-A binding CKP comprises the amino acid sequence GCNIX1LPYWGCGRDF-D/E-CME-N/K/X2-CICQYY-QSCG (SEQ ID NO: 538) wherein X1 is norleucine and X2 is ornithine. In certain embodiments, the non-naturally occurring VEGF-A binding CKP comprises the amino acid sequence GCNIXLPYWGCGRDFECMEKCICQYYQSCG (SEQ ID NO: 543), wherein X is norleucine. In certain embodiments, the non-naturally occurring VEGF-A binding CKP comprises the amino acid sequence GCNIX1LPYWGCGRDFECMEX2CICQYYQSCG (SEQ ID NO: 544), wherein X1 is norleucine and X2 is ornithine.

In certain embodiments, the non-naturally occurring VEGF-A binding CKP comprises the amino acid sequence GCNIX1LPYWGCGRDF-N/K/X2-CME-D/E-CICQYY-QSCG (SEQ ID NO: 539) wherein X1 is norleucine and X2 is ornithine. In certain embodiments, the non-naturally occurring VEGF-A binding CKP comprises the amino acid sequence GCNIXLPYWGCGRDFKCME-D/E-CICQYY-QSCG (SEQ ID NO: 555) wherein X is norleucine.

In certain embodiments, the non-naturally occurring VEGF-A binding CKP comprises the amino acid sequence GCNIXLPYWGCGRDFKCMEDCICQYYQSCG (SEQ ID NO: 556) wherein X is norleucine. In certain embodiments, the non-naturally occurring VEGF-A binding CKP comprises the amino acid sequence GCNIXLPYWGCGRD-FKCMEECICQYYQSCG (SEQ ID NO: 557) wherein X is norleucine. In certain embodiments, the non-naturally occurring VEGF-A binding CKP comprises the amino acid sequence GCNIX1LPYWGCGRDFX2CME-D/E-CIC-QYYQSCG (SEQ ID NO: 558) wherein X1 is norleucine and X2 is ornithine. In certain embodiments, the non-naturally occurring VEGF-A binding CKP comprises the amino acid sequence GCNIX1LPYWGCGRDFX2CMEDCICQYYQSCG (SEQ ID NO: 559) wherein X1 is norleucine and X2 is ornithine. In certain embodiments, the non-naturally occurring VEGF-A binding CKP comprises the amino acid sequence GCNIX1LPYWGCGRDFX2CMEECICQYYQSCG (SEQ ID NO: 560) wherein X1 is norleucine and X2 is ornithine.

In certain embodiments the non-naturally occurring VEGF-A binding CKP comprises the amino acid sequence GCDVX1QPYWGCGPDI-D/E-CLS-N/K/X2-CICHWYN-SCG (SEQ ID NO: 534), wherein X1 is norleucine and X2 is ornithine. In certain embodiments the non-naturally occurring VEGF-A binding CKP comprises the amino acid sequence GCDVXQPYWGCGPDIDCLSKCICHWYN-SCG (SEQ ID NO: 536), wherein X is norleucine. In certain embodiments, the non-naturally occurring VEGF-A binding CKP comprises the amino acid sequence GCDVX1QPYWGCGPDIDCLSX2CICHWYNSCG (SEQ ID NO: 537), wherein X1 is norleucine and X2 is ornithine. In certain embodiments the non-naturally occurring VEGF-A binding CKP comprises the amino acid sequence GCDVX1QPYWGCGPDI-N/K/X2-CLS-D/E-CICHWYN-SCG (SEQ ID NO: 535), wherein X1 is norleucine and X2 is ornithine. In certain embodiments the non-naturally occurring VEGF-A binding CKP comprises the amino acid sequence GCDVXQPYWGCGPDIDCLSNCICHWYN-SCG (SEQ ID NO: 224), wherein X is norleucine. In certain embodiments the non-naturally occurring VEGF-A binding CKP comprises the amino acid sequence GCDVXQPY-WGCGPDIKCLS-D/E-CICHWYNSCG (SEQ ID NO: 549), wherein X is norleucine. In certain embodiments the non-naturally occurring VEGF-A binding CKP comprises the amino acid sequence GCDVXQPYWGCGPDIKCLSD-CICHWYNSCG (SEQ ID NO: 550), wherein X is norleucine. In certain embodiments the non-naturally occurring VEGF-A binding CKP comprises the amino acid sequence GCDVXQPYWGCGPDIKCLSECICHWYNSCG (SEQ ID NO: 551), wherein X is norleucine. In certain embodiments the non-naturally occurring VEGF-A binding CKP comprises the amino acid sequence GCDVX1QPYWGCGPDIX2CLS-D/E-CICHWYNSCG (SEQ ID NO: 552), wherein X1 is norleucine and X2 is ornithine. In certain embodiments the non-naturally occurring VEGF-A binding CKP comprises the amino acid sequence GCDVX1QPYWGCGPDIX2CLSDCICHWYNSCG (SEQ ID NO: 553), wherein X1 is norleucine and X2 is ornithine In certain embodiments the non-naturally occurring VEGF-A binding CKP comprises the amino acid sequence GCDVX1QPYWGCGPDIX2CLSECICHWYNSCG (SEQ ID NO: 554), wherein X1 is norleucine and X2 is ornithine.

In certain embodiments, the non-naturally occurring VEGF-A binding CKP comprises the amino acid sequence GCNIMLXFWGCGRDFECLAGCVCQYYQSCG (SEQ ID NO: 413), wherein X is gamma-benzyl-L-proline. In certain embodiments, the non-naturally occurring VEGF-A binding CKP comprises the amino acid sequence GCNIMLXFWGCGRDFECLAGCVCQYYQSCG (SEQ ID NO: 413), wherein X is gamma-(4-fluoro-benzyl)-L-proline. In certain embodiments, the non-naturally occurring VEGF-A binding CKP comprises the amino acid sequence GCNIMLXFWGCGRDFECLAGCVCQYYQSCG (SEQ ID NO: 413), wherein X is 4-OH-L-proline. In certain embodiments, the non-naturally occurring VEGF-A binding CKP comprises the amino acid sequence GCNIMLXFWGCGRDFECLAGCVCQYYQSCG (SEQ ID NO: 413), wherein X is 4-fluoro-L-proline. In certain embodiments, the non-naturally occurring VEGF-A binding CKP comprises the amino acid sequence GCNIMLXFWGCGRDFECLAGCVCQYYQSCG (SEQ ID NO: 413), wherein X is 4-[4-(trifluoromethyl)benzyl]-L-proline.

In certain embodiments, the non-naturally occurring VEGF-A binding CKP comprises the amino acid sequence GCNIMLPYXGCGRDFECLAGCVCQYYQSCG (SEQ ID NO: 417), wherein X is N-methyl indole. In certain embodiments, the non-naturally occurring VEGF-A binding CKP comprises the amino acid sequence GCNIMLPYXGCGRDFECLAGCVCQYYQSCG (SEQ ID NO: 417), wherein X is N-ethyl indole. In certain embodiments, the non-naturally occurring VEGF-A binding CKP comprises the amino acid sequence GCNIMLPYXGCGRDFECLAGCVCQYYQSCG (SEQ ID NO: 417), wherein X is N-isopropyl indole. In certain embodiments, the non-naturally occurring VEGF-A binding CKP comprises the amino acid sequence GCNIMLPYXGCGRDFECLAGCVCQYYQSCG (SEQ ID NO: 417), wherein X is 5-aza-indole.

In certain embodiments, the non-naturally occurring VEGF-A binding CKP comprises the amino acid sequence GCNIMLPYWGCGRDXECLAGCVCQYYQSCG (SED ID NO: 419), wherein X is 4-methyl-L-phenylalanine. In certain embodiments, the non-naturally occurring VEGF-A binding CKP comprises the amino acid sequence GCNIMLPYWGCGRDXECLAGCVCQYYQSCG (SED ID NO: 419), wherein X is 2-naphthyl-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 2-quinolyl-Alanine. In certain embodiments, the non-naturally occurring VEGF-A binding CKP comprises the amino acid sequence GCNIMLPYWGCGRDXECLAGCVCQYYQSCG (SED ID NO: 419), wherein X is 4,4'-biphenyl-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 3-(3-quinolinyl)-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 3-(2-quinolinyl)-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 3-(2-quinoxalinyl)-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 4-methyl-2-pyridyl-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 4-ethyl-2-pyridyl-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is benzothiazole-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is benzothiophene-L-alanine. In certain embodiments, the non-naturally occurring VEGF-A binding CKP comprises the amino acid sequence GCNIMLPYWGCGRDXECLAGCVCQYYQSCG (SED ID NO: 419), wherein X is 3-(3-isoquinolinyl)-L-alanine.

In certain embodiments, the non-naturally occurring VEGF-A binding CKP comprises the amino acid sequence GCNIMLPYWGCGRDFECXAGCVCQYYQSCG (SEQ ID NO: 420), wherein X is t-butyl-L-alanine (also known as L-Nepentylglycine). In certain embodiments, the non-naturally occurring VEGF-A binding CKP comprises the amino acid sequence GCNIMLPYWGCGRDFECXAGCVCQYYQSCG (SEQ ID NO: 420), wherein X is 3-cyclobutyl-L-alanine. In certain embodiments, the non-naturally occurring VEGF-A binding CKP comprises the amino acid sequence GCNIMLPYWGCGRDFECXAGCVCQYYQSCG (SEQ ID NO: 420), wherein X is 3-cyclopentyl-L-alanine. In certain embodiments, the non-naturally occurring VEGF-A binding CKP comprises the amino acid sequence GCNIMLPYWGCGRDFECXAGCVCQYYQSCG (SEQ ID NO: 420), wherein X is 5,5,5-Trifluoro-L-leucine.

In certain embodiments, the non-naturally occurring VEGF-A binding CKP comprises the amino acid sequence GCNIMLPYWGCGRDFECLAGCXCQYYQSCG (SEQ ID NO: 426), wherein X is L-tert-Leucine. In certain embodiments, the non-naturally occurring VEGF-A binding CKP comprises the amino acid sequence GCNIMLPYWGCGRDFECLAGCXCQYYQSCG (SEQ ID NO: 426), wherein X is t-butyl-L-alanine (also known as L-Nepentylglycine). In certain embodiments, the non-naturally occurring VEGF-A binding CKP comprises the amino acid sequence GCNIMLPYWGCGRDFECLAGCXCQYYQSCG (SEQ ID NO: 426), wherein X is L-cyclopentylglycine. In certain embodiments, the non-naturally occurring VEGF-A binding CKP comprises the amino acid sequence GCNIMLPYWGCGRDFECLAGCXCQYYQSCG (SEQ ID NO: 426), wherein X is 3-cyclopentyl-L-alanine. In certain embodiments, the non-naturally occurring VEGF-A binding CKP comprises the amino acid sequence GCNIMLPYWGCGRDFECLAGCXCQYYQSCG (SEQ ID NO: 426), wherein X is L-cyclobutyl-L-glycine. In certain embodiments, the non-naturally occurring VEGF-A binding CKP comprises the amino acid sequence GCNIMLPYWGCGRDFECLAGCXCQYYQSCG (SEQ ID NO: 426), wherein X is 3-cyclobutyl-L-alanine. In certain embodiments, the non-naturally occurring VEGF-A binding CKP comprises the amino acid sequence GCNIMLPYWGCGRDFECLAGCXCQYYQSCG (SEQ ID NO: 426), wherein X is 5,5,5-Trifluoro-L-leucine.

In certain embodiments, the non-naturally occurring VEGF-A binding CKP comprises the amino acid sequence GCNIMLPYWGCGRDFECLAGCVCQXYQSCG (SEQ ID NO: 428), wherein X is 2-pyridone. In certain embodiments, the non-naturally occurring VEGF-A binding CKP comprises the amino acid sequence GCNIMLPYWGCGRDFECLAGCVCQXYQSCG (SEQ ID NO: 428), wherein X is 3,4-hydroxy-L-phenylalanine. In certain embodiments, the non-naturally occurring VEGF-A binding CKP comprises the amino acid sequence GCNIMLPY- WGCGRDFECLAGCVCQXYQSCG (SEQ ID NO: 428), wherein X is 3,4-fluoro phenylalanine. In certain embodiments, the non-naturally occurring VEGF-A binding CKP comprises the amino acid sequence GCNIMLPYWGCGRDFECLAGCVCQXYQSCG (SEQ ID NO: 428), wherein X is 3-fluoro,4-OH-L-phenylalanine.

In certain embodiments, the non-naturally occurring VEGF-A binding CKP comprises the amino acid sequence GCNIMLPYWGCGRDFECLAGCVCQYXQSCG (SEQ ID NO: 430), wherein X is 2-Chloro-L-Tyrosine. In certain embodiments, the non-naturally occurring VEGF-A binding CKP comprises the amino acid sequence GCNIMLPYWGCGRDFECLAGCVCQYXQSCG (SEQ ID NO: 430), wherein X is 2-methyl-L-tyrosine. In certain embodiments, the non-naturally occurring VEGF-A binding CKP comprises the amino acid sequence GCNIMLPYWGCGRDFECLAGCVCQYXQSCG (SEQ ID NO: 430), wherein X is 2-ethyl-L-tyrosine, or 4-(naphthalen-1-ol-)-L-alanine.

In certain embodiments, the non-naturally occurring VEGF-A binding CKP comprises the amino acid sequence GCNIMLPYWGCGRDFECLAGCVCQYYQSCX (SEQ ID NO: 432), wherein X is D-serine, L-beta-homoserine, L-beta-alanine, N-alpha-methylglycine, glycine with its carboxy terminus converted to an ester of glycerol, glycine with its carboxy terminus converted to an ester of glycol, glycine with its carboxy terminus converted to an ester of oxetanyl alcohol, or glycine morpholine amide.

In certain embodiments, the non-naturally occurring VEGF-A binding CKP comprises the amino acid sequence GCNIXQPYWGCGRDFECMEQCICQYYQSCG (SEQ ID NO: 436), wherein X is norleucine.

In certain embodiments, the non-naturally occurring VEGF-A binding CKP comprises the amino acid sequence GCNIX$_1$LPYWGCGRDFECX$_2$EQCICQYYQSCG (SEQ ID NO: 437). In certain embodiments, $X_1$ and $X_2$ are the same unnatural amino acid. In certain embodiments, $X_1$ and $X_2$ are different unnatural amino acids. In certain embodiments, $X_1$ and $X_2$ are norleucine. In certain embodiments, $X_1$ is norleucine and $X_2$ is 3-cyclobutyl-L-alanine.

In certain embodiments, the non-naturally occurring VEGF-A binding CKP comprises the amino acid sequence GCNIXLPYWGCGRDFECLEQCICQYYQSCG (SEQ ID NO: 438), wherein X is norleucine.

In certain embodiments, the non-naturally occurring VEGF-A binding CKP comprises the amino acid sequence GCNIX$_1$LPYWGCGRDFECX$_2$EQCX$_3$CQYYQSCG (SEQ ID NO: 439). In certain embodiments, $X_1$, $X_2$, and/or $X_3$ are the same unnatural amino acid. In certain embodiments, $X_1$, $X_2$, and/or $X_3$ are not the same unnatural amino acid. In certain embodiments, $X_1$ is norleucine, $X_2$ is 3-cyclobutyl-L-alanine, and $X_3$ is cyclobutyl-L-glycine. In certain embodiments, $X_1$ is norleucine, $X_2$ is 3-cyclobutyl-L-alanine, and $X_3$ is 3-cyclobutyl-L-alanine. In certain embodiments, $X_1$ is norleucine, $X_2$ is 3-cyclobutyl-L-alanine, and $X_3$ is norleucine.

In certain embodiments, the non-naturally occurring VEGF-A binding CKP comprises the amino acid sequence CNIX$_1$QPYWGCGRDFECX$_2$EQCX$_3$CQYYQSCG (SEQ ID NO: 440). In certain embodiments, $X_1$, $X_2$, and/or $X_3$ are the same unnatural amino acid. In certain embodiments, $X_1$, $X_2$, and/or $X_3$ are not the same unnatural amino acid. In certain embodiments, $X_1$ is norleucine, $X_2$ is 3-cyclobutyl-L-alanine, and $X_3$ is cyclobutyl-L-glycine. In certain embodiments, $X_1$ is norleucine, $X_2$ is 3-cyclobutyl-L-alanine, and $X_3$ is 3-cyclobutyl-L-alanine.

In certain embodiments, the non-naturally occurring VEGF-A binding CKP comprises the amino acid sequence GCNILLPYWGCGRDFECXEQCICQYYQSCG (SEQ ID NO: 441), wherein X is 3-cyclobutyl-L-alanine or t-butyl-L-alanine (also known as L-Nepentylglycine).

In certain embodiments, the non-naturally occurring VEGF-A binding CKP comprises the amino acid sequence GCNILLPYWGCGRDFECMEQCXCQYYQSCG (SEQ ID NO: 442), wherein X is cyclobutyl-L-glycine or 3-cyclobutyl-L-alanine.

In certain embodiments, the non-naturally occurring VEGF-A binding CKP comprises the amino acid sequence X$_1$CNIX$_2$LPYWGCGRDFECMEQCICQYYQSCX$_3$ (SEQ ID NO: 443). In certain embodiments, $X_1$, $X_2$, and/or $X_3$ are the same unnatural amino acid. In certain embodiments, $X_1$, $X_2$, and/or $X_3$ are not the same unnatural amino acid. In certain embodiments, $X_1$ is N-acetylglycine, $X_2$ is norleucine, and $X_3$ is glycine amide.

In certain embodiments, the non-naturally occurring VEGF-A binding CKP comprises the amino acid sequence X$_1$CNILLPYWGCGRDFECMEQCICQYYQSCX$_2$ (SEQ ID NO: 444). In certain embodiments, $X_1$ and $X_2$ are the same unnatural amino acid. In certain embodiments, $X_1$ and $X_2$ are different unnatural amino acids. In certain embodiments, $X_1$ is N-acetylglycine and $X_2$ is glycine amide.

In certain embodiments, the non-naturally occurring VEGF-A binding CKP comprises the amino acid sequence X$_1$CNILQPYWGCGRDFECMEQCICQYYQSCX$_2$ (SEQ ID NO: 445). In certain embodiments, $X_1$ and $X_2$ are the same unnatural amino acid. In certain embodiments, $X_1$ and $X_2$ are different unnatural amino acids. In certain embodiments, $X_1$ is N-acetylglycine and $X_2$ is glycine amide.

In certain embodiments, the non-naturally occurring VEGF-A binding CKP comprises the amino acid sequence X$_1$CNILQPYWGCGRDFECLEQCICQYYQSCX$_2$ (SEQ ID NO: 446). In certain embodiments, $X_1$ and $X_2$ are the same unnatural amino acid. In certain embodiments, $X_1$ and $X_2$ are different unnatural amino acids. In certain embodiments, $X_1$ is N-acetylglycine and $X_2$ is glycine amide.

In certain embodiments, the non-naturally occurring VEGF-A binding CKP comprises the amino acid sequence GCDVLQPYWGCGPDIDCXSNCICHWYNSCG (SEQ ID NO: 447), wherein X is 3-cyclobutyl-L-alanine or t-butyl-L-alanine (L-Nepentylglycine).

In certain embodiments, the non-naturally occurring VEGF-A binding CKP comprises the amino acid sequence GCDVLQPYWGCGPDIDCLSNCXCHWYNSCG (SEQ ID NO: 448), wherein X is cyclobutyl-L-glycine.

In certain embodiments, the non-naturally occurring VEGF-A binding CKP comprises the amino acid sequence GCDVX$_1$QPYWGCGPDIDCX$_2$SNC2X$_3$CHWYNSCG (SEQ ID NO: 449). In certain embodiments, $X_1$, $X_2$, and/or $X_3$ are the same unnatural amino acid. In certain embodiments, $X_1$, $X_2$, and/or $X_3$ are not the same unnatural amino acid. In certain embodiments, $X_1$ is norleucine, $X_2$ is 3-cyclobutyl-L-alanine, and $X_3$ is cyclobutyl-L-glycine. In certain embodiments, $X_1$ is norleucine, $X_2$ is 3-cyclobutyl-L-alanine, and $X_3$ is 3-cyclobutyl-L-alanine.

In certain embodiments, the non-naturally occurring VEGF-A binding CKP comprises the amino acid sequence GCDVLQPYWGCGPDIDCX$_1$SNC2X$_2$CHWYNSCG (SEQ ID NO: 450). In certain embodiments, $X_1$ and $X_2$ are the same unnatural amino acid. In certain embodiments, $X_1$ and $X_2$ are different unnatural amino acids. In certain embodiments, $X_1$ is 3-cyclobutyl-L-alanine, and $X_2$ is cyclobutyl-L-glycine. In certain embodiments, $X_1$ is 3-cyclobutyl-L-alanine, and $X_2$ is 3-cyclobutyl-L-alanine.

In certain embodiments, the non-naturally occurring VEGF-A binding CKP comprises the amino acid sequence X₁CDVLQPYWGCGPDIDCX₂SNC2X₃CHWYNSCX₄ (SEQ ID NO: 451). In certain embodiments, X₁, X₂, X₃, and/or X₄ are the same unnatural amino acid. In certain embodiments, X₁, X₂, X₃, and/or X₄ are not the same unnatural amino acid. In certain embodiments, X₁ is N-acetylglycine, X₂ is 3-cyclobutyl-L-alanine, X₃ is cyclobutyl-L-glycine, and X₄ is glycine amide In certain embodiments, X₁ is acetylglycine, X₂ is cyclobutyl-L-alanine, X₃ is cyclobutyl-L-alanine, and X₄ is glycine amide In certain embodiments, the non-naturally occurring VEGF-A binding CKP comprises the amino acid sequence X₁CDVX₂QPYWGCGPDIDCLSNCICHWYNSCX₃(SEQ ID NO: 452). In certain embodiments, X₁, X₂, and/or X₃ are the same unnatural amino acid. In certain embodiments, X₁, X₂, and/or X₃ are not the same unnatural amino acid. In certain embodiments, X₁ is N-acetylglycine, X₂ is norleucine, and X₃ is glycine amide In certain embodiments, the non-naturally occurring VEGF-A binding CKP comprises the amino acid sequence X₁CDVLQPYWGCGPDIDCLSNCICHWYNSCX₂ (SEQ ID NO: 453). In certain embodiments, X₁ and X₂ are the same unnatural amino acid. In certain embodiments, X₁ and X₂ are different unnatural amino acids. In certain embodiments, X₁ is N-acetylglycine and X₂ is glycine amide In certain embodiments, the C-terminus of the non-naturally occurring cystine knot peptide (CKP) that binds to VEGF-A is modified (such as capped). In certain embodiments, the N-terminus of the non-naturally occurring cystine knot peptide (CKP) that binds to VEGF-A is modified (such as capped). In certain embodiments, both the C- and N-termini of the non-naturally occurring cystine knot peptide (CKP) that binds to VEGF-A are modified (such as capped). In certain embodiments, the C-terminal carboxyl group of the non-naturally occurring cystine knot peptide (CKP) that binds to VEGF-A is amidated. In certain embodiments, the N-terminal amine of the non-naturally occurring cystine knot peptide (CKP) that binds to VEGF-A is acetylated. In certain embodiments, the C-terminal carboxyl group of the non-naturally occurring cystine knot peptide (CKP) that binds to VEGF-A is amidated and the N-terminal amine of the non-naturally occurring cystine knot peptide (CKP) that binds to VEGF-A is acetylated.

Structural Characteristics

In certain embodiments, the structure of a non-naturally occurring VEGF-Abinding CKP provided herein has a disulfide bond connectivity that is different from the WT EETI-II protein, i.e., different from the C1-C4, C2-O5, and C3-C6 disulfide bond pattern characteristic of WT EETI-II. In certain embodiments, a non-naturally occurring VEGF-A binding CKP provided herein has a disulfide bond connectivity of C1-C4, C2-C3, and C5-C6. Methods of determining the disulfide bond connectivity of, e.g., a non-naturally occurring VEGF-A binding CKP, include, e.g., by solving and analyzing the co-crystal structure of a non-naturally occurring VEGF-A binding CKP in complex with VEGF-A, via mass spectrometry following partial reduction alkylation, or via mass spectrometry following proteolytic digestion, performing structure calculations as described in Sampoli et al. (2000) *Proteins Struct Funct Gen.* 40, 168-174, etc.

In certain embodiments, the non-naturally occurring VEGF-A binding CKP and has an alpha helix content of at least about 10%, at least about 15%, at least about 20%, at least about 25%, at least about 30%, at least about 35%, at least about 40%, at least about 45%, or at least about 50%, including any range in between these values. In certain embodiments, at least 7, at least 8, at least 9, at least 10, at least 11, at least 12, at least 13, at least 14, at least 15, at least 16, at least 17, or at least 18 amino acids of the non-naturally occurring VEGF-A binding CKP form the alpha helix. In certain embodiments, the non-naturally occurring VEGF-A binding CKP has a disulfide bond connectivity of C1-C4, C2-C3, and C5-C6 and an alpha helix content of at least about 10%, at least about 15%, at least about 20%, at least about 25%, at least about 30%, at least about 35%, at least about 40%, at least about 45%, or at least about 50%, including any range in between these values. In certain embodiments, the alpha helix content of a non-naturally occurring VEGF-A binding CKP is determined by, e.g., circular dichroism (CD), optical rotary dispersion (ORD), nuclear magnetic resonance (NMR), by solving and analyzing the co-crystal structure of a non-naturally occurring VEGF-A binding CKP in complex with VEGF-A, via mass spectrometry following partial reduction alkylation, or via mass spectrometry following proteolytic digestion.

In certain embodiments, a non-naturally occurring VEGF-A binding CKP provided herein competes for binding to VEGF-A with a second non-naturally occurring VEGF-A binding CKP, wherein the second non-naturally occurring VEGF-A binding CKP comprises an L1 comprising the amino acid sequence NIMLPFWG (SEQ ID NO: 33); an L2 comprising the amino acid sequence KQDSD (SEQ ID NO: 93); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A binding CKP provided herein competes for binding to VEGF-A with a second non-naturally occurring VEGF-A binding CKP, wherein the second non-naturally occurring VEGF-A binding CKP comprises the amino acid sequence GCNIMLPFWGCKQDSDCLAGCVCQYYQSCG (SEQ ID NO: 52).

In certain embodiments, a non-naturally occurring VEGF-A binding CKP provided herein binds the same epitope on VEGF-A bound by a second non-naturally occurring VEGF-A binding CKP, wherein the second non-naturally occurring VEGF-A binding CKP comprises an L1 comprising the amino acid sequence NIMLPFWG (SEQ ID NO: 33); an L2 comprising the amino acid sequence KQDSD (SEQ ID NO: 93); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A binding CKP provided herein binds the same epitope on VEGF-A bound by a second non-naturally occurring VEGF-A binding CKP, wherein the second non-naturally occurring VEGF-A binding CKP comprises the amino acid sequence GCNIMLPFWGCKQDSDCLAGCVCQYYQSCG (SEQ ID NO: 52).

In certain embodiments, the non-naturally VEGF-A binding CKP provided herein competes for binding to VEGF-A with a second non-naturally occurring VEGF-A binding CKP, wherein the second VEGF-A binding CKP comprises an L1 comprising the amino acid sequence NIMLPFWG (SEQ ID NO: 33); an L2 comprising the amino acid sequence GRDFE (SEQ ID NO: 97); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A binding CKP provided herein competes for binding to VEGF-A with a second non-naturally occurring VEGF-A binding CKP, wherein the second non-naturally occurring VEGF-A binding CKP comprises the amino acid sequence GCNIMLPFWGCGRDFECLAGCVCQYYQSCG (SEQ ID NO: 102).

In certain embodiments, the non-naturally occurring VEGF-A binding CKP provided herein binds the same epitope on VEGF-A bound by a second non-naturally occurring VEGF-A binding CKP, wherein the second non-naturally occurring VEGF-A-binding CKP comprises an L1 comprising the amino acid sequence NIMLPFWG (SEQ ID NO: 33); an L2 comprising the amino acid sequence GRDFE (SEQ ID NO: 97); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A-binding CKP provided herein binds the same epitope on VEGF-A bound by a second non-naturally occurring VEGF-A-binding CKP, wherein the second non-naturally occurring VEGF-A-binding CKP comprises the amino acid sequence GCNIMLPFWGCGRDFECLAGCVCQYYQSCG (SEQ ID NO: 102).

In certain embodiments, the non-naturally occurring VEGF-A-binding CKP provided herein competes for binding to VEGF-A with a second non-naturally occurring VEGF-A-binding CKP, wherein the second non-naturally occurring VEGF-A-binding CKP comprises an L1 comprising the amino acid sequence DVMQPYWG (SEQ ID NO: 35); an L2 comprising the amino acid sequence KQDSD (SEQ ID NO: 93); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP provided herein competes for binding to VEGF-A with a second non-naturally occurring VEGF-A-binding CKP, wherein the second non-naturally occurring VEGF-A-binding CKP comprises the amino acid sequence GCDVMQPYWGCKQDSDCLAGCVCHWYNSCG (SEQ ID NO: 55).

In certain embodiments, the non-naturally occurring VEGF-A-binding CKP provided herein binds the same epitope on VEGF-A bound by a second non-naturally occurring VEGF-A-binding CKP, wherein the second non-naturally occurring VEGF-A-binding CKP comprises an L1 comprising the amino acid sequence DVMQPYWG (SEQ ID NO: 35); an L2 comprising the amino acid sequence KQDSD (SEQ ID NO: 93); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP provided herein binds the same epitope on VEGF-A bound by a second non-naturally occurring VEGF-A-binding CKP, wherein the second non-naturally occurring VEGF-A-binding CKP comprises the amino acid sequence GCDVMQPYWGCKQDSDCLAGCVCHWYNSCG (SEQ ID NO: 55).

In certain embodiments, the non-naturally occurring VEGF-A-binding CKP protein provided herein competes for binding to VEGF-A with a second non-naturally occurring VEGF-A-binding CKP, wherein the second VEGF-A-binding CKP comprises an L1 comprising the amino acid sequence DVMQPYWG (SEQ ID NO: 35); an L2 comprising the amino acid sequence GPDID (SEQ ID NO: 118); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP provided herein competes for binding to VEGF-A with a second non-naturally occurring VEGF-A-binding CKP, wherein the second non-naturally occurring VEGF-A-binding CKP comprises the amino acid sequence GCDVMQPYWGCGPDID-CLAGCVCHWYNSCG (SEQ ID NO: 123).

In certain embodiments, the non-naturally occurring VEGF-A-binding CKP provided herein binds the same epitope on VEGF-A bound by a second non-naturally occurring VEGF-A-binding CKP, wherein the second non-naturally occurring VEGF-A-binding CKP comprises an L1 comprising the amino acid sequence DVMQPYWG (SEQ ID NO: 35); an L2 comprising the amino acid sequence GPDID (SEQ ID NO: 118); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP provided herein binds the same epitope on VEGF-A bound by a second non-naturally occurring VEGF-A-binding CKP, wherein the second non-naturally occurring VEGF-A-binding CKP comprises the amino acid sequence GCDVMQPYWGCGPDIDCLAGCVCHWYNSCG (SEQ ID NO: 123).

In certain embodiments, a non-naturally occurring VEGF-A-binding CKP provided herein binds an epitope of VEGF-A comprising at least one, at least two, at least three, at least four, at least five, at least six, at least seven, at least eight, at least nine, at least ten, or more than ten amino acids selected from the group consisting of V14, V15, F17, D19, Y21, Q22, Y25, I46, K48, N62, D63, L66, M81, I83, K84, P85, H86, Q87, G88, Q89, I91, C104, R105, and P106. In certain embodiments, a non-naturally occurring VEGF-A-binding CKP provided herein binds an epitope of VEGF-A comprising K48, N62, and D63. In certain embodiments, a non-naturally occurring VEGF-A-binding CKP provided herein binds an epitope of VEGF-A comprising H86. In certain embodiments, non-naturally occurring VEGF-A-binding CKP provided herein binds an epitope of VEGF-A comprising Y21, Y25, and P106. In certain embodiments, a non-naturally occurring VEGF-A-binding CKP provided herein binds an epitope of VEGF-A comprising M81, D19, and Q22. In certain embodiments, a non-naturally occurring VEGF-A-binding CKP provided herein binds an epitope of VEGF-A comprising F17, M81, and I91. In certain embodiments, non-naturally occurring VEGF-A-binding CKP provided herein binds an epitope of VEGF-A comprising V14, F17, D19, Q22, M81, and I91. In certain embodiments, a non-naturally occurring VEGF-A-binding CKP provided herein binds an epitope of VEGF-A comprising Q22 and Y25.

In certain embodiments, a non-naturally occurring VEGF-A-binding CKP provided herein binds an epitope on VEGF-A that overlaps the epitope of VEGF-A bound by the anti-VEGF-A antibody G6.31 (Fuh et al. (2006) *J. Biol. Chem.* 281, 6625-6631). In certain embodiments, a non-naturally occurring VEGF-A-binding CKP provided herein binds an epitope on VEGF-A that overlaps with the epitope of VEGF-A bound by Flt-1. In certain embodiments, a non-naturally occurring VEGF-A-binding CKP provided herein binds an epitope on VEGF-A that overlaps with the epitope of VEGF-A bound by bevacizumab.

Functional Characteristics

In certain embodiments, a non-naturally occurring CKP that "specifically binds" VEGF-A (such as a human VEGF-A, a mouse VEGF-A, and/or a rat VEGF-A) has a binding affinity (Kd) value of no more than about $1 \times 10^{-7}$ M, preferably no more than about 1×10⁻⁸ and most preferably no more than about 1×10⁻⁹ M) but has a binding affinity for a homologue of VEGF-A or other growth factor which is at least about 50-fold, or at least about 500-fold, or at least about 1000-fold, weaker than its binding affinity for VEGF-A.

In certain embodiments, the extent of binding of a non-naturally occurring VEGF-A-binding CKP provided herein to, e.g., a non-target protein (e.g., a homolog of VEGFA such as VEGF-B, VEGF-C and VEGF-D) or other growth factors (such as P1GF, EGF, NGF, IGF and PDGF) is less than about 10% of the binding of the non-naturally occurring VEGF-A-binding CKP to VEGF-A as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. Other methods of assessing the binding of a non-naturally occurring CKP that "specifically binds" VEGF-A are described in the Examples.

The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In certain embodiments, the non-naturally occurring VEGF-A-binding CKP binds VEGF-A with a Kd between about 1 pM to about 500 nM. In certain embodiments, the non-naturally occurring VEGF-A-binding CKP binds VEGF-A with a Kd between about 1 pM to about 50 pM, between about 50 pM to about 250 pM, between about 250 pM to about 500 pM, between about 500 pM to about 750 pM, between about 750 pM to about 1 nM, between about 1 nM to about 25 nM, between about 25 nM to about 50 nM, between 50 nM to about 100 nM, between about 100 nM to about 250 nM, or between about 250 nM to about 500 nM.

In certain embodiments, the non-naturally occurring VEGF-A-binding CKP binds human VEGF-A, a mouse VEGF-A, and/or a rat VEGF-A. In certain embodiments, non-naturally occurring VEGF-A-binding CKP that binds human VEGF-A, a mouse VEGF-A, and a rat VEGF-A comprises an L1 comprising the amino acid sequence NIMLPFWG (SEQ ID NO: 33); an L2 comprising the amino acid sequence KQDSD (SEQ ID NO: 93); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A-binding CKP that binds human VEGF-A, a mouse VEGF-A, and a rat VEGF-A comprises the amino acid sequence GCNIMLPFWGCKQDSDCLAGCVCQYYQSCG (SEQ ID NO: 52).

In certain embodiments, non-naturally occurring VEGF-A-binding CKP binds human VEGF-A, a mouse VEGF-A, and a rat VEGF-A comprises an L1 comprising the amino acid sequence NIMLPFWG (SEQ ID NO: 33); an L2 comprising the amino acid sequence GRDFE (SEQ ID NO: 97); an L3 comprising the amino acid sequence LAG; an L4 comprising the amino acid V, and an L5 comprising the amino acid sequence QYYQS (SEQ ID NO: 45), with reference to scaffold structure I. In certain embodiments, the non-naturally occurring VEGF-A-binding CKP that binds human VEGF-A, a mouse VEGF-A, and a rat VEGF-A comprises the amino acid sequence GCNIMLPFWGCGRDFECLAGCVCQYYQSCG (SEQ ID NO: 102).

In certain embodiments, non-naturally occurring VEGF-A-binding CKP that binds human VEGF-A, a mouse VEGF-A, and a rat VEGF-A comprises an L1 comprising the amino acid sequence DVMQPYWG (SEQ ID NO: 35); an L2 comprising the amino acid sequence KQDSD (SEQ ID NO: 93); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP that binds human VEGF-A, a mouse VEGF-A, and a rat VEGF-A comprises the amino acid sequence GCDVMQPYWGCKQDSDCLAGCVCHWYNSCG (SEQ ID NO: 55).

In certain embodiments, non-naturally occurring VEGF-A-binding CKP that binds human VEGF-A, a mouse VEGF-A, and a rat VEGF-A comprises an L1 comprising the amino acid sequence DVMQPYWG (SEQ ID NO: 35); an L2 comprising the amino acid sequence GPDID (SEQ ID NO: 118); an L3 comprising the amino acid sequence LAG; an L4 comprising the amino acid V, and an L5 comprising the amino acid sequence HWYNS (SEQ ID NO: 46), with reference to scaffold structure I. In certain embodiments, the non-naturally occurring VEGF-A-binding CKP that binds human VEGF-A, a mouse VEGF-A, and a rat VEGF-A comprises the amino acid sequence GCDVMQPYWGCGPDIDCLAGCVCHWYNSCG (SEQ ID NO: 123).

In certain embodiments, the non-naturally occurring VEGF-A-binding CKP described herein has an $IC_{50}$ value of less than about 0.5 nM, less than about 0.6 nM, less than about 0.7 nM, less than about 0.8 nM, less than about 0.9 nM, or less than about 1.0 nM, including any range in between these values.

In certain embodiments, the non-naturally occurring VEGF-A-binding CKP does not inhibit trypsin protease activity as measured in a peptide substrate cleavage assay (e.g., the peptide substrate cleavage assay described in the Examples).

In certain embodiments, the non-naturally occurring VEGF-A-binding CKP is resistant to trypsin digestion. In certain embodiments, about 30% or less, about 25% or less, or about 20% or less of the non-naturally occurring VEGF-A-binding CKP is cleaved at Arg13 within loop 2 after 24 h incubation with trypsin at 37° C.

Nucleic acid molecules encoding non-naturally occurring VEGF-A-binding CKPs described herein, expression vectors comprising nucleic acid molecules encoding the non-naturally occurring VEGF-A-binding CKP, and cells comprising the nucleic acid molecules are also contemplated. Also provided herein are methods of producing a non-naturally occurring VEGF-A-binding CKP described herein by culturing such cells, expressing the non-naturally occurring VEGF-A-binding CKP, and recovering the non-naturally occurring VEGF-A-binding CKP from the cell culture.

In certain embodiments, a non-naturally occurring VEGF-A-binding CKP is produced via in vitro translation, as described elsewhere herein.

In certain embodiments, a non-naturally occurring VEGF-A-binding CKP is generated via chemical peptide synthesis, e.g., by grafting chemically synthesized L1, L2, L3, L4, and/or L5 peptides onto an scaffold framework (such as scaffold structure I), or by chemically synthesizing the entire non-naturally occurring VEGF-A-binding CKP.

Non-Naturally Occurring Cystine Knot Peptides (CKPs) that Bind Human Low Density Lipoprotein Receptor (LDL)-Related Protein 6 (LRP6)

LDL receptors are transmembrane cell surface proteins involved in receptor-mediated endocytosis of lipoprotein and protein ligands. Human LDL receptor-related protein 6 (LRP6) (Accession Nos: NM_002336 (mRNA) and NP_002327 (protein); UniProtKB: O75581) functions as a receptor or, with Frizzled, a co-receptor for Wnt and thereby transmits the canonical Wnt/beta-catenin signaling cascade (Katoh et al. (2007) *Clin Cancer Res* 13:4042-4045). Through its interaction with the Wnt/beta-catenin signaling cascade, LRP6 plays a role in the regulation of cell differentiation, proliferation, and migration, and in the development of many cancer types (Li et al. (2004) *Oncogene* 23:9129-9135; Tung et al. (2012) PLoS ONE 7(5): e36565. doi:10.1371/journal.pone.0036565; Liu et al. (2010) *Proc Natl Acad Sci USA* 107:5136-5141).

Wnt signaling is involved in many biological pathways. With respect to diseases it is involved with cancer and metastatic disease, osteoporosis and other bone metabolism and disease, neuronal and neurodegenerative disease, rheumatoid arthritis and other inflammatory disease. This inhibition of Wnt signaling by blockade of LRP6 may have a wide range of therapeutic utility. Bone loss is a serious medical problem, not only during postmenopausal osteoporosis, but also in rheumatoid arthritis. Bone is degraded in multiple myeloma and in bone metastases. Therapeutic strategies aimed at strengthening bone, fracture prevention, or restoration of damaged bone are therefore of very high interest (Kawai et al. (2011) *Nat. Rev. Drug Discov.* 10, 141-156; Mason and Williams (2010) *J. Osteoporosis*, vol. 2010, Article ID 460120, 9 pages; doi:10.4061/2010/460120). The Wnt pathway inhibitors DKK1 and SOST, because of their roles in suppressing new bone formation, are considered highly promising therapeutic targets; antibodies with neutralizing the function of SOST show significant preclinical activity (Ominsky et al. (2010) *J. Bone Miner. Res.* 25, 948-959) and are now in human clinical trials (Padhi et al. (2011) *J. Bone Miner. Res.* 26, 19-26.

Misregulated Wnt signaling is implicated in diseases ranging from osteoporosis to cancer (Clevers (2006) *Cell* 127: 469-80; MacDonald et al. 2009. *Dev Cell* 17: 9-26; Nusse (2008) *Cell Res* 18: 523-7; Polakis (2007) *Curr Opin Genet Dev* 17: 45-51). This list has expanded to include metabolic disorders (Mani et al. (2007) *Science* 315: 1278-82 and neurodegeneration (Caricasole et al. (2004) *J Neurosci* 24: 6021-7; De Ferrari et al. (2007) *Proc Natl Acad Sci USA* 104: 9434-9). An especially clear link exists between mutations of the protein adenomatous polyposis *coli* (APC), which prevent effective regulation of β-catenin levels, and colorectal cancers (Polakis (2007) *Curr Opin Genet Dev* 17: 45-51). Also of particular note is the strong genetic relationship between LRP5 and bone homeostasis. Loss-of-function mutations in LRP5 cause the autosomal recessive disorder osteoporosispseudoglioma syndrome (OPPG), characterized by low bone mass, ocular defects and a predisposition to fractures (Gong et al. (2001) *Cell* 107: 513-23.

Provided herein is a non-naturally occurring CKP that binds to human low density lipoprotein receptor-related protein 6 (LRP6), wherein the non-naturally CKP comprises the following cystine scaffold structure (i.e., scaffold structure I):

$$Z_1C_1L1C_2L2C_3L3C_4L4C_5L5C_6Z_2 \quad (I)$$

wherein:

$Z_1$ and $Z_2$ are any amino acid;

L1 is Loop 1 and has a structure selected from the group consisting of: $X_1X_2X_3X_4X_5X_6$, $X_1X_2X_3X_4X_5X_6X_7$, $X_1X_2X_3X_4X_5X_6X_7X_8$, $X_1X_2X_3X_4X_5X_6X_7X_8X_9$, and $X_1X_2X_3X_4X_5X_6X_7X_8X_9X_{10}$, wherein each of $X_1$-$X_{10}$ is any amino acid;

L2 is Loop 2 and has the structure: $X_1X_2X_3X_4X_5$, wherein each of $X_1$-$X_5$ is any amino acid;

L3 is Loop 3 and has the structure: $X_1X_2X_3$ wherein each of $X_1$-$X_3$ is any amino acid;

L4 is Loop 4 and has the structure: $X_1$, wherein $X_1$ is any amino acid; and

L5 is Loop 5 and has the structure: $X_1X_2X_3X_4X_5$, wherein each of $X_1$-$X_5$ is any amino acid.

In certain embodiments, $Z_1$ and/or $Z_2$ of the non-naturally occurring cystine knot peptide (CKP) that binds to LRP6 is G. In certain embodiments, $Z_1$ and/or $Z_2$ comprise more than one amino acid. In certain embodiments, $Z_1$ and/or $Z_2$ comprise 4 amino acids. In certain embodiments, $Z_1$ and/or $Z_2$ comprise 5 amino acids.

In certain embodiments, the non-naturally occurring LRP6-binding CKP comprises an L1 wherein $X_1$ is an amino acid selected from R, V, M, A, G, N, S, and E; wherein $X_2$ is an amino acid selected from T, N, S, G, R, and A; wherein $X_3$ is an amino acid selected from N, R, H, V, K, S, G, I, and Y; wherein $X_4$ is an amino acid selected from R, V, N, I, K, S, and T; wherein $X_5$ is an amino acid selected from V, R, K, I, T, S, L, and N; and wherein $X_6$ is an amino acid selected from K, G, A, I, R, N, S, and V. In certain embodiments, the non-naturally occurring LRP6-binding CKP comprises an L1 wherein $X_7$ is an amino acid selected from G, R, K, E, P, and T. In certain embodiments, the non-naturally occurring LRP6-binding CKP comprises an L1 wherein $X_8$ is an amino acid selected from G, R, K, Q, A, and S. In certain embodiments, the non-naturally occurring LRP6-binding CKP comprises an L1 wherein $X_9$ is an amino acid selected from R or G. In certain embodiments, the non-naturally occurring LRP6-binding CKP comprises an L1 wherein $X_{10}$ is an amino acid selected from E, W, and G. In certain embodiments, the non-naturally occurring LRP6-binding CKP comprises an L5 wherein $X_1$ is an amino acid selected from G, S, N, Y, A, and R; wherein $X_2$ is an amino acid selected from P, G, S, V, E, R, F, and D; wherein $X_3$ is an amino acid selected from N, G, S, E, P, K, H, and R; wherein $X_4$ is an amino acid selected from G, R, H, S, Q, V, and D; and wherein $X_5$ is an amino acid selected from F, D, N, R, G, Y, S, and T. In certain embodiments, the non-naturally occurring LRP6-binding CKP comprises an L2 wherein $X_1$ is K, $X_2$ is Q, $X_3$ is D, $X_4$ is S, and $X_5$ is D. In certain embodiments, the non-naturally occurring LRP6-binding CKP comprises an L3 wherein $X_1$ is L, $X_2$ is A, and $X_3$ is G. In certain embodiments, the non-naturally occurring LRP6-binding CKP comprises an L4 wherein $X_1$ is V.

In certain embodiments, the non-naturally occurring LRP6-binding CKP competitively inhibits the binding of a competing molecule to human LRP6. In certain embodiments, the competing molecule is an anti-LRP6 antibody. In certain embodiments, the competing molecule is a second non-naturally occurring LRP6-binding CKP.

Non-naturally occurring LRP6-binding CKPs that bind to overlapping or similar areas on a target can be identified by competitive inhibition/binding assays. Such assays are well known in the art and are described in, e.g., S. J. Mather (ed.) 1996. *Current Directions in Radiopharmaceutical Research and Development,* 169-179, Kluwer Academic Publishers; Zettner (1973) *Clin. Chem.* 19, 699-705; Gao (2012) *Analytical Methods* 4, 3718-3723.

In certain embodiments, the non-naturally occurring LRP6-binding CKP binds the same epitope of human LRP6 bound by a second non-naturally occurring LRP6-binding CKP comprising an L1 that comprises the amino acid sequence V/R/N/S/E/G-N/S/G/R-R/V/K/S/N/I/Y-V/N/I/R/S/T-R/K/I/N-G/I/R/K/S/A (SEQ ID NO: 185) or A/R/M/V/G/S-N/T/S/A-R/N/H-V/R/K-K/V/I-R/K/A/N/S/V-T/G/R/K/P-S/G/R/A (SEQ ID NO: 186) or R/A/Q-S/A-G/S/N/I-N/K-T/S/L/R-I/R/V-R/E/K-K/Q/A-R/G/Q-E/W/G/R (SEQ ID NO: 187); an L2 that comprises the amino acid sequence KQDSD (SEQ ID NO: 93); an L3 that comprises the amino acid sequence LAG; an L4 that comprises the amino acid V; and an L5 that comprises the amino acid sequence G/S/N/Y/A/R-P/G/S/V/E/R/F/D-N/G/S/E/P/K/H/R-G/R/H/S/Q/V/D-F/D/N/R/G/Y/S/T (SEQ ID NO: 188), with reference to scaffold structure I.

In certain embodiments, the non-naturally occurring LRP6-binding CKP comprises an L1 that comprises the amino acid sequence V/R/N/S/E/G-N/S/G/R-R/V/K/S/N/I/Y-V/N/I/R/S/T-R/K/I/N-G/I/R/K/S/A (SEQ ID NO: 185) or A/R/M/V/G/S-N/T/S/A-R/N/H-V/R/K-K/V/I-R/K/A/N/S/V-T/G/R/K/P-S/G/R/A (SEQ ID NO: 186) or R/A-S-G/S/N-N/K-T/S/L-I/R-R/E-K/Q/A-R/G-E/W/G (SEQ ID NO: 187)), with reference to scaffold structure I. In certain embodiments, the non-naturally occurring LRP6-binding CKP further comprises an L2 that comprises the amino acid sequence KQDSD (SEQ ID NO: 93). In certain embodiments, the non-naturally occurring LRP6-binding CKP further comprises an L3 that comprises the amino acid sequence LAG. In certain embodiments, the non-naturally occurring LRP6-binding CKP further comprises an L4 that comprises the amino acid V. In certain embodiments, the non-naturally occurring LRP6-binding CKP further comprises an L5 that comprises the amino acid sequence G/S/N/Y/A/R-P/G/S/V/E/R/F/D-N/G/S/E/P/K/H/R-G/R/H/S/Q/V/D-F/D/N/R/G/Y/S/T (SEQ ID NO: 188

In certain embodiments, the non-naturally occurring LRP6-binding CKP comprises an L1 and/or L5 of any one of the non-naturally occurring LRP6-binding CKPs disclosed herein. In certain embodiments, the non-naturally occurring LRP6-binding CKP comprises an L1 that comprises an amino acid sequence set forth in any one of SEQ ID NOs: 147-168 and 367, with respect to scaffold structure I. In certain embodiments, the non-naturally occurring LRP6-binding CKP further comprises an L2 that comprises the amino acid sequence set forth in SEQ ID NO: 93. In certain embodiments, the non-naturally occurring LRP6-binding CKP further comprises an L3 that comprises the amino acid sequence LAG. In certain embodiments, the non-naturally occurring LRP6-binding CKP further comprises an L4 comprising the amino acid V. In certain embodiments, the non-naturally occurring LRP6-binding CKP further comprises an L5 that comprises an amino acid sequence set forth in any one of SEQ ID NOs: 19 and 169-184.

The L1 and L5 amino acid sequences described above are provided in Table 18 below:

TABLE 18

| | |
|---|---|
| RTNRVKGG (SEQ ID NO: 147) | GPNGF (SEQ ID NO: 19) |
| VNRVRG (SEQ ID NO: 148) | SGGRD (SEQ ID NO: 169) |
| MNHVKARR (SEQ ID NO: 149) | GPNGF (SEQ ID NO: 19) |
| RSVNKI (SEQ ID NO: 150) | GSSRN (SEQ ID NO: 170) |
| VNKIKG (SEQ ID NO: 151) | GVEGR (SEQ ID NO: 171) |
| RNSIKR (SEQ ID NO: 152) | SVGHG (SEQ ID NO: 172) |
| VSNRVNKG (SEQ ID NO: 153) | GPNGF (SEQ ID NO: 19) |
| RGNIIK (SEQ ID NO: 154) | NESRG (SEQ ID NO: 173) |
| RSGNTIRKRE (SEQ ID NO: 155) | GGPGG (SEQ ID NO: 174) |
| ASSNSIRQGW (SEQ ID NO: 156) | GPKSN (SEQ ID NO: 175) |
| RSNRIR (SEQ ID NO: 157) | YGHGD (SEQ ID NO: 176) |
| RSNKLREARG (SEQ ID NO: 158) | GSRQD (SEQ ID NO: 177) |
| VNSVKR (SEQ ID NO: 159) | SRGVN (SEQ ID NO: 178) |
| GSNKIRPR (SEQ ID NO: 160) | GPNDF (SEQ ID NO: 179) |
| NRIRNS (SEQ ID NO: 161) | GRGDY (SEQ ID NO: 180) |
| SRNSIK (SEQ ID NO: 162) | ASGSS (SEQ ID NO: 181) |
| SNYVKR (SEQ ID NO: 163) | SPGGR (SEQ ID NO: 182) |
| RANRVSGR (SEQ ID NO: 164) | GPNGF (SEQ ID NO: 19) |
| SNRVKVRA (SEQ ID NO: 165) | GPNGF (SEQ ID NO: 19) |
| ENRTKG (SEQ ID NO: 166) | GFRGT (SEQ ID NO: 183) |
| GNKIRA (SEQ ID NO: 167) | RDRVG (SEQ ID NO: 184) |
| ANRVKRTS (SEQ ID NO: 168) | GPNGF (SEQ ID NO: 19) |
| QAINRVKRQR (SEQ ID NO: 367) | |
| V/R/N/S/E/G-N/S/G/R-R/V/K/S/N/I/Y-V/N/I/R/S/T-R/K/I/N-G/I/R/K/S/A (SEQ ID NO: 185) | A/R/M/M/G/S-N/T/S/A-R/N/H-V/R/K-K/V/I-R/K/A/N/S/V-T/G/R/K/P-S/G/R/A (SEQ ID NO: 186) |
| R/A-S-G/S/N-N/K-T/S/L-I/R-R/E-K/Q/A-R/G-E/W/G (SEQ ID NO: 187) | G/S/N/Y/A/R-P/G/S/V/E/R/F/D-N/G/S/E/P/K/H/R-G/R/H/S/Q/V/D-F/D/N/R/G/Y/S/T (SEQ ID NO: 188) |

In certain embodiments, the non-naturally occurring LRP6-binding CKP comprises an L1 that comprises the amino acid sequence RTNRVKGG (SEQ ID NO: 147); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to with reference to scaffold structure I.

In certain embodiments, the non-naturally occurring LRP6-binding CKP comprises an L1 that comprises the amino acid sequence VNRVRG (SEQ ID NO: 148); an L2 that comprises the amino acid sequence KQDSD (SEQ ID NO: 93); an L3 that comprises the amino acid sequence LAG; an L4 that comprises the amino acid V; and an L5 that comprises the amino acid sequence SGGRD (SEQ ID NO: 169), with reference to with reference to scaffold structure I.

In certain embodiments, the non-naturally occurring LRP6-binding CKP comprises an L1 that comprises the amino acid sequence MNHVKARR (SEQ ID NO: 149); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an L1 that comprises the amino acid sequence RSVNKI (SEQ ID NO: 150); an L2 that comprises the amino acid sequence KQDSD (SEQ ID NO: 93); an L3 that comprises the amino acid sequence LAG; an L4 that comprises the amino acid V; and an L5 that comprises the amino acid sequence GSSRN (SEQ ID NO: 170), with reference to scaffold structure I.

In certain embodiments, the non-naturally occurring LRP6-binding CKP comprises an L1 that comprises the amino acid sequence VNKIKG (SEQ ID NO: 151); an L2 that comprises the amino acid sequence KQDSD (SEQ ID NO: 93); an L3 that comprises the amino acid sequence LAG; an L4 that comprises the amino acid V; and an L5 that comprises the amino acid sequence GVEGR (SEQ ID NO: 29), with reference to scaffold structure I.

In certain embodiments, the non-naturally occurring LRP6-binding CKP comprises an L1 that comprises the amino acid sequence RNSIKR (SEQ ID NO: 152); an L2 that comprises the amino acid sequence KQDSD (SEQ ID NO: 93); an L3 that comprises the amino acid sequence LAG; an L4 that comprises the amino acid V; and an L5 that comprises the amino acid sequence SVGHG (SEQ ID NO: 172), with reference to scaffold structure I.

In certain embodiments, the non-naturally occurring LRP6-binding CKP comprises an L1 that comprises the amino acid sequence VSNRVNKG (SEQ ID NO: 153); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an L1 that comprises the amino acid sequence RGNIIK (SEQ ID NO: 154); an L2 that comprises the amino acid sequence KQDSD (SEQ ID NO: 93); an L3 that comprises the amino acid sequence LAG; an L4 that comprises the amino acid V; and an L5 that comprises the amino acid sequence NESRG (SEQ ID NO: 173), with reference to scaffold structure I.

In certain embodiments, the non-naturally occurring LRP6-binding CKP comprises an L1 that comprises the amino acid sequence RSGNTIRKRE (SEQ ID NO: 155); an L2 that comprises the amino acid sequence KQDSD (SEQ ID NO: 93); an L3 that comprises the amino acid sequence LAG; an L4 that comprises the amino acid V; and an L5 that comprises the amino acid sequence GGPGG (SEQ ID NO: 174), with reference to scaffold structure I.

In certain embodiments, the non-naturally occurring LRP6-binding CKP comprises an L1 that comprises the amino acid sequence ASSNSIRQGW (SEQ ID NO: 156); an L2 that comprises the amino acid sequence KQDSD (SEQ ID NO: 93); an L3 that comprises the amino acid sequence LAG; an L4 that comprises the amino acid V; and an L5 that comprises the amino acid sequence GPKSN (SEQ ID NO: 175), with reference to scaffold structure I.

In certain embodiments, the non-naturally occurring LRP6-binding CKP comprises an L1 that comprises the amino acid sequence RSNRIR (SEQ ID NO: 157); an L2 that comprises the amino acid sequence KQDSD (SEQ ID NO: 93); an L3 that comprises the amino acid sequence LAG; an L4 that comprises the amino acid V; and an L5 that comprises the amino acid sequence YGHGD (SEQ ID NO: 176), with reference to scaffold structure I.

In certain embodiments, non-naturally occurring LRP6-binding CKP an L1 that comprises the amino acid sequence RSNKLREARG (SEQ ID NO: 158); an L2 that comprises the amino acid sequence KQDSD (SEQ ID NO: 93); an L3 that comprises the amino acid sequence LAG; an L4 that comprises the amino acid V; and an L5 that comprises the amino acid sequence GSRQD (SEQ ID NO: 177), with reference to scaffold structure I.

In certain embodiments, the non-naturally occurring LRP6-binding CKP comprises an L1 that comprises the amino acid sequence VNSVKR (SEQ ID NO: 159); an L2 that comprises the amino acid sequence KQDSD (SEQ ID NO: 93); an L3 that comprises the amino acid sequence LAG; an L4 that comprises the amino acid V; and an L5 that comprises the amino acid sequence SRGVN (SEQ ID NO: 178), with reference to scaffold structure I.

In certain embodiments, the non-naturally occurring LRP6-binding CKP comprises an L1 that comprises the amino acid sequence GSNKIRPR (SEQ ID NO: 160); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNDF (SEQ ID NO: 179), with reference to scaffold structure I.

In certain embodiments, the non-naturally occurring LRP6-binding CKP comprises an L1 that comprises the amino acid sequence NRIRNS (SEQ ID NO: 161); an L2 that comprises the amino acid sequence KQDSD (SEQ ID NO: 93); an L3 that comprises the amino acid sequence LAG; an L4 that comprises the amino acid V; and an L5 that comprises the amino acid sequence GRGDY (SEQ ID NO: 180), with reference to scaffold structure I.

In certain embodiments, the non-naturally occurring LRP6-binding CKP comprises an L1 that comprises the amino acid sequence SRNSIK (SEQ ID NO: 162); an L2 that comprises the amino acid sequence KQDSD (SEQ ID NO: 93); an L3 that comprises the amino acid sequence LAG; an L4 that comprises the amino acid V; and an L5 that comprises the amino acid sequence ASGSS (SEQ ID NO: 181), with reference to scaffold structure I.

In certain embodiments, the non-naturally occurring LRP6-binding CKP comprises an L1 that comprises the amino acid sequence SNYVKR (SEQ ID NO: 163); an L2 that comprises the amino acid sequence KQDSD (SEQ ID NO: 93); an L3 that comprises the amino acid sequence LAG; an L4 that comprises the amino acid V; and an L5 that comprises the amino acid sequence SPGGR (SEQ ID NO: 182), with reference to scaffold structure I.

In certain embodiments, the non-naturally occurring LRP6-binding CKP comprises an L1 that comprises the amino acid sequence RANRVSGR (SEQ ID NO: 164); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an L1 that comprises the amino acid sequence SNRVKVRA (SEQ ID NO: 165); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an L1 that comprises the amino acid sequence ENRTKG (SEQ ID NO: 166); an L2 that comprises the amino acid sequence KQDSD (SEQ ID NO: 93); an L3 that comprises the amino acid sequence LAG; an L4 that comprises the amino acid V; and an L5 that comprises the amino acid sequence GFRGT (SEQ ID NO: 183), with reference to with reference to scaffold structure I.

In certain embodiments, the non-naturally occurring LRP6-binding CKP comprises an L1 that comprises the amino acid sequence GNKIRA (SEQ ID NO: 167); an L2 that comprises the amino acid sequence KQDSD (SEQ ID NO: 93); an L3 that comprises the amino acid sequence LAG; an L4 that comprises the amino acid V; and an L5 that comprises the amino acid sequence RDRVG (SEQ ID NO: 184), with reference to scaffold structure I.

In certain embodiments, the non-naturally occurring LRP6-binding CKP comprises an L1 that comprises the amino acid sequence ANRVKRTS (SEQ ID NO: 168); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an L1 that comprises the amino acid sequence QAINRVKRQR (SEQ ID NO: 367); an L2 that comprises the amino acid sequence KQDSD (SEQ ID NO: 93); an L3 that comprises the amino acid sequence LAG; an L4 that comprises the amino acid V; and an L5 that comprises the amino acid sequence GPNGF (SEQ ID NO: 19), with reference to scaffold structure I.

In certain embodiments, the non-naturally occurring LRP6-binding CKP comprises an amino acid sequence set forth in any one of SEQ ID NOs: 189-210 and 366. SEQ ID NOs: 189-210 and 366 are provided below.

```
GCRTNRVKGGCKQDSDCLAGCVCGPNGFCG (SEQ ID NO: 189)

GCVNRVRGCKQDSDCLAGCVCSGGRDCG (SEQ ID NO: 190)

GCMNHVKARRCKQDSDCLAGCVCGPNGFCG (SEQ ID NO: 191)

GCRSVNKICKQDSDCLAGCVCGSSRNCG (SEQ ID NO: 192)

GCVNKIKGCKQDSDCLAGCVCGVEGRCG (SEQ ID NO: 193)

GCRNSIKRCKQNSDCLAGCVCSVGHGCG (SEQ ID NO: 194)

GCVSNRVNKGCKQDSDCLAGCVCGPNGFCG (SEQ ID NO: 195)

GCRGNIIKCKQDSDCLAGCVCNESRGCG (SEQ ID NO: 196)

GCRSGNTIRKRECKQDSDCLAGCVCGGPGGCG (SEQ ID NO: 197)

GCASSNSIRQGWCKQDSDCLAGCVCGPKSNCG (SEQ ID NO: 198)

GCRSNRIRCKQDSDCLAGCVCYGHGDCG (SEQ ID NO: 199)

GCRSNKLREARGCKQDSDCLAGCVCGSRQDCG (SEQ ID NO: 200)

GCVNSVKRCKQDSDCLAGCVCSRGVNCG (SEQ ID NO: 201)

GCGSNKIRPRCKQDSDCLAGCVCGPNDFCG (SEQ ID NO: 202)

GCNRIRNSCKQDSDCLAGCVCGRGDYCG (SEQ ID NO: 203)

GCSRNSIKCKQDSDCLAGCVCASGSSCG (SEQ ID NO: 204)
```

-continued
```
GCSNYVKRCKQDSDCLAGCVCSPGGRCG (SEQ ID NO: 205)

GCRANRVSGRCKQDSDCLAGCVCGPNGFCG (SEQ ID NO: 206)

GCSNRVKVRACKQDSDCLAGCVCGPNGFCG (SEQ ID NO: 207)

GCENRTKGCKQDSDCLAGCVCGFRGTCG (SEQ ID NO: 208)

GCGNKIRACKQDSDCLAGCVCRDRVGCG (SEQ ID NO: 209)

GCANRVKRTSCKQDSDCLAGCVCGPNGFCG (SEQ ID NO: 210)

GCQAINRVKRQRCKQDSDCLAGCVCGPNGFCG (SEQ ID NO: 366)
```

In certain embodiments, the non-naturally occurring LRP6-binding CKP is a variant of a non-naturally occurring LRP6-binding CKP described herein. In certain embodiments, such a variant comprises at least 1, at least 2, at least 3, at least 4, at least 5, at least 6, at least 7, at least 8, at least 9, or at least 10 amino acid substitutions in one or more of the sequences set forth in SEQ ID NOs: 19, 93, 147-168, 169-184, and 189-210 and/or in the amino acid sequence LAG. In certain embodiments, the amino acid substitution(s) are conservative amino acid substitution(s). In certain embodiments, the amino acid substitutions do not substantially reduce the ability of the non-naturally occurring LRP6-binding CKP to bind human LRP6. For example, conservative alterations (e.g., conservative substitutions as provided herein) that do not substantially reduce LRP6 binding affinity may be made. The binding affinity of a variant of a non-naturally occurring LRP6-binding CKP can be assessed using a method described in the Examples below.

Conservative substitutions are shown in Table 17 above under the heading of "conservative substitutions." More substantial changes are provided in Table 17 under the heading of "exemplary substitutions," and as further described below in reference to amino acid side chain classes. Amino acid substitutions may be introduced into a variant of a non-naturally occurring LRP6-binding CKP and the products screened for a desired activity, e.g., retained/improved LRP6 binding.

Non-conservative substitutions will entail exchanging a member of one of these classes for another class. An exemplary substitutional variant is an affinity matured non-naturally occurring LRP6-binding CKP, which may be conveniently generated, e.g., using phage display based affinity maturation techniques such as those described herein. Briefly, one or more residues in L1, L2, L3, L4, and/or L5 is altered (i.e., added, deleted, or substituted) and the variant LRP6-binding CKP is displayed on phage and screened for LRP6 binding affinity. In certain embodiments of affinity maturation, diversity is introduced into the variable genes chosen for maturation by any of a variety of methods (e.g., error-prone PCR, loop shuffling, or oligonucleotide-directed mutagenesis). A secondary library is then created. The library is then screened to identify any non-naturally occurring CKP variants with the desired affinity for LRP6. In certain embodiments, introducing diversity involves loop-directed approaches, in which several residues in L1, L2, L3, L4, and/or L5 (e.g., about 5, about 4-6, or about 6-10 residues at a time) are randomized. L1, L2, L3, L4, and/or L5 residues involved in binding a target ligand may be identified, e.g., using alanine scanning mutagenesis or modeling.

In certain embodiments, a non-naturally occurring CKP that "specifically binds" human LRP6 (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for another LRP protein which is at least about 50-fold, or at least about 500-fold, or at least about 1000-fold, weaker than its binding affinity for LRP6.

In certain embodiments, the extent of binding of the non-naturally occurring LRP6-binding CKP to a non-target protein (e.g., a LRP6 homolog such as LRP1, LRP1B, LRP2, LRP3, LRP4, LRP5, LRP8, LRP10, LRP11, and LRP12) is less than about 10% of the binding of the non-naturally occurring LRP6-binding CKP to human LRP6 as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In certain embodiments, the non-naturally occurring LRP6-binding CKP binds a human LRP6 with a Kd between about 1 pM to about 500 nM. In certain embodiments, the non-naturally occurring LRP6-binding CKP protein that specifically binds LRP6 binds a human LRP6 with a Kd between about 1 pM to about 50 pM, between about 50 pM to about 250 pM, between about 250 pM to about 500 pM, between about 500 pM to 750 pM, between about 750 pM to about 1 nM, between about 1 nM to about 25 nM, between about 25 nM to 50 nM, between 50 nM to about 100 nM, between about 100 nM to about 250 nM, or between about 250 nM to about 500 nM, including any range in between these values.

In certain embodiments, the non-naturally occurring LRP6-binding CKP inhibits Wnt1 signaling, e.g., as determined using methods described in the Examples below.

Nucleic acid molecules encoding the non-naturally occurring LRP6-binding CKPs described, expression vectors comprising nucleic acid molecules encoding the non-naturally occurring LRP6-binding CKPs, and cells comprising the nucleic acid molecules are also contemplated. Also provided herein are methods of producing a non-naturally occurring LRP6-binding CKP by culturing such cells, expressing the non-naturally occurring LRP6-binding CKP, and recovering the non-naturally occurring LRP6-binding CKP from the cell culture.

In certain embodiments, a non-naturally occurring LRP6-binding CKP is produced via in vitro translation, as described elsewhere herein.

As described elsewhere herein, a non-naturally occurring LRP6-binding CKP is generated via chemical peptide synthesis, e.g., by grafting chemically synthesized L1, L2, L3, L4, and/or L5 peptides onto an EETI-II framework, or by chemically synthesizing the entire non-naturally occurring LRP6-binding CKP.

In certain embodiments, the non-naturally occurring LRP6-binding CKP is as a therapeutic agent in the treatment of diseases or conditions wherein excessive LRP6 activity is involved.

Methods of Production

In certain embodiments, a non-naturally occurring VEGF-A-binding CKP or a non-naturally occurring LRP6-binding CKP is generated via genetic engineering. A variety of methods for mutagenesis have been previously described (along with appropriate methods for screening or selection). Such mutagenesis methods include, but are not limited to, e.g., error-prone PCR, loop shuffling, or oligonucleotide-directed mutagenesis, random nucleotide insertion or other methods prior to recombination. Further details regarding these methods are described in, e.g., Abou-Nadler et al. (2010) *Bioengineered Bugs* 1, 337-340; Firth et al. (2005) *Bioinformatics* 21, 3314-3315; Cirino et al. (2003) *Methods Mol Biol* 231, 3-9; Pirakitikulr (2010) *Protein Sci* 19, 2336-2346; Steffens et al. (2007) *J. Biomol Tech* 18, 147-149; and others. Accordingly, in certain embodiments, provided is a non-naturally occurring VEGF-A-binding CKP or a non-naturally occurring LRP6-binding CKP generated via genetic engineering techniques.

In certain embodiments, a non-naturally occurring VEGF-A-binding CKP or a non-naturally occurring LRP6-binding CKP is generated via in vitro translation. Briefly, in vitro translation entails cloning the protein-coding sequence(s) into a vector containing a promoter, producing mRNA by transcribing the cloned sequence(s) with an RNA polymerase, and synthesizing the protein by translation of this mRNA in vitro, e.g., using a cell-free extract. A desired variant protein can be generated simply by altering the cloned protein-coding sequence. Many mRNAs can be translated efficiently in wheat germ extracts or in rabbit reticulocyte lysates. Further details regarding in vitro translation are described in, e.g., Hope et al. (1985) *Cell* 43, 177-188; Hope et al. (1986) *Cell* 46, 885-894; Hope et al. (1987) *EMBO J.* 6, 2781-2784; Hope et al. (1988) *Nature* 333, 635-640; and Melton et al. (1984) *Nucl. Acids Res.* 12, 7057-7070.

Accordingly, provided are nucleic acid molecules encoding a non-naturally occurring VEGF-A-binding CKP or a non-naturally occurring LRP6-binding CKP described herein. An expression vector operably linked to a nucleic acid molecule encoding a non-naturally occurring VEGF-A-binding CKP or a non-naturally occurring LRP6-binding CKP is also provided. Host cells (including, e.g., prokaryotic host cells such as *E. coli*, eukaryotic host cells such as yeast cells, mammalian cells, CHO cells, etc.) comprising a nucleic acid encoding a non-naturally occurring VEGF-A-binding CKP or a non-naturally occurring LRP6-binding CKP are also provided.

In certain embodiments, non-naturally occurring VEGF-A-binding CKP or a non-naturally occurring LRP6-binding CKP is generated via in vitro translation. Briefly, in vitro translation entails cloning the protein-coding sequence(s) into a vector containing a promoter, producing mRNA by transcribing the cloned sequence(s) with an RNA polymerase, and synthesizing the protein by translation of this mRNA in vitro, e.g., using a cell-free extract. A desired mutant protein can be generated simply by altering the cloned protein-coding sequence. Many mRNAs can be translated efficiently in wheat germ extracts or in rabbit reticulocyte lysates. Further details regarding in vitro translation are described in, e.g., Hope et al. (1985) *Cell* 43, 177-188; Hope et al. (1986) *Cell* 46, 885-894; Hope et al. (1987) *EMBO J.* 6, 2781-2784; Hope et al. (1988) *Nature* 333, 635-640; and Melton et al. (1984) *Nucl. Acids Res.* 12, 7057-7070.

In certain embodiments, a non-naturally occurring VEGF-A-binding CKP or a non-naturally occurring LRP6-binding CKP is generated via chemical synthesis. In certain embodiments, chemically synthesized L1, L2, L3, L4, and/or L5 peptides are grafted onto an EETI-II-based framework (such as scaffold structure I) to generate non-naturally occurring VEGF-A-binding CKP or a non-naturally occurring LRP6-binding CKP. In certain embodiments the entire non-naturally occurring VEGF-A-binding CKP or the entire non-naturally occurring LRP6-binding CKP is chemically synthesized. Methods of solid phase and liquid phase peptide synthesis are well known in the art and described in detail in, e.g., Methods of Molecular Biology, 35, Peptide Synthesis Protocols, (M. W. Pennington and B. M. Dunn Eds), Springer, 1994; Welsch et al. (2010) *Curr Opin Chem Biol* 14, 1-15; Methods of Enzymology, 289, Solid Phase Peptide Synthesis, (G. B. Fields Ed.), Academic Press, 1997; Chemical Approaches to the Synthesis of Peptides and Proteins, (P. Lloyd-Williams, F. Albericio, and E. Giralt Eds), CRC Press, 1997; Fmoc Solid Phase Peptide Synthesis, A Practical Approach, (W. C. Chan, P. D. White Eds), Oxford University Press, 2000; Solid Phase Synthesis, A Practical Guide, (S. F. Kates, F Albericio Eds), Marcel Dekker, 2000; P. Seneci, Solid-Phase Synthesis and Combinatorial Technologies, John Wiley & Sons, 2000; Synthesis of Peptides and Peptidomimetics (M. Goodman, Editor-in-chief, A. Felix, L. Moroder, C. Tmiolo Eds), Thieme, 2002; N. L. Benoiton, Chemistry of Peptide Synthesis, CRC Press, 2005; Methods in Molecular Biology, 298, Peptide Synthesis and Applications, (J. Howl Ed) Humana Press, 2005; and Amino Acids, Peptides and Proteins in Organic Chemistry, Volume 3, Building Blocks, Catalysts and Coupling Chemistry, (A. B. Hughs, Ed.) Wiley-VCH, 2011.

Chimeric Molecules Comprising a Non-Naturally Occurring EETI-II Protein

A non-naturally occurring CKP described herein (such as a non-naturally occurring VEGF-A-binding CKP or a non-naturally occurring LRP6-binding CKP) can also be modified if advantageous in a way to form a chimeric molecule comprising the non-naturally occurring CKP fused (e.g., recombinantly fused) to another, heterologous polypeptide or amino acid sequence. In certain embodiments, such a chimeric molecule comprises a fusion of a non-naturally occurring CKP described herein (such as a non-naturally occurring VEGF-A-binding CKP or a non-naturally occurring LRP6-binding CKP) with an antibody to form, e.g., a divalent molecule or a bispecific molecule.

In certain embodiments, a chimeric molecule comprises a fusion of a non-naturally occurring CKP described herein (such as a non-naturally occurring VEGF-A-binding CKP or a non-naturally occurring LRP6-binding CKP) with a second moiety (such as a protein transduction domain) which targets the chimeric molecule for delivery to various tissues, or, e.g., across brain blood barrier, using, for example, the protein transduction domain of human immunodeficiency virus TAT protein (Schwarze et al., 1999, *Science* 285: 1569-72).

In embodiments, the non-naturally occurring CKP provided herein can be used as bi- or multi-specific (for different target ligands or different epitopes on the same target ligand) in multimer form. For example, a dimeric bispecific non-naturally occurring CKP has one subunit with specificity for a first target protein or epitope and a second subunit with specificity for a second target protein or epitope. Non-naturally occurring CKP protein subunits can be joined in a variety of conformations that can increase the valency and thus the avidity of binding to a target ligand.

In certain embodiments a chimeric molecule provided herein comprises two or more (such as three, four, five, six, seven, eight, nine, ten, or more than ten) non-naturally occurring CKP proteins. In certain embodiments, a nucleic acid can be engineered to encode two or more copies of a single non-naturally occurring CKP, which copies are transcribed and translated in tandem to produce a covalently linked multimer of identical subunits. In certain embodiments, the nucleic acid can be engineered to encode two or more different non-naturally occurring CKPs, which copies are transcribed and translated in tandem to produce a covalently linked multimer of different subunits that bind, e.g., different epitopes of a single target ligand, or, e.g., different target ligands.

In another embodiment, such a chimeric molecule comprises a fusion of a non-naturally occurring CKP described herein (such as a non-naturally occurring VEGF-A-binding CKP or a non-naturally occurring LRP6-binding CKP) with a tag polypeptide which provides an epitope to which an anti-tag antibody can selectively bind. The epitope tag is generally placed at the amino- or carboxyl-terminus of the non-naturally occurring CKP. The presence of such epitope-tagged forms of the non-naturally occurring CKP protein can be detected using an antibody against the tag polypeptide. Also, provision of the epitope tag enables the non-naturally occurring CKP to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-Gly) tags; the flu HA tag polypeptide and its antibody 12CA5 (Field et al. (1988) *Mol. Cell. Biol.* 8, 2159-2165); the c-myc tag and the 8F9, 3C7, 6E10, G4, B7 and 9E10 antibodies thereto (Evan et al. (1985) *Mol. Cell. Biol.* 5, 3610-3616]; and the Herpes Simplex virus glycoprotein D (gD) tag and its antibody (Paborsky et al. (1990) *Protein Eng.,* 3, 547-553). Other tag polypeptides include the Flag-peptide (Hopp et al. (1988) *BioTechnology,* 6, 1204-1210); the KT3 epitope peptide (Martin et al. (1992) *Science,* 255, 192-194]; an α-tubulin epitope peptide (Skinner et al. (1991) *J. Biol. Chem.* 266, 15163-15166); and the T7 gene 10 protein peptide tag (Lutz-Freyermuth et al. (1990) *Proc. Natl. Acad. Sci. USA* 87, 6393-6397].

In certain embodiments, the chimeric molecule can comprise a fusion of a non-naturally occurring CKP protein described herein (such as a non-naturally occurring VEGF-A-binding CKP or a non-naturally occurring LRP6-binding CKP) with an immunoglobulin or a particular region of an immunoglobulin. For a bivalent form of the chimeric molecule (e.g., an "immunoadhesin"), such a fusion could be to the Fc region of an IgG molecule. Ig fusions provided herein include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995. In certain embodiments, a non-naturally occurring CKP described herein (such as a non-naturally occurring VEGF-A-binding CKP or a non-naturally occurring LRP6-binding CKP) is fused, e.g., at the N or C terminus, to the constant region of an IgG (Fc). In certain embodiments, the non-naturally occurring CKP/Fc fusion molecule activates the complement component of the immune response. In certain embodiments, the non-naturally occurring CKP/Fc fusion protein increases the therapeutic value of the non-naturally occurring CKP. In certain embodiments, a non-naturally occurring CKP protein described herein (such as a non-naturally occurring VEGF-A-binding CKP or a non-naturally occurring LRP6-binding CKP) is fused (such as recombinantly fused), e.g., at the N or C terminus, to a complement protein, such as C1q. Various publications describe methods for obtaining non-naturally occurring proteins whose half-lives are modified either by introducing an FcRn-binding polypeptide into the molecules (WO 1997/43316, U.S. Pat. Nos. 5,869,046, 5,747,035, WO 1996/32478, WO 1991/14438) or by fusing the proteins with antibodies whose FcRn-binding affinities are preserved but affinities for other Fc receptors have been greatly reduced (WO 1999/43713) or fusing with FcRn binding domains of antibodies (WO 2000/09560, U.S. Pat. No. 4,703,039). Specific techniques and methods of increasing half-life of physiologically active molecules (e.g., non-naturally occurring CKP) can also be found in U.S. Pat. No. 7,083,784. In certain embodiments, a non-naturally occurring CKP protein described herein (such as a non-naturally occurring VEGF-A-binding CKP or a non-naturally occurring LRP6-binding CKP) is fused to an Fc region from an IgG that comprises amino acid residue mutations (as numbered by the EU index in Kabat): M252Y/S254T/T256E or H433K/N434F/Y436H.

In certain embodiments, non-naturally occurring CKP proteins described herein (such as a non-naturally occurring VEGF-A-binding CKP or a non-naturally occurring LRP6-binding CKP) are fused with molecules that increase or extend in vivo or serum half-life. In certain embodiments, a non-naturally occurring CKP described herein (such as a non-naturally occurring VEGF-A-binding CKP or a non-naturally occurring LRP6-binding CKP) is fused with albumin, such as human serum albumin (HSA), polyethylene glycol (PEG), polysaccharides, immunoglobulin molecules (IgG), complement, hemoglobin, a binding peptide, lipoproteins or other factors to increase its half-life in the bloodstream and/or its tissue penetration.

Additional chimeric molecules comprising non-naturally occurring VEGF-A-binding CKPs or non-naturally occurring LRP6-binding CKPs may be generated through the techniques of gene-shuffling, motif-shuffling, exon-shuffling, and/or codon-shuffling (collectively referred to as "DNA shuffling"). DNA shuffling may be employed to alter the activities of the non-naturally occurring CKPs (e.g., non-naturally occurring CKPs with higher affinities and lower dissociation rates). See, generally, U.S. Pat. Nos. 5,605,793, 5,811,238, 5,830,721, 5,834,252, 5,837,458, Patten et al. (1997) *Curr. Opinion Biotechnol.* 8, 724-33; Harayama (1998) *Trends Biotechnol.* 16, 76-82; Hansson, et al., (1999) *J. Mol. Biol.* 287, 265-76; and Lorenzo and Blasco, (1998) *Biotechniques* 24, 308-313

In certain embodiments, a non-naturally occurring VEGF-A-binding CKP or a non-naturally occurring LRP6-binding CKP provided herein is altered by being subjected to random mutagenesis by error-prone PCR, random nucleotide insertion or other methods prior to recombination. One or more portions of a polynucleotide encoding a scaffold that binds to a specific target may be recombined with one or more components, motifs, sections, parts, domains, fragments, etc. of one or more heterologous molecules.

Any of these fusions can be generated by standard techniques, for example, by expression of the fusion protein from a recombinant fusion gene constructed using publicly available gene sequences, or by chemical peptide synthesis.

Conjugates Comprising a Non-Naturally Occurring VEGF-A-Binding CKP or a Non-Naturally Occurring LRP6-binding CKP)

Provided herein are immunoconjugates comprising a non-naturally occurring CKP described herein (such as a non-naturally occurring VEGF-A-binding CKP or a non-naturally occurring LRP6-binding CKP) conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes. Other toxins include maytansine and maytansinoids, calicheamicin and other cytotoxic agents. A variety of radionuclides are available for the production of radioconjugated non-naturally occurring CKPs. Examples include $^{212}$Bi, $^{131}$I, $^{131}$In, $^{90}$Y, and $^{186}$Re.

Conjugates of a non-naturally occurring CKP described herein (such as a non-naturally occurring VEGF-A-binding CKP or a non-naturally occurring LRP6-binding CKP) and, e.g., cytotoxic agent, are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionuclide to a non-naturally occurring CKP provided herein. See, WO94/11026.

In another embodiment, the non-naturally occurring CKP described herein (such as a non-naturally occurring VEGF-A-binding CKP or a non-naturally occurring LRP6-binding CKP) can be conjugated to a "receptor" (such as streptavidin) for utilization in ocular "pre-targeting" wherein the non-naturally occurring EETI-II scaffold protein-receptor conjugate is administered to the eye patient, followed by removal of unbound conjugate from the circulation using a clearing agent and then administration of a "ligand" (e.g., avidin) that is conjugated to a cytotoxic agent (e.g., a radionuclide) or a therapeutic agent.

In certain embodiments, the non-naturally occurring CKPs provided herein (such as a non-naturally occurring VEGF-A-binding CKP or a non-naturally occurring LRP6-binding CKP) can be used as bi- or multi-specific (for different target ligands or different epitopes on the same target ligand) in multimer form. The attachments may be covalent or non-covalent. For example, a dimeric bispecific non-naturally occurring CKP has one subunit with specificity for a first target protein or epitope and a second subunit with specificity for a second target protein or epitope. Non-naturally occurring CKP subunits can be joined, e.g., via conjugation, in a variety of conformations that can increase the valency and thus the avidity of binding to a target ligand or to bind multiple target ligands.

In certain embodiments, non-naturally occurring CKPs provided herein are engineered to provide reactive groups for conjugation. In certain embodiments, the N-terminus and/or C-terminus may also serve to provide reactive groups for conjugation. In certain embodiments, the N-terminus is conjugated to one moiety (such as, but not limited to PEG) while the C-terminus is conjugated to another moiety (such as, but not limited to biotin), or vice versa.

Provided is a non-naturally occurring CKP described herein (such as a non-naturally occurring VEGF-A-binding CKP or a non-naturally occurring LRP6-binding CKP) conjugated to one or more moieties, including but not limited to, peptides, polypeptides, proteins, fusion proteins, nucleic acid molecules, small molecules, mimetic agents, synthetic drugs, inorganic molecules, and organic molecules. Also provided is the use of a non-naturally occurring CKP described herein (such as a non-naturally occurring VEGF-A-binding CKP or a non-naturally occurring LRP6-binding CKP) chemically conjugated (including both covalent and non-covalent conjugations) to a heterologous protein or polypeptide (or fragment thereof, to a polypeptide of at least 10, at least 20, at least 30, at least 40, at least 50, at least 60, at least 70, at least 80, at least 90 or at least 100 amino acids). The fusion does not necessarily need to be direct, but may occur through linker sequences described herein.

In certain embodiments, a non-naturally occurring CKP described herein (such as a non-naturally occurring VEGF-A-binding CKP or a non-naturally occurring LRP6-binding CKP), or analogs or derivatives thereof may be conjugated to a diagnostic or detectable agent. Such non-naturally occurring CKP conjugates can be useful for monitoring or prognosing the development or progression of a disease as part of a clinical testing procedure, such as determining the efficacy of a particular therapy. Such diagnosis and detection can be accomplished by coupling the non-naturally occurring CKP to detectable substances including, but not limited to various enzymes, such as but not limited to horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tn; positron emitting metals using various positron emission tomographies, nonradioactive paramagnetic metal ions, and molecules that are radiolabeled or conjugated to specific radioisotopes.

Also provided is a non-naturally occurring CKPs (such as a non-naturally occurring VEGF-A-binding CKP or a non-naturally occurring LRP6-binding CKP) conjugated to a therapeutic moiety. In certain embodiments, a non-naturally occurring CKP may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

In certain embodiments, a non-naturally occurring CKP described herein (such as a non-naturally occurring VEGF-A-binding CKP or a non-naturally occurring LRP6-binding CKP is conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$Lu, $^{131}$Y, $^{131}$Ho, $^{131}$Sm, to polypeptides. In certain embodiments, the macrocyclic chelator is 1, 4, 7, 10-tetraazacyclododecane-N,N', N",N"'-tetra-acetic acid (DOTA) which can be attached to the non-naturally occurring CKP via a linker molecule. Such linker molecules are commonly known in the art and described in, e.g., Denardo et al. (1998) *Clin Cancer Res.* 4, 2483-90; Peterson et al. (1999) *Bioconjug. Chem.* 10, 553-557; and Zimmerman et al. (1999) *Nucl. Med. Biol.* 26, 943-50.

Techniques for conjugating therapeutic moieties to antibodies are well known and can be applied to the non-naturally CKPs disclosed herein, see, e.g., Amon et al., "Monoclonal Antibodies For Immunotargeting Of Drugs In Cancer Therapy," in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radio labeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58. Similar approaches may be adapted for use with the non-naturally occurring CKPs provided herein.

The therapeutic moiety or drug conjugated to a non-naturally CKP described herein (such as a non-naturally occurring VEGF-A-binding CKP or a non-naturally occurring LRP6-binding CKP) should be chosen to achieve the desired prophylactic or therapeutic effect(s) for a particular disorder in a subject. A clinician or other medical personnel should consider the following when deciding on which therapeutic moiety or drug to conjugate to a scaffold: the nature of the disease, the severity of the disease, and the condition of the subject.

In certain embodiments, non-naturally occurring CKPs described herein (such as a non-naturally occurring VEGF-A-binding CKP or a non-naturally occurring LRP6-binding CKP) can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Covalent Modifications

Covalent modifications of non-naturally occurring CKPs described herein (such as a non-naturally occurring VEGF-A-binding CKP or a non-naturally occurring LRP6-binding CKP) are also contemplated. One type of covalent modification includes reacting targeted amino acid residues of a non-naturally occurring CKP with an organic derivatizing agent that is capable of reacting with selected side chains or the N- or C-terminal residues of the non-naturally occurring CKP. Derivatization with bifunctional agents is useful, for instance, for crosslinking the non-naturally occurring CKP to a water-insoluble support matrix or surface for use in the method for purifying a target ligand, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T.E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of a non-naturally occurring CKP comprises linking the non-naturally occurring CKP to one of a variety of nonproteinaceous polymers, e.g., polyethylene glycol (PEG), polypropylene glycol, or polyoxyalkylenes, in the manner set forth in U.S. Pat. Nos. 4,640,835, 4,496,689, 4,301,144, 4,670,417, 4,791,192 or 4,179,337

The term "polyethylene glycol" or "PEG" means a polyethylene glycol compound or a derivative thereof, with or without coupling agents, coupling or activating moieties (e.g., with thiol, triflate, tresylate, azirdine, oxirane, N-hydroxysuccinimide or a maleimide moiety). The term "PEG" is intended to indicate polyethylene glycol of a molecular weight between 500 and 150,000 Da, including analogues thereof, wherein for instance the terminal OR-group has been replaced by a methoxy group (referred to as mPEG).

In certain embodiments, non-naturally occurring CKPs described herein (such as a non-naturally occurring VEGF-A-binding CKP or a non-naturally occurring LRP6-binding CKP) are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the non-naturally occurring CKPs described herein can be either branched or unbranched (for example, Monfardini, C. et al. 1995 Bioconjugate Chem 6:62-69). PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

In certain embodiments, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), diimadozle, an anhydride reagent (for example, a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a non-naturally occurring CKP herein (such as a non-naturally occurring VEGF-A-binding CKP or a non-naturally occurring LRP6-binding CKP) to produce a non-naturally occurring CKP derivatized with a polymer. Alternatively, a functional group in the non-naturally occurring CKP provided herein can be activated for reaction with the polymer, or the two groups can be joined in a concerted coupling reaction using known coupling methods. It will be readily appreciated that the non-naturally occurring CKPs provided herein can be derivatized with PEG using a myriad of other reaction schemes known to and used by those of skill in the art.

Liposomes

Non-naturally occurring CKPs disclosed herein (such as a non-naturally occurring VEGF-A-binding CKP or a non-naturally occurring LRP6-binding CKP) can also be formulated as liposomes. Liposomes containing a non-naturally occurring EETI-II scaffold protein described herein can be prepared by methods known in the art, such as described in Epstein et al., *Proc Natl Acad Sci USA*, 82: 3688 (1985); Hwang et al., *Proc Natl Acad Sci USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. A second therapeutic agent is optionally also contained within the liposome. See, Gabizon et al., *J. National Cancer Inst.*, 81(19): 1484 (1989). Pharmaceutical Compositions and Formulations Comprising Non-Naturally Cystine Knot Peptides (CKPs) That Bind Human Vascular Endothelial Growth Factor A(VEGF-A)

In certain embodiments, provided herein is a pharmaceutical composition comprising a non-naturally occurring VEGF-A-binding CKP and a pharmaceutically acceptable excipient. In certain embodiments the composition may also contain, buffers, carriers, stabilizers, preservatives and/or bulking agents, to render the composition suitable for ocular administration to a patient to achieve a desired effect or result. In certain embodiments, the pharmaceutical composition comprises one or more permeability enhancers that permit a non-naturally occurring VEGF-A-binding CKP to penetrate the cornea. Examples of such permeability enhancers include, e.g., surfactants, bile acids, chelating agents, preservatives, cyclodextrins (i.e., cylindrical oligonucleotides with a hydrophilic outer surface and a lipophilic inner surface that form complexes with lipophilic drugs), etc. Such permeability enhancers increase chemical stability and bioavailability and decrease local irritation. In certain embodiments, a pharmaceutical composition provided herein additionally comprises agents that increase the absorption and distribution of non-naturally occurring VEGF-A-binding CKP in various ocular compartments. In certain embodiments, a pharmaceutical composition provided herein comprises a cross-linked polyacrylic acid, which can enhance ocular bioavailability by virtue of its mucoadhesive properties. In certain embodiments, a pharmaceutical composition provided herein comprises a bioadhesive polymer.

In certain embodiments, a pharmaceutical composition provided herein is formulated as an in-situ gelling system, e.g., a viscous polymer-based liquid that exhibits sol-to-gel phase transition on the ocular surface due to change in a specific physicochemical parameter (ionic strength, temperature, pH, or solvent exchange) when the composition comes into contact with tear fluid. In certain embodiments, a pharmaceutical composition provided herein is formulated as an eye spray. In certain embodiments, a pharmaceutical composition provided is formulated as liposomes. In certain embodiments, a pharmaceutical composition provided herein is formulated as niosomes (i.e., non-ionic surfactant-based vesicles containing, e.g., cholesterol as an excipient). In certain embodiments, a pharmaceutical composition provided herein is formulated as pharmacosomes (i.e., vesicles formed by amphiphilic drugs). In certain embodiments, a pharmaceutical composition provided herein is formulated as a microemulsion. Further details regarding various ophthalmic pharmaceutical formulations are provided in, e.g., Gaikwad et al. (2013) *Indo Amer J Pharm Res.* 3, 3216-3232; Achouri et al. (2012) *Drug Dev Indust Pharm.* 39, 1599-1617; Lu (2010) *Recent Pat Drug Deliv Formul.* 4, 49-57; Baranowski et al. (2014) *Sci World J.* doi.org/10.1155/2014/861904; Lang (1995) *Adv Drug Deliv Rev.* 16, 39-43; Short (2008) *Toxicologic Path.* 36, 49-62; and others.

In certain embodiments, a pharmaceutical composition comprising non-naturally occurring VEGF-A-binding CKP described herein is stable at room temperature (such as at about 20-25° C.) for about 0.5 weeks, about 1.0 weeks, about 1.5 weeks, about 2.0 weeks, about 2.5 weeks, 3.5 weeks, about 4.0 weeks, about 1 month, about 2 months about 3 months, about 4 months about 5 months, about 6 months, or greater than 6 months, including any range in between these values. In certain embodiments, a pharmaceutical composition comprising non-naturally occurring VEGF-A-binding CKP described herein is stable under accelerated conditions (such as storage at about 37° C.) for about 0.5 weeks, about 1.0 weeks, about 1.5 weeks, about 2.0 weeks, about 2.5 weeks, 3.5 weeks, about 4.0 weeks, about 1 month, about 2 months about 3 months, about 4 months about 5 months, about 6 months, or greater than 6 months, including any range in between these values.

Methods of Treatment Using Non-Naturally Occurring Cystine Knot Peptides (CKPs) that Bind Vascular Endothelial Growth Factor A (VEGF-A)

Vascular endothelial growth factor (VEGF-A), a dimeric glycoprotein of approximately 40 kDa, is a potent, endothelial cell mitogen that stimulates proliferation, migration and tube formation leading to angiogenic growth of new blood vessels and increased vascular permeability. Low oxygen conditions in the retina or cornea induce the expression of vascular endothelial growth factor (VEGF-A), and the abnormal (such as excessive or otherwise inappropriate) growth of leaky blood vessels contributes to the pathology of several debilitating ocular diseases including, e.g., diabetic blindness, retinopathies, primarily diabetic retinopathy, age-related macular degeneration (AMD), proliferative diabetic retinopathy (PDR), retinopathy of prematurity (ROP), choroidal neovascularization (CNV), diabetic macular edema, pathological myopia, von Rippel-Lindau disease, histoplasmosis of the eye, retinal vein occlusion (both branched retinal vein occlusion (BRVO) and central retinal vein occlusion (CRVO), corneal neovascularization, retinal neovascularization and rubeosis. The VEGF-A-induced formation of new blood vessels is detrimental, and retinal, intertrabecular or corneal neovascularization can ultimately lead to vision loss.

In certain embodiments, provided herein is a method of treating an ocular disease or disorder in a subject comprising administering to the subject an effective amount of a non-naturally occurring VEGF-A-binding CKP described herein or a composition (such as a pharmaceutical composition) comprising a non-naturally occurring VEGF-A-binding CKP described herein. In certain embodiment, provided are compositions (such as pharmaceutical compositions) comprising a non-naturally occurring VEGF-A-binding CKP described herein for use in treating an ocular disease or disorder in a subject. In certain embodiments, provided is the use of a non-naturally occurring VEGF-A-binding CKP described herein (or composition comprising such non-naturally occurring CKP) in the manufacture of a medicament for the treatment of an ocular disease or disorder in a subject.

In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having an ocular disease or disorder characterized by abnormal angiogenesis and/or abnormal vascular permeability (such as those described herein). In certain embodiments, the subject has been diagnosed with an ocular disease or disorder characterized by abnormal angiogenesis and/or abnormal vascular permeability (such as those described herein).

In certain embodiments, the ocular disease or disorder is an ocular vascular proliferative disease, such as an ocular vascular proliferative disease selected from the group consisting of diabetic blindness, retinopathies, primarily diabetic retinopathy, age-related macular degeneration (AMD), proliferative diabetic retinopathy (PDR), retinopathy of prematurity (ROP), choroidal neovascularization (CNV), diabetic macular edema, pathological myopia, von Rippel-Lindau disease, histoplasmosis of the eye, retinal vein occlusion (both branched retinal vein occlusion (BRVO) and central retinal vein occlusion (CRVO), corneal neovascularization, retinal neovascularization, and rubeosis. In certain embodiments, the corneal neovascularization results infection of the eye, inflammation in the eye, trauma to the eye (including chemical burns), or loss of the limbal stem cell barrier. In certain embodiments, the corneal neovascularization results from herpetic keratitis, trachoma, or onchocerciasis.

In certain embodiments, the effective amount of the non-naturally occurring VEGF-A-binding CKP described herein (or composition comprising such non-naturally occurring VEGF-A-binding CKP described herein) is administered directly to the eye of the subject (such as intravitreally or topically), as described in further detail elsewhere herein.

In certain embodiments, the non-naturally occurring VEGF-A-binding CKP described herein (or composition comprising such non-naturally occurring CKP) is administered in combination with a second agent. For patients in whom the ocular disease or disorder is triggered by an inflammatory response, combination therapy with an anti-inflammatory agent can be considered. For example, the combined use of steroids and a non-naturally occurring VEGF-A-binding CKP described herein (or composition comprising such non-naturally CKP) to reduce inflammation and prevent formation of new blood vessels, respectively, may be particularly advantageous in patients with, e.g., corneal neovascularization. Patients who suffer from an ocular disease or disorder secondary to bacterial, viral, fungal or acanthamoebal infection may benefit from administration of a non-naturally occurring VEGF-A-binding CKP described herein (or composition comprising such non-naturally occurring CKP) in combination with an antimicrobial agent and optionally an anti-inflammatory agent. Patients with corneal stromal blood vessels as a result of an ocular disease or disorder are at a significant risk for immune rejection after corneal transplantation. Administration of a non-naturally occurring VEGF-A-binding CKP described herein (or composition comprising such non-naturally occurring CKP) prior to (and optionally also subsequent to) corneal transplantation therefore may be particularly beneficial to patients with corneal stromal blood vessels as successful reduction of corneal vascularization will reduce the risk of graft rejection. In certain embodiments, the non-naturally occurring VEGF-A-binding CKP described herein (or composition comprising such non-naturally occurring CKP) is administered in combination with a second anti-angiogenic agent. In certain embodiments, the non-naturally occurring VEGF-A-binding CKP described herein (or composition comprising such non-naturally occurring CKP) is administered in combination with a matrix metalloprotease (MMP) inhibitor.

In certain embodiments, the non-naturally occurring VEGF-A-binding CKP described herein (or composition comprising such non-naturally occurring CKP) is administered in combination with a second therapy. In certain embodiments, the second therapy is laser photocoagulation therapy (LPT). LPT uses laser light to cause controlled damage of the retina to produce a beneficial therapeutic effect. Small bursts of laser light can seal leaky blood vessels, destroy abnormal blood vessels, seal retinal tears, or destroy abnormal tissue in the back of the eye. It is quick, non-invasive, and usually requires no anesthesia other than an anesthetic eye drop. LPT techniques and apparatuses are readily available to ophthalmologists (see Lock et al. (2010) *Med J Malaysia* 65:88-94). Additional details regarding LPT can be found in, e.g., WO 2014/033184.

In certain embodiments, the second therapy is photodynamic therapy (PDT). PDT uses a light-activated molecule to cause localized damage to neovascular endothelium, resulting in vessel occlusion. Light is delivered to the retina as a single circular spot via a fiber optic cable and a slit lamp, using a suitable ophthalmic magnification lens (laser treatment). The light-activated compound is injected into the circulation prior to the laser treatment, and damage is inflicted by photoactivation of the compound in the area afflicted by neovascularization. One commonly used light-activated compound is verteporfin (Visudyne®). Verteporfin is transported in the plasma primarily by lipoproteins. Once verteporfin is activated by light in the presence of oxygen, highly reactive, short-lived singlet oxygen and reactive oxygen radicals are generated which damages the endothelium surrounding blood vessels. Damaged endothelium is known to release procoagulant and vasoactive factors through the lipo-oxygenase (leukotriene) and cyclooxygenase (eicosanoids such as thromboxane) pathways, resulting in platelet aggregation, fibrin clot formation and vasoconstriction. Verteporfin appears to somewhat preferentially accumulate in neovasculature. The wavelength of the laser used for photoactivation of the light-activated compound may vary depending on the specific light-activated compound used. Additional details regarding PDT can be found in, e.g., WO 2014/033184.

In certain embodiments, the second therapy is diathermy and cautery, wherein vessels are occluded either by application of a coagulating current through a unipolar diathermy unit or by thermal cautery using an electrolysis needle inserted into feeder vessels at the limbus.

Administration

In certain embodiments the non-naturally occurring VEGF-A-binding CKP (or composition comprising such non-naturally occurring CKP) is administered, e.g., via injection, e.g., subconjunctival injection, intracorneal injection, or intravitreal injection. Administration in aqueous form is usual, with a typical volume of 20-150 µl e.g. 40-60 µl, or 50 µl. Injection can be via a 30-gaugex½-inch (12.7 mm) needle. In certain embodiments, the non-naturally occurring VEGF-A-binding CKP (or composition comprising such non-naturally occurring CKP) is provided in a pre-filled sterile syringe ready for administration. In certain embodiments, the syringe has low silicone content or is silicone free. The syringe may be made of glass. Using a pre-filled syringe for delivery has the advantage that any contamination of the sterile antagonist solution prior to administration can be avoided. Pre-filled syringes also provide easier handling for the administering ophthalmologist. See, e.g., WO 2014/033184, Fagan et al. (2013) *Clin Exp Ophthalmol*. 41, 500-507; Avery et al. (2014) *Retina*. 34 Suppl 12, S1-S18; and Doshi et al. (2015) *Seminar Ophthalmol*. 26, 104-113 for further details regarding intravitreal administration.

In certain embodiments, the non-naturally occurring VEGF-A-binding CKP (or composition comprising such non-naturally occurring CKP) is administered topically, e.g. in form of eye drops. Additional details regarding topical drug delivery to the eye are found in, e.g., Loftsson et al. (2012) Acta Ophthalmologica. 90, 603-608; Patel et al. (2013) World J. Pharmacol. 2, 47-64; Freeman et al. (2009) Exp Rev Ophthalmol. 4, 59-64; and Boddu et al. (2014) Recent Patents on Drug Delivery and Formulation. 8, 27-36.

In certain embodiments, an intravitreal device is used to continuously deliver the non-naturally occurring VEGF-A-binding CKP (or composition comprising such non-naturally occurring CKP) into the eye. In certain embodiments, the non-naturally occurring VEGF-A-binding CKP (or composition comprising such non-naturally occurring CKP) is administered via ocular insert (including, but not limited to, e.g., Ocuserts, Lactisers, Soluble Ocular Drug Inserts (SODIs), Minidiscs, contact lenses, films, filter paper strips, artificial tear inserts, and collagen shields). See, e.g., Gaikwad et al. (2013) *Indo Amer J Pharm Res*. 3, 3216-3232). In certain embodiments, the non-naturally occurring VEGF-A-binding CKP (or composition comprising such non-naturally occurring CKP) is administered as a slow-release depot, an ocular plug/reservoir, an ocular implant (such as a scleral or vitreal implant). Various scleral and intravitreal delivery systems are known in the art. These delivery systems are typically non-biodegradable, and may be active or passive. For example, WO 2010/088548 describes a delivery system having a rigid body using passive diffusion to deliver a therapeutic agent. WO 2002/100318 discloses a delivery system having a flexible body that allows active administration via a pressure differential. Alternatively, active delivery can be achieved by implantable miniature pumps. An example for an intravitreal delivery system using a miniature pump to deliver a therapeutic agent is the Ophthalmic MicroPump System™ marketed by Replenish, Inc. which can be programmed to deliver a set amount of a therapeutic agent for a pre-determined number of times. In certain embodiments, the non-naturally occurring VEGF-A-binding CKP (or composition comprising such non-naturally occurring CKP) is encased in a small capsule-like container (e.g., a silicone elastomer cup). The container is usually implanted in the eye above the iris. The container comprises a release opening. Release of the non-naturally occurring VEGF-A-binding CKP (or composition comprising such non-naturally occurring CKP) may be controlled by a membrane positioned between the non-naturally occurring VEGF-A-binding CKP (or composition comprising such non-naturally occurring CKP) and the opening, or by means of a miniature pump connected to the container. Alternatively, the non-naturally occurring VEGF-A-binding CKP (or composition comprising such non-naturally occurring CKP) may be deposited in a slow-release matrix that prevents rapid diffusion of the antagonist out of the container. Preferably, the intravitreal device is designed to release the non-naturally occurring VEGF-A-binding CKP (or composition comprising such non-naturally occurring CKP) at an initial rate that is higher in the first month. The release rate slowly decreases, e.g., over the course of the first month after implantation, to a rate that is about 50% less than the initial rate. The container may have a size that is sufficient to hold a supply of the non-naturally occurring VEGF-A-binding CKP (or composition comprising such non-naturally occurring CKP) that lasts for about four to six months. Since a reduced dose of the non-naturally occurring VEGF-A-binding CKP (or composition comprising such non-naturally occurring CKP) may be sufficient for effective treatment when administration is continuous, the supply in the container may last for one year or longer, preferably about two years, more preferably about three years. Because only a small surgery is required to implant a delivery system and intravitreal injections are avoided, patient compliance issues with repeated intravitreal injections can be avoided. Intravitreal concentrations of the non-naturally occurring VEGF-A-binding CKP (or composition comprising such non-naturally occurring CKP) are reduced, and therefore the potential risk of side-effects from the non-naturally occurring VEGF-A-binding CKP (or composition comprising such non-naturally occurring CKP) entering the circulation is decreased.

In certain embodiments, the non-naturally occurring VEGF-A-binding CKP (or composition comprising such non-naturally occurring CKP) is administered via iontophoresis. Iontophoresis is a noninvasive technique in which a small electric current is applied to enhance ionized drug penetration into tissue (see, e.g., Myles et al. (2005) *Adv Drug Deliv Rev* 57, 2063-79 and Eljarrat-Binstock et al. (2006) *J Controlled Release* 110, 479-89). The drug is applied with an electrode carrying the same charge as the drug, and the ground electrode, which is of the opposite charge, is placed elsewhere on the body to complete the circuit. The drug serves as the conductor of the current through the tissue.

Additional details regarding administration of drug to the eye are provided in, e.g., Kuno et al. (2011) *Polymers* 3, 193-221; Short (2008) *Toxicologic Path.* 36, 49-62; Ghate et al. (2006) *Expert Opin Drug Deliv* 3, 275-87; Davis et al. (2004) *Curr Opin Mol Therap* 6, 195-205; Gaudana et al. (2010) *AAPS J.* 12, 348-360; and others.

Slow Release/Long Acting Delivery Formulations

In certain embodiments, the non-naturally occurring VEGF-A-binding CKP (or composition comprising such non-naturally occurring CKP) is provided as slow-release formulations. Slow-release formulations are typically obtained by mixing a therapeutic agent with a biodegradable polymer or encapsulating it into microparticles.

A slow-release formulation in accordance with the invention typically comprises the non-naturally occurring VEGF-A-binding CKP (or composition comprising such non-naturally occurring CKP), a polymeric carrier, and a release modifier for modifying a release rate of the non-naturally occurring VEGF-A-binding CKP (or composition comprising such non-naturally occurring CKP) from the polymeric carrier. By varying the manufacture conditions of polymer-based delivery compositions, the release kinetic properties of the resulting compositions can be modulated. The polymeric carrier usually comprises one or more biodegradable polymers or copolymers or combinations thereof. For example, the polymeric carrier may be selected from poly-lactic acid (PLA), poly-glycolic acid (PGA), polylactide-co-glycolide (PLGA), polyesters, poly (orthoester), poly(phosphazine), poly (phosphate ester), polycaprolactones, or a combination thereof.

In certain embodiments the polymeric carrier is PLGA. The release modifier is typically a long chain fatty alcohol, preferably comprising from 10 to 40 carbon atoms. Commonly used release modifiers include capryl alcohol, pelargonic alcohol, capric alcohol, lauryl alcohol, myristyl alcohol, cetyl alcohol, palmitoleyl alcohol, stearyl alcohol, isostearyl alcohol, elaidyl alcohol, oleyl alcohol, linoleyl alcohol, polyunsaturated elaidolinoleyl alcohol, polyunsaturated linolenyl alcohol, elaidolinolenyl alcohol, polyunsaturated ricinoleyl alcohol, arachidyl alcohol, behenyl alcohol, erucyl alcohol, lignoceryl alcohol, ceryl alcohol, montanyl alcohol, cluytyl alcohol, myricyl alcohol, melissyl alcohol, and geddyl alcohol.

In certain embodiments, the non-naturally occurring VEGF-A-binding CKP (or composition comprising such non-naturally occurring CKP) is incorporated into a microsphere-based sustained release composition. In certain embodiments, the microspheres are prepared from PLGA. The amount of the non-naturally occurring VEGF-A-binding CKP (or composition comprising such non-naturally occurring CKP) incorporated in the microspheres and the release rate of the non-naturally occurring VEGF-A-binding CKP (or composition comprising such non-naturally occurring CKP) can be controlled by varying the conditions used for preparing the microspheres. Processes for producing such slow-release formulations are described in US 2005/0281861 and US 2008/0107694.

In certain embodiments, the non-naturally occurring VEGF-A-binding CKP (or composition comprising such non-naturally occurring CKP) is incorporated into a biodegradable implant (such as a microneedle). Matrix implants (such as microneedles) are typically used to treat ocular diseases that require a loading dose followed by tapering doses of the drug during a 1-day to 6-month time period (Davis et al. (2004) *Curr Opin Mol Therap* 6, 195-205). They are most commonly made from the copolymers poly-lactic-acid (PLA) and/or poly-lactic-glycolic acid (PLGA), which degrade to water and carbon dioxide. The rate and extent of drug release from the implant can be decreased by altering the relative concentrations of lactide (slow) and glycolide (fast), altering the polymer weight ratios, adding additional coats of polymer, or using hydrophobic, insoluble drugs. The release of drug generally follows first-order kinetics with an initial burst of drug release followed by a rapid decline in drug levels. Biodegradable implants do not require removal, as they dissolve over time (Hsu (2007) *Curr Opin Ophthalmol* 18, 235-9). Biodegradable implants also allow flexibility in dose and treatment from short duration (weeks) to longer duration (months to a year), depending on the polymer PLA/PLGA ratio, which is another benefit in tailoring drug delivery to disease progression, because dose and treatment requirements may change over time. Additional details regarding the manufacture and implantation of biodegradable implants (such as PLGA or PLA implants) for the ocular administration are provided in, e.g., WO 2006/093758, US 2006/0182783, WO 2009/026461, US 2008/0181929, US 2009/0263460, US 2010/0015158, US 2011/0207653, and US 2014/0154321. Additional details regarding microneedles for ocular drug delivery are provided in, e.g., Donnelly et al. (2010) *Drug Deliv* 14, 187-207; U.S. Pat. No. 7,918,814, Yavux et al. (2013) *Sci World J*. doi.org/10.1155/2013/732340, and elsewhere.

Articles of Manufacture and Kits

In certain embodiments, provided is an article of manufacture containing a non-naturally occurring VEGF-A-binding CKP described herein and materials useful for the treatment of an ocular disease or disorder (such as an ocular vascular proliferative disease or ocular disorder characterized by excessive angiogenesis). The article of manufacture can comprise a container and a label or package insert on or associated with the container. Suitable containers include, for example, bottles, vials, syringes, etc. The containers may be formed from a variety of materials such as glass or plastic. In certain embodiments, the container holds a composition which is effective for treating the ocular disease or disorder (such as an ocular vascular proliferative disease or ocular disorder characterized by excessive angiogenesis) and may have a complete set of items needed to implant a slow release ocular or intraocular drug delivery system, including, but not limited to, injection devices, topical and injectable medications, surgical instruments, sutures and suturing needles, and eye covers. In certain embodiments, the container fold sterile unit-dose packages. At least one active agent in the composition is non-naturally occurring VEGF-A-binding CKP described herein. The label or package insert indicates that the composition is used for treating an ocular disease or disorder (such as an ocular vascular proliferative disease or ocular disorder characterized by excessive angiogenesis). The label or package insert will further comprise instructions for administering the non-naturally occurring VEGF-A-binding CKP (or composition comprising such non-naturally occurring CKP) to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition comprising the non-naturally occurring VEGF-A-binding CKP is used for treating an ocular disease or disorder (such as an ocular vascular proliferative disease or ocular disorder characterized by excessive angiogenesis described herein).

Kits are also provided that are useful for various purposes, e.g., for isolation or detection VEGF-A, optionally in combination with the articles of manufacture. For isolation and purification of VEGF-A, the kit can contain non-naturally occurring VEGF-A-binding CKP described herein coupled to beads (e.g., sepharose beads). Kits can be provided which contain the non-naturally occurring VEGF-A-binding CKP described herein for detection and quantitation of VEGF-A in vitro, e.g. in an ELISA or blot. As with the article of manufacture, the kit comprises a container and a label or package insert on or associated with the container. For example, the container holds a composition comprising at least one non-naturally occurring VEGF-A-binding CKP described herein. Additional containers may be included that contain, e.g., diluents and buffers, control antibodies, etc. The label or package insert may provide a description of the composition as well as instructions for the intended in vitro or diagnostic use.

EXAMPLES

Example 1

Materials and Methods for Examples 2-3

Display of EETI-II on M13 Phage.

EETI-II was displayed on the surface of M13 bacteriophage by modifying a previously described phagemid pS2202b (Skelton, N. J., Koehler, M. F., Zobel, K., Wong, W. L., Yeh, S., Pisabarro, M. T., Yin, J. P., Lasky, L. A., and Sidhu, S. S. (2003) Origins of PDZ domain ligand specificity. Structure determination and mutagenesis of the Erbin PDZ domain. *J Biol Chem* 278, 7645-7654). Standard molecular biology techniques were used to replace the fragment of pS2202d encoding Erbin PDZ domain with a DNA fragment encoding for EETI-II. The resulting phagemid (p8EETI-II) contained an open reading frame that encoded for the maltose binding protein secretion signal, followed by a gD tag and EETI-II and ending with M13 major coat protein p8. *E. Coli* harboring p8EETI-II were co-infected with M13-KO7 helper phage and cultures were grown in 30 ml 2YT medium supplemented with 50 µg/ml Carbenecillin and 25 µg/ml Kanamycin at 30° C. overnight. The propagated phage was purified according to the standard protocol (Tonikian, R., Zhang, Y., Boone, C., and Sidhu, S. S. (2007) Identifying specificity profiles for peptide recognition modules from phage-displayed peptide libraries. *Nat Protoc* 2, 1368-1386) and re-suspended in 1 ml PBT buffer (PBS, 0.5% BSA and 0.1% TWEEN®20), resulting in the production of phage particles that encapsulated p8EETI-II DNA and displayed EETI-II. The display level was analyzed using a phage ELISA.

Library Construction and Sorting.

The EETI-II libraries were constructed following Kunkel mutagenesis method (Kunkel, T. A., Roberts, J. D., and Zakour, R. A. (1987) Rapid and efficient site-specific mutagenesis without phenotypic selection. *Methods Enzymol* 154, 367-382). Three libraries were constructed: Library 1, in which loop 1 (3-8) was randomized with the degenerated codon encoding all natural amino acids except Cys at 6, 8 or 10 amino acids in length; or Library 2, in which loop 5 (22-26) was randomized with the same set of degenerated codon with fixed length of 5 amino acids; or Library 3, in which both loop 1 were randomized with 6, 8, and 10 amino acids and loop 5 with 5 amino acids simultaneously with degenerated codon encoding for 19 amino acids. Oligonucleotides for mutagenesis were synthesized using custom mixes of trimer phosphoramidites encoding for 19 amino acids at equimolar concentration. (Glen Research, Sterling, Va.). The stop template is the single strand DNA of p8EETI-II containing three stop codons in region of 3-26 and was used to construct all three libraries. The pool of three libraries contained ~3×10$^{10}$ unique members and was cycled through rounds of binding selection against hVEGF (8-109) captured on plate for four rounds following the standard protocol (Tonikian, R., Zhang, Y., Boone, C., and Sidhu, S. S. (2007) Identifying specificity profiles for peptide recognition modules from phage-displayed peptide libraries. *Nat Protoc* 2, 1368-1386) with the variation that, 25 ug/ml of hVEGF(8-109) was used to coat the plate and eluted phage were propagated by growing the overnight culture at 30° C.

Spot Phage ELISA.

After four rounds of binding selection, individual phage clones were picked and inoculated into 450 µl 2YT media containing 50 µg/ml Carbenecillin and M13-KO7 helper phage in 96-well blocks, which were grown at 37° C. overnight. The supernatant was analyzed with spot phage ELISA as follows: hVEGF(8-109) or BSA were coated on 384-well MAXISORP™ immunoplates and phage supernatant diluted (1:3) with PBT buffer was added to the wells. The plates were washed and bound phage was detected with anti-M13-HRP followed by TMB substrate. In these assays, phage binding to BSA alone was tested in parallel to assess background binding. Clones whose binding signals for hVEGF-A (8-109) were more than 3 times higher than to BSA (background) were considered positive. Positive clones were subjected to DNA sequence analysis.

Crystallography.

To form a stable complex, VEGF-A was concentrated to 7 mg/ml and incubated with a 6-fold molar excess of VEGF_CKP9.54.90 variant. VEGFA/VEGF_CKP9.54.90 crystals of the primitive monoclinic space group $P12_11$ were grown at 19° C. by the hanging-drop vapor diffusion method using a drop ratio of 2:1 protein: reservoir solution. Reservoir solution contained 100 mM HEPES pH 7.4 and 26% PEG 3350. Crystals were cryoprotected in reservoir solution supplemented with 25% PEG 200 and flash-frozen in liquid nitrogen prior to data collection.

Data Collection and Structure Determination.

X-ray diffraction data were collected to 1.64 Å at beamline 21IDF at the Advanced Photon Source. Data were processed using iMosflm. The structure was solved by molecular replacement using Phaser in Phenix with the previously published apo VEGF-A structure (PDB: 1VPF) as a search model and one VEGF-A dimer in the asymmetric unit. Clear $F_o-F_c$ density was present for the VEGF_CKP9.54.90 variant, so the structure of this variant was built into the density manually using Coot and then subjected to iterative rounds of refinement and rebuilding using Phenix and Coot.

KDR-CHO VEGF Assay to Determine Cellular $IC_{50}$

KDR-CHO cells (CHO cells stably transfected with gD tagged-KDR) were grown in cell growth medium (DMEM/Ham's F-12, 10% diafiltered FBS (GIBCO catalog no. 26400), 25 mM HEPES, 2 mM L-GLUTAMAX™). For VEGF stimulation assay, $5 \times 10^4$ cells/well were plated in 100 µl of cell plating medium (DMEM/Ham's F-12, 0.2% BSA, 0.25% diafiltered FBS, 25 mM HEPES, 2 mM L-GLUTAMAX™) in 96-well tissue culture plate and incubated at 37° C. overnight. The medium was replaced with 100 µl of serum-free cell stimulation medium (DMEM/Ham's F-12, 0.5% BSA, 25 mM HEPES) and cells were incubated at 37° C. for 2 hr. One hour before stimulation, the medium was replaced with 50 µl of serum-free cell stimulation medium. Concurrently, VEGF (50 ng/ml for hVEGF, 100 ng/ml for mVEGF and rVEGF) was pre-incubated with titrated amount of CKP or anti-VEGF in 50 µl of serum-free cell stimulation medium at 37° C. for 1 hour and added to the cells. The cells were stimulated for 15 min at 37 C and the medium is removed. The cells were lysed with 130 µl of ice-cold cell lysis buffer (150 mM NaCl, 50 mM HEPES, 0.5% Triton-X 100, HALT protease and phosphatase inhibitor cocktail (ThermoFisher Scientific, Inc. catalog no. 78444), 5 mM EDTA). VEGF mediated Tyr phosphorylation of KDR was determined by ELISA-based assay. Briefly, MAXISORP™ 96 well plates (ThermoFisher Scientific, Inc. catalog no. 439454) were coated with 100 µl of anti-gD antibody diluted in PBS (1 µg/ml) at 4° C. overnight and washed three times with washing buffer (PBS, 0.05% TWEEN®20, pH 7.4). The plates were blocked with 300 µl of blocking buffer (PBS, 0.5% BSA) at room temperature for 1 hour followed by washing three times with washing buffer. The above KDR-CHO cell lysate (100 µl) was added to each well and incubated at room temperature for 2 hours. The plates were washed four times with washing buffer followed by incubation with 100 µl of 0.5 µg/ml biotin-conjugated anti-phosphotyrosine (clone 4G10, Millipore catalog no. 16-103) in blocking buffer at room temperature for 2 hours. After washing four times, the plates were incubated with 100 µl of HRP-conjugated streptavidin in blocking buffer at room temperature for 30 min. After washing four times, the plates were developed with 100 µl of TMB substrate (BD Biosciences) at room temperature for 20~30 min and stopped by addition of 50 µl of $H_2SO_4$ solution. The optical density of each well was determined using a microplate reader set to 450 nm.

Competition ELISAs

Binding specificity of each peptide was established by competition ELISA. First, binding of each growth factor to their corresponding receptor in a plate-ELISA format was confirmed by coating VEGF-A, VEGF-B, VEGF-C, VEGF-D, PlGf-2, NGF, EGF, PDGF-ββ, or IGF-1 at 2 or 5 µg/mL in MAXISORP™ plates overnight at 4° C. in PBS. After blocking with block buffer (PBS with 0.5% BSA and 0.05% TWEEN®20) for 2 hours at room temperature, the receptor-Fc fusions or biotinylated receptors were serially diluted using assay buffer (PBS with 0.5% BSA and 0.05% TWEEN®20) and incubated for 1 hour at room temperature. Amount of bound receptor-Fc or biotinylated receptor was detected by incubating with anti-human-Fc-HRP (Life Technologies) or high affinity streptavidin-HRP (ThermoFisher Scientific, Inc.) respectively for 30 min. Competition ELISA was conducted in an identical fashion as described above except after blocking, a mixture of serially diluted peptide containing a constant concentration of receptor-Fc fusion or biotinylated receptor (concentration of receptor was set to $EC_{60}$) was added and incubated for 1 hour. All recombinant human proteins and antibodies were purchased from R &D Systems (Minneapolis, Minn.).

SPR Binding Assays.

Binding kinetics and affinities of inhibitors of VEGF-A were assessed using surface plasmon resonance technology on a BIACORE™ 3000 instrument (GE Healthcare) at 37° C. using HBS-EP buffer (10 mM HEPES pH 7.4, 150 mM NaCl, 3 mM EDTA and 0.005% v/v surfactant P20) containing 0.1% DMSO (v/v). Depending on the format of the assay either a streptavidin sensor (SA) or a dextran-coated (CM5) sensor was utilized as described below.

For use with the SA sensor, VEGF-A was first biotinylated (no more than 2 biotin/VEGF-A) by incubating the protein with EZ-link NHS-PEG4-Biotin (Pierce) in a 1:1.5 molar ratio respectively, in PBS for 2 hours on ice. Reaction was then quenched by addition of 10 molar excess of Glycine pH 8.0 and the sample was buffer exchanged into PBS using an Amicon 0.5 mL 3000 MWCO ultra-centrifugal filters (EMD Millipore). The biotinylation state of the protein was verified by LC-MS analysis. Biotinylated VEGF-A was then captured on the surface until a resonance unit (RU) signal of about ~400. For immobilization of VEGF-A on CMS sensor, the surface was first activated with a mixture of N-ethyl-N'-(3-dimethylaminopropyl)carbodiimide hydrochloride and N-hydroxysuccinimide (EDC/NHS) according to the supplier instructions. VEGF-A was then diluted into coupling buffer (0.1 M Acetate Buffer, pH 5.0) and injected until the signal reached about ~400 RU followed by a wash with 1 M ethanolamine pH 8.0 to quench remaining activated sites.

Following the capture step, a series of the peptide concentrations were prepared in HBS-EP buffer with matching DMSO concentrations to 0.1% and injected at a flow rate of 80 μL/min. The resulting sensorgrams were then analyzed using a 1:1 binding model to obtain kinetic data and affinities using Scrubber 2.0 (BioLogic Software).

CKP Synthesis and Folding.

Linear precursor LRP6 peptides were dissolved into DMSO (0.5 mg/mL) into 0.1M ammonium bicarbonate (pH 9), 1 mM reduced glutathione in 50% DMSO and incubated while shaking at room temperature for 24 h. Folded CKPs were purified by RP-HPLC on a C18 column and then collected fractions were analyzed by mass spectrometry, pooled and lyophilized prior to use.

Cell Culture and Transfection.

HEK293 cells stably transfected with a firefly luciferase Wnt reporter (Gong et al. (2010) *PLoS ONE* 5,9: e12682). and pRL-SV40 *Renilla* luciferase (Promega) were grown to 90% confluence in DMEM:F12 (50:50) supplemented with 10% FBS, 2 mM GLUTAMAX™ and 40 μg/ml hygromycin. Cells were incubated in a 5% $CO_2$ humidified incubator at 37° C. for 24 h. Following the incubation, the cells were trypsinized (0.05% Gibco 15400-54 in PBS) then diluted to $4 \times 10^5$ cells/ml in DMEM:F12 (50:50) supplemented with 10% FBS, 2 mM GLUTAMAX™. 20,000 cells were loaded into individual wells of white microtest 96-well optilux plates (catalog no. 353947) and incubated for ~24 h. Each well was transfected using FUGENE® HD with Wnt1-pCDNA3.2 (5 ng/well) or Wnt3a-pCDNA3.2 (25 ng/well) then grown for 24 h. All LRP6-binding variants were diluted in DMSO and added to cells at a final DMSO concentration of 1% at peptide concentrations of 0, 0.1, 0.1, 1.0, 10, and 100 μM for 6 hours. For stimulation with recombinant Wnt3a (5036-WN-010/CF, R&D Systems) was diluted in PBS to 50 ng/mL and added to the incubation media with the indicated CKP.

Luciferase response in all assays was then measured with Promega's DUAL-GLO® kit according to the manufacturer's instructions, except using half the volume of each reagent. Firefly luminescence and *Renilla* luminescence were measured on a Perkin Elmer ENVISION™ Multilabel Reader. The ratios of firefly luminescence: *Renilla* luminescence were calculated and normalized to the ratio in control cells expressing or treated with the indicated Wnt protein. Inhibitory constants were calculated using normalized data in Prism Graphpad using the using the log(inhibitor) vs. normalized response–variable slope $Y=100/(1+10^{\wedge}((Log IC_{50}-X)*HillSlope))$. Statistical significance was determined using the Holm-Sidak method, with alpha=5.000%. Computations assume that all rows are sample from populations with the same scatter (SD) and $IC_{50}$ were identified as significantly different using the Extra sum-of-squares F test where P<0.05 when significant.

Example 2A

Generation of Non-Naturally Occurring EETI-II Variants that Bind VEGF-A

EETI-II (FIG. 1) was chosen as a scaffold for display on the surface of M13 bacteriophage. EETI-II was fused to the N terminus of M13 major coat protein p8. Furthermore, a gD-tag was engineered N terminal of EETI-II sequence in order to verify display levels. Three peptide phage libraries were generated based on the EETI-II framework as follows: library I in which loop 1 amino acid residues were randomized and the loop length was varied (6, 8, 10 residues); library II in which loop 5 amino acid residues were randomized and the native loop length was fixed; and library III in which both loops 1 and 5 were randomized in amino acid content simultaneously and loop 1 length was varied from 6 to 10 amino acid residues while loop 5 length was fixed. Altogether, the three libraries contained $3 \times 10^{10}$ unique members and were cycled through rounds of selection against VEGF-A.

Panning against VEGF-A generated thirteen unique variants that bound to $hVEGF_{8-109}$ (see Table 19). These variants contained variations in amino acid composition in loop 1 or both loops 1 and 5 simultaneously. Also, a number of variants had a longer loop compared to the native loop present in EETI-II. A conserved YXS motif was also apparent in loop 5. We generated soluble folded cystine-knot peptides that correspond to seven of these unique variants, and they all demonstrated binding to hVEGF-A in a phage competition ELISA (Table 19). Moreover, we assessed some of the variants in a cellular assay and they demonstrated cross-species inhibition of human, mouse and rat VEGF-A activity with $IC_{50}$ in low μM.

TABLE 19

| EETI-II-based binders against hVEGF-A | | | | | |
|---|---|---|---|---|---|
| VARIANT | LOOP 1 | LOOP 5 | n | ELISA | S/N* |
| EETI-II | PRILMR (SEQ ID NO: 92) | GPNGF (SEQ ID NO: 15) | | 0.01 | 1.11 |
| VEGF_CKP1 | ETDWYPHQID (SEQ ID NO: 225) | GPNGF (SEQ ID NO: 15) | 2 | 0.9 | 16.9 |
| VEGF_CKP2 | GETVFEQFLW (SEQ ID NO: 226) | GPNGF (SEQ ID NO: 15) | 2 | 3.2 | 48.1 |
| VEGF_CKP3 | HMMYDY (SEQ ID NO: 227) | EMYDA (SEQ ID NO: 235) | 2 | 3.1 | 42.9 |

TABLE 19-continued

EETI-II-based binders against hVEGF-A

| VARIANT | LOOP 1 | LOOP 5 | n | ELISA | S/N* |
|---|---|---|---|---|---|
| VEGF_CKP4 | KKWQWWYM (SEQ ID NO: 228) | YPWTE (SEQ ID NO: 236) | 5 | 2.6 | 35.3 |
| VEGF_CKP5 | PAIQNWKEHP (SEQ ID NO: 229) | SWWPSL (SEQ ID NO: 237) | 2 | 1.9 | 28.4 |
| VEGF_CKP6 | PTTRFKQY (SEQ ID NO: 8) | GPNGF (SEQ ID NO: 15) | 28 | 3.5 | 51.9 |
| VEGF_CKP7 | QDPTFNWALY (SEQ ID NO: 9) | QMYQS (SEQ ID NO: 16) | 2 | 3.4 | 54.5 |
| VEGF_CKP8 | QLMHPFWG (SEQ ID NO: 230) | HWYRS (SEQ ID NO: 238) | 2 | 3.9 | 59.4 |
| VEGF_CKP9 | QLMQPFWG (SEQ ID NO: 10) | HWYQS (SEQ ID NO: 17) | 11 | 3.3 | 36.0 |
| VEGF_CKP10 | RDLDVKWD (SEQ ID NO: 11) | QYYSS (SEQ ID NO: 18) | 3 | 3.2 | 43.7 |
| VEGF_CKP11 | RTPWEPHDIT (SEQ ID NO: 12) | GPNGF (SEQ ID NO: 15) | 16 | 4.1 | 57.5 |
| VEGF_CKP12 | TTPWPPHEIM (SEQ ID NO: 13) | GPNGF (SEQ ID NO: 15) | 75 | 3.5 | 55.2 |
| VEGF_CKP13 | VTPWKPHWIN (SEQ ID NO: 14) | GPNGF (SEQ ID NO: 15) | 2 | 3.5 | 56.3 |

*S/N = signal to noise ratio as compared to BSA control

TABLE 20

Phage Competition ELISA and cellular inhibitory activities of soluble EETI-II-based binders against hVEGF-A

| VARIANT | In vitro IC$_{50}$ (µM) | Cellular Assay hVEGF-A (25 ng/ml) | mVEGF (50 ng/ml) | rVEGF (50 ng/ml) |
|---|---|---|---|---|
| VEGF_CKP6 | 3 | 47 | 169 | 711.2 (partial) |
| VEGF_CKP7 | 12 | 18 | 39 | 7 |
| VEGF_CKP9 | 0.6 | 12 | 10 | 1 |
| VEGF_CKP10 | 1 | 45 | ND* | 18 |
| VEGF_CKP11 | 80 | ND* | ND* | ND* |
| VEGF_CKP12 | 60 | 102 | 243 | 1220 (partial) |
| VEGF_CKP13 | 80 | ND* | ND* | ND* |

*ND = not determined

To further improve the potency of these variants, we followed up on VEGF_CKP7 and VEGF_CKP9. Soft randomization was done on loops 1 and 5 within the VEGF-CKP7 framework, resulting in 16 unique variants that bound to human VEGF-A (see Table 21 below).

TABLE 21

CKP_7 Affinity-matured binders against hVEGF-A

| VARIANT | LOOP 1 | LOOP 5 | n | ELISA | S/N* |
|---|---|---|---|---|---|
| VEGF_CKP7 | QDPTFNWALY (SEQ ID NO: 9) | QMYQS (SEQ ID NO: 16) | 1 | 0.1 | 1.3 |
| VEGF_CKP7.2 | DDPSFDWSVY (SEQ ID NO: 287) | RMYDS (SEQ ID NO: 292) | 1 | 1.2 | 21.5 |
| VEGF_CKP7.8 | KNPLFNWALY (SEQ ID NO: 60) | QLFDS SEQ ID NO: 71) | 2 | 0.5 | 7.5 |

TABLE 21-continued

CKP_7 Affinity-matured binders against hVEGF-A

| VARIANT | LOOP 1 | LOOP 5 | n | ELISA | S/N* |
|---|---|---|---|---|---|
| VEGF_CKP7.17 | QDPTVNWAVY (SEQ ID NO: 61) | QFYQS (SEQ ID NO: 72) | 1 | 0.8 | 13.4 |
| VEGF_CKP7.19 | QDPTFNWAEY (SEQ ID NO: 62) | QLYQS (SEQ ID NO: 73) | 2 | 0.6 | 11.1 |
| VEGF_CKP7.24 | WDPTFNWALY (SEQ ID NO: 288) | QMYDS (SEQ ID NO: 76) | 2 | 0.8 | 13.4 |
| VEGF_CKP7.35 | QDPTFNWAEY (SEQ ID NO: 62) | QMYQS (SEQ ID NO: 16) | 3 | 0.6 | 10.6 |
| VEGF_CKP7.43 | QDPTLNWATY (SEQ ID NO: 289) | QMYQS (SEQ ID NO: 16) | 1 | 0.5 | 6.3 |
| VEGF_CKP7.46 | EDPTVDWAQY (SEQ ID NO: 290) | QMYQS (SEQ ID NO: 16) | 1 | 0.3 | 4.9 |
| VEGF_CKP7.50 | QDPSLNWADY (SEQ ID NO: 63) | QMHQS (SEQ ID NO: 74) | 1 | 0.8 | 14.3 |
| VEGF_CKP7.54 | LDRTLNWALY (SEQ ID NO: 64) | QMYNS (SEQ ID NO: 75) | 1 | 0.5 | 9.3 |
| VEGF_CKP7.57 | LDPSFNWSLY (SEQ ID NO: 65) | QMYDS (SEQ ID NO: 76) | 2 | 1.0 | 17.4 |
| VEGF_CKP7.73 | RDLTINWALF (SEQ ID NO: 66) | QMFNS (SEQ ID NO: 274) | 1 | 1.2 | 19.2 |
| VEGF_CKP7.78 | KDTTFNWGLF (SEQ ID NO: 291) | QLYQS (SEQ ID NO: 73) | 1 | 0.7 | 11.8 |
| VEGF_CKP7.81 | LDPTVNWALF (SEQ ID NO: 67) | QHYKT (SEQ ID NO: 77) | 1 | 1.1 | 18.6 |
| VEGF_CKP7.88 | QDPKLNWAVY (SEQ ID NO: 68) | QLFNS (SEQ ID NO: 78) | 2 | 0.5 | 7.7 |
| LRP6_CKP7.89 | LDPSFDWALY (SEQ ID NO: 69) | QLYNS (SEQ ID NO: 79) | 1 | 0.5 | 8.1 |

*S/N = signal to noise ratio as compared to BSA control

Soft randomization was done on loops 1 and 5 within the VEGF-CKP9 framework, resulting in 16 unique variants that bound to human VEGF-A (see Tables 22-24 below).

TABLE 22

VEGF_CKP9 Loop1 Affinity-Matured Variants Against VEGF-A

| VARIANT | L1 SEQUENCE | n | ELISA | S/N* |
|---|---|---|---|---|
| VEGF_CKP9 | QLMQPFWG (SEQ ID NO: 10) | | 0.4 | 7.4 |
| VEGF_CKP9.L1.2 | HLFEPLWG (SEQ ID NO: 245) | 17 | 1.6 | 12.5 |
| VEGF_CKP9.L1.7 | QVMRPFWG (SEQ ID NO: 246) | 3 | 1.5 | 8.9 |
| VEGF_CKP9.L1.8 | QVMQPAWG (SEQ ID NO: 247) | 1 | 1.2 | 12.8 |

TABLE 22-continued

VEGF_CKP9 Loop1 Affinity-Matured Variants Against VEGF-A

| VARIANT | L1 SEQUENCE | n | ELISA | S/N* |
|---|---|---|---|---|
| VEGF_CKP9.L1.19 | HRLQPLWG (SEQ ID NO: 248) | 3 | 1.4 | 11.6 |
| VEGF_CKP9.L1.26 | ELLQPSWG (SEQ ID NO: 249) | 4 | 1.7 | 11.9 |
| VEGF_CKP9.L1.57 | NPMLPFWG (SEQ ID NO: 368) | 3 | 3.7 | 31.8 |
| VEGF_CKP9.L1.64 | NVLLPLWG (SEQ ID NO: 250) | 1 | 2.3 | 19.9 |
| VEGF_CKP9.L1.68 | DIMQPLWG (SEQ ID NO: 36) | 1 | 2.0 | 23.2 |
| VEGF_CKP9.L1.76 | DLMQPLWG (SEQ ID NO: 251) | 2 | 2.5 | 17.4 |
| VEGF_CKP9.L1.78 | NPMLPLWG (SEQ ID NO: 252) | 1 | 3.0 | 25.1 |
| VEGF_CKP9.L1.79 | QVLQPSWG (SEQ ID NO: 253) | 1 | 1.2 | 10.0 |

*S/N = signal to noise ratio as compared to BSA control

TABLE 23

VEGF_CKP9 Loop5 Affinity-Matured Variants Against VEGF-A

| VARIANT | L5 SEQUENCE | n | ELISA | S/N* |
|---|---|---|---|---|
| VEGF_CKP9 | HWYQS (SEQ ID NO: 17) |  | 0.9 | 11.6 |
| VEGF_CKP9.L5.7 | RWYNS (SEQ ID NO: 133) | 11 | 1.4 | 18.9 |
| VEGF_CKP9.L5.18 | HWYQS (SEQ ID NO: 17) | 1 | 1.6 | 20.4 |
| VEGF_CKP9.L5.43 | RWYHS (SEQ ID NO: 43) | 2 | 0.9 | 13.6 |

*S/N = signal to noise ratio as compared to BSA control

TABLE 24

VEGF_CKP9 Loop1/Loop5 Affinity-Matured Variants Against VEGF-A

| VARIANT | Loop 1 | LOOP 5 | n | ELISA | S/N* |
|---|---|---|---|---|---|
| VEGF_CKP9 | QLMQPFWG (SEQ ID NO: 10) | HWYQS (SEQ ID NO: 17) |  | 0.4 | 7.4 |
| VEGF_CKP9.2 | DVLQPFWG (SEQ ID NO: 28) | HWYQS (SEQ ID NO: 17) | 20 | 2.4 | 31.1 |
| VEGF_CKP9.3 | QISQPFWG (SEQ ID NO: 29) | HFYNS (SEQ ID NO: 41) | 1 | 1.6 | 24.5 |
| VEGF_CKP9.4 | DRMQPLWG (SEQ ID NO: 30) | LWYKS (SEQ ID NO: 42) |  | N/D | N/D |
| VEGF_CKP9.9 | QLLEPMWG (SEQ ID NO: 254) | HWYNS (SEQ ID NO: 46) | 1 | 1.1 | 19.7 |
| VEGF_CKP9.14 | KLLQPMWG (SEQ ID NO: 255) | RWYQS (SEQ ID NO: 44) | 1 | 2.0 | 30.1 |
| VEGF_CKP9.11 | DRMQPYWG (SEQ ID NO: 256) | QWYKS (SEQ ID NO: 262) | 1 | 1.1 | 14.1 |
| VEGF_CKP9.20 | NLMLPFWG (SEQ ID NO: 31) | RWYHS (SEQ ID NO: 43) | 1 | 1.7 | 13.3 |
| VEGF_CKP9.22 | QRTQPFWG (SEQ ID NO: 32) | RWYQS (SEQ ID NO: 44) | 1 | 1.2 | 17.2 |
| VEGF_CKP9.47 | KIMQPLWG (SEQ ID NO: 257) | LWYDS (SEQ ID NO: 263) | 1 | 1.0 | 14.6 |
| VEGF_CKP9.51 | NLMHPFWG (SEQ ID NO: 258) | HWYQS (SEQ ID NO: 17) | 1 | 1.0 | 11.0 |

TABLE 24-continued

VEGF_CKP9 Loop1/Loop5 Affinity-Matured Variants Against VEGF-A

| VARIANT | Loop 1 | LOOP 5 | n | ELISA | S/N* |
|---|---|---|---|---|---|
| VEGF_CKP9.54 | NIMLPFWG (SEQ ID NO: 33) | QYYQS (SEQ ID NO: 45) | 1 | 2.1 | 28.4 |
| VEGF_CKP9.59 | DPMQPFWG (SEQ ID NO: 34) | RWYQS (SEQ ID NO: 44) | | N/D | N/D |
| VEGF_CKP9.63 | DVMQPYWG (SEQ ID NO: 35) | HWYNS (SEQ ID NO: 46) | 1 | 2.0 | 29.7 |
| VEGF_CKP9.69 | ALLQPLWG (SEQ ID NO: 259) | RWYNS (SEQ ID NO: 133) | 1 | 1.0 | 14.3 |
| VEGF_CKP9.71 | QLLQPLWG (SEQ ID NO: 37) | RWYQS (SEQ ID NO: 44) | 1 | 1.0 | 16.5 |
| VEGF_CKP9.72 | RLLEPSWG (SEQ ID NO: 260) | QWYQS (SEQ ID NO: 264) | 1 | 0.6 | 10.0 |
| VEGF_CKP9.76 | HLLLPLWG (SEQ ID NO: 261) | RWYHS (SEQ ID NO: 43) | 1 | 1.3 | 15.5 |
| VEGF_CKP9.96 | KLFEPLWG (SEQ ID NO: 39) | RWYES (SEQ ID NO: 567) | 1 | 1.2 | 18.4 |

*S/N = signal to noise ratio as compared to BSA control

These clones were selected for further validation in a phage titration assay, and soluble folded forms corresponding to ten of these sequences were generated for further in vitro assessment (see Table 25 below). From this set of variants, VEGF_CKP9.2, VEGF_CKP9.54 and VEGF_CKP9.63 exhibited improved potency against VEGF-A compared to parent VEGF-CKP9 in in vitro and cellular assays, with $IC_{50}$ in 100-200 nM range (see Table 25).

TABLE 25

| Inhibitory activity in phage competition ELISA and VEGF-A-KDR interaction ELISA | | |
|---|---|---|
| VARIANT | phage ELISA $IC_{50}$ (μM) | Cellular $IC_{50}$ (nM) |
| VEGF_CKP9 | 1.36 | 11700 |
| VEGF_CKP9.2 | 0.168 | 270 |
| VEGF_CKP9.3 | 1.50 | N/D |
| VEGF_CKP9.4 | 1.95 | N/D |
| VEGF_CKP9.20 | 1.34 | N/D |

TABLE 25-continued

| Inhibitory activity in phage competition ELISA and VEGF-A-KDR interaction ELISA | | |
|---|---|---|
| VARIANT | phage ELISA $IC_{50}$ (μM) | Cellular $IC_{50}$ (nM) |
| VEGF_CKP9.22 | >100 | N/D |
| VEGF_CKP9.54 | 0.45 | 188 |
| VEGF_CKP9.59 | 5.82 | N/D |
| VEGF_CKP9.63 | 0.146 | 140 |
| VEGF_CKP9.96 | 49.00 | N/D |

To enhance potency, we selected the lead 9.54 and 9.63 molecules and generated new phage libraries based on these frameworks in which loop 2 was randomized. The new libraries were panned against hVEGF-A and yielded a number of loop 2 variants which demonstrated significantly improved potency against VEGF-A compared to parent 9.54 and 9.63 molecules (see Tables 26 and 27 below, respectively), with the most potent molecules exhibiting $IC_{50}$ in 0.5-2 nM range (see Table 28 below).

TABLE 26

| Affinity-matured VEGF-A binding loop 2 variants based on 9.54 framework | | | | | | |
|---|---|---|---|---|---|---|
| VARIANT | LOOP 1 | LOOP 2 | LOOP 5 | n | ELISA | S/N* |
| VEGF_CKP9 | QLMQPFWG (SEQ ID NO: 10) | KQDSD (SEQ ID NO: 93) | HWYQS (SEQ ID NO: 17) | | | |
| VEGF_CKP9.54 | NIMLPFWG (SEQ ID NO: 33) | KQDSD (SEQ ID NO: 93) | QYYQS (SEQ ID NO: 45) | | | |
| VEGF_CKP9.54.1 | NIMLPFWG (SEQ ID NO: 33) | GQSFE (SEQ ID NO: 94) | QYYQS (SEQ ID NO: 45) | 80 | 2.4 | 29.9 |
| VEGF_CKP9.54.2 | NIMLPFWG (SEQ ID NO: 33) | GLDYD (SEQ ID NO: 95) | QYYQS (SEQ ID NO: 45) | 1 | 0.1 | 26 |

TABLE 26-continued

Affinity-matured VEGF-A binding loop 2 variants based on 9.54 framework

| VARIANT | LOOP 1 | LOOP 2 | LOOP

TABLE 27-continued

Affinity-matured VEGF-A binding loop 2 variants based on VEGF_CKP9.63 framework
*S/N = signal to noise ratio as compared to BSA control

| VARIANT | LOOP 1 | LOOP 2 | Loop5 | ELISA | S/N* |
|---|---|---|---|---|---|
| VEGF_CKP9.63.1 | DVMQPYWG (SEQ ID NO: 35) | GPDID (SEQ ID NO: 118) | HWYNS (SEQ ID NO: 46) | 2.0 | 25.2 |
| VEGF_CKP9.63.2 | DVMQPYWG (SEQ ID NO: 35) | GDDLE (SEQ ID NO: 324) | HWYNS (SEQ ID NO: 46) | 2.0 | 15.0 |
| VEGF_CKP9.63.3 | DVMQPYWG (SEQ ID NO: 35) | GVDMT (SEQ ID NO: 325) | HWYNS (SEQ ID NO: 46) | 1.7 | 20.7 |
| VEGF_CKP9.63.12 | DVMQPYWG (SEQ ID NO: 35) | GMDIE (SEQ ID NO: 326) | HWYNS (SEQ ID NO: 46) | 2.6 | 39.9 |
| VEGF_CKP9.63.14 | DVMQPYWG (SEQ ID NO: 35) | DGDYQ (SEQ ID NO: 327) | HWYNS (SEQ ID NO: 46) | 1.5 | 21.3 |
| VEGF_CKP9.63.15 | DVMQPYWG (SEQ ID NO: 35) | GNDVS (SEQ ID NO: 328) | HWYNS (SEQ ID NO: 46) | 1.5 | 21.4 |
| VEGF_CKP9.63.16 | DVMQPYWG (SEQ ID NO: 35) | GRDMD (SEQ ID NO: 119) | HWYNS (SEQ ID NO: 46) | 2.2 | 10.3 |
| VEGF_CKP9.63.18 | DVMQPYWG (SEQ ID NO: 35) | AGDEL (SEQ ID NO: 329) | HWYNS (SEQ ID NO: 46) | 2.3 | 17.3 |
| VEGF_CKP9.63.24 | DVMQPYWG (SEQ ID NO: 35) | GLDEE (SEQ ID NO: 330) | HWYNS (SEQ ID NO: 46) | 1.6 | 20.4 |
| VEGF_CKP9.63.27 | DVMQPYWG (SEQ ID NO: 35) | DGDFD (SEQ ID NO: 331) | HWYNS (SEQ ID NO: 46) | 2.1 | 26.0 |
| VEGF_CKP9.63.30 | DVMQPYWG (SEQ ID NO: 35) | AGDFE (SEQ ID NO: 332) | HWYNS (SEQ ID NO: 46) | 2.0 | 26.0 |
| VEGF_CKP9.63.37 | DVMQPYWG (SEQ ID NO: 35) | EMDFD (SEQ ID NO: 120) | HWYNS (SEQ ID NO: 46) | 0.6 | 8.6 |
| VEGF_CKP9.63.39 | DVMQPYWG (SEQ ID NO: 35) | GNSFE (SEQ ID NO: 333) | HWYNS (SEQ ID NO: 46) | 1.6 | 18.9 |
| VEGF_CKP9.63.42 | DVMQPYWG (SEQ ID NO: 35) | GQDLT (SEQ ID NO: 334) | HWYNS (SEQ ID NO: 46) | 1.7 | 23.1 |
| VEGF_CKP9.63.44 | DVMQPYWG (SEQ ID NO: 35) | GENLA (SEQ ID NO: 335) | HWYNS (SEQ ID NO: 46) | 1.7 | 19.5 |
| VEGF_CKP9.63.47 | DVMQPYWG (SEQ ID NO: 35) | GQDYN (SEQ ID NO: 336) | HWYNS (SEQ ID NO: 46) | 1.7 | 20.7 |
| VEGF_CKP9.63.50 | DVMQPYWG (SEQ ID NO: 35) | GADLS (SEQ ID NO: 337) | HWYNS (SEQ ID NO: 46) | 0.9 | 12.7 |
| VEGF_CKP9.63.54 | DVMQPYWG (SEQ ID NO: 35) | GFDMD (SEQ ID NO: 338) | HWYNS (SEQ ID NO: 46) | 1.4 | 19.9 |

TABLE 27-continued

Affinity-matured VEGF-A binding loop 2 variants based on VEGF_CKP9.

TABLE 28-continued

Inhibitory activity of VEGF_CKP9.54- and VEGF_CKP9.63-derived loop 2 variants against VEGF-A

| VARIANT | LOOP 1 | LOOP 2 | LOOP 5 | KDR-VEGF IC$_{50}$ (nm) | Cellular IC$_{50}$ (nm) |
|---|---|---|---|---|---|
| VEGF_CKP9.63.69 | DVMQPYWG (SEQ ID NO: 35) | GESLS (SEQ ID NO: 211) | HWYNS (SEQ ID NO: 46) | 2.1 | 26.4 |
| VEGF_CKP9.63.12 | DVMQPYWG (SEQ ID NO: 35) | GPDID (SEQ ID NO: 118) | HWYNS (SEQ ID NO: 46) | 0.7 | 1.83 |

The affinities/potencies of VEGF_CKP9.63.1, VEGF_CKP9.63.27, VEGF_CKP9.63.44, VEGF_CKP9.63.69, and VEGF_CKP9.63.12 for hVEGF-A (8-109) are shown below in Table 29.

TABLE 29

| VARIANT | k$_a$ | k$_d$ | K$_D$ |
|---|---|---|---|
| EM63 | 0.16 ± 0.03 | 1.6 ± 0.5 | 100 ± 9 nM |
| L2.9.63.1 | 6 ± 1 | 0.37 ± 0.13 | 5.8 ± 1.2 |
| L2.9.63.12 | 8 ± 1 | 0.10 ± 0.04 | 1.1 ± 0.2 |
| L2.9.63.27 | 11 ± 4 | 0.15 ± 0.04 | 1.4 ± 0.2 |
| L2.9.63.44 | 10 ± 2 | 0.11 ± 0.02 | 1.2 ± 0.2 |
| L2.9.63.69 | 3 ± 1 | 0.20 ± 0.04 | 6.9 ± 0.7 |

Variants VEGF_CKP9.54.90 (see row 2 of Table 26) and VEGF_CKP9.63.12 (see row 6 of Table 27), as well as parental variants VEGF_CKP9.54 (see row 12 of Table 24) and VEGF_CKP9.63 (see row 15 of Table 24), bind with similar affinity to human, mouse, rat and rabbit VEGF-A, as determined by surface plasmon resonance. See Table 30 below.

TABLE 30

Binding kinetics and affinities of VEGF_CKP9.54.90, VEGF_CKP9.63.12, VEGF_CKP9.54, and VEGF_CKP9.63 for various VEGF isoforms.

| VARIANT | VEGF Isoform | ka | ka (error) | kd | kd (error) | KD (nM) | KD (error) |
|---|---|---|---|---|---|---|---|
| 9.54 | human 8-109 | $1.26 \times 10^6$ | $1.10 \times 10^5$ | $2.18 \times 10^{-1}$ | $1.19 \times 10^{-2}$ | 175.88 | 18.21 |
| | human 165 | $8.23 \times 10^5$ | $1.11 \times 10^5$ | $1.49 \times 10^{-1}$ | $1.29 \times 10^{-2}$ | 189.67 | 34.57 |
| | mouse 164 | $8.26 \times 10^5$ | $2.93 \times 10^4$ | $2.07 \times 10^{-1}$ | $2.44 \times 10^{-2}$ | 249.87 | 21.19 |
| | rat | $1.93 \times 10^6$ | $8.91 \times 10^5$ | $2.96 \times 10^{-1}$ | $9.36 \times 10^{-2}$ | 175.64 | 26.27 |
| | rabbit | $2.10 \times 10^6$ | $7.12 \times 10^5$ | $2.74 \times 10^{-1}$ | $9.14 \times 10^{-2}$ | 133.22 | 9.47 |
| 9.54.90 | human 8-109 | $5.15 \times 10^7$ | $1.62 \times 10^7$ | $4.05 \times 10^{-2}$ | $8.77 \times 10^{-3}$ | 0.87 | 0.13 |
| | human 165 | $1.58 \times 10^7$ | $3.87 \times 10^6$ | $1.33 \times 10^{-2}$ | $1.70 \times 10^{-3}$ | 0.89 | 0.10 |
| | mouse 164 | $8.71 \times 10^6$ | $2.79 \times 10^6$ | $1.01 \times 10^{-2}$ | $2.12 \times 10^{-3}$ | 1.31 | 0.24 |
| | rat | $1.72 \times 10^7$ | $7.43 \times 10^6$ | $1.35 \times 10^{-2}$ | $3.33 \times 10^{-3}$ | 0.90 | 0.14 |
| | rabbit | $5.15 \times 10^7$ | $1.36 \times 10^7$ | $6.75 \times 10^{-2}$ | $8.99 \times 10^{-3}$ | 1.14 | 0.18 |
| 9.63 | human 8-109 | $6.62 \times 10^5$ | $9.83 \times 10^4$ | $1.81 \times 10^{-1}$ | $2.56 \times 10^{-2}$ | 281.44 | 43.53 |
| | human 165 | $3.40 \times 10^5$ | $2.79 \times 10^4$ | $1.30 \times 10^{-1}$ | $1.33 \times 10^{-2}$ | 381.89 | 19.15 |
| | mouse 164 | $5.57 \times 10^5$ | $4.60 \times 10^4$ | $1.60 \times 10^{-1}$ | $1.35 \times 10^{-2}$ | 288.75 | 11.08 |
| | rat | $4.56 \times 10^5$ | $1.49 \times 10^5$ | $2.46 \times 10^{-1}$ | $9.23 \times 10^{-2}$ | 523.93 | 25.06 |
| | rabbit | $4.24 \times 10^5$ | $3.22 \times 10^4$ | $1.30 \times 10^{-1}$ | $1.95 \times 10^{-2}$ | 311.43 | 52.25 |
| 9.63.12 | human 8-109 | $6.54 \times 10^6$ | $7.25 \times 10^5$ | $2.50 \times 10^{-2}$ | $3.45 \times 10^{-3}$ | 3.20 | 0.22 |
| | human 165 | $4.65 \times 10^6$ | $8.39 \times 10^5$ | $2.01 \times 10^{-2}$ | $3.95 \times 10^{-3}$ | 4.32 | 0.15 |
| | mouse 164 | $1.04 \times 10^6$ | $2.81 \times 10^5$ | $1.32 \times 10^{-2}$ | $3.04 \times 10^{-3}$ | 13.07 | 1.74 |
| | rat | $6.44 \times 10^6$ | $3.87 \times 10^6$ | $2.59 \times 10^{-2}$ | $1.01 \times 10^{-2}$ | 5.74 | 1.54 |
| | rabbit | $6.91 \times 10^6$ | $1.35 \times 10^6$ | $1.78 \times 10^{-2}$ | $4.46 \times 10^{-3}$ | 2.54 | 0.40 |

Figure 2A:
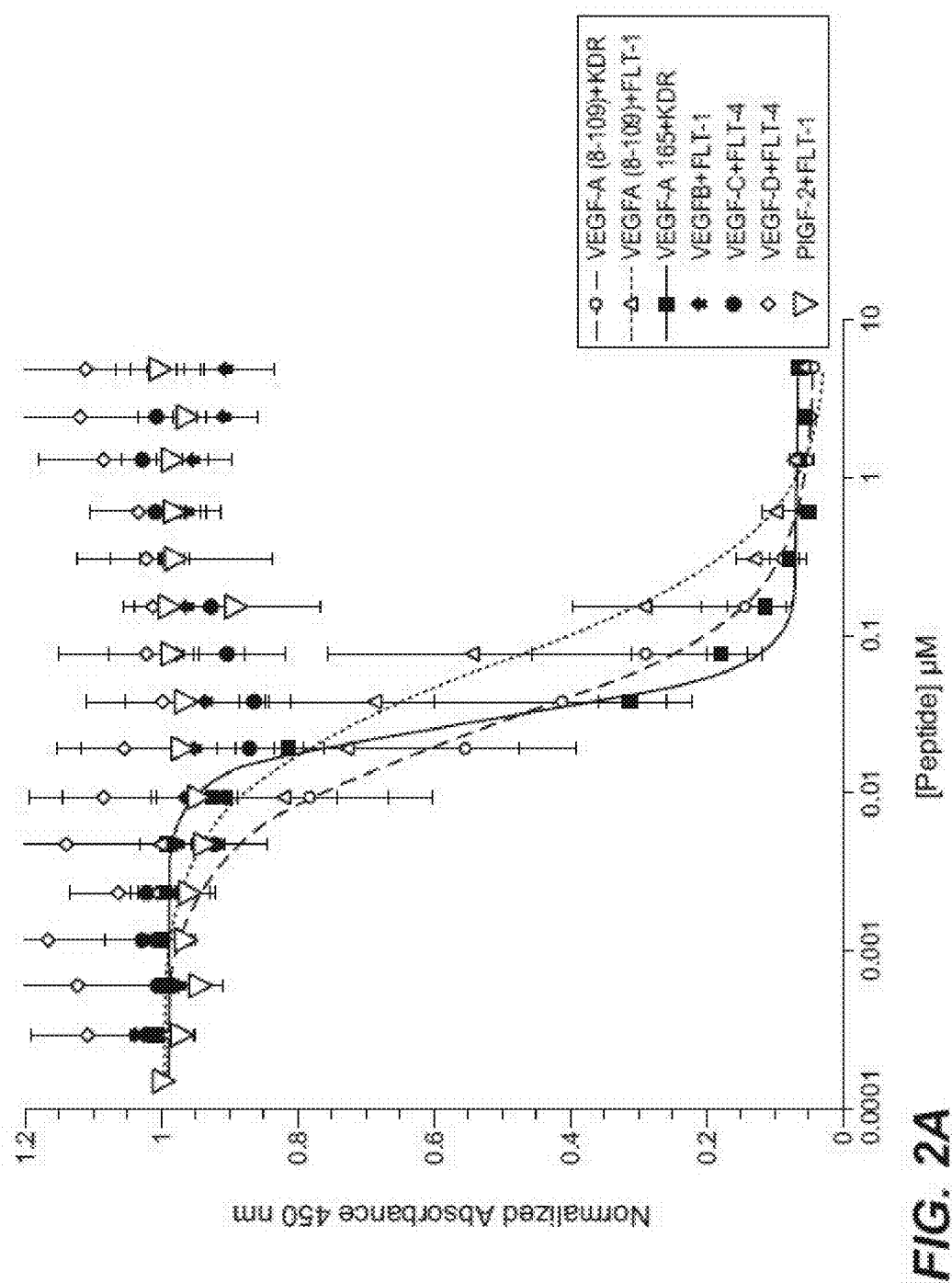
FIG. 2A shows the results of experiments that were performed to determine whether EGF_CKP9.54.90 disrupts the interaction between VEGF-A(8-109) and KDR; VEGF-A(8-109) and Flt-1; VEGF-A 165 and KDR; VEGF-B and Flt-1; VEGF-C and Flt-4; VEGF-D and Flt-4; and PlGF-2 and FLT-1.
Figure 2B:
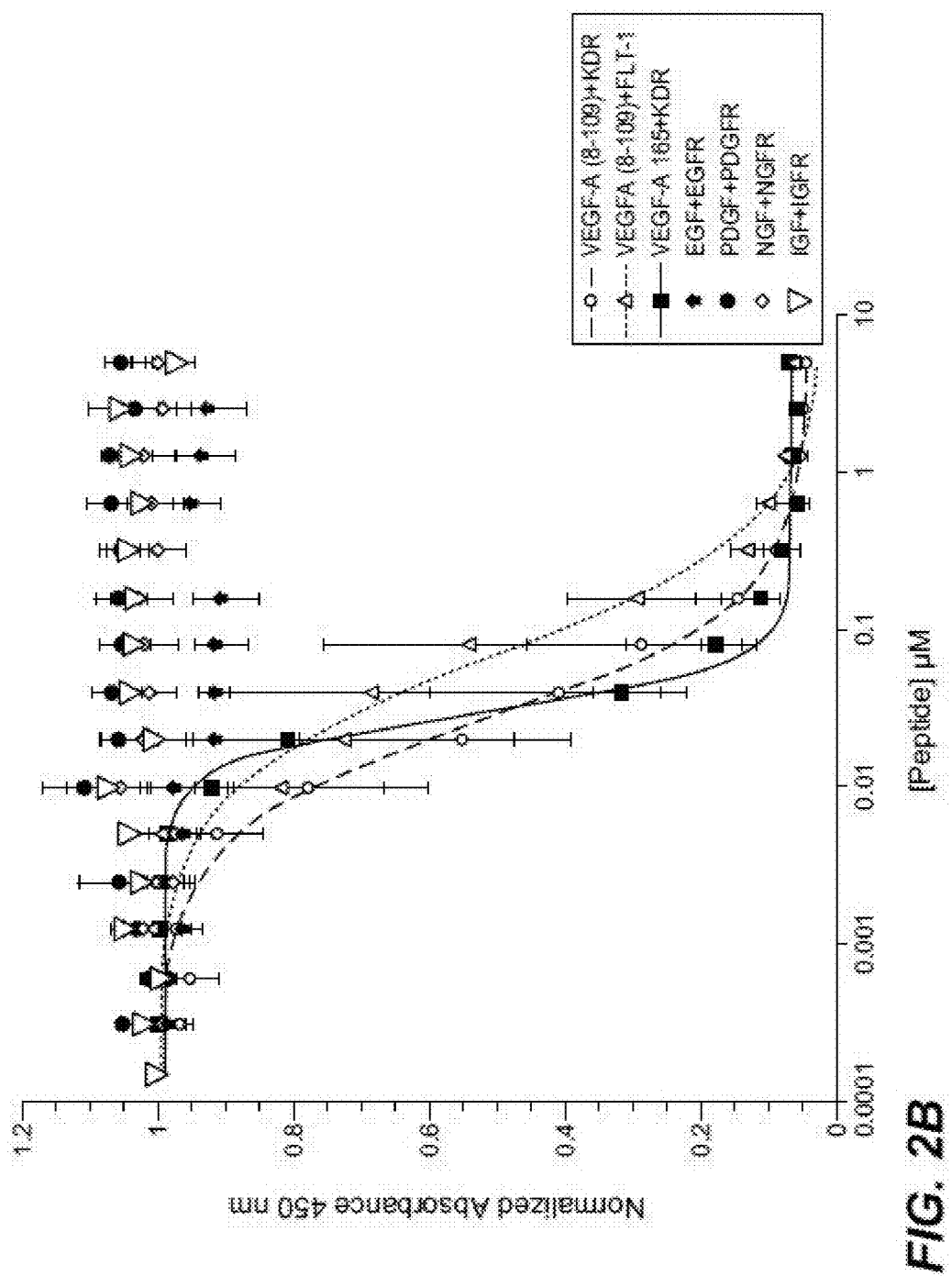
FIG. 2B shows the results of experiments that were performed to determine whether EGF_CKP9.54.90 disrupts the interaction between VEGF-A(8-109) and KDR; VEGF-A(8-109) and Flt-1; VEGF-A 165 and KDR; EGF and EGFR; PDGF and PDGFR; NGF and NGFR; and IGF and IGFR.

VEGF_CKP9.54.90 is also highly selective to VEGF-A and does not bind to or inhibit the activity of other VEGF isoforms such as VEGF-B, VEGF-C and VEGF-D or other growth factors such as P1GF, EGF, NGF, IGF and PDGF. As shown in FIGS. 2A and 2B, the variant VEGF_CKP9.54.90 disrupts the interaction between VEGF-A and KDR as well as the interaction between VEGF-A and Flt-1, but not disrupt the interaction between VEGF-B and Flt-1, between VEGF-C and Flt-4, between VEGF-D and Flt-4, between PIGF-2 and Flt-1, between EGF and EGFR, between PDGF and PDGFR, between NGF and NGFR, or between IGF and IGFR.

Figures 3A, 3B:
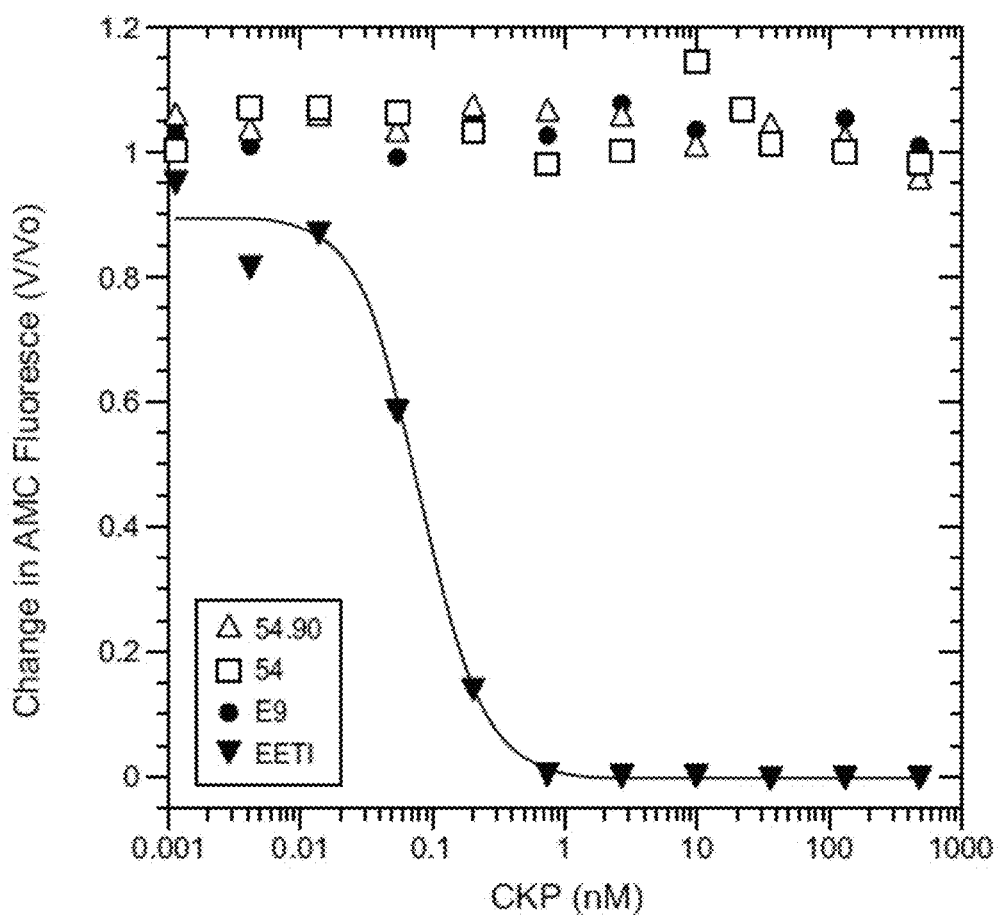
FIG. 3A provides the Loop 1, Loop 2, and Loop 5 amino acid sequences of wild type EETI, VEGF_CKP9 (also referred to as E9), VEGF_CKP9.54 (also referred to as EM54), and VEGF_CKP9.54.90 (also referred to as V_L2.9.54.90).
FIG. 3B shows the results of experiments performed to determine whether VEGF_CKP9.54.90, VEGF_CKP9.54, and VEGF_CKP9.63.12 inhibit trypsin protease activity.
Figures 4A, 4B, 4C:
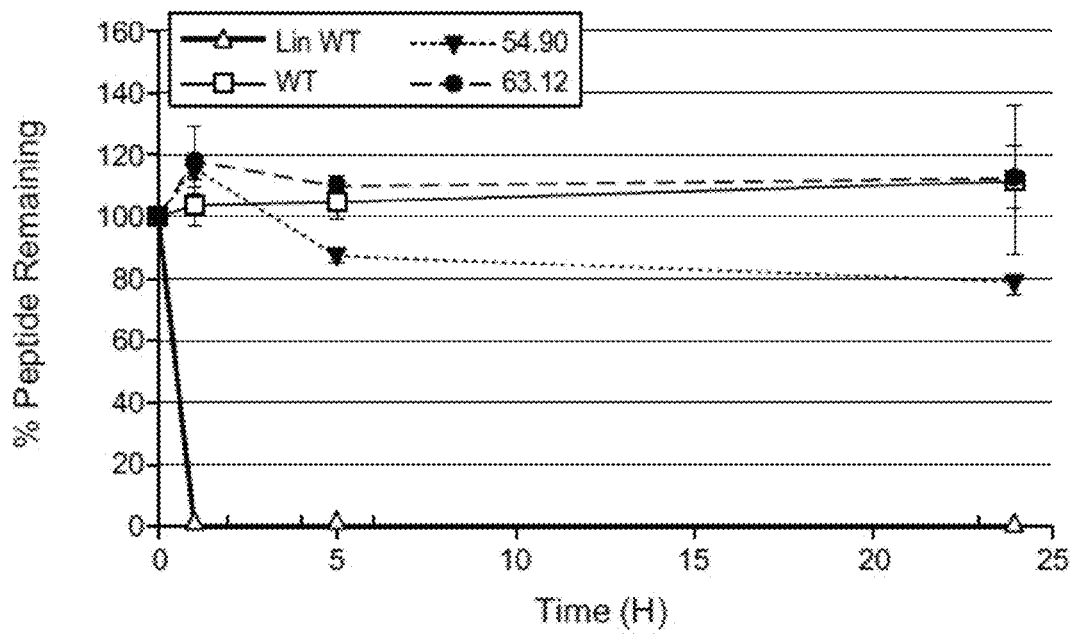
FIG. 4A provides schematics that compare the disulfide bond connectivity pattern of VEGF_CKP9.54.90 (also referred to as 54.90) to that of wild type EETI-II.
FIG. 4B provides the Loop 1, Loop2, and Loop 5 amino acid sequences of VEGF_CKP9 (also referred to as E9), VEGF_CKP9.54 (also referred to as EM54), VEGF_CKP9.54.1 (also referred to as V_L2.9.54.1), VEGF_CKP9.54.90 (also referred to as V_L2.9.54.90), VEGF_CKP9.63 (also referred to as EM63), VEGF_CKP9.63.1 (also referred to as V_L2.9.63.1), VEGF_CKP9.63.44 (also referred to as V_L2.9.63.44), and VEGF_CKP9.63.12 (also referred to as V_L2.9.63.12).
FIG. 4C shows the results of experiments performed to determine whether VEGF_CKP9.54.90 and VEGF_CKP9.63.12 are resistant to trypsin digestion.

Unlike EETI-II, VEGF_CKP9.54.90, VEGF_CKP9.54, and VEGF_CKP9.63.12 do not inhibit trypsin protease activity as measured in a peptide substrate cleavage assay (Stanger et al. (2014) *FEBS Lett.* 588 (23), 4487-96). See FIGS. 3A and 3B. However, VEGF_CKP9.54.90 and VEGF_CKP9.63.12 maintain a degree of resistance to trypsin digestion (see FIGS. 4A, 4B, and 4C). Approximately 20% of VEGF_CKP9.54.90 was cleaved at Arg13 within loop 2 after 24 h incubation with trypsin at 37° C.

Figure 5A:
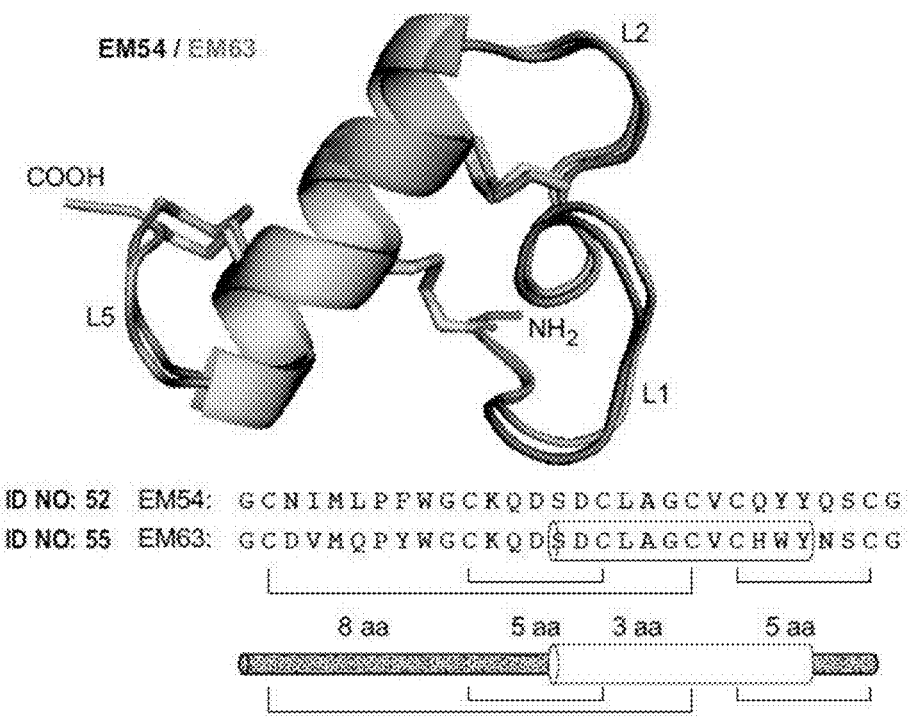
FIG. 5A depicts the structure of VEGF_CKP9.54 (also referred to as EM54) superimposed upon the structure of VEGF_CKP9.54 (also referred to as EM63) and provides schematics of VEGF_CKP9.54's and VEGF_CKP9.63's disulfide bond connectivity patterns.
Figure 5B:
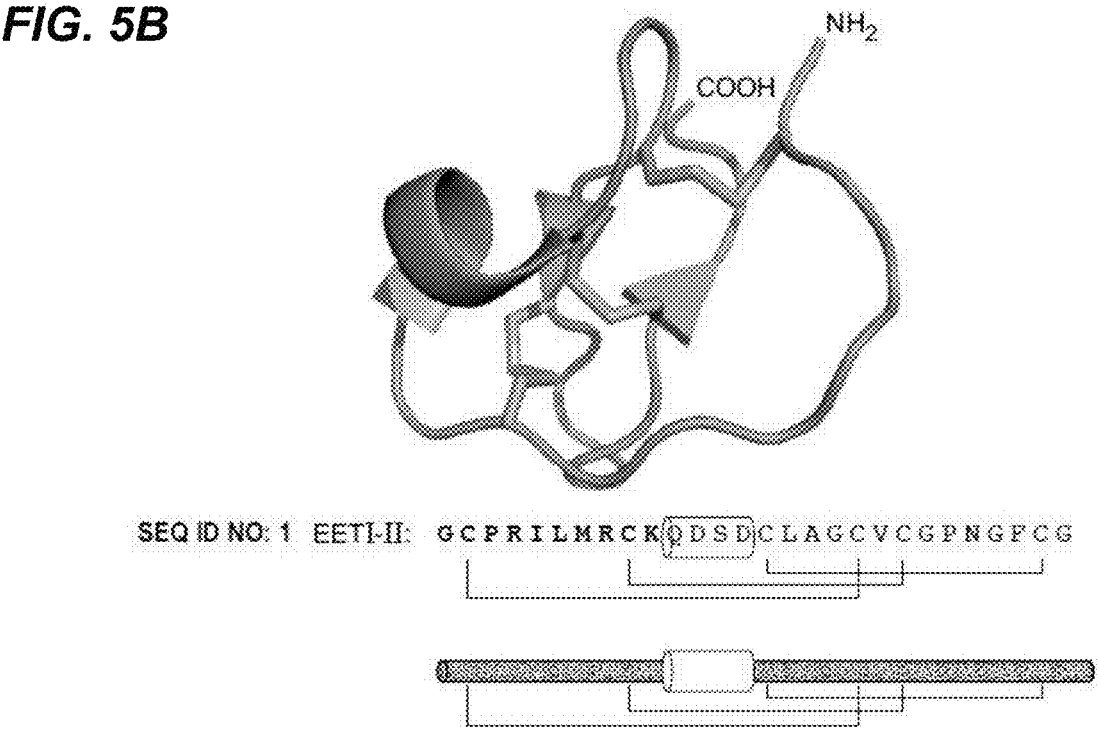
FIG. 5B depicts the structure of wild type EETI-II, and provides a schematic of wild type EETI's disulfide bond connectivity pattern.
Figure 7A:
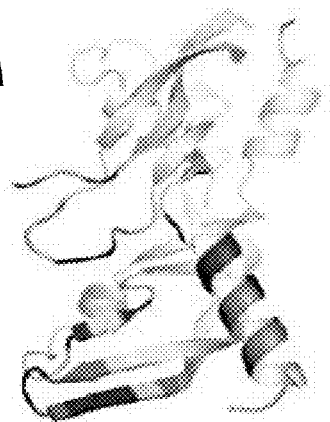
FIG. 7A is a ribbon diagram model showing the binding interface of VEGF_CKP9.54.90 on VEGF-A.
Figure 7B:
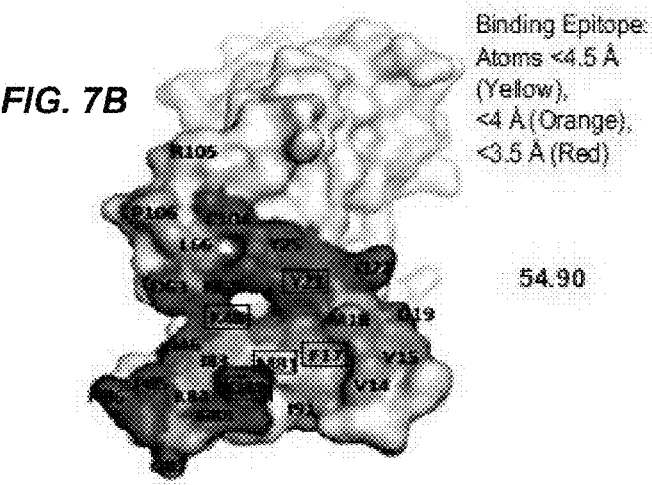
FIG. 7B depicts space a filling model of FIG. 7A.
Figure 7C:
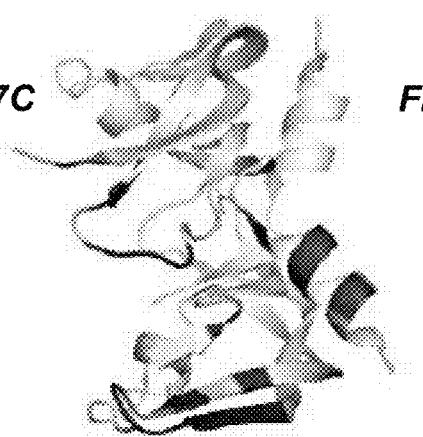
FIG. 7C is a ribbon diagram model showing the binding interface of antibody G6.31 on VEGF-A.
Figure 7D:
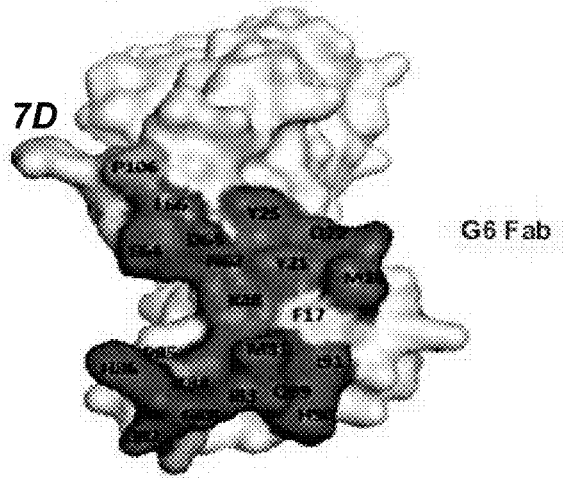
FIG. 7D depicts space a filling model of FIG. 7C.
Figure 7E:
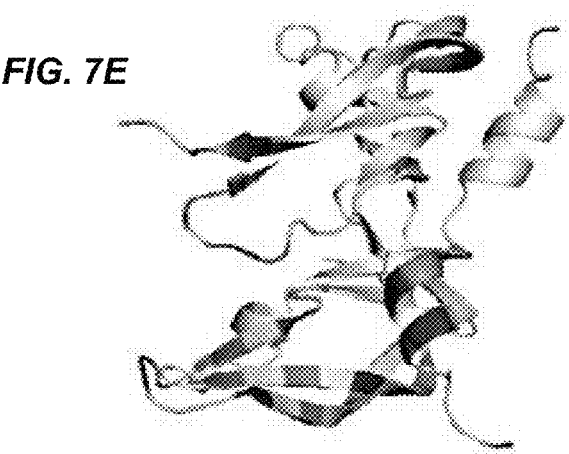
FIG. 7E is a ribbon diagram model showing the binding interface of domain 2 of Flt-2 on VEGF-A.
Figure 7F:
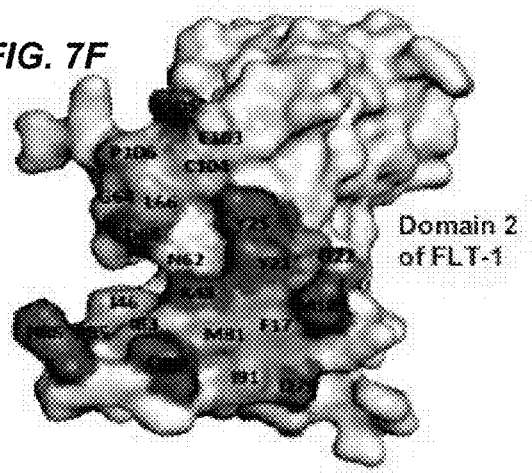
FIG. 7F depicts space a filling model of FIG. 7E.
Figures 8A, 8B, 8C:
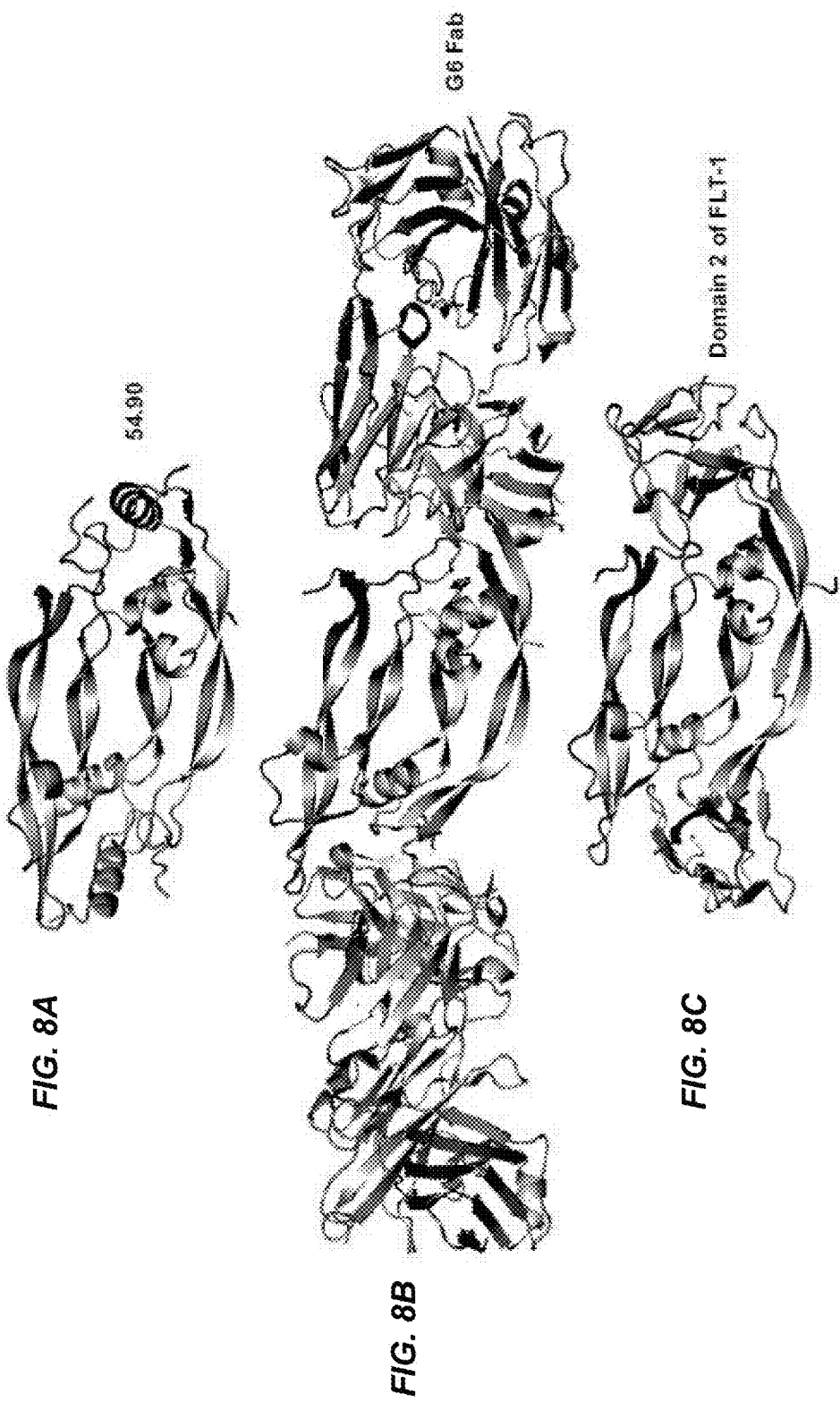
FIG. 8A depicts a ribbon diagram model that shows the binding interface of VEGF_CKP9.54.90, on VEGF-A.
FIG. 8B depicts a ribbon diagram model that shows the binding interface of antibody G6.31 on VEGF-A.
FIG. 8C depicts a ribbon diagram model that shows the binding interface of domain 2 of Flt-2 on VEGF-A.

VEGF_CKP9.54, VEGF_CKP9.63, and VEGF_CKP9.54.90 each contains roughly a 3-turn alpha-helix and each adopts a disulfide signature that is distinct from that of wild-type EETI-II (C1-C4, C2-C3, C5-C6 for VEGF_CKP9.54.90 vs. C1-C4, C2-O5, C3-C6 for wild-type EETI-II). See FIGS. 5A and 5B. On one side of the helix, VEGF_CKP9.54.90 forms a fused bicyclic structure that is bridged by two disulfide bonds (C1-C4 and C2-C3), encompassing loops 1, 2 and 3, and ~1.5 turn of the alpha-helix. Loop 5 forms on the opposite side of the helix and is constrained by C5-C6 disulfide bond.

The co-crystal structures of VEGF_CKP9.54, VEGF_CKP9.63, and VEGF_CKP9.54.90 in complex with VEGF-A were obtained. co-crystal structures of VEGF_CKP9.54, VEGF_CKP9.63, and VEGF_CKP9.54.90 in complex with VEGF-A are highly similar. See FIGS. 5A, 5B, 6A and 6B for the co-crystal structure of VEGF_CKP9.54 in complex with VEGF-A. Given that the structures of VEGF_CKP9.54, VEGF_CKP9.63, and VEGF_CKP9.54.90 are highly similar, (see FIGS. 5A, 5B, 6A and 6B) further studies were performed with VEGF_CKP9.54.90. The helix defined by residues Phe15-Tyr26 of VEGF_CKP9.54.90 forms extensive hydrophobic and polar interactions with the VEGF-A surface (see Table 31 below). Additionally, there is a network of backbone H-bonds which forms within and stabilizes the ~3-turn alpha-helix. In general, VEGF_CKP9.54.90 exhibits a compact and rigid structure, stabilized by intramolecular polar and hydrophobic contacts, including backbone-backbone, side chain-backbone and side chain-side chain interactions (Table 32). The surface of VEGF_CKP9.54.90 that contacts VEGF-A is mainly hydrophobic in nature with few polar side chains (Table 31), whereas the opposite surface of the peptide that is not interacting with VEGF-A is solvent-exposed and primarily polar in nature.

TABLE 31

VEGF_CKP9.54.90 residues that are within 4 Å of the VEGF-A dimer
VEGF_CKF9.54.90 residues within 4 Å of VEGFA

| VEGF_CKP9.54.90 (Chain 1) | VEGF_CKP9.54.90 (Chain 2) |
|---|---|
| I4 | I4 |
| M5 | M5 |
| L6 | L6 |
| P7 | P7 |
| F8 | F8 |
| W9 | W9 |
| R13 | R13 |
| D14 | D14 |
| F15 | F15 |
| L18 | L18 |
| A19 | A19 |
| V22 | V22 |
| C23 | C23 |
| Y25 | Y25 |
| Y26 | Y26 |
| Q27 | Q27 |
| S28 | S28 |
| G30 | G30 |

TABLE 32

Summary of VEGF_CKP9.54.90 intra-molecular interactions

| Residue 1 | Residue 2 | Comments |
|---|---|---|
| Cys2 | Cys21 | Disulfide |
| Asn3 | Trp9 | Main chain H-bond |
| Asn3 | Met5 | Asp3 makes H-bond with M5 main chain nitrogen |
| Asn3 | Leu6 | Main chain H-bond |
| Leu6 | Trp9 | Main chain H-bond |
| Pro7 | Gly10 | Main chain H-bond |
| Phe8 | Cys11 | Main chain H-bond |
| Phe8 | Leu18 | Van der Waals interaction |

TABLE 32-continued

Summary of VEGF_CKP9.54.90 intra-molecular interactions

| Residue 1 | Residue 2 | Comments |
|---|---|---|
| Trp9 | Ile4, Leu18, Val22, Tyr25, Tyr26 | Core Trp makes a network of Van der Waals interactions |
| Cys11 | Cys17 | Disulfide |
| Gly12 | Asp14 | Main chain H-bond |
| Asp14 | Glu16, C17 | Asp14 makes stabilizing H-bond with N-terminus of helix |
| Phe15 | Leu18, Ala19 | Van der Waals interactions stabilizing helix |
| Leu18 | Val22 | Van der Waals interactions stabilizing helix |
| Val22 | Tyr26 | Van der Waals interactions stabilizing helix |
| Phe15-Tyr26 | | Network of backbone H-bonds form stabilizing a ~3-turn helix |
| Cys23 | Cys29 | Disulfide |
| Tyr25 | Tyr26 | Van der Waals interactions stabilizing helix |
| Gln27 | Cys23 | Main chain H-bond |
| Ser28 | Cys23 | Main chain H-bond |

Figure 9:
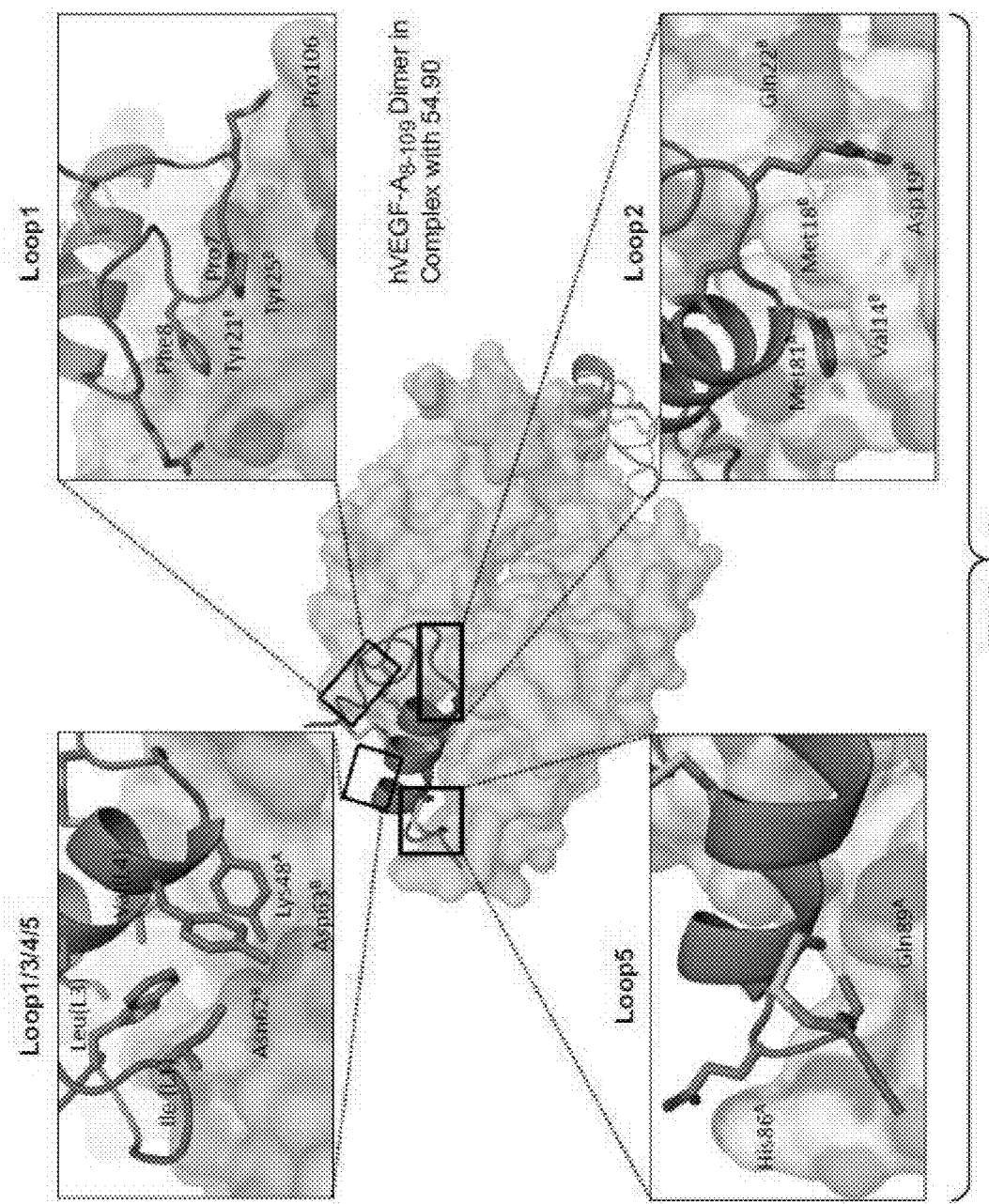
FIG. 9 shows contact residues on VEGF-A at the interacting surface between VEGF-A and VEGF_CKP9.54.90.
Figure 10C:
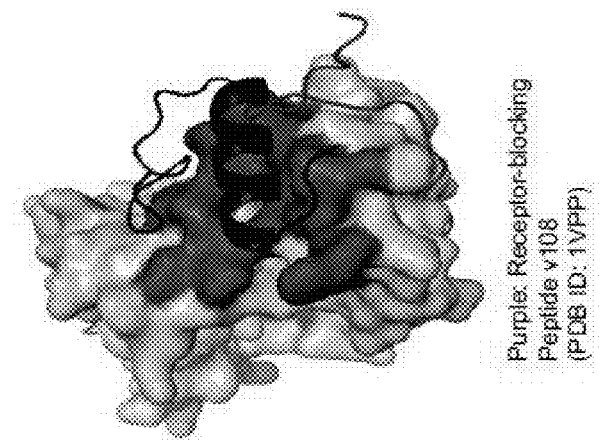
FIG. 10C shows the binding interface of receptor-blocking peptide v108 on VEGF-A.
Figure 10B:
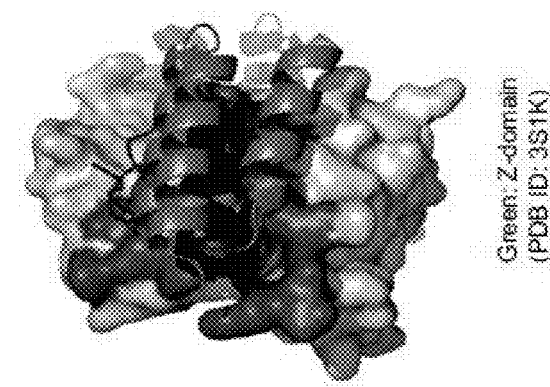
FIG. 10B shows the binding interface of Z-domain on VEGF-A.
Figure 10A:
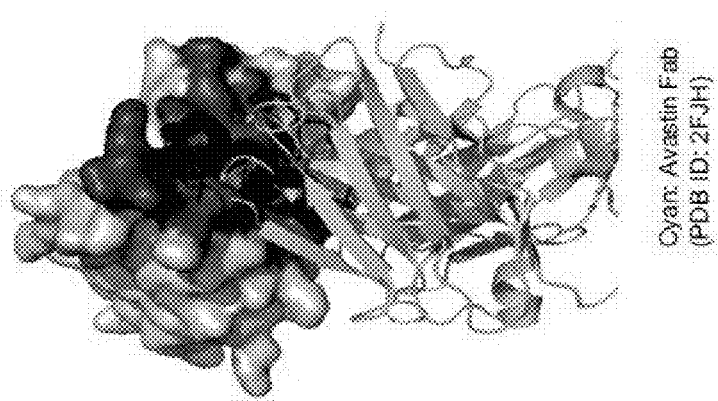
FIG. 10A shows the binding interface of bevacizumab Fab on VEGF-A.
Figure 11A:
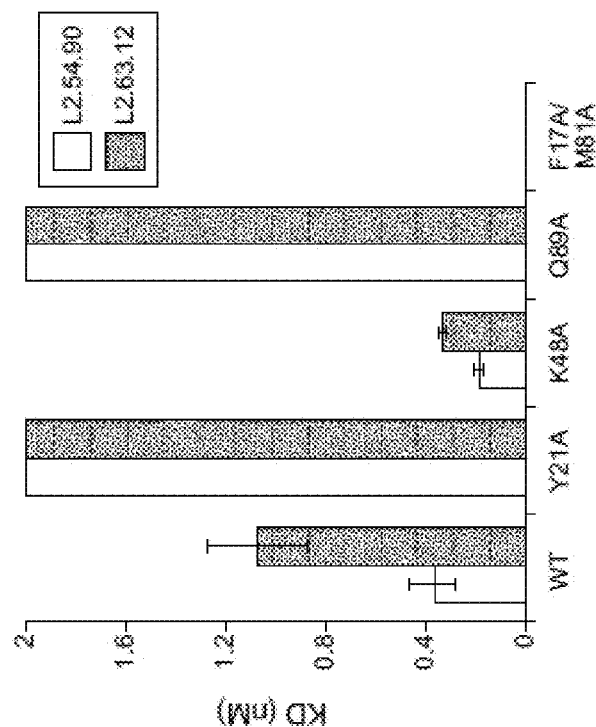
FIG. 11A provides the results of an experiment that was performed to determine the effects of amino acid substitution mutations in VEGF-A on binding of VEGF_CKP9.54.90 to VEGF-A and on the binding of VEGF_CKP9.63.12 to VEGFA.
Figure 11B:
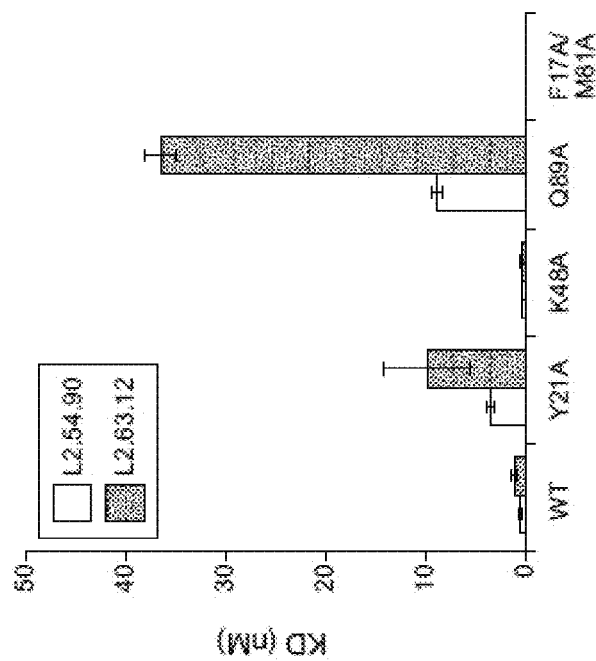
FIG. 11B provides the results of FIG. 11A on a different y axis.

The binding interface of VEGF_CKP9.54.90 on VEGF-A overlaps with that of the natural receptors and G6.31 antibody (FIGS. 7A-7F and 8A-C). Contact residues on VEGF-A that are in the peptide interface are summarized in Table 33 and shown in FIG. 9. The binding epitope of VEGF_CKP9.54.90 on VEGF-A is distinct from that of ranibizumab and bevacizumab (FIGS. 10A, 10B, and 10C), which do not bind to mouse or rat VEGF-A because their interaction with human VEGF-A is dependent on a key Gly88 residue that is substituted with Ser in rodents. The binding mode of VEGF_CKP9.54.90 suggests that it is not substantially dependent on Gly88, and this notion is validated by the observation that the peptide bound efficiently to both human and rodent VEGF-A. Site-directed mutagenesis was utilized to validate a number of contacts in the protein—peptide interface observed from the crystal structure. As expected, Y21A, Q89A and F17A/M81A mutations on VEGF-A led to reduced binding of VEGF_CKP9.54.90 on VEGF-A. See FIGS. 11A and 11B. However, K48A mutation enhanced the binding of VEGF_CKP9.54.90 by ~2-3 fold, a behavior that is similar to that observed with the G6.31 antibody (Fuh et al. (2006) *J. Biol. Chem.* 281, 6625-6631). See Table 34 below and FIGS. 11A and 11B.

TABLE 33

VEGF-A dimer residues that are within 4 Å of VEGF_CKP9.54.90
VEGF-A residues within 4 Å of VEGF_CKP9.54.90

| VEGF-A (Dimer Chain A) | VEGF-A (Dimer Chain B) |
|---|---|
|  | V14 |
|  | V15 |
| F17 | F17 |
| M18 | M18 |
|  | D19 |
| Y21 | Y21 |
| Q22 | Q22 |
| Y25 | Y25 |
| I46 | I46 |
| K48 | K48 |
| N62 | N62 |
| D63 | D63 |
| L66 | L66 |
| M81 | M81 |
| I83 | I83 |
| K84 | K84 |

TABLE 33-continued

VEGF-A dimer residues that are within 4 Å of VEGF_CKP9.54.90
VEGF-A residues within 4 Å of VEGF_CKP9.54.90

Figure 12:
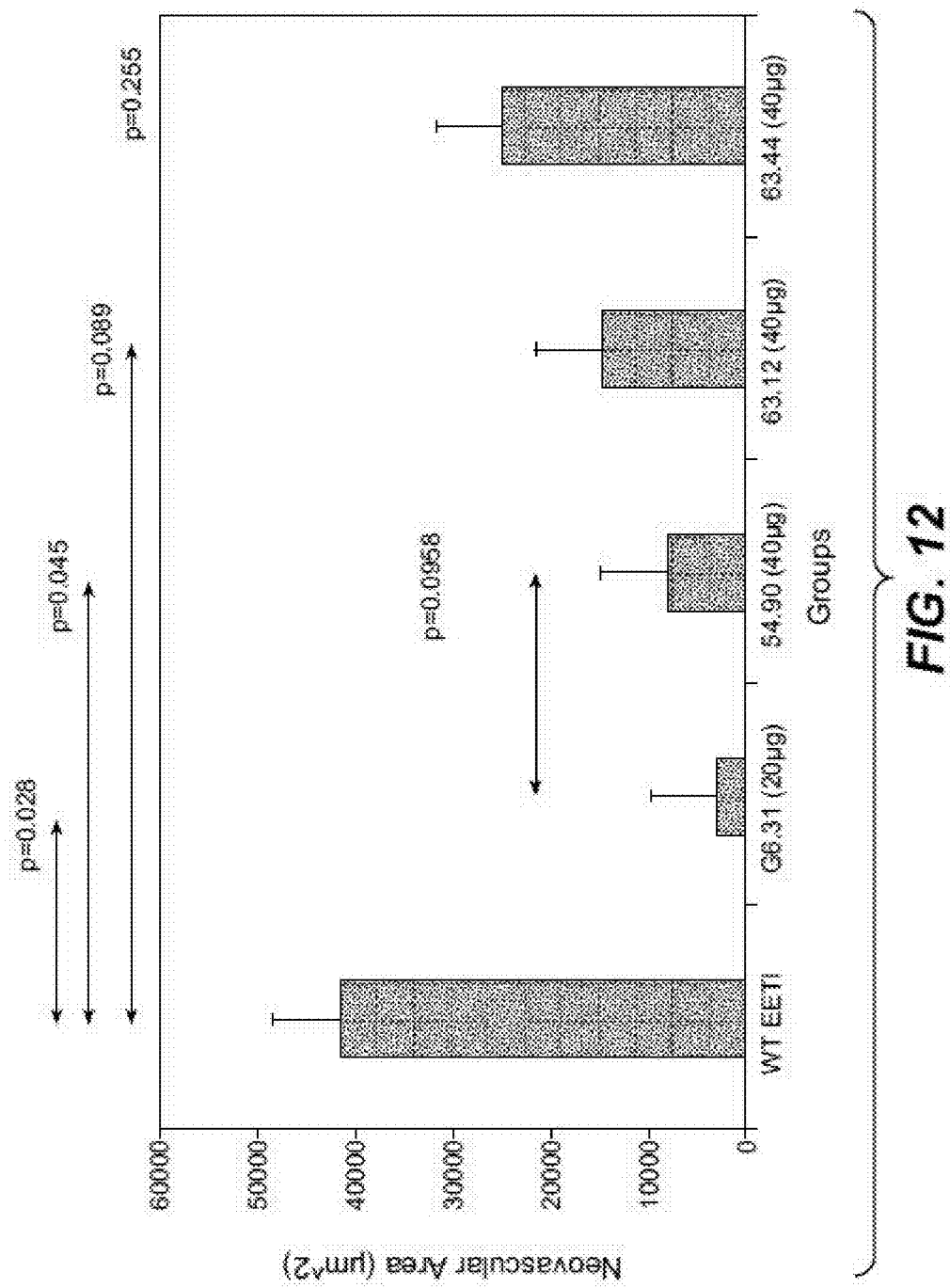
FIG. 12 provides the results of experiments that were performed to determine the effects of VEGF_CKP9.54.90 on CNV in rat eyes.

| VEGF-A (Dimer Chain A) | VEGF-A (Dimer Chain B) |
|---|---|
| P85 | P85 |
| H86 | H86 |
| Q87 | Q87 |
| G88 | G88 |
| Q89 | Q89 |
| I91 | |
| | C104 |
| | R105 |
| P106 | P106 | observed in neovascular area in peptide-treated eyes compared to control eyes. See FIG. 12.

The co-crystal structure of VEGF_CKP9.54.90 in complex with VEGF-A revealed that the native amino acid residues in loops 3 and 4 are not necessarily in optimal orientations for binding to VEGF-A (see FIG. 9) and could be modified to enhance their interaction with the VEGF-A surface or to elicit intramolecular interactions within the peptide that could improve peptide folding and stability. Therefore, with the goal of further improving the potency and behavior of the lead molecules, new phage libraries were constructed based on the sequences of 9.54, 54.1 and 9.63, 63.12 in which only loops 3 and 4 were randomized. These specific frameworks, though slightly weaker than the lead molecules, were selected in order to allow for a

TABLE 34

Binding kinetics and affinities of VEGF_CKP9.54.90, VEGF_CKP9.63.12, VEGF_CKP9.54, and VEGF_CKP9.63 for various hVEGF-A mutants.

| VARIANT | VEGF MUTANT | ka | ka (error) | kd | kd (error) | KD (nM) | KD (error) |
|---|---|---|---|---|---|---|---|
| 9.54.90 | WT | $7.81 \times 10^7$ | $1.86 \times 10^7$ | 0.0300 | $9.79 \times 10^{-3}$ | 0.37 | 0.09 |
| | Y21A | $3.72 \times 10^7$ | $1.30 \times 10^7$ | 0.1202 | $2.44 \times 10^{-2}$ | 3.50 | 0.30 |
| | K48A | $6.04 \times 10^7$ | $2.12 \times 10^7$ | 0.0116 | $3.77 \times 10^{-3}$ | 0.19 | 0.02 |
| | Q89A F17A/M81A | $1.71 \times 10^7$ | $8.38 \times 10^6$ | 0.1458 | $5.99 \times 10^{-2}$ | 8.80 | 0.45 |
| 9.63.12 | WT | $8.43 \times 10^6$ | $1.47 \times 10^6$ | 0.0096 | 0.0035 | 1.07 | 0.20 |
| | Y21A | $1.99 \times 10^7$ | $6.84 \times 10^6$ | $1.48 \times 10^{-1}$ | $3.13 \times 10^{-2}$ | 9.84 | 4.41 |
| | K48A | $5.30 \times 10^7$ | $3.77 \times 10^7$ | 0.017 | 0.013 | 0.33 | 0.01 |
| | Q89A F17A/M81A | $7.43 \times 10^6$ | $2.09 \times 10^6$ | 0.47 | $2.71 \times 10^{-1}$ | 36.49 | 1.62 |
| 9.54 | WT | $4.10 \times 10^6$ | $8.59 \times 10^5$ | 0.2349 | 0.0778 | 55 | 7 |
| | Y21A | $6.63 \times 10^5$ | $6.39 \times 10^3$ | 0.2101 | 0.0389 | 317 | 56 |
| | K48A | $2.64 \times 10^6$ | $2.24 \times 10^5$ | 0.0587 | 0.0010 | 22 | 3 |
| | Q89A F17A/M81A | $3.37 \times 10^5$ | $1.41 \times 10^5$ | 0.7932 | 0.5101 | 1882 | 460 |
| 9.63 | WT | $1.57 \times 10^6$ | $3.14 \times 10^5$ | 0.1624 | 0.05 | 100.34 | 9.40 |
| | Y21A | $7.52 \times 10^5$ | $2.45 \times 10^5$ | 0.4814 | $2.13 \times 10^{-1}$ | 584.85 | 112.171 |
| | K48A | $5.72 \times 10^5$ | $1.75 \times 10^5$ | 0.02 | $5.24 \times 10^{-3}$ | 28.4 | 4.8 |
| | Q89A F17A/M81A | $2.66 \times 10^5$ | $8.01 \times 10^4$ | 0.51 | $1.22 \times 10^{-1}$ | 1999.8 | 127.5 |

Next, VEGF-A binding variants VEGF_CKP9.54.90, VEGF_CKP9.63.12, and VEGF_CKP9.63.44 were assessed for their in vivo efficacy in a VEGF-A driven model of choroidal neovascularization. Laser-burnt spots were created in rat eyes and the formation of new vessels was monitored after a 14-day period in the presence and absence of peptide that was administered intravitreally at different intervals. Peptide VEGF_CKP9.54.90 demonstrated effective inhibition of laser-induced choroidal neovascularization in rat eyes, as measured by the significant reduction sufficient dynamic range in the assay to detect improvement in affinity. Many new clones containing variations in loops 3 and 4 only were identified that showed improved binding to VEGF-A. Fourteen of the obtained sequences were selected and grafted onto loops 3 and 4 within the lead VEGF_CKP9.54.90 or VEGF_CKP9.63.12 molecules, and the corresponding soluble molecules were then generated in folded form. The amino acid sequences of the fourteen affinity-matured variants are provided in Table 35 below.

TABLE 35

Affinity-matured VEGF-A binding loop 3/loop 4 variants based on VEGF_CKP9.54.90 or VEGF_CKP9.63.12 frameworks

| VARIANT | LOOP 1 | LOOP 2 | LOOP 3 | LOOP 4 | LOOP 5 |
|---|---|---|---|---|---|
| 9.54.90.7 | NIMLPFWG (SEQ ID NO: 33) | GRDFE (SEQ ID NO: 97) | LQQ | I | QYYQS (SEQ ID NO: 45) |
| 9.54.90.10 | NIMLPFWG (SEQ ID NO: 33) | GRDFE (SEQ ID NO: 97) | VER | I | QYYQS (SEQ ID NO: 45) |
| 9.54.90.12 | NIMLPFWG (SEQ ID NO: 33) | GRDFE (SEQ ID NO: 97) | MSD | I | QYYQS (SEQ ID NO: 45) |

TABLE 35-continued

Affinity-matured VEGF-A binding loop 3/loop 4 variants based on VEGF_CKP9.54.90 or VEGF_CKP9.63.12 frameworks

| VARIANT | LOOP 1 | LOOP 2 | LOOP 3 | LOOP 4 | LOOP 5 |
|---|---|---|---|---|---|
| 9.54.90.13 | NIMLPFWG (SEQ ID NO: 33) | GRDFE (SEQ ID NO: 97) | MNQ | I | QYYQS (SEQ ID NO: 45) |
| 9.54.90.25 | NIMLPFWG (SEQ ID NO: 33) | GRDFE (SEQ ID NO: 97) | MQT | I | QYYQS (SEQ ID NO: 45) |
| 9.54.90.31 | NIMLPFWG (SEQ ID NO: 33) | GRDFE (SEQ ID NO: 97) | VYQ | I | QYYQS (SEQ ID NO: 45) |
| catalog no. 100110) in water was added to 50 uL of variant peptide sample (prepared as 1 mg/mL peptide in 20 mM histidine acetate pH 5.5) and the mix was incubated for 16 hours at 40° C. At the end of the incubation, the sample was quenched by addition of 27.5 uL of 40 mM methionine, followed by addition of 160 ul of 20 mM Histidine acetate, 100 mM sucrose at pH 5.5 to dilute the samples. The reactions were analyzed by LC-MS.

It was observed that VEGF_CKP9.54.90 underwent ~30% oxidation at Met5 within loop 1. Replacement of Met 5 with the unnatural amino acid norleucine rendered VEGF_CKP9.54.90 completely resistant to oxidation. The replacement of Met5 with norleucine also had a favorable effect on binding efficiency (~2-fold improvement). Variants VEGF_CKP9.54.90.67 F8Y M5Nle, VEGF_CKP9.54.90.53 M5Nle and VEGF_CKP9.63.12.12 M5Nle were produced. All three Met5Nle of the Met5Nle variants showed modest improvement in cellular potency by ~1.5-2× compared to their parent molecules.

Next, the effect of naphthalene-based amino acid substitutions at Trp9 in loop 1 of VEGF_CKP9.54.90 on VEGF-A binding affinity was assessed. The crystal structures of VEGF_CKP9.54.90 complexed with VEGF indicate that the Trp9 residue of VEGF_CKP9.54.90 (and variants derived therefrom) interacts with the VEGF-A surface, with residual space that might allow larger ring systems to fit in. To test this hypothesis, we generated soluble variants of VEGF_CKP9.54.90 in which the indole ring of Trp9 was replaced with 1- or 2-naphthyl isomers. These molecules showed reduced cellular potency relative to parent VEGF_CKP9.54.90. Further data regarding the potency of VEGF_CKP9.54.90-derived variants comprising the F8Y substitution and/or an unnatural amino acid substitution are provided in Table 38:

TABLE 38

$IC_{50}$ values for VEGF_CKP9.54.90-derived variants comprising the F8Y substitution and/or an unnatural amino acid substitution.

| VARIANT | Cellular $IC_{50}$ (nM) | FOLD IMPROVEMENT RELATIVE TO VARIANT 9.54.90 |
|---|---|---|
| 9.54.90 | 1.35 | 1 |
| 9.54.90.F8Y | 1.58 | 0.85 |
| 9.54.90.F7Y.Δ2G | 3.01 | 0.44 |
| 9.54.90.M5.Nle | 1.95 | 0.69 |
| 9.54.90.Naph1 | 5.42 | 0.24 |
| 9.54.90.Naph2 | 17.1 | 0.08 |
| 9.54.90.13 | 0.96 | 1.41 |
| 9.54.90.13.F8Y | 2.02 | 0.67 |
| 9.54.90.62 | 0.92 | 1.47 |
| 9.54.90.62.F8Y | 1.14 | 1.18 |
| 9.54.90.67 | 1.1 | 1.23 |
| 9.54.90.67.F8Y | 0.66 | 2.05 |

Shortening the lead VEGF_CKP9.54.90. F8Y by trimming the two glycine residues at the N- and C-termini to generate variant VEGF_CKP9.54.90 F7Y Δ2G) resulted in a slight reduction of cellular potency relative to VEGF_CKP9.54.90. See Table 38 above.

Example 2B

Generation of VEGF-A-binding Non-Naturally Occurring EETI-II Variants Comprising C-Terminal Amino Acid Extensions To identify additional peptide variants with enhanced affinity for VEGF-A, we selected the 9.54 (SEQ ID NO: 52), 9.54.1 (SEQ ID NO: 99) molecules and generated new phage libraries based on these frameworks in which two additional amino acids were added to their C-termini.

From the 9.54 library, twenty-two clones whose binding signals for hVEGF-A (8-109) were more than 3 times higher than to BSA (background) were identified (Table 39). These hits contained variations in amino acid composition within loop 2, within loops 2 and 4, or within loops 2, 4, and 5.

TABLE 39

C-terminal Two-residue Extension Variants Based on 9.54

| CLONE ID | AMINO ACID SEQUENCE | SEQ ID NO |
|---|---|---|
| 9.54 | GCNIMLPFWGCKQDSDCLAGCVCQYYQSCG | 52 |
| 9.54-28 | GCNIMLPFWGCKQDFDCLAGCICQYYQSCGFH | 455 |
| 9.54-39 | GCNIMLPFWGCKQDFDCLAGCICQYYQSCGGE | 457 |
| 9.54-10 | GCNIMLPFWGCKQDSDCLVGCICQYYQSCGSI | 458 |
| 9.54-32 | GCNIMLPFWGCKQDFDCLAGCVCQYYQSCGGR | 459 |
| 9.54-13 | GCNIMLPFWGCKQDFDCLAGCVCQYYQSCGRP | 460 |
| 9.54-6 | GCNIMLPFWGCKQDFDCLAGCVCQYYQSCGQY | 461 |
| 9.54-24 | GCNIMLPFWGCKQDSDCLAGCVCQYYQSCGEN | 462 |
| 9.54-34 | GCNIMLPFWGCKQDFDCLAGCVCQYYQSCGDT | 463 |
| 9.54-9 | GCNIMLPFWGCKQDFDCLAGCVCQYYQSCGQH | 464 |
| 9.54-12 | GCNIMLPFWGCKQDSDCLAGCICQYYQSCGQN | 465 |
| 9.54-17 | GCNIMLPFWGCKQDSDCLAGCVCQYYQSCGEE | 466 |
| 9.54-19 | GCNIMLPFWGCKQDSDCLAGCVCQYYQSCGDD | 467 |
| 9.54-43 | GCNIMLPFWGCKQDSDCLAGCVCQYYQSCGDG | 468 |
| 9.54-5 | GCNIMLPFWGCKQDFDCLAGCVCQYYQSCGLE | 469 |
| 9.54-1 | GCNIMLPFWGCKQDSDCLAGCVCQYYQSCGTD | 470 |
| 9.54-4 | GCNIMLPFWGCKQDSDCLAGCVCQYYQSCGSE | 471 |
| 9.54-15 | GCNIMLPFWGCKQDSDCLAGCVCQYYQSCGPE | 472 |
| 9.54-42 | GCNIMLPFWGCKQDSDCLAGCVCQYYQSCGTN | 473 |
| 9.54-27 | GCNIMLPFWGCKQDSDCLAGCVCQYYQSCGPH | 474 |
| 9.54-2 | GCNIMLPFWGCKQDSDCLAGCVCQYYQSCGMD | 475 |
| 9.54-21 | GCNIMLPFWGCKQDSDCLAGCVCQYYQSCGSD | 476 |

From the 9.54.1 library, clones whose binding signals for hVEGF-A (8-109) were more than 3 times higher than to BSA (background) were identified (Table 40).

TABLE 40

C-terminal Two-residue Extension Variants Based on 9.54.1

| CLONE ID | AMINO ACID SEQUENCE | SEQ ID NO |
|---|---|---|
| 9.54.1 | GCNIMLPFWGCGQSFECLAGCVCQYYQSCG | 99 |
| 9.54.1-2 | GCNIMLPFWGCGQSFECLAGCICQYYQSCGIA | 477 |

TABLE 40-continued

C-terminal Two-residue Extension Variants Based on 9.54.1

| CLONE ID | AMINO ACID SEQUENCE | SEQ ID NO |
|---|---|---|
| 9.54.1-63 | GCNIMLPFWGCGQSFECLAGCICQYYQSCGGS | 478 |
| 9.54.1-36 | GCNIMLPFWGCGQSFECLAGCICQYYQSCGTR | 479 |
| 9.54.1-42 | GCNIMLPFWGCGQSFECLAGCICQYYQSCGLS | 533 |
| 9.54.1-90 | GCNIMLPFWGCGQSFECLAGCICQYYQSCGVH | 480 |

Figure 15:
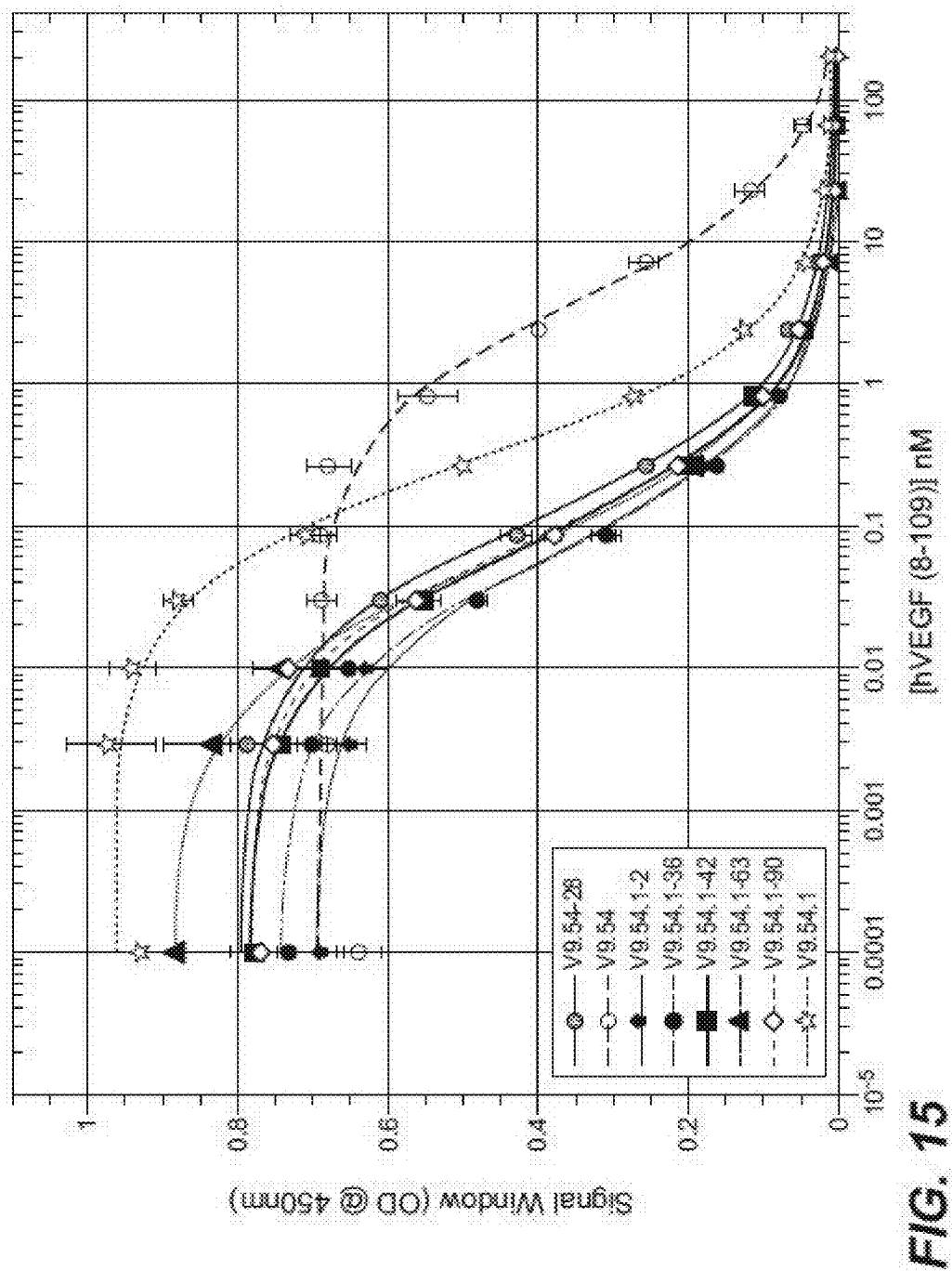
FIG. 15 shows the results of phage competition ELISA experiments that were performed to assess the binding affinity of clones 9.54-28, 9.54, 9.54.1-2, 9.54.1-36, 9.54.1-42, 9.54.1-63, 9.54.1-90, and 9.54.1 for hVEGF(8-109).

Clone 9.54-28 (in Table 39) showed approximately 10-fold improved binding affinity for hVEGF-A (8-109) compared to 9.54, as determined by phage competition ELISA (described above). (See FIG. 15). Clones 9.54.1-2, 9.54.1-36, 9.54.1-42, 9.54.1-63, and 9.54.1-90 (in Table 40) also showed approximately 10-fold improved binding affinity for hVEGF-A (8-109) compared to 9.54.1, as determined by phage competition ELISA. (See FIG. 15).

Peptides 9.63 (SEQ ID NO: 55), and 9.63.44 (SEQ ID NO: 125) were selected for further modification as described above. New phage libraries based on these frameworks were generated in which two additional amino acids were added to their C-termini.

From the 9.63 library, 28 clones whose binding signals for hVEGF-A (8-109) were more than 3 times higher than to BSA (background) were identified (Table 41). These hits contained variations in amino acid composition within loops 2 and 4.

TABLE 41

C-terminal Two-residue Extension Variants Based on 9.63

| CLONE ID | AMINO ACID SEQUENCE | SEQ ID NO |
|---|---|---|
| 9.63 | GCDVMQPYWGCKQDSDCLAGCVCHWYNSCG | 55 |
| 9.63-1 | GCDVMQPYWGCKQDFDCLAGCVCHWYNSCGPS | 481 |
| 9.63-4 | GCDVMQPYWGCEMDFDCLAGCICHWYNSCGFS | 482 |
| 9.63-7 | GCDVMQPYWGCEMDFDCLAGCVCHWYNSCGGK | 483 |
| 9.63-10 | GCDVMQPYWGCKQDFDCLAGCICHWYNSCGYL | 484 |
| 9.63-16 | GCDVMQPYWGCEMDFDCLAGCVCHWYNSCGDL | 485 |
| 9.63-17 | GCDVMQPYWGCEMDFDCLAGCVCHWYNSCGEK | 486 |
| 9.63-19 | GCDVMQPYWGCKQDSDCLAGCICHWYNSCGTD | 487 |
| 9.63-20 | GCDVMQPYWGCEMDFDCLAGCICHWYNSCGQV | 488 |
| 9.63-21 | GCDVMQPYWGCEMDFDCLAGCVCHWYNSCGRL | 489 |
| 9.63-22 | GCDVMQPYWGCEMDFDCLAGCICHWYNSCGYA | 490 |
| 9.63-23 | GCDVMQPYWGCEMDFDCLAGCICHWYNSCGAS | 491 |
| 9.63-25 | GCDVMQPYWGCEMDFDCLAGCICHWYNSCGSR | 492 |
| 9.63-30 | GCDVMQPYWGCEMDFDCLAGCICHWYNSCGPT | 493 |
| 9.63-36 | GCDVMQPYWGCEMDFDCLAGCVCHWYNSCGSL | 456 |
| 9.63-40 | GCDVMQPYWGCEMDFDCLAGCVCHWYNSCGWD | 494 |
| 9.63-45 | GCDVMQPYWGCEMDFDCLAGCVCHWYNSCGSM | 495 |
| 9.63-61 | GCDVMQPYWGCEMDFDCLAGCICHWYNSCGTR | 496 |
| 9.63-62 | GCDVMQPYWGCKQDSDCLAGCVCHWYNSCGEN | 497 |
| 9.63-65 | GCDVMQPYWGCEMDFDCLAGCVCHWYNSCGNN | 498 |
| 9.63-66 | GCDVMQPYWGCEMDFDCLAGCICHWYNSCGPE | 499 |
| 9.63-67 | GCDVMQPYWGCEMDFDCLAGCVCHWYNSCGGI | 500 |
| 9.63-68 | GCDVMQPYWGCEMDFDCLAGCVCHWYNSCGVE | 501 |
| 9.63-70 | GCDVMQPYWGCEMDFDCLAGCVCHWYNSCGPL | 503 |
| 9.63-72 | GCDVMQPYWGCEMDFDCLAGCICHWYNSCGTS | 527 |
| 9.63-74 | GCDVMQPYWGCEMDFDCLAGCICHWYNSCGRP | 504 |
| 9.63-77 | GCDVMQPYWGCEMDFDCLAGCVCHWYNSCGND | 505 |
| 9.63-79 | GCDVMQPYWGCEMDFDCLAGCICHWYNSCGLQ | 506 |
| 9.63-93 | GCDVMQPYWGCEMDFDCLAGCICHWYNSCGDE | 507 |

From the 9.63.44 library, 17 clones whose binding signals for hVEGF-A (8-109) were more than 3 times higher than to BSA (background) were identified (Table 42). These hits contained a variation in amino acid composition within loop 4. Clone 9.63.44-55 contained a variation in amino acid composition within loop 2, and clone 9.63.44-10 contained a variation in amino acid composition within loop 3. Interestingly clone 9.63.44-12 in Table 42 and clone 9.63-70 in Table 41 have the same amino acid sequence.

TABLE 42

C-terminal Two-residue Extension Variants Based on 9.63.44

| CLONE ID | AMINO ACID SEQUENCE | SEQ ID NO |
|---|---|---|
| 9.63.44 | GCDVMQPYWGCEMDFDCLAGCVCHWYNSCG | 125 |
| 9.63.44-2-A | GCDVMQPYWGCEMDFDCLAGCICHWYNSCGRT | 508 |
| 9.63.44-55 | GCDVMQPYWGCEIDFDCLAGCVCHWYNSCGQV | 509 |
| 9.63.44-10-A | GCDVMQPYWGCEMDFDCLAGCVCHWYNSCGGI | 510 |
| 9.63.44-54 | GCDVMQPYWGCEMDFDCLAGCVCHWYNSCGYM | 511 |
| 9.63.44-19 | GCDVMQPYWGCEMDFDCLAGCVCHWYNSCGGQ | 512 |
| 9.63.44-44 | GCDVMQPYWGCEMDFDCLAGCVCHWYNSCGTP | 513 |
| 9.63.44-14 | GCDVMQPYWGCEMDFDCLAGCVCHWYNSCGVN | 514 |
| 9.63.44-73 | GCDVMQPYWGCEMDFDCLAGCVCHWYNSCGFN | 515 |
| 9.63.44-16 | GCDVMQPYWGCEMDFDCLAGCVCHWYNSCGEP | 516 |
| 9.63.44-80 | GCDVMQPYWGCEMDFDCLAGCVCHWYNSCGNS | 517 |

TABLE 42-continued

C-terminal Two-residue Extension Variants Based on 9.63.44

| CLONE ID | AMINO ACID SEQUENCE | SEQ ID NO |
|---|---|---|
| 9.63.44-41 | GCDVMQPYWGCEMDFDCLAGCVCHWYNSCGST | 518 |
| 9.63.44-82 | GCDVMQPYWGCEMDFDCLAGCVCHWYNSCGRY | 519 |
| 9.63.44-1 | GCDVMQPYWGCEMDFDCLAGCICHWYNSCGFS | 520 |
| 9.63.44-2 | GCDVMQPYWGCEMDFDCLAGCICHWYNSCGQV | 521 |
| 9.63.44-3 | GCDVMQPYWGCEMDFDCLAGCICHWYNSCGYA | 522 |
| 9.63.44-4 | GCDVMQPYWGCEMDFDCLAGCICHWYNSCGSR | 523 |
| 9.63.44-5 | GCDVMQPYWGCEMDFDCLAGCICHWYNSCGPT | 524 |
| 9.63.44-6 | GCDVMQPYWGCEMDFDCLAGCVCHWYNSCGSM | 525 |
| 9.63.44-7 | GCDVMQPYWGCEMDFDCLAGCVCHWYNSCGGI | 526 |
| 9.63.44-8 | GCDVMQPYWGCEMDFDCLAGCICHWYNSCGTS | 527 |
| 9.63.44-9 | GCDVMQPYWGCEMDFDCLAGCICHWYNSCGLQ | 528 |
| 9.63.44-10 | GCDVMQPYWGCEMDFDCLVGCVCHWYNSCGDE | 529 |
| 9.63.44-11 | GCDVMQPYWGCEMDFDCLAGCVCHWYNSCGDL | 530 |
| 9.63.44-12 | GCDVMQPYWGCEMDFDCLAGCVCHWYNSCGPL | 503 |
| 9.63.44-13 | GCDVMQPYWGCEMDFDCLAGCVCHWYNSCGQF | 531 |
| 9.63.44-14 | GCDVMQPYWGCEMDFDCLAGCICHWYNSCGWK | 532 |

Figure 16A:
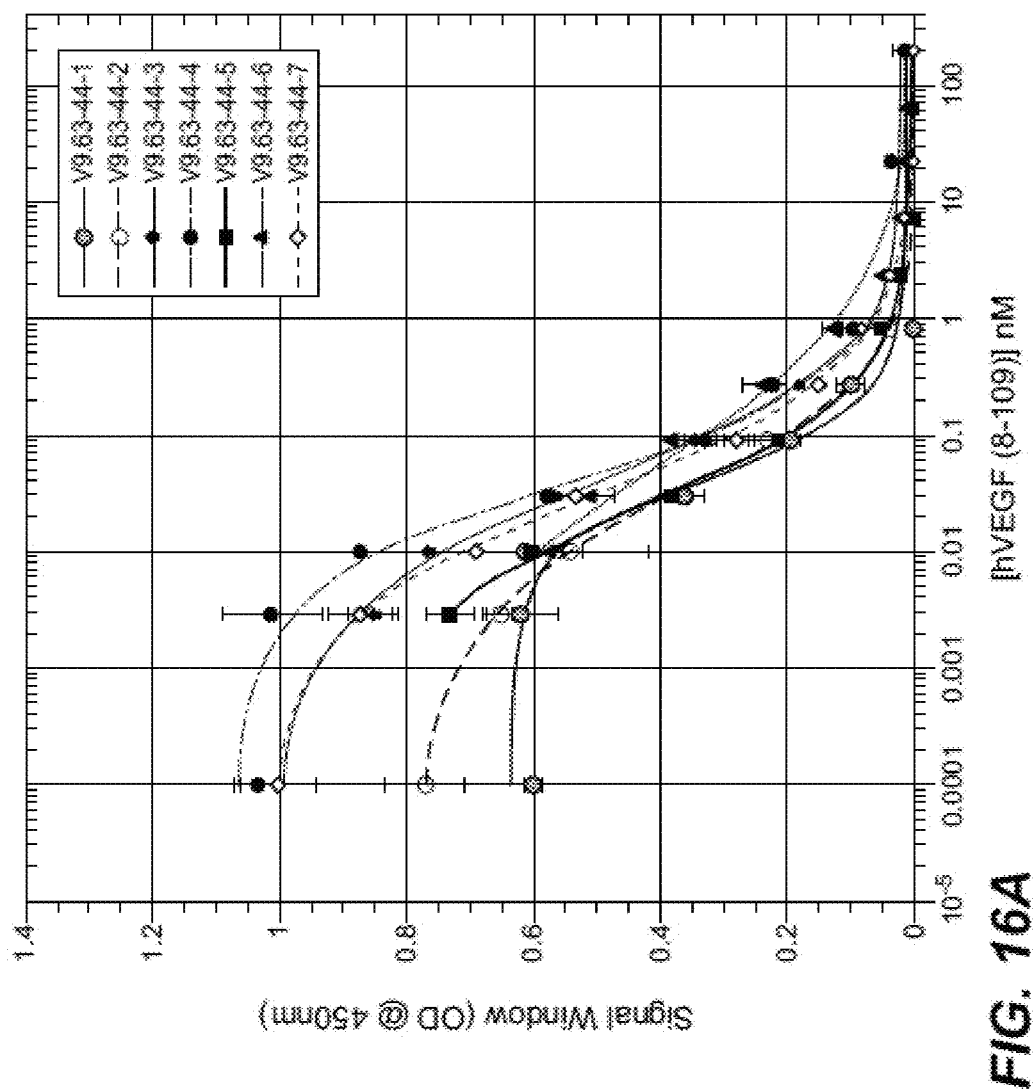
FIG. 16A shows the results of phage competition ELISA experiments that were performed to assess the binding affinity of clones 9.63.44-1 to 9.63.44-7.
Figure 16B:
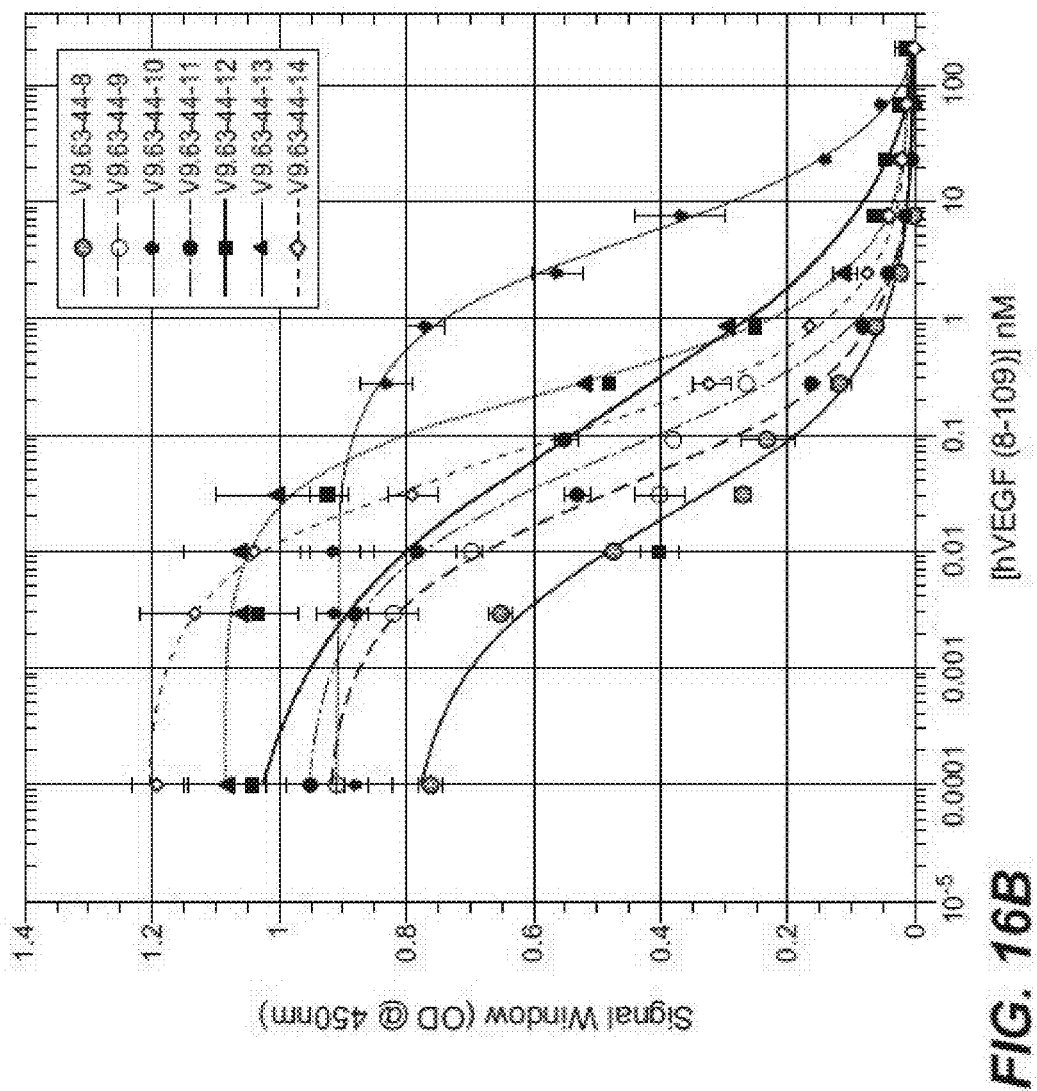
FIG. 16B shows the results of phage competition ELISA experiments that were performed to assess the binding affinity of clones 9.63.44-8 to 9.63.44-14.

Clones 9.63.44-1 through 9.63.44-14 (in Table 42) showed improved binding affinity for hVEGF-A (8-109) compared to 9.63.44, as determined by phage competition ELISA. (See FIGS. 16A and 16B).

Taken together, the results above indicate that extending lead peptides 9.54 (SEQ ID NO: 52), 9.54.1 (SEQ ID NO: 99), 9.63 (SEQ ID NO: 55), and 9.63.44 by adding two amino acids to their C-termini produced variants having ~10-fold greater binding affinity for hVEGF-A (8-109).

Next, peptides 9.54.90 (SEQ ID NO: 102) and 63.12.12.M5L (SEQ ID NO: 386) were selected for further modification as described above. Briefly new phage libraries were generated based on 9.54.90 in which two additional amino acids, three additional amino acids, or four additional amino acids were added at the C-terminus. A second set of libraries was generated based on 63.12.12.M5L in which two additional amino acids were added at the C-terminus.

From the 9.54.90 libraries comprising 2-amino acid C-terminal extensions, 6 clones whose binding signals for hVEGF-A (8-109) were more than 3 times higher than to BSA (background) were identified (Table 43).

TABLE 43

C-terminal Two-residue Extension Variants Based on 9.54.90

| CLONE ID | AMINO ACID SEQUENCE | SEQ ID NO |
|---|---|---|
| 9.54.90 | GCNIMLPFWGCGRDFECLAGCVCQYYQSCG | 102 |
| 9.54.90-2x28 | GCNIMLPFWGCGRDFECLAGCVCQYYQSCGFH | 379 |
| 9.54.90-2x2 | GCNIMLPFWGCGRDFECLAGCVCQYYQSCGIA | 380 |
| 9.54.90-2x63 | GCNIMLPFWGCGRDFECLAGCVCQYYQSCGGS | 381 |
| 9.54.90-2x36 | GCNIMLPFWGCGRDFECLAGCVCQYYQSCGTR | 382 |
| 9.54.90-2x90 | GCNIMLPFWGCGRDFECLAGCVCQYYQSCGVH | 383 |
| 9.54.90-2x42 | GCNIMLPFWGCGRDFECLAGCVCQYYQSCGLS | 384 |

From the 9.54.90 libraries comprising 3-amino acid C-terminal extensions, 10 clones whose binding signals for hVEGF-A (8-109) were more than 3 times higher than to BSA (background) were identified (Table 44).

TABLE 44

C-terminal Three-residue Extension Variants Based on 9.54.90

| CLONE ID | AMINO ACID SEQUENCE | SEQ ID NO |
|---|---|---|
| 9.54.90 | GCNIMLPFWGCGRDFECLAGCVCQYYQSCG | 102 |
| 9.54.90-3X83 | GCNIMLPFWGCGRDFECLAGCVCQYYQSCGPLI | 369 |
| 9.54.90-3X50 | GCNIMLPFWGCGRDFECLAGCVCQYYQSCGNYQ | 370 |
| 9.54.90-3x49 | GCNIMLPFWGCGRDFECLAGCVCQYYQSCGPLQ | 371 |
| 9.54.90-3x10 | GCNIMLPFWGCGRDFECLAGCVCQYYQSCGTFQ | 372 |
| 9.54.90-3x91 | GCNIMLPFWGCGRDFECLAGCVCQYYQSCGDLV | 373 |
| 9.54.90-3x42 | GCNIMLPFWGCGRDFECLAGCVCQYYQSCGEHK | 374 |
| 9.54.90-3x88 | GCNIMLPFWGCGRDFECLAGCVCQYYQSCGYLS | 375 |
| 9.54.90-3x9 | GCNIMLPFWGCGRDFECLAGCVCQYYQSCGWDY | 376 |
| 9.54.90-3x13 | GCNIMLPFWGCGRDFECLAGCVCQYYQSCGWPH | 377 |
| 9.54.90-3x33 | GCNIMLPFWGCGRDFECLAGCVCQYYQSCGPHQ | 378 |

All peptides from the 9.54.90 libraries comprising 4-amino acid C-terminal extensions, contained 3 amino acid C-terminal extensions.

From the 63.12.12.M5L libraries comprising 2-amino acid C-terminal extensions, 9 clones whose binding signals for hVEGF-A (8-109) were more than 3 times higher than to BSA (background) were identified (Table 45).

TABLE 45

C-terminal Two-residue Extension Variants Based on 63.12.12.M5L

| CLONE ID | AMINO ACID SEQUENCE | SEQ ID NO |
|---|---|---|
| 63.12.12.M5L | GCDVLQPYWGCGPDIDCLSNCICHWYNSCG | 386 |
| 63.12.12.M5L.2x2 | GCDVLQPYWGCGPDIDCLSNCICHWYNSCGRT | 387 |
| 63.12.12.M5L.2x77 | GCDVLQPYWGCGPDIDCLSNCICHWYNSCGWK | 388 |
| 63.12.12.M5L.2x48 | GCDVLQPYWGCGPDIDCLSNCICHWYNSCGPL | 389 |
| 63.12.12.M5L.2x25 | GCDVLQPYWGCGPDIDCLSNCICHWYNSCGDE | 390 |
| 63.12.12.M5L.2x69 | GCDVLQPYWGCGPDIDCLSNCICHWYNSCGQF | 391 |
| 63.12.12.M5L.2x12 | GCDVLQPYWGCGPDIDCLSNCICHWYNSCGEQ | 392 |
| 63.12.12.M5L.2x30 | GCDVLQPYWGCGPDIDCLSNCICHWYNSCGPT | 393 |
| 63.12.12.M5L.2x21 | GCDVLQPYWGCGPDIDCLSNCICHWYNSCGRL | 394 |
| 63.12.12.M5L.2x29 | GCDVLQPYWGCGPDIDCLSNCICHWYNSCGSL | 395 |

Example 2C

Characterization of VEGF-A-binding Non-Naturally Occurring EETI-II Variants Comprising C-Terminal Amino Acid Extensions The variants provided in Tables 43-45 above are assayed via phage competition ELISA as described above to identify variants with greater binding affinity for hVEGF-A (8-109).

Clones (e.g., such as those provided in Tables 39-45) demonstrating greater affinity for hVEGF (8-109), including, e.g., 9.54.1-2, 9.54.1-36, 9.54.1-42, 9.54.1-63, and 9.54.1-90, and 9.63.44-1-9.63.44-14, are then selected for further in vitro assessments, such as inhibitory activity in phage competition ELISAs and VEGF-KDR interaction ELISAs, as described above.

Clones are then analyzed via surface plasmon resonance to determine their affinities for various VEGF isoforms, including hVEGF-A (8-109), hVEGF-A 165, mouse VEGF-A 164, rat VEGF-A, and rabbit VEGF-A.

Further analyses are performed to assess the clones specificity for VEGF-A. For example, competition ELISAs are performed as described above with VEGF-A, VEGF-B, VEGF-C, VEGF-D, PlGf-2, NGF, EGF, PDGF-β, or IGF-1.

The clones are also assayed for their abilities to inhibit trypsin protease activity as measured in a peptide substrate cleavage assay (Stanger et al. (2014) *FEBS Lett.* 588 (23), 4487-96).

Binding kinetics and affinities of the clones for various hVEGF mutants, including, e.g., Y21A, K48A, Q89A, and F17A/M81A, are determined as described above.

Next, the clones are assessed for their in vivo efficacy in a VEGF-A driven model of choroidal neovascularization, as described above.

The oxidative stability of the variants is assayed as described above.

Example 3

Generation of Non-naturally Occurring EETI-II Variants that Bind LRP6

The naïve EETI-II libraries described in Example 2A were cycled through rounds of selection against LRP6 E1E2 protein. Twenty-two unique clones were identified which bound LRP6 E1E2 (Table 46). These initial hits contained variations in amino acid content within loops 1 and 5. In several variants, loop 1 exhibited a longer length compared to that of the native EETI-II framework. Notably, the newly evolved sequences that bound to LRP6 contained a consensus motif in loop 1 (NXI) that is similar to a motif (NAI) present within the native Dkk1 molecules which are endogenous LRP6 ligands. The newly evolved variants recapitulated a motif which occurs in natural ligands.

TABLE 46

EETI-II-based binders against LRP6 E1E2

| VARIANT | LOOP 1 | LOOP 2 | ELISA | S/N* |
|---|---|---|---|---|
| LRP6_CKP1 | RTNRVKGG (SEQ ID NO: 147) | GPNGF (SEQ ID NO: 19) | 3.23 | 45.49 |
| LRP6_CKP2 | VNRVRG (SEQ ID NO: 148) | SGGRD (SEQ ID NO: 169) | 3.41 | 41.62 |
| LRP6_CKP3 | MNHVKARR (SEQ ID NO: 149) | GPNGF (SEQ ID NO: 19) | 2.93 | 40.18 |
| LRP6_CKP4 | RSVNKI (SEQ ID NO: 150) | GSSRN (SEQ ID NO: 170) | 2.82 | 25.39 |
| LRP6_CKP5 | VNKIKG (SEQ ID NO: 151) | GVEGR (SEQ ID NO: 171) | 3.04 | 35.71 |
| LRP6_CKP6 | RNSIKR (SEQ ID NO: 152) | SVGHG (SEQ ID NO: 172) | 3.10 | 37.36 |

TABLE 46-continued EETI-II-based binders against LRP6 E1E2

| VARIANT | LOOP 1 | LOOP 2 | ELISA | S/N* |
|---|---|---|---|---|
| LRP6_CKP7 | VSNRVNKG (SEQ ID NO: 153) | GPNGF (SEQ ID NO: 19) | 3.30 | 28.96 |
| LRP6_CKP8 | RGNIIK (SEQ ID NO: 154) | NESRG (SEQ ID NO: 173) | 3.23 | 37.56 |
| LRP_CKP9 | RSGNTIRKRE (SEQ ID NO: 155) | GGPGG (SEQ ID NO: 174) | 2.97 | 37.62 |
| LRP6_CKP10 | ASSNSIRQGW (SEQ ID NO: 156) | GPKSN (SEQ ID NO: 175) | 3.29 | 37.38 |
| LRP6_CKP11 | RSNRIR (SEQ ID NO: 157) | YGHGD (SEQ ID NO: 176) | 2.65 | 36.76 |
| LRP_CKP12 | RSNKLREARG (SEQ ID NO: 158) | GSRQD (SEQ ID NO: 177) | 0.60 | 6.78 |
| LRP6_CKP13 | VNSVKR (SEQ ID NO: 159) | SRGVN (SEQ ID NO: 178) | 3.28 | 37.75 |
| LRP6_CKP14 | GSNKIRPR (SEQ ID NO: 160) | GPNDF (SEQ ID NO: 179) | 3.18 | 43.53 |
| LRP6_CKP15 | NRIRNS (SEQ ID NO: 161) | GRGDY (SEQ ID NO: 180) | 2.03 | 26.31 |
| LRP6_CKP16 | SRNSIK (SEQ ID NO: 162) | ASGSS (SEQ ID NO: 181) | 3.36 | 31.11 |
| LRP6_CKP17 | SNYVKR (SEQ ID NO: 163) | SPGGR (SEQ ID NO: 182) | 3.09 | 35.88 |
| LRP6_CKP18 | RANRVSGR (SEQ ID NO: 164) | GPNGF (SEQ ID NO: 19) | 1.67 | 18.32 |
| LRP6_CKP19 | SNRVKVRA (SEQ ID NO: 165) | GPNGF (SEQ ID NO: 19) | 3.27 | 41.96 |
| LRP6_CKP20 | ENRTKG (SEQ ID NO: 166) | GFRGT (SEQ ID NO: 183) | 3.10 | 38.69 |
| LRP6_CKP21 | GNKIRA (SEQ ID NO: 167) | RDRVG (SEQ ID NO: 184) | 2.80 | 33.69 |
| LRP6_CKP22 | ANRVKRTS (SEQ ID NO: 168) | GPNGF (SEQ ID NO: 19) | 3.43 | 42.86 |

*S/N = signal to noise ratio as compared to BSA control

The extracellular domain of the LRP6 consists of four propeller domains (E1-E4) that interact with Frizzled receptors and Wnt proteins to propagate Wnt signaling. Utilizing a modular approach, LRP6 distinguishes between Wnt1 or Wnt3a signaling through selective binding of either its E1-E2 or E3-E4 domains to specific Wnt isoforms, respectively (Hannoush et al. (2010) J. Biol. Chem. 285, 9172-9179). To pharmacologically delineate Wnt1 and Wnt3a signaling arms, we sought to identify ligands that bind selectively to LRP6 E1-E2.

Of the identified sequences, R1, LRP6 CKP6 and LRP6 CKP19 were generated in soluble folded form in order to test their pharmacological activity against either Wnt1 or Wnt3a signaling. As shown in Tables 47 and 48 below, no significant selectivity was observed by R77 towards Wnt1 or Wnt3a in a cell-based signaling reporter assay. On the other hand, R1 and R19 showed selective inhibition towards Wnt1 signaling relative to Wnt3a (160-fold and 11-fold for Wnt1 over Wnt3a, respectively) as measured in a luciferase reporter assay, supporting the notion that these variants do not target the LRP6 E3-E4 domains (IC$_{50}$>44 µM). Altogether, the data highlight the specificity of the newly evolved variants and their effects in mimicking a motif which occurs in natural ligands. More importantly, the identified variants provide a pharmacological means to interrogate Wnt1 and Wnt3 signaling.

TABLE 47

Inhibitory activity of LRP6-binding CKP variants against Wnt1 signaling

| Lrp6-CKP (n = 4) | Best Fit IC$_{50}$ (nM) for Wnt1 (5 ng/well) | 95% confidence interval (nM) |
|---|---|---|
| R1 F1 | 241.7 | 185.8 to 314.5 |
| R1 F2 | 193.8 | 140.1 to 268.2 |
| LRP6_CKP6 F1 | 22,866 | 13,593 to 38,463 |
| LRP6_CKP6 F2 | 23,760 | 14,458 to 39,046 |
| LRP6_CKP6 F3 | 4,625 | 3,037 to 7,044 |
| LRP6_CKP19 F1 | 23,132 | 15,397 to 34,754 |
| LRP6_CKP19 F2 | 49,330 | 31,391 to 77,520 |

TABLE 48

Inhibitory activity of LRP6-binding
CKP variants against Wnt3a signaling

| Lrp6-CKP (n = 4) | Best Fit IC$_{50}$ (nM) for Wnt3a (25 ng/well) | 95% confidence interval (nM) |
|---|---|---|
| R1 F1 | 38,594 | 16,093 to 92,554 |
| R1 F2 | 16,596 | 9,037 to 30,478 |
| LRP6_CKP6 F1 | 350,240 | 11840 to 1.036 × 10$^7$ |
| LRP6_CKP6 F2 | 275,584 | 24,695 to 3.075 × 10$^6$ |
| LRP6_CKP6 F3 | Not converge | Not converge |
| LRP6_CKP19 F1 | 59,287 | 32,600 to 107,823 |
| LRP6_CKP19 F2 | 69,827 | 26,179 to 186,252 |

F1, F2, and F3 in Tables 47 and 48 refer to peak fractions 1, 2, and 3, respectively that were obtained during the purification of R1, LRP6_CKP6, and LRP6_CKP19.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

The invention claimed is:

1. A peptide that binds to vascular endothelial growth factor A (VEGF-A), and comprises the scaffold structure:

$$Z_1C_1L1C_2L2C_3L3C_4L4C_5L5C_6Z_2$$

wherein:

$Z_1$ corresponds to the N-terminus of the peptide and is selected from the group consisting of: G, no amino acid, and X, wherein X is acetylglycine or $PEG_6$-propargylglycine;

$Z_2$ corresponds to the C-terminus of the peptide and is selected from the group consisting of G, no amino acid, L-serine, D-serine, X, wherein X is selected from the group consisting of: L-beta-homoserine, L-beta-alanine, N-alpha-methyl-glycine, glycine comprising amidated carboxyl group, glycine ester of glycerol, glycine ester of glycol, glycine ester of oxetane-3-yl, glycine amide, and glycine morpholine amide, GFH, GIA, GGS, GTR, GVH, GLS and amino acids 30-33 of any one of SEQ ID NOs: 369-378;

$C_1$-$C_6$ are cysteine residues; and

L1 is loop 1 , L2 is loop 2 , L3 is loop 3 , L4 is loop 4 , and L5 is loop 5;

wherein

L1 is selected from the group consisting of SEQ ID NOs: 33, 141, 143, 212, 213, 277, 396-404, 414, 416, 433, 434, and amino acids 3 to 8 of SEQ ID NO: 548;

L2 is selected from the group consisting of SEQ ID NO: 97, 418, and amino acids 12-16 of SEQ ID NOs: 538, 539, 540, and 541;

L3 is selected from the group consisting of LAG, LQQ, VER, MSD, MNQ, MQT, VYQ, FIN, VSQ, VTE, FYE, MEQ, LEQ, VYR, VSD, VSE, VSK, VSN, VSX, wherein X is ornithine, LAK, MED, MEE, MEK, MEN, and MEX wherein X is ornithine, LAX wherein X is ornithine, LSG, LTG, LEG, and XAG wherein X is selected from the group consisting of: t-butyl-L-alanine, cyclobutyl-L-alanine, cyclopentyl-L-alanine, and 5,5,5-trifluoro-L-leucine, and XEQ wherein X is selected from the group consisting of: norleucine, t-butyl-L-alanine, and cyclobutyl-L-alanine;

L4 is selected from the group consisting of: V, L, I, and X wherein X is selected from the group consisting of: norleucine, butyl-L-glycine, t-butyl-L-alanine, L-cyclopentylglycine, cyclopentyl-L-alanine, cyclobutyl-L-glycine, cyclobutyl-L-alanine, and 5,5,5-trifluoro-L-leucine; and L5 is selected from the group consisting of SEQ ID NOs: 45, 220, 427, and 429; and wherein $C_1$ forms a disulfide bond with $C_4$, $C_2$ forms a disulfide bond with $C_3$, and $C_5$ forms a disulfide bond with $C_6$.

2. A peptide comprising the amino acid sequence selected from the group consisting of: GCNIMLPFWGCGRDFECMEQCICQYYQSCG (SEQ ID NO: 113), GCNIMLPFWGCGRDFECVYRCICQYYQSCG (SEQ ID NO: 114), GCDVMQPYWGCGPDIDCFVRCLCHWYNSCG (SEQ ID NO: 139), GCDVMQPYWGCGPDIDCLSNCICHWYNSCG (SEQ ID NO: 140), GCNIMLPYWGCGRDFECMEQCICQYYQSCG (SEQ ID NO: 142), GCNIXLPFWGCGRDFECMSDCICQYYQSCG (SEQ ID NO: 144) , wherein X is norleucine (Nle), GCNIXLPFWGCGRDFECVSQCICQYYQSCG (SEQ ID NO: 145), wherein X is norleucine (Nle), GCNIXLPYWGCGRDFECMEQCICQYYQSCG (SEQ ID NO: 146), wherein X is norleucine (Nle), GCDVXQPYWGCGPDIDCLSNCICHWYNSCG (SEQ ID NO: 224), wherein X is norleucine, and GCNILLPYWGCGRDFECMEQCICQYYQSCG (SEQ ID NO: 435).

3. The peptide of claim 2, wherein the peptide binds VEGF-A.

4. The peptide of claim 1, wherein:

(a) the C-terminal carboxyl group of the peptide is capped;

(b) the N-terminal amine of the peptide is capped; or
(c) the C-terminal carboxyl group and the N-terminal amine of the peptide is capped.

5. The peptide of claim 2 conjugated to a therapeutic agent.

6. The peptide of claim 2 conjugated to a label.

7. A composition comprising the peptide of claim 2 and a pharmaceutically acceptable carrier.

8. The peptide of claim 2, wherein the peptide is formulated for long acting delivery.

9. A formulation comprising the peptide of any of claim 2 and PLGA.

10. The peptide of claim 1, wherein:
Z1 and Z2 are G;
L1 is SEQ ID NO: 33;
L2 is SEQ ID NO: 97;
L3 is LAG, LQQ, VER, MSD, MNQ, MQT, VYQ, FIN, VSQ, VTE, FYE, MEQ, or VYR;
L4 is I; and
L5 is SEQ ID NO: 45.

11. The peptide of claim 1, wherein:
Z1 and Z2 are G;
L1 is selected from the group consisting of: SEQ ID NOs: 33, 277, and 396-403;
L2 is SEQ ID NO: 97;
L3 is LAG;
L4 is V; and
L5 is SEQ ID NO: 45.

12. The peptide of claim 1, wherein:
Z1 and Z2 are G;
L1 is SEQ ID NO: 404,
L2 is SEQ ID NO: 97;
L3 is LAG;
L4 is V; and
L5 is SEQ ID NO: 45.

13. The peptide of claim 1, wherein:
Z1 is G, no amino acid, or X, wherein X is selected from the group consisting of acetylglycine and PEG$_6$-prop-argylglycine;
Z2 is G or no amino acid
L1 is SEQ ID NO: 33, 141, 212, or 414;
L2 is SEQ ID NO: 97;
L3 is LAG;
L4 is V; and
L5 is SEQ ID NO: 45.

14. The peptide of claim 1, wherein:
Z1 and Z2 are G;
L1 is SEQ ID NO: 213 or 416;
L2 is SEQ ID NO: 97;
L3 is LAG;
L4 is V; and
L5 is SEQ ID NO: 45.

15. The peptide of claim 1, wherein:
Z1 and Z2 are G;
L1 is SEQ ID NO: 141,
L2 is SEQ ID NO: 418;
L3 is LAG;
L4 is V; and
L5 is SEQ ID NO: 45.

16. The peptide of claim 1, wherein:
Z1 and Z2 are G;
L1 is SEQ ID NO: 141,
L2 is SEQ ID NO: 97;
L3 is LAK, LAX wherein X is ornithine, or XAG wherein X is selected from the group consisting of: t-butyl-L-alanine, cyclobutyl-L-alanine, cyclopentyl-L-alanine, and 5,5,5-trifluoro-L-leucine;
L4 is V; and
L5 is SEQ ID NO: 45.

17. The peptide of claim 1, wherein:
Z1 and Z2 are G;
L1 is SEQ ID NO: 33;
L2 is SEQ ID NO: 97;
L3 is LSG, LTG, or LEG;
L4 is V; and
L5 is SEQ ID NO: 45.

18. The peptide of claim 1, wherein:
Z1 and Z2 are G;
L1 is SEQ ID NO: 141;
L2 is SEQ ID NO: 97;
L3 is LAG;
L4 is L, I, or X, wherein X is an unnatural amino acid selected from the group consisting of: butyl-L-glycine, t-butyl-L-alanine, L-cyclopentylglycine, cyclopentyl-L-alanine, L-cyclobutyl-L-glycine, cyclobutyl-L-alanine, and 5,5,5-trifluoro-L-leucine; and
L5 is SEQ ID NO: 45.

19. The peptide of claim 1, wherein:
Z1 and Z2 are G;
L1 is SEQ ID NO: 141;
L2 is SEQ ID NO: 97;
L3 is LAG;
L4 is V and
L5 is SEQ ID NO: 220, 427, or 429.

20. The peptide of claim 1, wherein
Z1 is G;
Z2 is X, wherein X is selected from the group consisting of: L-serine, D-serine, L-beta-homoserine, L-beta-alanine, N-alpha-methyl-glycine, glycine amide, glycine ester of glycerol, glycine ester of glycol, glycine ester of oxetane-3-yl alcohol, or glycine morpholine amide;
L1 is SEQ ID NO: 141,
L2 is SEQ ID NO: 97;
L3 is LAG;
L4 is V; and
L5 is SEQ ID NO: 45.

21. The peptide of claim 1, wherein:
Z1 is G;
Z2 is amino acids 30-33 of any one of SEQ ID NOs: 369-378;
L1 is SEQ ID NO: 33;
L2 is SEQ ID NO: 97;
L3 is LAG;
L4 is V; and
L5 is SEQ ID NO: 45.

22. The peptide of claim 1, wherein:
Z1 is G;
Z2 is GFH, GIA, GGS, GTR, GVH, GLS;
L1 is SEQ ID NO: 33;
L2 is SEQ ID NO: 97;
L3 is LAG;
L4 is V; and
L5 is SEQ ID NO: 45.

23. The peptide of claim 1, wherein:
Z1 and Z2 are G;
L1 is SEQ ID NO: 33, 141, 143, 397, or 433;
L2 is SEQ ID NO: 97;
L3 is MEQ;
L4 is I; and
L5 is SEQ ID NO: 45.

24. The peptide of claim 1, wherein:
Z1 and Z2 are G;
L1 is SEQ ID NO: 143 or 433;
L2 is SEQ ID NO: 97;

L3 is LEQ or XEQ wherein X is selected from the group consisting of: norleucine and cyclobutyl-L-alanine;
L4 is I or X wherein X is selected from the group consisting of: cyclobutyl-L-glycine, cyclobutyl-L-alanine and norleucine; and
L5 is SEQ ID NO: 45.

25. The peptide of claim 1, wherein
Z1 and Z2 are G;
L1 is SEQ ID NO: 397;
L2 is SEQ ID NO: 97;
L3 is MEQ or XEQ, wherein X is selected from the group consisting of: cyclobutyl-L-alanine and t-butyl-L-alanine;
L4 is I or X, wherein X is selected from the group consisting of: cyclobutyl-L-glycine and cyclobutyl-L-alanine; and
L5 is SEQ ID NO: 45.

26. The peptide of claim 1, wherein
Z1 is X, wherein X is acetylglycine;
Z2 is X, wherein X is glycine amide;
L1 is SEQ ID NO: 143, 397 or 434;
L2 is SEQ ID NO: 97;
L3 is MEQ or LEQ;
L4 is I; and
L5 is SEQ ID NO: 45.

27. The peptide of claim 1, wherein
Z1 and Z2 are G;
L1 is SEQ ID NO: 33, 396, or amino acids 3 to 8 of SEQ ID NO: 548;
L2 is SEQ ID NO: 97;
L3 is VSQ;
L4 is I; and
L5 is SEQ ID NO: 45.

28. The peptide of claim 1, wherein
Z1 and Z2 are G;
L1 is SEQ ID NO: 141, 143, or 277;
L2 is SEQ ID NO: 97;
L3 is MSD, MNQ, FYE, or VSQ;
L4 is I; and
L5 is SEQ ID NO: 45.

29. The peptide of claim 1, wherein
Z1 and Z2 are G;
L1 is SEQ ID NO: 143;
L2 is SEQ ID NO: 97, amino acids 12-16 of SEQ ID NO: 538 or amino acids 12-16 of SEQ ID NO: 539
L3 is MED, MEE, MEK, MEN, and MEX wherein X is ornithine;
L4 is I; and
L5 is SEQ ID NO: 45.

30. The peptide of claim 1, wherein
Z1 and Z2 are G;
L1 is SEQ ID NO: 277;
L2 is SEQ ID NO: 97, amino acids 12-16 of SEQ ID NO: 540 or amino acids 12-16 of SEQ ID NO: 541
L3 is VSD, VSE, VSK, VSN, or VSX wherein X is ornithine;
L4 is I; and
L5 is SEQ ID NO: 45.

31. The peptide of claim 2, comprising the amino acid sequence of SED ID NO: 139.

32. The peptide of claim 2, comprising the amino acid sequence of SED ID NO: 142.

33. The peptide of claim 2, comprising the amino acid sequence of SED ID NO: 146.

34. The peptide of claim 2, comprising the amino acid sequence of SED ID NO: 435.

35. An isolated nucleic acid encoding the peptide of claim 1.

36. An expression vector encoding the nucleic acid molecule of claim 35.

37. A cell comprising the expression vector of claim 36.

38. A method of producing the peptide of claim 1 comprising culturing the cell of claim 37 and recovering the peptide from the cell culture.

39. A method of producing the peptide of claim 1, comprising chemically synthesizing the peptide.

* * * * *